US012576109B2

(12) United States Patent
Alshamleh et al.

(10) Patent No.: US 12,576,109 B2
(45) Date of Patent: Mar. 17, 2026

(54) ALLOGENEIC HUMAN PLASMA AND PLATELET DERIVED PRODUCTS AND USES THEREOF

(71) Applicant: Consano Bio, Inc., Lewes, DE (US)

(72) Inventors: Ehab Mosa Alshamleh, Bedford (CA); Barbara Bennett, Wakefield, MA (US); Karen Fu, Lexington, MA (US); Andrew James Hall, Gillette, NJ (US); Vishwesh Ashok Patil, Arlington, MA (US); Jennifer Louise Schmitke, Belmont, MA (US); Teresa Leah Wright, Lexington, MA (US); Jennifer Newman, Burlington, MA (US); William Kane Grier, Ashland, MA (US)

(73) Assignee: Consano Bio, Inc., Lewes, DE (US)

( * ) Notice: Subject to any disclaimer, the term of this patent is extended or adjusted under 35 U.S.C. 154(b) by 0 days.

(21) Appl. No.: 19/194,993

(22) Filed: Apr. 30, 2025

(65) Prior Publication Data

US 2025/0302873 A1 Oct. 2, 2025

Related U.S. Application Data

(63) Continuation of application No. PCT/US2025/017819, filed on Feb. 28, 2025.

(60) Provisional application No. 63/722,936, filed on Nov. 20, 2024, provisional application No. 63/559,536, filed on Feb. 29, 2024.

(51) Int. Cl.
| | |
|---|---|
| *A61K 35/16* | (2015.01) |
| *A61K 35/19* | (2015.01) |
| *A61K 38/18* | (2006.01) |
| *A61K 38/19* | (2006.01) |
| *A61K 38/36* | (2006.01) |
| *A61K 38/38* | (2006.01) |
| *A61K 39/395* | (2006.01) |
| *A61P 25/02* | (2006.01) |

(52) U.S. Cl.
CPC .............. *A61K 35/16* (2013.01); *A61K 35/19* (2013.01); *A61K 38/1808* (2013.01); *A61K 38/1825* (2013.01); *A61K 38/1833* (2013.01); *A61K 38/1841* (2013.01); *A61K 38/1858* (2013.01); *A61K 38/1866* (2013.01); *A61K 38/19* (2013.01); *A61K 38/363* (2013.01); *A61K 38/385* (2013.01); *A61K 39/39516* (2013.01); *A61P 25/02* (2018.01)

(58) Field of Classification Search
None
See application file for complete search history.

(56) References Cited

U.S. PATENT DOCUMENTS

| | | | |
|---|---|---|---|
| 8,603,541 | B2 | 12/2013 | Weissman et al. |
| 8,993,733 | B2 | 3/2015 | Anitua Aldecoa |
| 9,682,104 | B2 | 6/2017 | Patel |
| 9,757,430 | B2 | 9/2017 | Woods et al. |
| 9,943,546 | B2 | 4/2018 | Weissman et al. |
| 9,950,035 | B2 | 4/2018 | Binder et al. |
| 10,166,258 | B2 | 1/2019 | Dietz et al. |
| 10,357,513 | B2 | 7/2019 | Braithwaite et al. |
| 10,874,692 | B2 | 12/2020 | Braithwaite et al. |
| 10,925,901 | B2 | 2/2021 | Dietz et al. |
| 10,980,837 | B2 | 4/2021 | Patel |
| 10,993,965 | B2 | 5/2021 | Patel |
| 11,326,144 | B2 | 5/2022 | Patel |
| 11,413,308 | B2 | 8/2022 | Braithwaite et al. |
| 12,370,218 | B2 | 7/2025 | Delorme et al. |
| 12,371,657 | B2 | 7/2025 | Dietz et al. |
| 2009/0220482 | A1* | 9/2009 | Higgins ............. A61K 38/1709 424/94.64 |
| 2021/0154234 | A1 | 5/2021 | Dietz et al. |
| 2021/0290683 | A1 | 9/2021 | Sutton et al. |
| 2021/0361718 | A1 | 11/2021 | Srinivasan |
| 2022/0127573 | A1 | 4/2022 | Hosoe |
| 2022/0249612 | A1 | 8/2022 | Palanivel et al. |
| 2022/0339190 | A1 | 10/2022 | Palanivel et al. |
| 2022/0395558 | A1 | 12/2022 | Palanivel et al. |
| 2023/0404923 | A1 | 12/2023 | Chen et al. |
| 2024/0350556 | A1 | 10/2024 | Rizzo et al. |
| 2025/0186499 | A1 | 6/2025 | Chen et al. |
| 2025/0186500 | A1 | 6/2025 | Chen et al. |
| 2025/0320456 | A1 | 10/2025 | Coutinho Da Costa et al. |
| 2025/0360168 | A1 | 11/2025 | Hodler et al. |

FOREIGN PATENT DOCUMENTS

| | | | |
|---|---|---|---|
| CA | 2695398 | A1 | 2/2009 |
| CA | 2919314 | A1 | 2/2015 |
| EP | 2740486 | A1 | 6/2014 |
| EP | 3095856 | A1 | 11/2016 |

(Continued)

OTHER PUBLICATIONS

Mishra et al (Tissue Eng Part C Methods. Feb. 10, 2009;15(3):431-435) (Year: 2009).*

Ahmadpoor et al., "Self-Assembled Nanoflowers from Natural Building Blocks with Antioxidant, Antibacterial, and Antibiofilm Properties." ACS Applied Bio Materials 8(1) (2025): 152-165. doi:10.1021/acsabm.4c00788.

Alizadeh et al., "Autologous platelet-rich plasma eye drops accelerate re-epithelialization of post-keratoplasty persistent corneal epithelial defects." Journal of Ophthalmic & Vision Research 14(2) (2019): 131.

Anitua et al., "Potential Use of Plasma Rich in Growth Factors in Age-Related Macular Degeneration: Evidence from a Mouse Model." Medicina 60 (2024): 2036.

(Continued)

*Primary Examiner* — Brian Gangle
*Assistant Examiner* — Andrea K McCollum
(74) *Attorney, Agent, or Firm* — Foley Hoag LLP; Amy E. Mandragouras; Ariana D. Harris

(57) ABSTRACT

Provided herein are compositions comprising allogeneic human plasma and platelet derived product, and methods for making the compositions and using the compositions as a therapeutic for example, in orthopedic indications.

30 Claims, 28 Drawing Sheets

(56) References Cited

FOREIGN PATENT DOCUMENTS

| | | | |
|----|----------------|----|---------|
| EP | 3254684 | A1 | 12/2017 |
| EP | 2334785 | B2 | 8/2019 |
| EP | 3584310 | A1 | 12/2019 |
| EP | 4458363 | A1 | 11/2024 |
| EP | 4358979 | B1 | 10/2025 |
| WO | WO-2014/126931 | A1 | 8/2014 |
| WO | WO-2021/009659 | A1 | 1/2021 |
| WO | WO-2021/009662 | A1 | 1/2021 |
| WO | WO-2021/009663 | A1 | 1/2021 |
| WO | WO-2023/026213 | A1 | 3/2023 |
| WO | WO-2024/159177 | A1 | 8/2024 |
| WO | WO-2024/233577 | A1 | 11/2024 |
| WO | WO-2025/184489 | A1 | 9/2025 |
| WO | WO-2025/217615 | A1 | 10/2025 |

OTHER PUBLICATIONS

Anonymous, "Blood Protein—Wikipedia," Nov. 14, 2022. Retrieved from: https://web.archive.org/web/20221114044803/https://en.wikipedia.org/wiki/Blood_protein.

Berry et al., "A review of lumbar radiculopathy, diagnosis, and treatment." Cureus 11(10) (2019).

Bieback et al., "Gaps in the knowledge of human platelet lysate as a cell culture supplement for cell therapy: a joint publication from the AABB and the International Society for Cell & Gene Therapy." Cytotherapy 21(9) (2019): 911-924.

Burnouf et al., "Expanding applications of allogeneic platelets, platelet lysates, and platelet extracellular vesicles in cell therapy, regenerative medicine, and targeted drug delivery." Journal of Biomedical Science 30(1) (2023): 79.

Camussi et al., "The importance of controlled clinical trials with extracellular vesicles." Journal of Extracellular Vesicles 12 (2023): e12347.

Centeno et al., "The use of lumbar epidural injection of platelet lysate for treatment of radicular pain." Journal of Experimental Orthopaedics 4 (2017): 1-11.

Choi et al., "Effect of injectate viscosity on epidural distribution in lumbar transforaminal epidural steroid injection." Pain Research and Management 2019 (2019): 2651504.

Chou et al., "Current methods to manufacture human platelet lysates for cell therapy and tissue engineering: possible trends in product safety and standardization." ISBT Science Series 12 (2017): 168-175.

Cohen et al., "Immunogenicity risk assessment for biotherapeutics through in vitro detection of CD134 and CD137 on T helper cells." MAbs, 13(1) (2021).

Delabie et al., "Single step method for high yield human platelet lysate production." Transfusion 63(2) (2023): 373-383.

Delila et al., "Extensive characterization of the composition and functional activities of five preparations of human platelet lysates for dedicated clinical uses." Platelets 32(2) (2021): 259-272.

Dewberry et al., "High frequency alternating current neurostimulation decreases nocifensive behavior in a disc herniation model of lumbar radiculopathy." Bioelectronic Medicine 9 (2023): 15.

Everts et al., "Profound properties of protein-rich, platelet-rich plasma matrices as novel, multi-purpose biological platforms in tissue repair, regeneration, and wound healing." International Journal of Molecular Sciences 25 (2024): 7914.

He et al., "Comparison of allogeneic platelet-rich plasma with autologous platelet-rich plasma for the treatment of diabetic lower extremity ulcers." Cell Transplantation 29 (2020): 0963689720931428.

Hong et al., "Epidural injection method for long-term pain management in rats with spinal stenosis." Biomedicines 11(5) (2023): 1390.

International Search Report and Written Opinion for International Application No. PCT/US25/17819 dated Jun. 16, 2025.

Invitation to Pay Additional Fees for International Application No. PCT/US25/17819 dated Apr. 22, 2025.

Johnson et al., "First-in-human clinical trial of allogeneic, platelet-derived extracellular vesicles as a potential therapeutic for delayed wound healing." Journal of Extracellular Vesicles 12 (2023): 12332.

Kawabata et al., "Advances in platelet-rich plasma treatment for spinal diseases: a systematic review." International Journal of Molecular Sciences 24 (2023): 7677.

Khongjaroensakun et al., "A simple and applicable method for human platelet lysate preparation using citrate blood." Laboratory Medicine 53 (2022): e109-e112.

Kocaoemer et al., "Human AB serum and thrombin-activated platelet-rich plasma are suitable alternatives to fetal calf serum for the expansion of mesenchymal stem cells from adipose tissue." Stem Cells 25 (2007): 1270-1278.

Lopez et al., "Platelet-rich plasma in treating peripheral neuropathic pain. Preliminary report," Revista de la Sociedad Espanola del Dolor 25.5 (2018): 263-270.

Mathur et al., "Adding to platelet safety and life: Platelet additive solutions." Asian Journal of Transfusion Science 12(2) (2018): 136-140.

Nebie et al., "Human platelet lysate biotherapy for traumatic brain injury: preclinical assessment." Brain 144(10) (2021): 3142-3158.

Noh et al., "Effects of different doses of complete Freund's adjuvant on nociceptive behaviour and inflammatory parameters in polyarthritic rat model mimicking rheumatoid arthritis." PloS one 16.12 (2021): e0260423.

Oeller et al. "Human platelet lysate for good manufacturing practice-compliant cell production." International Journal of Molecular Sciences 22 (2021): 5178.

Peng et al., "Efficacy of platelet-rich plasma and platelet-rich fibrin in arthroscopic rotator cuff repair: A systematic review and meta-analysis." PM&R 15.12 (2023): 1643-1653.

Peng et al., "Platelet-derived biomaterial with hyaluronic acid alleviates temporal-mandibular joint osteoarthritis: clinical trial from dish to human." Journal of Biomedical Science 30.1 (2023): 77.

Rawson, "Platelet-Rich Plasma and Epidural Platelet Lysate: Novel Treatment for Lumbar Disk Herniation." The Journal of the American Osteopathic Association 120(3) (2020): 201-207. doi:10.7556/jaoa.2020.032.

Rizzo et al., "Safety results for geographic atrophy associated with age-related macular degeneration using subretinal cord blood platelet-rich plasma." Ophthalmology Science 4.6 (2024): 100476.

Ruiz et al., "Method to obtain a plasma rich in platelet- and plasma-growth factors based on water evaporation," PLoS One 19(2) (2024): e0297001.

Schallmoser et al., "Production and quality requirements of human platelet lysate: a position statement from the working party on cellular therapies of the international society of blood transfusion." Trends in Biotechnology 38.1 (2020): 13-23.

Seghatchian, "Platelet therapy: Current opinions on laboratory and clinical aspects." Transfusion Science 18(3 (1997): 345-350.

Shariati et al., "Investigation into antibacterial and wound healing properties of platelets lysate against Acinetobacter baumannii and Klebsiella pneumoniae burn wound infections." Annals of Clinical Microbiology and Antimicrobials 20 (2021): 40.

Shih et al., "Preparation, quality criteria, and properties of human blood platelet lysate supplements for ex vivo stem cell expansion." New Biotechnology 32 (2015): 199-211.

Strandberg et al., "Standardizing the freeze-thaw preparation of growth factors from platelet lysate." Transfusion 57(40 (2017): 1058-1065.

Sugimoto et al., "Generation and manipulation of human iPSC-derived platelets." Cellular and Molecular Life Sciences 78 (2021): 3385-3401.

Tavakoli et al., "Advanced strategies for the regeneration of lumbar disc annulus fibrosus." International Journal of Molecular Sciences 21 (2020): 4889.

Torre et al., "Annulus fibrosus cell phenotypes in homeostasis and injury: implications for regenerative strategies." Annals of the New York Academy of Sciences 1442.1 (2019): 61-78.

Trial to Reduce Alloimmunization to Platelets Study Group. "Leukocyte reduction and ultraviolet B irradiation of platelets to prevent alloimmunization and refractoriness to platelet transfusions." New England Journal of Medicine 337(26) (1997): 1861-1870.

(56) References Cited

OTHER PUBLICATIONS

Van der Meer, "PAS or plasma for storage of platelets? A concise review." Transfusion Medicine 26(5) (2016): 339-342.

Whelan, "What Are Hydrocolloid Bandages Made Of?" Healthline, (2022) https://www.healthline.com/health/what-is-in-hydrocolloid-bandages.

Widyaningrum et al., "A purified human platelet pellet lysate rich in neurotrophic factors and antioxidants repairs and protects corneal endothelial cells from oxidative stress." Biomedicine & Pharmacotherapy 142 (2021): 112046.

Xu et al., "Ultrasound-Guided Transforaminal Injections of Platelet-Rich Plasma Compared with Steroid in Lumbar Disc Herniation: A Prospective, Randomized, Controlled Study." Neural Plasticity 2021.1 (2021): 5558138.

Zunino et al., "A human plasma fraction alleviates cold allodynia in the mouse oxaliplatin-induced peripheral neuropathy model of pain." PSTR477.10 Charles River (2023).

Zunino et al., "A human plasma fraction alleviates cold allodynia in the mouse oxaliplatin-induced peripheral neuropathy model of pain." Society of Neuroscience. Nov. 11-15, 2023, Washington DC.

* cited by examiner

Lane
1. Hypo-osmotic 1
2. Hypo-osmotic 2
3. Hypo-osmotic 3
4. Hyper-osmotic
5. Detergent
6. Freeze-Thaw

FIG. 15

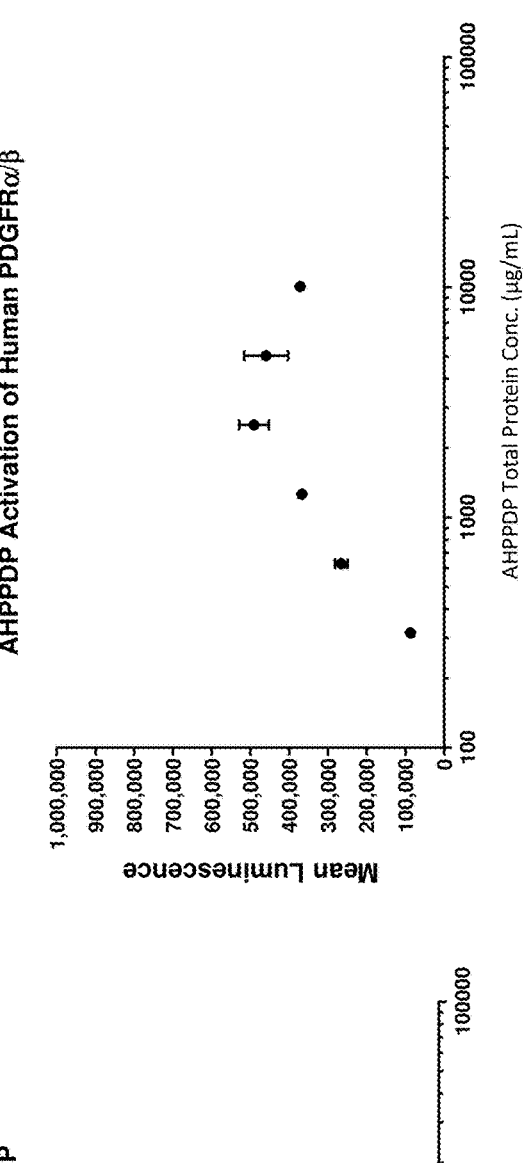
FIG. 21B
FIG. 21A

1

ALLOGENEIC HUMAN PLASMA AND PLATELET DERIVED PRODUCTS AND USES THEREOF

CROSS REFERENCE TO RELATED APPLICATIONS

This application is a continuation application of International Application No. PCT/US25/17819 filed on Feb. 28, 2025, which claims the benefit of U.S. Provisional Application 63/559,536, filed Feb. 29, 2024, and U.S. Provisional Application 63/722,936, filed Nov. 20, 2024, the contents of each are hereby incorporated by reference.

BACKGROUND OF THE DISCLOSURE

Painful joint conditions are commonly occurring and debilitating with many different etiologies. These diseases and the symptoms of pain and reduced function can be due to problems with the bone, nerves and connective tissue. Orthopedic and nervous tissue injuries such as painful lumbar radiculopathy, osteoarthritis, tendon or ligament injuries (such as to the rotator cuff), nerve injury (such as carpal tunnel, spinal cord or other traumatic nerve injury), and chemotherapy-induced peripheral neuropathy cause pain and disability across many demographic groups (Centeno, J Exp Orthop. 2017 Nov. 25; 4(1):38; Peng B Y, et al., J Biomed Sci. 2023; 30(1):77; Peng Y, et al., P M R. 2023; 15(12):1643-1653; Kawabata S, et al., Int J Mol Sci. 2023; 24(8):7677; Zunino, G. et al., Society of Neuroscience. Nov. 11-15, 2023, Washington DC). In particular, low back pain is one of the highest burden of diseases, and in 2016 was the leading cause of disability-adjusted-life-years (DALY) in 2016 (Mokdad A H, et al., JAMA. 2018 Apr. 10; 319(14): 1444-1472). Painful lumbosacral radiculopathy (PLSR) is a disease that typically involves compression of the lumbar spinal nerve root, and it can manifest in several ways such as weakness, pain, or numbness. Non-steroidal anti-inflammatory drugs (NSAIDs) are the first line of treatment, providing short-term pain relief (van der Gaag W H, et al., Cochrane Database Syst Rev. 2020 Apr. 16; 4(4): CD013581), but may increase the risk of developing chronic pain (Parisien M, et al., Sci Transl Med. 2022 May 11; 14(644):eabj9954C). Steroids are often used to treat PLSR, despite no proven efficacy and significant side effects, including bone loss and increased spinal fracture risks. Opioids are also used to manage PLSR, but do not treat the cause and have significant addictive potential.

Autologous preparations of platelet rich plasma and human platelet lysate has been shown to be a promising regenerative therapy, which is attributed to the presence of cytokines and growth factors. Platelet rich plasma and human platelet lysates may be used locally to treat orthopedic, tendon or nerve injuries. Autologous platelet lysate has been administered epidurally to treat PLSR and was shown to reduce lumbar radicular pain (Centeno, J Exp Orthop. 2017 Nov. 25; 4(1):38). While the results with the autologous platelets demonstrate the potential pharmacological activity of a regenerative medicine in PLSR, there is inherent variability in the process of preparing the platelet lysate. The biological activity and identity of the autologous preparation is unknown, and there may be variability in the potency between individuals.

SUMMARY OF THE DISCLOSURE

In some aspects, the disclosure provides a pharmaceutical composition comprising an allogeneic human plasma and platelet derived product comprising:

2

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFb1, TGFb2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some aspects, the disclosure provides a pharmaceutical composition comprising an allogeneic human plasma and platelet derived product comprising:

(a) human plasma proteins comprising at least one of albumin, globulins, and fibrinogen; and (b) human platelet proteins comprising at least one of PDGF-AB, PDGF-AA, PDGF-BB, TGFb1, TGFb2, BDNF, VEGF, FGF, EGF and HGF, wherein the total protein concentration of the composition is greater than 50 mg/mL and less than or about 500 mg/mL.

In some aspects, the disclosure provides a pharmaceutical composition comprising an allogeneic human plasma and platelet derived product comprising:

(a) human plasma proteins comprising at least one of albumin, globulins, and fibrinogen; and (b) human platelet proteins comprising at least one of PDGF-AB, PDGF-AA, PDGF-BB, TGFb1, TGFb2, VEGF, FGF, EGF and HGF, wherein the total protein concentration of the composition is greater than 50 mg/mL and less than or about 500 mg/mL.

In some aspects, the disclosure provides a pharmaceutical composition comprising an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFb1, TGFb2, VEGF, FGF, EGF and HGF, wherein the total protein concentration of the composition is greater than 50 mg/mL and less than or about 500 mg/mL.

In some aspects, the disclosure provides a pharmaceutical composition comprising an allogeneic human plasma and platelet derived product comprising:

(a) human plasma proteins comprising fibrinogen; and (b) human platelet proteins comprising PDGF-AB wherein the total protein concentration of the composition is greater than 50 mg/mL and less than or about 500 mg/mL.

In some aspects, the disclosure provides a pharmaceutical composition comprising an allogeneic human plasma and platelet derived product comprising:

(a) human plasma proteins comprising fibrinogen, human serum albumin and immunoglobulin; and (b) human platelet proteins comprising PDGF-AB, TGF-β, VEGF, EGF, FGF and HGF, wherein:

(i) the total protein concentration of the composition is greater than 50 mg/mL and less than or about 500 mg/mL, (ii) the concentration of fibrinogen is about 0.25 mg/mL to about 5 mg/mL, (iii) the concentration of human serum albumin is about 60% to about 70% w/w total protein, (iv) the concentration of immunoglobulin is about 10% to about 20% w/w total protein, and (v) the concentration of PDGF-AB is about 5 ng/mL to about 200 ng/mL.

In some aspects, the disclosure provides a pharmaceutical composition comprising an allogeneic human plasma and platelet derived product comprising: (a) human plasma proteins comprising fibrinogen at a concentration of about 1 mg/mL to about 2 mg/mL, and (b) human platelet proteins comprising about 20 to about 70 μg/mL PDGF-AB, wherein the total protein concentration is about 50 mg/mL to about 160 mg/mL. In some aspects, the disclosure provides a pharmaceutical composition comprising an allogeneic human plasma and platelet derived product comprising: (a) human plasma proteins comprising fibrinogen at a concentration of about 0.77 mg/mL, and (b) human platelet proteins comprising about 21 to about 67 μg/mL PDGF-AB, wherein the total protein concentration is about 56 mg/mL to about 156 mg/mL. In some aspects, the disclosure provides a pharmaceutical composition comprising an allogeneic human plasma and platelet derived product as characterized in Examples 11 and 14.

In some aspects, the disclosure provides a pharmaceutical composition comprising an allogeneic human plasma and platelet derived product comprising: (a) human plasma proteins comprising about 1 mg/mL to about 2 mg/mL fibrinogen, and about 60% to about 70% w/w albumin, about 10% to about 20% w/w immunoglobulin, and (b) human platelet proteins comprising about 50 to about 60 ng/mL PDGF-AB, about 350 to about 450 ng/mL TGF-β, about 450 to about 650 pg/mL VEGF, about 1000 to about 3000 pg/mL EGF, about 750 to about 1000 pg/mL FGF, and about 300 to about 800 pg/mL HGF, wherein the total protein concentration is about 50 mg/mL to about 160 mg/mL, wherein the total protein concentration is about 100 mg/mL to about 150 mg/mL. In some aspects, the disclosure provides a pharmaceutical composition comprising an allogeneic human plasma and platelet derived product as characterized in Example 31.

In other aspects, the disclosure provides a pharmaceutical composition comprising an allogeneic human plasma and platelet derived product comprising:
- (a) human plasma proteins comprising albumin, globulins, and fibrinogen; and
- (b) human platelet proteins comprising PDGF-AB, PDGF-AA, PDGF-BB, TGFβ1, TGFβ2, BDNF, VEGF, FGF, EGF and HGF,
- wherein the concentration of PDGF-AB is greater than 50 pg/mL and less than 1,000 pg/mL.

In other aspects, the disclosure provides a pharmaceutical composition comprising an allogeneic human plasma and platelet derived product comprising:
- (a) human plasma proteins comprising at least one of albumin, globulins, and fibrinogen; and
- (b) human platelet proteins comprising at least one of PDGF-AB, PDGF-AA, PDGF-BB, TGFβ1, TGFβ2, BDNF, VEGF, FGF, EGF and HGF,
- wherein the concentration of PDGF-AB is greater than 50 pg/mL and less than 1,000 pg/mL.

In other aspects, the disclosure provides a pharmaceutical composition comprising an allogeneic human plasma and platelet derived product comprising:
- (a) human plasma proteins comprising at least one of albumin, globulins, and fibrinogen; and
- (b) human platelet proteins comprising at least one of PDGF-AB, PDGF-AA, PDGF-BB, TGFβ1, TGFβ2, VEGF, FGF, EGF and HGF, wherein the concentration of PDGF-AB is greater than 50 pg/mL and less than 1,000 pg/mL.

In other aspects, the disclosure provides a pharmaceutical composition comprising an allogeneic human plasma and platelet derived product comprising:
- (a) human plasma proteins comprising albumin, globulins, and fibrinogen; and
- (b) human platelet proteins comprising PDGF-AB, PDGF-AA, PDGF-BB, TGFβ1, TGFβ2, VEGF, FGF, EGF and HGF,
- wherein the concentration of PDGF-AB is greater than 50 pg/mL and less than 1,000 pg/mL.

In other aspects, the disclosure provides a pharmaceutical composition comprising an allogeneic human plasma and platelet derived product comprising:
- (a) human plasma proteins comprising albumin, globulins, and fibrinogen; and
- (b) human platelet proteins comprising PDGF-AB, wherein the concentration of PDGF-AB is greater than 50 pg/mL and less than 1,000 pg/mL.

In other aspects, the disclosure provides a pharmaceutical composition comprising an allogeneic human plasma and platelet derived product comprising:
- (a) human plasma proteins comprising fibrinogen, wherein the concentration of fibrinogen is about 20 μg/mL to about 10 mg/mL, or about 1 mg/mL to about 5 mg/mL; and
- (b) human platelet proteins comprising PDGF-AB, wherein the concentration of PDGF-AB is greater than 50 pg/mL and less than 1,000 pg/mL,
- wherein the total protein concentration of the composition is greater than 50 mg/mL and less than or about 500 mg/mL.

In some embodiments, the total protein concentration of the composition is greater than 50 mg/mL and less than or about 500 mg/mL. In some embodiments, the total protein concentration is less than or about 250 mg/mL. In some embodiments, the total protein concentration is about 100 mg/mL to about 250 mg/mL.

In some embodiments, the composition has a viscosity of 50 cP or less. In some embodiments, the composition comprises a viscosity of less than 25 cP, less than 20 cP, less than 15 cP, or less than 10 cP. In some embodiments, the viscosity is about 1 to about 5 cP, 5 to about 10 cP, about 10 to about 15 cP, or about 15 to about 20 cP.

In some embodiments, the composition has a pH of about 4.5 to about 8.5. In some embodiments, the composition has an osmolality of about 200 to about 500 mOsmo/kg.

In some embodiments, the concentration of albumin is about 100 to about 1,400 mg/mL. In some embodiments, the concentration of albumin is greater than or about 40% w/w. In some embodiments, albumin is human serum albumin. In some embodiments, the concentration of albumin is about 60% to about 70% w/w.

In some embodiments, the concentration of fibrinogen is about 20 μg/mL to about 10 mg/mL, or about 1 mg/mL to about 5 mg/mL.

In some embodiments, the globulins comprise immunoglobulins. In some embodiments, the concentration of immunoglobulins is greater than or about 20% w/w. In some embodiments, the concentration of immunoglobulins is about 10% to about 20% w/w. In some embodiments, the globulins comprise alpha-2-macroglobulin (A2M). In some embodiments, the concentration of A2M is greater than or about 200 mg/mL.

In some embodiments, the concentration of albumin and/or immunoglobulin is determined by capillary electrophoresis sodium dodecyl sulfate (CE-SDS), enzyme-linked immunosorbent assay (ELISA), size exclusion high performance liquid chromatography (SEC-HPLC), or SDS polyacrylamide gel electrophoresis (SDS-PAGE).

In some embodiments, the concentration of PDGF-AB is about 5 ng/mL to about 200 ng/mL. In some embodiments, the concentration of PDGF-AB is about 20 ng/mL to about 160 ng/mL, about 20 ng/mL to about 40 ng/mL, about 40 ng/mL to about 80 ng/mL, or about 80 ng/mL to about 160 ng/mL.

In some embodiments, the human platelet proteins comprise one or more of PDGF-AB, PDGF-AA, PDGF-BB, TGF-β1, TGF-β2, VEGF, FGF, EGF, and HGF. In some embodiments, the concentration of TGF-β is about 50 ng/mL to about 1000 ng/mL, the concentration of VEGF is about 50 pg/mL to about 1500 pg/mL, the concentration of EGF is about 100 pg/mL to about 6000 pg/mL, the concentration of FGF is about 100 pg/mL to about 3000 pg/mL, and/or the concentration of HGF is about 25 pg/mL to about 2500 pg/mL. In some embodiments, (i) the concentration of TGF-β is about 175 ng/mL to about 225 ng/mL, about 350 ng/mL to about 450 ng/mL, or about 700 ng/mL to about 900 ng/mL; (ii) the concentration of VEGF is about 225 pg/mL to about 325 pg/mL, 450 pg/mL to about 650 pg/mL, or about 900 pg/mL to about 1300 pg/mL; (iii) the concentration of EGF is about 500 pg/mL to about 1500 pg/mL, about 1000 pg/mL to about 3000 pg/mL, or about 2000 pg/mL to about 6000 pg/mL; (iv) the concentration of FGF is about 350 pg/mL to about 500 pg/mL, about 700 pg/mL to about 1000 pg/mL, or about 1400 pg/mL to about 2000 pg/mL; (v) the concentration of HGF is about 125 pg/mL to about 425 pg/mL, about 250 pg/mL to about 850 pg/mL, or about 500 pg/mL to about 1700 pg/mL; or (vi) any combination of (i)-(v).

In some embodiments, the total protein concentration is about 50 mg/mL to about 80 mg/mL, the fibrinogen concentration is about 0.5 mg/mL to about 1 mg/mL, the PDGF-AB concentration is about 20 ng/mL to about 40 ng/mL, the TGF-β concentration is about 150 ng/mL to about 300 ng/mL, the VEGF concentration is about 200 pg/mL to about 400 pg/mL, the EGF concentration is about 1000 pg/mL to about 2000 pg/mL, the FGF concentration is about 300 pg/mL to about 600 pg/mL, and the HGF concentration is about 150 pg/mL to about 300 pg/mL. In some embodiments, the total protein concentration is about 80 mg/mL to about 160 mg/mL, the fibrinogen concentration is about 1 mg/mL to about 2 mg/mL, the PDGF-AB concentration is about 40 ng/mL to about 80 ng/mL, the TGF-β concentration is about 350 ng/mL to about 450 ng/mL, the VEGF concentration is about 400 pg/mL to about 800 pg/mL, the EGF concentration is about 2000 pg/mL to about 4000 pg/mL, the FGF concentration is about 600 pg/mL to about 1200 pg/mL, and the HGF concentration is about 300 pg/mL to about 1000 pg/mL. In some embodiments, the total protein concentration is about 160 mg/mL to about 320 mg/mL, the fibrinogen concentration is about 2 mg/mL to about 5 mg/mL, the PDGF-AB concentration is about 80 ng/mL to about 160 ng/mL, the TGF-β concentration is about 500 ng/mL to about 1000 ng/mL, the VEGF concentration is about 800 pg/mL to about 1500 pg/mL, the EGF concentration is about 4000 pg/mL to about 6000 pg/mL, the FGF concentration is about 1200 pg/mL to about 3000 pg/mL, and the HGF concentration is about 1000 pg/mL to about 2500 pg/mL.

In some embodiments, the composition comprises an anti-inflammatory protein. In some embodiments, the platelet proteins comprise an anti-inflammatory protein. In some embodiments, the anti-inflammatory protein is selected from interleukin 1 (IL-1), receptor antagonist protein (IRAP), IL-10, TIMP-1, and any combination thereof. In some embodiments, the anti-inflammatory proteins comprise at least two of IL-1, IRAP, IL-10 and TIMP-1. In some embodiments, the anti-inflammatory proteins comprise at least three of IL-1, IRAP, IL-10 and TIMP-1. In some embodiments, the anti-inflammatory proteins comprise IL-1, IRAP, IL-10 and TIMP-1. In some embodiments, the composition comprises an antioxidant protein. In some embodiments, the platelet proteins comprise an antioxidant protein. In some embodiments, the antioxidant protein is selected from glutathione S-transferase, glutathione peroxide, catalase, and any combination thereof. In some embodiments, the antioxidant proteins comprise glutathione S-transferase, glutathione peroxide, and catalase. In some embodiments, the antioxidant proteins comprise any two of glutathione S-transferase, glutathione peroxide, and catalase.

In some embodiments, the pharmaceutical composition comprises one or more cytokines selected from IL-5, IL-1b, IL-6, IL-1Ra, IL-10, IL-13, TNFα, IL-8, IL-12p40, and MCP-1.

In some embodiments, the composition comprises a buffer which maintains plasma proteins in solution. In some embodiments, the buffer comprises citrate or phosphate buffer comprising NaCl.

In some embodiments, the composition forms a depot at a site of injection. In some embodiments, the composition comprises one or more plasma proteins, e.g., fibrinogen, capable of forming a matrix following administration to a subject in vivo.

In some embodiments, the composition is formulated for epidural injection. In some embodiments, the composition is formulated for intraarticular injection. In some embodiments, the composition is formulated for intrathecal injection. In some embodiments, the composition is formulated for intramuscular injection. In some embodiments, the composition is formulated for intravitreal injection. In some embodiments, the composition is formulated for subretinal injection. In some embodiments, the composition is formulated for suprachoroidal injection. In some embodiments, the composition is formulated for systemic injection. In some embodiments, the composition is formulated for intravenous injection. In some embodiments, the composition is formulated for intraosseous injection. In some embodiments, the composition is formulated for local administration.

In some aspects, the disclosure provides a method for treating pain in a subject, comprising administering to the subject a pharmaceutical composition described herein.

In some aspects, the disclosure provides a method for treating an orthopedic indication or injury in a subject, comprising administering to the subject a pharmaceutical composition described herein. In some aspects, the disclosure provides use of a pharmaceutical composition described herein for treating an orthopedic indication or injury in a subject.

In some embodiments, the orthopedic indication or injury is selected from painful lumbar radiculopathy, a spinal cord injury, osteoarthritis, ligament laxity, a rotator cuff injury, and a muscle injury. In some embodiments, the pharmaceutical composition is administered locally. In some embodiments, local administration is epidural, intrathecal, intraarticular, intramuscular, direct injection into a tendon, or direction injection into a ligament.

In some aspects, the disclosure provides a method for treating painful lumbar radiculopathy in a subject, comprising administering to the subject a pharmaceutical composition formulated for epidural injection described herein. In some embodiments, the method comprises x-ray guided needle injection.

In some aspects, the disclosure provides use of a pharmaceutical composition formulated for epidural injection described herein for treating painful lumbar radiculopathy in a subject. In some embodiments, the use comprises x-ray guided needle injection.

In some aspects, the disclosure provides a method for treating a spinal cord injury in a subject, comprising administering to the subject a pharmaceutical composition formulated for intrathecal injection described herein.

In some aspects, the disclosure provides use of a pharmaceutical composition formulated for intrathecal injection described herein for treating a spinal cord injury in a subject.

In some aspects, the disclosure provides a method for treating osteoarthritis in a subject, comprising administering to the subject a pharmaceutical composition formulated for intraarticular injection described herein.

In some aspects, the disclosure provides use of a pharmaceutical composition formulated for intraarticular injection described herein for treating osteoarthritis in a subject.

In some aspects, the disclosure provides a method for treating chemotherapy-induced peripheral neuropathy (CIPN), comprising administering to the subject a pharmaceutical composition described herein. In some embodiments, administering is systemic administration. In some embodiments, systemic administration is intravenous administration.

In some aspects, the disclosure provides a method for treating an ophthalmic condition or disease in a subject, comprising administering a pharmaceutical composition described herein.

In some aspects, the disclosure provides use of a pharmaceutical composition described herein for treating chemotherapy-induced peripheral neuropathy (CIPN). In some embodiments, the pharmaceutical composition is formulated for systemic administration. In some embodiments, systemic administration is intravenous administration.

In some embodiments, the pharmaceutical composition is diluted to a desired dose.

In some aspects, the disclosure provides a kit comprising a container comprising a pharmaceutical composition described herein and instructions for treating a subject with an orthopedic indication or injury. In some embodiments, orthopedic indication or injury is selected from painful lumbar radiculopathy, a spinal cord injury, osteoarthritis, ligament laxity, a rotator cuff injury, and a muscle injury. In some embodiments, the instructions comprise diluting the pharmaceutical composition to an appropriate dose. In some embodiments, the instructions comprise injecting the pharmaceutical composition into a site appropriate for the orthopedic indication or injury.

In some aspects, the disclosure provides a method for preparing a pharmaceutical composition described herein, the method comprising:

(a) providing a platelet suspension from one or more donor human subjects, wherein the platelet suspension comprises plasma and platelets, and wherein plasma comprises plasma proteins;

(b) maintaining the plasma and platelets under conditions appropriate to extract platelet proteins from the platelets, thereby generating a platelet extract comprising the plasma proteins and the platelet proteins;

(c) separating the platelet extract from cell debris, thereby generating a purified platelet extract comprising the plasma proteins and the platelet proteins, and (d) concentrating the purified platelet extract, thereby generating the allogeneic human plasma and platelet derived product.

In some aspects, the disclosure provides a method for preparing a pharmaceutical composition described herein, the method comprising:

(a) providing a platelet suspension from one or more donor human subjects, wherein the platelet suspension comprises plasma and platelets, and wherein plasma comprises plasma proteins;

(b) centrifuging and filtering the platelet suspension;

(c) maintaining the plasma and platelets under conditions appropriate to extract platelet proteins from the platelets, thereby generating a platelet extract comprising the plasma proteins and the platelet proteins;

(d) separating the platelet extract from cell debris comprising centrifuging and filtering the platelet extract, thereby generating a purified platelet extract comprising the plasma proteins and the platelet proteins;

(e) filtering the purified platelet extract; and (f) concentrating the purified platelet extract, thereby generating the allogeneic human plasma and platelet derived product.

In some aspects, the disclosure provides a method for preparing a pharmaceutical composition comprising an allogeneic human plasma and platelet derived product, wherein the method comprises:

(a) providing a platelet suspension from one or more donor human subjects, wherein the platelet suspension comprises plasma and platelets, and wherein plasma comprises plasma proteins;

(b) maintaining the plasma and platelets under conditions appropriate to extract platelet proteins from the platelets, thereby generating a platelet extract comprising the plasma proteins and the platelet proteins;

(c) separating the platelet extract from cell debris, thereby generating a purified platelet extract comprising the plasma proteins and the platelet proteins, wherein:

(i) the plasma proteins comprise albumin, globulins, and fibrinogen; and (ii) the platelet proteins comprise PDGF-AB, PDGF-AA, PDGF-BB, TGFβ1, TGFβ2, BDNF, VEGF, b-FGF, EGF and HGF, (d) concentrating the purified platelet extract, thereby generating the allogeneic human plasma and platelet derived product.

In some aspects, the disclosure provides a method for preparing a pharmaceutical composition comprising an allogeneic human plasma and platelet derived product, wherein the method comprises:

(a) providing a platelet suspension from one or more donor human subjects, wherein the platelet suspension comprises plasma and platelets, and wherein plasma comprises plasma proteins;

(b) maintaining the plasma and platelets under conditions appropriate to extract platelet proteins from the platelets, thereby generating a platelet extract comprising the plasma proteins and the platelet proteins;

(c) separating the platelet extract from cell debris, thereby generating a purified platelet extract comprising the plasma proteins and the platelet proteins, wherein:

(i) the plasma proteins comprise albumin, globulins, and fibrinogen; and (ii) the platelet proteins comprise PDGF-AB, PDGF-AA, PDGF-BB, TGFβ1, TGFβ2, VEGF, b-FGF, EGF and HGF, (d) concentrating the purified platelet extract, thereby generating the allogeneic human plasma and platelet derived product.

In some aspects, the disclosure provides a method for preparing a pharmaceutical composition comprising an allogeneic human plasma and platelet derived product, wherein the method comprises:

(a) providing a platelet suspension from one or more donor human subjects, wherein the platelet suspension comprises plasma and platelets, and wherein plasma comprises plasma proteins;

(b) maintaining the plasma and platelets under conditions appropriate to extract platelet proteins from the platelets, thereby generating a platelet extract comprising the plasma proteins and the platelet proteins;

(c) separating the platelet extract from cell debris, thereby generating a purified platelet extract comprising the plasma proteins and the platelet proteins, wherein:

(i) the plasma proteins comprise at least one of albumin, globulins, and fibrinogen; and (ii) the platelet proteins comprise at least one of PDGF-AB, PDGF-AA, PDGF-BB, TGFβ1, TGFβ2, BDNF, VEGF, b-FGF, EGF and HGF, (d) concentrating the purified platelet extract, thereby generating the allogeneic human plasma and platelet derived product.

In some aspects, the disclosure provides a method for preparing a pharmaceutical composition comprising an allogeneic human plasma and platelet derived product, wherein the method comprises:

(a) providing a platelet suspension from one or more donor human subjects, wherein the platelet suspension comprises plasma and platelets, and wherein plasma comprises plasma proteins;

(b) maintaining the plasma and platelets under conditions appropriate to extract platelet proteins from the platelets, thereby generating a platelet extract comprising the plasma proteins and the platelet proteins;

(c) separating the platelet extract from cell debris, thereby generating a purified platelet extract comprising the plasma proteins and the platelet proteins, wherein:

(i) the plasma proteins comprise at least one of albumin, globulins, and fibrinogen; and (ii) the platelet proteins comprise at least one of PDGF-AB, PDGF-AA, PDGF-BB, TGFβ1, TGFβ2, VEGF, b-FGF, EGF and HGF, (d) concentrating the purified platelet extract, thereby generating the allogeneic human plasma and platelet derived product.

In some aspects, the disclosure provides a method for preparing a pharmaceutical composition comprising an allogeneic human plasma and platelet derived product, wherein the method comprises:

(a) providing a platelet suspension from one or more donor human subjects, wherein the platelet suspension comprises plasma and platelets, and wherein plasma comprises plasma proteins;

(b) maintaining the plasma and platelets under conditions appropriate to extract platelet proteins from the platelets, thereby generating a platelet extract comprising the plasma proteins and the platelet proteins;

(c) separating the platelet extract from cell debris, thereby generating a purified platelet extract comprising the plasma proteins and the platelet proteins, wherein:

(i) the plasma proteins comprise at least one of albumin, globulins, and fibrinogen; and (ii) the platelet proteins comprise at least PDGF-AB, (d) concentrating the purified platelet extract, thereby generating the allogeneic human plasma and platelet derived product.

In some embodiments, the platelet suspension is from one or more donor human subjects at an age of 16 to 65 years old. In some embodiments, the platelet suspension is from one or more donor human subjects at an age of 16 to 35 years old. In some embodiments, the platelet suspension is from 10 or more donor human subjects. In some embodiments, the platelet suspension is from whole-blood. In some embodiments, the platelet suspension is from apheresis. In some embodiments, the platelet suspension has been treated with an anti-coagulant, optionally wherein the anti-coagulant is selected from an acid-citrate-dextrose solution, citrate, and heparin.

In some embodiments, step (b) comprises (i) applying at least one freeze-thaw cycle, (ii) contacting the platelet suspension with a detergent, (iii) applying osmotic pressure, (iv) sonication, (v) electroporation, (vi) high pressure microfluidics, or (vii) any combination of (i)-(vi).

In some embodiments, step (b) comprises applying at least one freeze-thaw cycle to the platelet suspension. In some embodiments, the at least one freeze-thaw cycle comprises freezing the source at about −210° C. to about −80° C. and thawing the platelet suspension at about 2-8° C., 15-25° C., or up to 37° C. In some embodiments, the at least one freeze-thaw cycle is three freeze-thaw cycles.

In some embodiments, step (b) comprises contacting the platelet suspension with a detergent to extract platelet proteins from platelets. In some embodiments, the detergent is an anionic detergent, a non-ionic detergent, a cationic detergent, or a zwitterionic detergent. In some embodiments, the detergent is non-denaturing, a mild lysis agent, or a strong lysis agent. In some embodiments, the detergent is sodium dodecyl sulphate (SDS), ethyl trimethyl ammonium bromide, Triton X-45, Triton X-100, Triton X-114, NP-40, Tween 20, Tween 80, CHAPS, or CHAPSO. In some embodiments, the platelet suspension is incubated with the detergent under continuous mixing or gentle rocking for about 10 minutes to about 24 hours, optionally at a temperature of about 4° C. to about 40° C.

In some embodiments, step (b) comprises applying osmotic pressure to the platelet suspension. In some embodiments, osmotic pressure is increased by salts, sugars, and/or buffers. In some embodiments, osmotic pressure is decreased by water, salts, sugars, and/or buffers. In some embodiments, osmotic pressure is from about 0.01 to about 1,000 mOsm/kg.

In some embodiments, the method comprises inactivating and/or removing or reducing viruses. In some embodiments, inactivating and/or removing or reducing viruses occurs in step (b), wherein conditions appropriate to extract platelet proteins inactivate viruses. In some embodiments, inactivating and/or removing or reducing viruses occurs after step (b). In some embodiments, inactivating viruses comprises heat-inactivation, ultraviolet radiation, chemical treatment, or low pH treatment. In some embodiments, removing or reducing viruses comprises nanofiltration or chromatography.

In some embodiments, step (b) occurs in the absence of a clotting agent. In some embodiments, step (b) does not include removing a clot.

In some embodiments, step (c) comprises micro-filtration, depth-filtration, or centrifugation.

In some embodiments, step (d) comprises tangential flow filtration of the purified platelet extract, optionally wherein a membrane for tangential flow filtration has a size of about 1 KDa to about 500 KDa. In some embodiments, step (d) comprises using spin filters to concentrate the purified platelet extract.

In some embodiments, the platelet suspension is diluted in a solution prior to step (b). In some embodiments, the purified platelet extract is diluted in a solution prior to step (d). In some embodiments, the solution is a buffer, optionally phosphate buffered saline (PBS) or a buffer comprising citrate.

In some embodiments, the metho comprises step (e) sterile filtering the allogeneic human plasma and platelet derived product. In some embodiments, step (e) comprises passing the allogeneic human plasma and platelet derived product through a filter of about 0.1 mm to about 0.22 mm.

In some embodiments, the method comprises reducing or removing blood cells from the platelet suspension prior to step (b). In some embodiments, blood cells comprise red blood cells and white blood cells. In some embodiments, white blood cells are reduced by about a 5-6 log reduction. In some embodiments, reducing or removing blood cells comprises passing the platelet suspension through a filter at a temperature of about 2° C. to about 8° C. In some embodiments, the filter is about 0.1 mm to about 40 mm.

In some embodiments, step (b) comprises maintaining the platelet suspension in conditions sufficient to maintain plasma proteins in solution.

In some embodiments, the human allogeneic plasma and platelet derived product is diluted to a dosage form. In some embodiments, the dosage form is for epidural injection, intramuscular injection, intrathecal injection, intraarticular injection, direct injection to a tendon, or direct injection to a ligament.

In some embodiments, the total protein concentration of the pharmaceutical composition is greater than 50 mg/mL and less than or about 500 mg/mL. In some embodiments, the total protein concentration is less than or about 250 mg/mL. In some embodiments, the total protein concentration is about 100 mg/mL to about 250 mg/mL.

In some embodiments, the pharmaceutical composition has a viscosity of 50 cP or less. In some embodiments, the pharmaceutical composition comprises a viscosity of less than 25 cP, less than 20 cP, less than 15 cP, or less than 10 cP. In some embodiments, the viscosity is about 1 to about 5 cP, 5 to about 10 cP, about 10 to about 15 cP, or about 15 to about 20 cP.

In some embodiments, the pharmaceutical composition has a pH of about 4.5 to about 8.5. In some embodiments, the composition has an osmolality of about 200 to about 500 mOsmo/kg.

In some embodiments, the concentration of albumin is about 100 to about 1,400 mg/mL. In some embodiments, the concentration of albumin is greater than or about 40% w/w. In some embodiments, albumin is human serum albumin.

In some embodiments, the concentration of fibrinogen is about 20 μg/mL to about 10 mg/mL, or about 1 mg/mL to about 5 mg/mL.

In some embodiments, the globulins comprise immunoglobulins. In some embodiments, the concentration of immunoglobulins is greater than or about 20% w/w. In some embodiments, the globulins comprise alpha-2-macroglobulin (A2M). In some embodiments, the concentration of A2M is greater than or about 200 mg/mL.

In some embodiments, the platelet proteins comprise an anti-inflammatory protein. In some embodiments, the anti-inflammatory protein is selected from interleukin 1 (IL-1), receptor antagonist protein (IRAP), IL-10, TIMP-1, and any combination thereof. In some embodiments, the platelet proteins comprise an antioxidant protein. In some embodiments, the antioxidant protein is selected from glutathione S-transferase, glutathione peroxide, catalase, and any combination thereof.

In some aspects, the disclosure provides a pharmaceutical composition comprising an allogeneic human plasma and platelet derived product produced by any of the methods described herein. In some embodiments, the composition forms a depot at a site of injection. In some embodiments, the composition is formulated for epidural injection. In some embodiments, the composition is formulated for intraarticular injection. In some embodiments, the composition is formulated for intrathecal injection. In some embodiments, the composition is formulated for intramuscular injection.

In some aspects, the disclosure provides a method for treating an orthopedic indication or injury in a subject, comprising administering to the subject a pharmaceutical composition described herein. In some aspects, the disclosure provides use of a pharmaceutical composition described herein for treating an orthopedic indication or injury in a subject.

In some embodiments, the orthopedic indication or injury is selected from painful lumbar radiculopathy, a spinal cord injury, osteoarthritis, ligament laxity, a rotator cuff injury, and a muscle injury. In some embodiments, the pharmaceutical composition is administered locally. In some embodiments, local administration is epidural, intrathecal, intraarticular, intramuscular, direct injection into a tendon, or direction injection into a ligament.

In some aspects, the disclosure provides a method for treating painful lumbar radiculopathy in a subject, comprising administering to the subject a pharmaceutical composition formulated for epidural injection described herein. In some embodiments, the method comprises x-ray guided needle injection.

In some aspects, the disclosure provides use of a pharmaceutical composition formulated for epidural injection described herein for treating painful lumbar radiculopathy in a subject. In some embodiments, the use comprises x-ray guided needle injection.

In some aspects, the disclosure provides a method for treating a spinal cord injury in a subject, comprising administering to the subject a pharmaceutical composition formulated for intrathecal injection described herein.

In some aspects, the disclosure provides use of a pharmaceutical composition formulated for intrathecal injection described herein for treating a spinal cord injury in a subject.

In some aspects, the disclosure provides a method for treating osteoarthritis in a subject, comprising administering to the subject a pharmaceutical composition formulated for intraarticular injection described herein.

In some aspects, the disclosure provides use of a pharmaceutical composition formulated for intraarticular injection described herein for treating osteoarthritis in a subject.

In some aspects, the disclosure provides a method for treating chemotherapy-induced peripheral neuropathy (CIPN), comprising administering to the subject a pharmaceutical composition described herein. In some embodiments, administering is systemic administration. In some embodiments, systemic administration is intravenous administration.

In some aspects, the disclosure provides use of a pharmaceutical composition described herein for treating chemotherapy-induced peripheral neuropathy (CIPN). In some embodiments, the pharmaceutical composition is formulated for systemic administration. In some embodiments, systemic administration is intravenous administration.

In some embodiments, the pharmaceutical composition is diluted to a desired dose.

In some aspects, the disclosure provides a kit comprising a container comprising a pharmaceutical composition described herein and instructions for treating a subject with an orthopedic indication or injury. In some embodiments, orthopedic indication or injury is selected from painful lumbar radiculopathy, a spinal cord injury, osteoarthritis, ligament laxity, a rotator cuff injury, and a muscle injury. In some embodiments, the instructions comprise diluting the pharmaceutical composition to an appropriate dose. In some embodiments, the instructions comprise injecting the pharmaceutical composition into a site appropriate for the orthopedic indication or injury.

BRIEF DESCRIPTION OF THE DRAWINGS

FIG. 15 is a graph showing paclitaxel-induced allodynia quantified by an acetone cooling test (ACT) score. Adult male C57BL6/J mice were administered paclitaxel or vehicle. Mice were placed into von Frey chambers and allowed to acclimate for 30 minutes. 10-15 μL of acetone spray was applied onto the medial area of the plantar hind paw using 0.5 mL syringes. Responses of each animal to acetone were monitored for 20 seconds, and the score was given based on a four-point scale. Data are presented as Mean±SEM; Group 1, n=10 and Group 2, n=15. Group 2 vs Group 1: *p<0.05 (Mann-Whitney test).

FIGS. 21A-21D provide graphs depicting the concentration of PDGF as a function of increasing concentrations of AHPPDP (FIG. 21A), activation of PDGFRα/β (FIG. 21B), the concentration of EGF as a function of increasing concentrations of AHPPDP (FIG. 21C), and activation of EGFR1 (FIG. 21D) after treatment with AHPPDP (CUR-001-20L-SEP24) in human cells.

DETAILED DESCRIPTION

Figure 1:
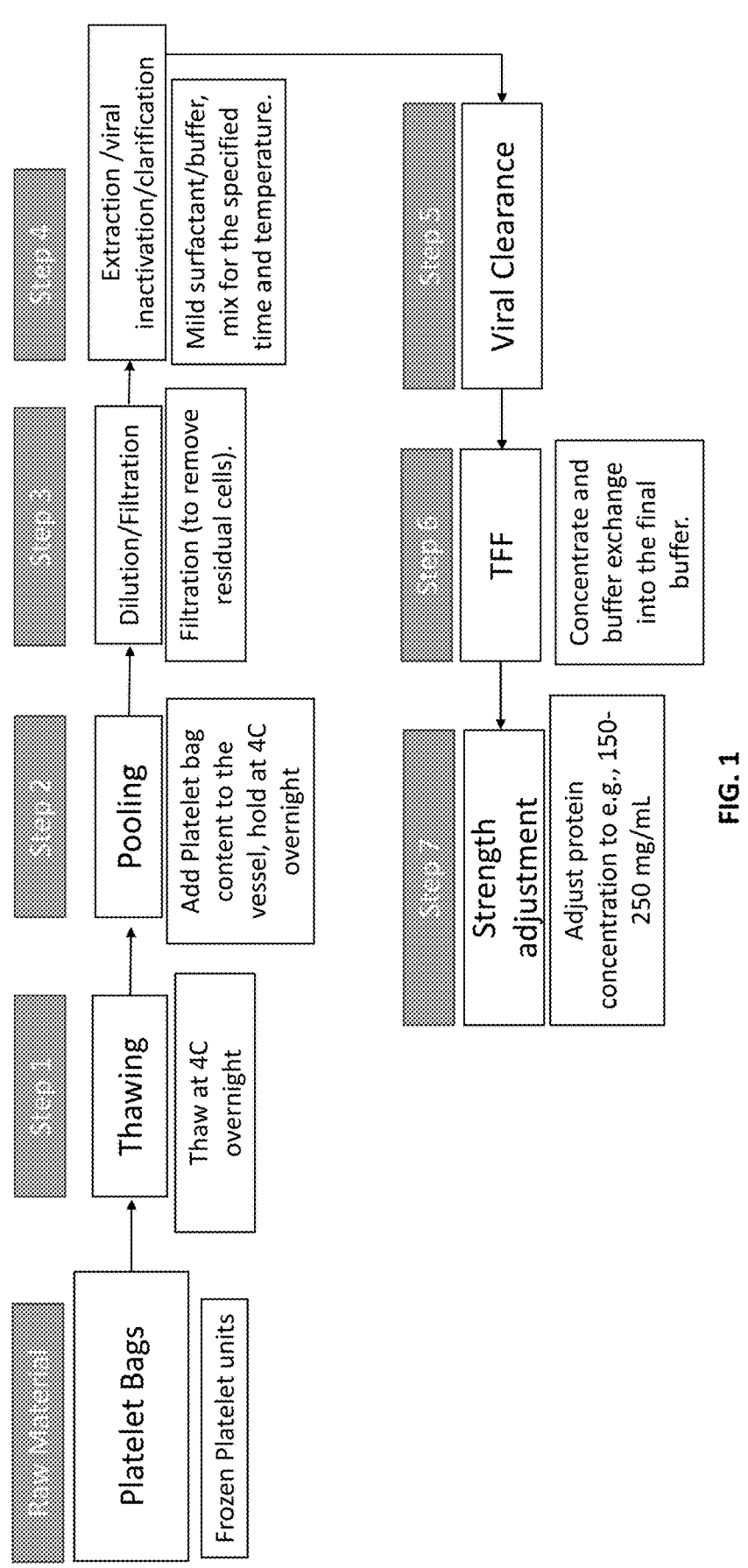
FIGS. 1-9 provide exemplary processes for producing allogeneic human plasma and platelet derived products (AHPPDP).

The present disclosure provides compositions comprising an allogeneic human plasma and platelet derived product, along with methods of making and using the compositions, for, e.g., orthopedic indications. In some aspects, the disclosure is based in part on the discovery of a composition suitable for therapeutic uses derived from allogenic human plasma and platelets having a high concentration of platelet proteins (e.g., PDGF-AB, PDGF-AA, and/or PDGF-BB). It has been demonstrated that the methods described herein result in a composition derived from allogenic human plasma and platelets with a high concentration of both plasma proteins (e.g., albumin, globulins, and fibrinogen) and platelet proteins (e.g., PGDF-AB, PDGF-AA, and PDGF-BB). In some aspects of the disclosure, human plasma proteins are reduced in the composition while a high concentration of human platelet proteins is maintained. Without wishing to be bound by theory, a composition comprising a high concentration of human plasma and platelet derived proteins is therapeutically beneficial for conditions such as orthopedic indications. In some aspects, the disclosure provides a composition wherein the concentration of human plasma and platelet derived proteins is greater than about 50 mg/mL.

In some aspects, the disclosure provides a composition comprising a high concentration of allogenic human plasma and platelet derived proteins having a viscosity which maintains both human plasma proteins and human platelet proteins at a site of injection (e.g., a viscosity of about 10 to about 40 cP or less than about 50 cP). As therapeutics generally diffuse from a site of injection, it is believed a high viscosity allows a high protein concentration composition of the disclosure to remain at the site of injection for a period of time sufficient to provide a therapeutic effect. In some aspects, the viscosity of a high protein concentration composition of the disclosure is reduced by for example, dilution, removal of some plasma proteins, and/or inclusion of viscosity modifiers, while maintaining a high total concentration of human plasma and platelet derived proteins.

In some aspects, the disclosure provides a composition comprising a high concentration of allogeneic human plasma and platelet derived proteins and citrate. Citrate acts as a stabilizer, cryoprotectant, and anticoagulant and is often added to blood-derived products. In some aspects, methods for generating the composition comprise using one or more buffers comprising citrate. In some aspects, methods for generating the composition comprise removing citrate through, e.g., buffer exchange.

In some aspects, the compositions of the disclosure having a high concentration of allogeneic human plasma and platelet derived proteins are formulated for epidural or intraarticular injection to treat orthopedic conditions. In some aspects, the compositions of the disclosure are used for treating pain. In some aspects, the compositions of the disclosure are used for treating orthopedic and nervous tissue injuries such as painful lumbar radiculopathy, osteoarthritis, tendon or ligament injuries (such as to the rotator cuff), nerve injury (such as carpal tunnel, spinal cord or other traumatic nerve injury), and chemotherapy-induced peripheral neuropathy. In some aspects, the compositions of the disclosure are used for treating ophthalmic conditions or diseases. In some aspects, the compositions of the disclosure are used for treating open wounds or traumatic injuries. In some aspects, the compositions of the disclosure are used for treating burn wounds.

Further, the disclosure is based in part on the discovery of a method for generating the compositions of the disclosure. As described herein, it has been demonstrated that a composition comprising concentrated allogeneic human plasma and platelet derived proteins is generated by processing platelet suspensions from one or more human donor subjects to extract and concentrate platelet proteins, while also removing unwanted cells (e.g., white blood cells), cell debris, and viruses.

Allogeneic Human Plasma and Platelet Derived Product

In some aspects, the disclosure provides compositions comprising an allogeneic human plasma and platelet derived product.

As used herein, "allogeneic human plasma and platelet derived product" refers to a composition comprising human plasma proteins and human platelet proteins that is derived from one or more donors of human platelets who are not the intended recipient of a composition of the disclosure (i.e. the platelet source is allogeneic, not autologous to the human recipient). In some embodiments, the plasma and platelet derived product is obtained from platelet suspension source of one or more human donors.

As used herein, "platelet suspension" is a frozen or liquid composition of plasma and platelets obtained from one or more human blood sources. In some embodiments, the platelet suspension is obtained from a whole blood source or from apheresis of one or more human donors.

Compositions of the Disclosure

In some aspects, the disclosure provides a composition comprising an allogeneic human plasma and platelet derived product prepared by the methods described herein. In some embodiments, the composition has a viscosity and total protein concentration suitable for the administration and treatment methods disclosed herein.

Plasma and Platelet Derived Components

In some embodiments, a composition of the disclosure comprises human plasma and platelet derived proteins. In some embodiments, the plasma proteins are selected from, albumin, fibrinogen, alpha-2-macroglobulin (A2M), immunoglobulins, and any combination thereof. In some embodiments, the composition comprises albumin. In some embodiments, the composition comprises fibrinogen. In some embodiments, the composition comprises A2M. In some embodiments, the composition comprises immunoglobulins.

In some embodiments, the plasma proteins of the composition comprising human plasma and platelet derived proteins comprise gel-forming associated proteins. Gel-forming associated proteins are also referred to as matrix-forming proteins, which are capable of forming a gel or a matrix in vivo following administration of to a subject. Gel-forming associated proteins, such as α-2-macroglobulin (A2M) help prevent protein lysis from proteases. Others, including fibrinogen, help initiate gel formation that creates a depot at the injection site during administration by interaction with other proteins in vivo. Specifically, a matrix is formed when thrombin protease cleaves fibrinogen to form fibrin monomers. The monomers are cross-linked by certain factors, such as Factor XIIIa, to form the matrix. Accordingly, fibrinogen in the composition described herein is modified by other proteins present in a subject to form a matrix, gel, or depot at the site of injection. Gel-forming associated proteins include, but are not limited to, A2M and fibrinogen. In some embodiments, the gel-forming associated protein is A2M. In some embodiments, the gel-forming associated protein is fibrinogen. In some embodiments, the composition comprises gel-forming associated proteins at a concentration of about 1 ng/mL to about 50 mg/mL. In some embodiments, the composition comprises gel-forming associated proteins at a concentration of about 1 ng/mL to about 500 ng/mL. In some embodiments, the composition comprises gel-forming associated proteins at a concentration of about 0.5 to about 1 μg/mL. In some embodiments, the composition comprises gel-forming associated proteins at a concentration of about 1 to about 100 μg/mL. In some embodiments, the composition comprises gel-forming associated proteins at a concentration of about 100 to about 500 μg/mL. In some embodiments, the composition comprises gel-forming associated proteins at a concentration of about 0.5 to about 1 mg/mL. In some embodiments, the composition comprises gel-forming associated proteins at a concentration of about 1 to about 5 mg/mL. In some embodiments, the composition comprises gel-forming associated proteins at a concentration of about 1 to about 10 mg/mL. In some embodiments, the composition comprises gel-forming associated proteins at a concentration of about 10 to about 25 mg/mL. In some embodiments, the composition comprises gel-forming associated proteins at a concentration of about 25 to about 50 mg/mL. In some embodiments, the composition comprises gel-forming associated proteins at a concentration of at least 25 mg/mL. In some embodiments, the composition comprises gel-forming associated proteins at a concentration of no more than 25 mg/mL.

In some embodiments, the composition comprising plasma and platelet derived proteins comprises fibrinogen at a concentration of at least 20 μg/mL. In some embodiments, the composition comprises fibrinogen at a concentration of about 20 μg/mL to about 10 mg/mL. In some embodiments, the composition comprises fibrinogen at a concentration of about 20 to about 100 μg/mL. In some embodiments, the composition comprises fibrinogen at a concentration of about 100 to about 500 μg/mL. In some embodiments, the composition comprises fibrinogen at a concentration of about 500 to about 1,000 μg/mL. In some embodiments, the composition comprises fibrinogen at a concentration of about 1 to about 5 mg/mL. In some embodiments, the composition comprises fibrinogen at a concentration of about 5 to about 10 mg/mL. In some embodiments, the composition comprises fibrinogen at a concentration no higher than 10 mg/mL.

In some embodiments, the composition comprising plasma and platelet derived proteins comprise stabilizing proteins. Stabilizing proteins help stabilize proteins and prevent aggregation. A stabilizing protein can include, but is not limited to, albumin. In some embodiments, a stabilizing protein is albumin. In some embodiments, the composition comprises stabilizing proteins at a concentration of about 0.1 ng/mL to about 500 mg/mL. In some embodiments, the composition comprises stabilizing proteins at a concentration of about 0.1 to about 500 ng/mL. In some embodiments, the composition comprises stabilizing proteins at a concentration of about 500 to about 1 pg/mL. In some embodiments, the composition comprises stabilizing proteins at a concentration of about 1 to about 500 μg/mL. In some embodiments, the composition comprises stabilizing proteins at a concentration of about 1 to about 500 μg/mL. In some embodiments, the composition comprises stabilizing proteins at a concentration of about 0.5 to about 1 mg/mL. In some embodiments, the composition comprises stabilizing proteins at a concentration of about 1 to about 50 mg/mL. In some embodiments, the composition comprises stabilizing proteins at a concentration of about 50 to about 100 mg/mL. In some embodiments, the composition comprises stabilizing proteins at a concentration of about 100 to about 250 mg/mL. In some embodiments, the composition comprises stabilizing proteins at a concentration of about 250 to about 500 mg/mL. In some embodiments, the composition comprises stabilizing proteins at a concentration of at least 500 mg/mL. In some embodiments, the composition comprises stabilizing proteins at a concentration of no more than 500 mg/mL.

In some embodiments, the composition comprising plasma and platelet derived proteins comprise immunoglobulins. Immunoglobulins are antibodies that recognize and bind antigens. In some embodiments, immunoglobulins are selected from immunoglobulin M (IgM), immunoglobulin G (IgG), immunoglobulin A (IgA), immunoglobulin E (IgE), and immunoglobulin D (IgD). In some embodiments, the immunoglobulin is IgM. In some embodiments the immunoglobulin is IgG. In some embodiments, the immunoglobulin is IgA. In some embodiments, the immunoglobulin IgE. In some embodiments, the immunoglobulin is IgD. In some embodiments, the composition comprises immunoglobulins at a concentration of about 50 ng/mL to about 2 mg/mL. In some embodiments, the composition comprises immunoglobulins at a concentration of about 50 to about 250 ng/mL. In some embodiments, the composition comprises immunoglobulins at a concentration of about 250 to about 500 ng/mL. In some embodiments, the composition comprises immunoglobulins at a concentration of about 500 to about 1,000 ng/mL. In some embodiments, the composition comprises immunoglobulins at a concentration of about 1 to about 100 μg/mL. In some embodiments, the composition comprises immunoglobulins at a concentration of about 250 to about 500 μg/mL. In some embodiments, the composition comprises immunoglobulins at a concentration of about 500 to about 1000 μg/mL. In some embodiments, the composition comprises immunoglobulins at a concentration of about 1 to about 2 mg/mL. In some embodiments, the composition comprises immunoglobulins at a concentration no higher than 2 mg/mL.

In some embodiments, the allogeneic human plasma and platelet suspension derived fraction comprises stabilizing lipids. Stabilizing lipids help stabilize the platelet and plasma proteins. In some embodiments, the stabilizing lipid found in platelet-rich plasma is selected from cholesterol and triglycerides. In some embodiments, the stabilizing lipid is cholesterol. In some embodiments, the stabilizing lipids are triglycerides. In some embodiments, the composition comprises stabilizing lipids at a concentration of about 0.1 ng/mL to about 100 mg/mL. In some embodiments, the composition comprises stabilizing lipids at a concentration of about 0.1 to about 500 ng/mL. In some embodiments, the composition comprises stabilizing lipids at a concentration of about 500 to about 1 μg/mL. In some embodiments, the composition comprises stabilizing lipids at a concentration of about 1 to about 500 μg/mL. In some embodiments, the composition comprises stabilizing lipids at a concentration of about 1 to about 500 μg/mL. In some embodiments, the composition comprises stabilizing lipids at a concentration of about 0.5 to about 1 mg/mL. In some embodiments, the composition comprises stabilizing lipids at a concentration of about 1 to about 50 mg/mL. In some embodiments, the composition comprises stabilizing lipids at a concentration of about 50 to about 100 mg/mL. In some embodiments, the composition comprises stabilizing lipids at a concentration of at least 100 mg/mL. In some embodiments, the composition comprises stabilizing lipids at a concentration of no more than 100 mg/mL.

In some embodiments, the composition comprises human plasma and platelet derived proteins, wherein the composition comprises greater than 40% w/w human serum albumin (HSA). In some embodiments, the composition comprises no more than 40% w/w HSA. In some embodiments, the composition comprises 40% w/w HSA. In some embodiments, the composition comprises about 60% to about 70% w/w albumin. In some embodiments, the composition comprises 60-70% w/w albumin. In some embodiments, the composition comprises 60-70% w/w HSA.

In some embodiments, the composition comprises human plasma and platelet derived proteins, wherein the composition comprises greater than 20% w/w immunoglobulins. In some embodiments, the composition comprises no more than 20% w/w immunoglobulins. In some embodiments, the composition comprises 20% w/w immunoglobulins. In some embodiments, the composition comprises about 10% to about 20% w/w immunoglobulin. In some embodiments, the composition comprises 10-20% w/w immunoglobulins.

In some embodiments, the composition comprises human plasma and platelet derived proteins, wherein the composition comprises greater than 200 µg/mL A2M. In some embodiments, the composition comprises no more than 200 µg/mL A2M. In some embodiments, the composition comprises 200 µg/mL A2M.

In some embodiments, the composition comprises human plasma and platelet derived proteins, wherein the composition comprises about 20 µg/mL to about 10 mg/mL fibrinogen. In some embodiments, the composition comprises 10 µg/mL to about 2 mg/mL fibrinogen. In some embodiments, the composition comprises no more than 10 mg/mL fibrinogen. In some embodiments, the composition comprises no less than 10 µg/mL fibrinogen. In some embodiments, the composition comprises no more than 10 mg/mL fibrinogen. In some embodiments, the composition comprises at least 10 mg/mL fibrinogen. In some embodiments, the composition comprises at least 20 µg/mL fibrinogen. In some embodiments, the composition comprises no more than 20 µg/mL fibrinogen. In some embodiments, the composition comprises at least 2 mg/mL fibrinogen. In some embodiments, the composition comprises no more than 2 mg/mL fibrinogen. In some embodiments, the composition comprises 0.25-5.0 mg/mL fibrinogen. In some embodiments, the composition comprises 0.25-0.5 mg/mL fibrinogen. In some embodiments, the composition comprises 0.5-1.0 mg/mL fibrinogen. In some embodiments, the composition comprises 1-2 mg/mL fibrinogen. In some embodiments, the composition comprises 2-5 mg/mL fibrinogen. In some embodiments, the composition comprises about 0.25 to about 5.0 mg/mL fibrinogen. In some embodiments, the composition comprises about 0.25 to about 0.5 mg/mL fibrinogen. In some embodiments, the composition comprises about 0.5 to about 1.0 mg/mL fibrinogen. In some embodiments, the composition comprises about 1 to about 2 mg/mL fibrinogen. In some embodiments, the composition comprises about 2 to about 5 mg/mL fibrinogen.

In some embodiments, the allogeneic human plasma and platelet derived product comprises platelet proteins. In some embodiments, the platelet proteins are selected from Adiponectin/Acrp30, IFN-gamma, CCL2/MCP-1, Angiogenin, IGFBP-2, CCL7/MCP-3, Angiopoietin-1, IGFBP-3 M-CSF, Angiopoietin-2, IL-1 alpha/IL-1F1, MIF, Apolipoprotein A1, IL-1 beta/IL-1F2, BAFF/BLyS/TNFSF13B, IL-1ra/IL-1F3, CCL3/CCL4, BDNF, IL-2, CCL20/MIP-3 alpha, CD14, IL-3, CCL19/MIP-3 beta, CD30, IL-4, MMP-9, CD31/PECAM-1, IL-5, Myeloperoxidase, CD40 Ligand/TNFSF5, IL-6, Osteopontin (OPN), Chitinase 3-like, IL-8, PDGF-AA, Complement Component C5/C5a, IL-10, PDGF-AB/BB, Complement Factor D, IL-11, Pentraxin 3/TSF-14, C-Reactive Protein/CRP, IL-12 p70, CXCL4/PF4, Cripto-1, IL-13, RAGE, Cystatin C, IL-15, CCL5/RANTES, Dkk-1, IL-16, RBP4, DPPIV/CD26, IL-17A, Relaxin-2, EGF, IL-18 BPa, Resistin, CXCL5/ENA-78, IL-19, CXCL12/SDF-1 alpha, Endoglin/CD105, IL-22, Serpin E1/PAI-1, EMMPRIN, SHBG, Fas Ligand, ST2/IL1, R4, FGF basic, IL-27, CCL17/TARC, KGF/FGF-7, IL-31, TFF3, FGF-19, IL-32 alpha/beta/gamma, TfR, Flt-3 Ligand, TGF-alpha, G-CSF, Thrombospondin-1, GDF-15, CXCL10/IP-10, TIM-1, GM-CSF, CXCL11/I-TAC, CXCL1/GRO alpha, Kallikrein 3/PSA, uPAR, Growth Hormone (GH), Leptin, VCAM-1, HGF, VEGF, ICAM-1/CD54, Lipocalin-2/NGAL, Vitamin D BP, and any combination thereof. In some embodiments, the platelet proteins are Adiponectin/Acrp30, IFN-gamma, CCL2/MCP-1, Angiogenin, IGFBP-2, CCL7/MCP-3, Angiopoietin-1, IGFBP-3 M-CSF, Angiopoietin-2, IL-1 alpha/IL-1F1, MIF, Apolipoprotein A1, IL-1 beta/IL-1F2, BAFF/BLyS/TNFSF13B, IL-1ra/IL-1F3, CCL3/CCL4, BDNF, IL-2, CCL20/MIP-3 alpha, CD14, IL-3, CCL19/MIP-3 beta, CD30, IL-4, MMP-9, CD31/PECAM-1, IL-5, Myeloperoxidase, CD40 Ligand/TNFSF5, IL-6, Osteopontin (OPN), Chitinase 3-like, IL-8, PDGF-AA, Complement Component C5/C5a, IL-10, PDGF-AB/BB, Complement Factor D, IL-11, Pentraxin 3/TSF-14, C-Reactive Protein/CRP, IL-12 p70, CXCL4/PF4, Cripto-1, IL-13, RAGE, Cystatin C, IL-15, CCL5/RANTES, Dkk-1, IL-16, RBP4, DPPIV/CD26, IL-17A, Relaxin-2, EGF, IL-18 BPa, Resistin, CXCL5/ENA-78, IL-19, CXCL12/SDF-1 alpha, Endoglin/CD105, IL-22, Serpin E1/PAI-1, EMMPRIN, SHBG, Fas Ligand, ST2/IL1, R4, FGF basic, IL-27, CCL17/TARC, KGF/FGF-7, IL-31, TFF3, FGF-19, IL-32 alpha/beta/gamma, TfR, Flt-3 Ligand, TGF-alpha, G-CSF, Thrombospondin-1, GDF-15, CXCL10/IP-10, TIM-1, GM-CSF, CXCL11/I-TAC, CXCL1/GRO alpha, Kallikrein 3/PSA, uPAR, Growth Hormone (GH), Leptin, VCAM-1, HGF, VEGF, ICAM-1/CD54, Lipocalin-2/NGAL, and Vitamin D BP.

In some embodiments, the platelet proteins of the composition comprising plasma and platelet derived proteins comprises comprise growth factors. Growth factors promote cell growth and division. In some embodiments, the composition comprising plasma and platelet derived proteins comprises growth factors selected from, platelet-derived growth factor (PDGF (AB, AA, BB)), transcription growth factor-β1 (TGFβ1), transcription growth factor-β2 (TGFβ2), vascular endothelial growth factor (VEGF), epidermal growth factor (EGF), brain-derived neurotrophic factor (BDNF), hepatocyte growth factor (HGF), basic-fibroblast growth factor (b-FGF), insulin-like growth factor 1 (IGF-1), glia maturation factor-β (GMFB), and any combination thereof. In some embodiments, the composition comprising plasma and platelet derived proteins comprises growth factors PDGF-AA, PDGF-BB, PDGF-AB, TGFβ, VEGF, EGF, BNDF, HGF, b-FGF, IGF-1, and GMFB. PDGF promotes cell growth and generation, repair of blood vessels and collagen production. VEGF promotes growth and generation of vascular endothelial cells. FGF promotes tissue repair, cell growth, collagen production and hyaluronic acid production. EGF promotes epithelial cell growth, angiogenesis and wound healing. TGF, especially TGF-β, promotes growth and neogenesis of epithelial cells and wound healing. In some embodiments, the composition comprising plasma and platelet derived proteins comprises growth factors at a concentration of about 0.1 to about 100 pg/mL. In some embodiments, the composition comprises growth factors at a concentration of about 100 to about 500 pg/mL. In some embodiments, the composition comprises growth factors at a concentration of about 0.1 to 100 ng/mL. In some embodiments, the composition comprises growth factors at a concentration of about 100 to about 500 ng/mL. In some embodiments the composition comprises growth factors at a concentration of about 0.5 to about 1 mg/mL. In some embodiments, the composition comprises growth factors at a concentration of about 1 to about 2 mg/mL. In some embodiments, the composition comprises growth factors at a concentration of about 2 to about 3 mg/mL. In some embodiments, the composition comprises growth factors at a concentration of about 3 to about 4 mg/mL. In some embodiments, the composition comprises growth factors at a concentration of about 4 to about 5 mg/mL. In some embodiments, the composition comprises growth factors at a concentration of at least 5 mg/mL. In some embodiments, the composition comprises growth factors at a concentration of more than 5 mg/mL.

In some embodiments, the composition comprising plasma and platelet derived proteins comprises PDGF-AB at a concentration of about 5 to about 200 ng/mL. In some embodiments, the composition comprising plasma and platelet derived proteins comprises PDGF-AB at a concentration of about 10 to about 20 ng/mL. In some embodiments, the composition comprising plasma and platelet derived proteins comprises PDGF-AB at a concentration of about 20 to about 40 ng/mL. In some embodiments, the composition comprising plasma and platelet derived proteins comprises PDGF-AB at a concentration of about 40 to about 80 ng/mL. In some embodiments, the composition comprising plasma and platelet derived proteins comprises PDGF-AB at a concentration of about 80 to about 160 ng/mL. In some embodiments, the composition comprising plasma and platelet derived proteins comprises PDGF-AB at a concentration of about 5 to about 200 ng/mL, +/−5%, 10%, 15%, 20%, 25%, or 30%. In some embodiments, the composition comprising plasma and platelet derived proteins comprises PDGF-AB at a concentration of about 10 to about 20 ng/mL, +/−5%, 10%, 15%, 20%, 25%, or 30%. In some embodiments, the composition comprising plasma and platelet derived proteins comprises PDGF-AB at a concentration of about 20 to about 40 ng/mL, +/−5%, 10%, 15%, 20%, 25%, or 30%. In some embodiments, the composition comprising plasma and platelet derived proteins comprises PDGF-AB at a concentration of about 40 to about 80 ng/mL, +/−5%, 10%, 15%, 20%, 25%, or 30%. In some embodiments, the composition comprising plasma and platelet derived proteins comprises PDGF-AB at a concentration of about 80 to about 160 ng/mL, +/−5%, 10%, 15%, 20%, 25%, or 30%.

In some embodiments, the composition comprising plasma and platelet derived proteins comprises TGFβ at a concentration of about 50 to about 1000 ng/mL. In some embodiments, the composition comprising plasma and platelet derived proteins comprises TGFβ at a concentration of about 50 to about 150 ng/mL. In some embodiments, the composition comprising plasma and platelet derived proteins comprises TGFβ at a concentration of about 150 to about 300 ng/mL. In some embodiments, the composition comprising plasma and platelet derived proteins comprises TGFβ at a concentration of about 300 to about 500 ng/mL. In some embodiments, the composition comprising plasma and platelet derived proteins comprises TGFβ at a concentration of about 500 to about 1000 ng/mL. In some embodiments, the composition comprising plasma and platelet derived proteins comprises TGFβ at a concentration of about 50 to about 1000 ng/mL, +/−5%, 10%, 15%, 20%, 25%, or 30%. In some embodiments, the composition comprising plasma and platelet derived proteins comprises TGFβ at a concentration of about 50 to about 150 ng/mL, +/−5%, 10%, 15%, 20%, 25%, or 30%. In some embodiments, the composition comprising plasma and platelet derived proteins comprises TGFβ at a concentration of about 150 to about 300 ng/mL, +/−5%, 10%, 15%, 20%, 25%, or 30%. In some embodiments, the composition comprising plasma and platelet derived proteins comprises TGFβ at a concentration of about 300 to about 500 ng/mL, +/−5%, 10%, 15%, 20%, 25%, or 30%. In some embodiments, the composition comprising plasma and platelet derived proteins comprises TGFβ at a concentration of about 500 to about 100 ng/mL, +/−5%, 10%, 15%, 20%, 25%, or 30%.

In some embodiments, the composition comprising plasma and platelet derived proteins comprises VEGF at a concentration of about 50 to about 1500 pg/mL. In some embodiments, the composition comprising plasma and platelet derived proteins comprises VEGF at a concentration of about 50 to about 200 pg/mL. In some embodiments, the composition comprising plasma and platelet derived proteins comprises VEGF at a concentration of about 200 to about 400 pg/mL. In some embodiments, the composition comprising plasma and platelet derived proteins comprises VEGF at a concentration of about 400 to about 800 pg/mL. In some embodiments, the composition comprising plasma and platelet derived proteins comprises VEGF at a concentration of about 800 to about 1500 pg/mL. In some embodiments, the composition comprising plasma and platelet derived proteins comprises VEGF at a concentration of about 50 to about 1500 pg/mL, +/−5%, 10%, 15%, 20%, 25%, or 30%. In some embodiments, the composition comprising plasma and platelet derived proteins comprises VEGF at a concentration of about 50 to about 200 pg/mL, +/−5%, 10%, 15%, 20%, 25%, or 30%. In some embodiments, the composition comprising plasma and platelet derived proteins comprises VEGF at a concentration of about 200 to about 400 pg/mL, +/−5%, 10%, 15%, 20%, 25%, or 30%. In some embodiments, the composition comprising plasma and platelet derived proteins comprises VEGF at a concentration of about 400 to about 800 pg/mL, +/−5%, 10%, 15%, 20%, 25%, or 30%. In some embodiments, the composition comprising plasma and platelet derived proteins comprises VEGF at a concentration of about 800 to about 1500 pg/mL, +/−5%, 10%, 15%, 20%, 25%, or 30%.

In some embodiments, the composition comprising plasma and platelet derived proteins comprises EGF at a concentration of about 100 to about 5000 pg/mL. In some embodiments, the composition comprising plasma and platelet derived proteins comprises EGF at a concentration of about 100 to about 1000 pg/mL. In some embodiments, the composition comprising plasma and platelet derived proteins comprises EGF at a concentration of about 1000 to about 2000 pg/mL. In some embodiments, the composition comprising plasma and platelet derived proteins comprises EGF at a concentration of about 2000 to about 4000 pg/mL. In some embodiments, the composition comprising plasma and platelet derived proteins comprises EGF at a concentration of about 4000 to about 6000 pg/mL. In some embodiments, the composition comprising plasma and platelet derived proteins comprises EGF at a concentration of about 100 to about 5000 pg/mL, +/−5%, 10%, 15%, 20%, 25%, or 30%. In some embodiments, the composition comprising plasma and platelet derived proteins comprises EGF at a concentration of about 100 to about 1000 pg/mL, +/−5%, 10%, 15%, 20%, 25%, or 30%. In some embodiments, the composition comprising plasma and platelet derived proteins comprises EGF at a concentration of about 1000 to about 2000 pg/mL, +/−5%, 10%, 15%, 20%, 25%, or 30%. In some embodiments, the composition comprising plasma and platelet derived proteins comprises EGF at a concentration of about 2000 to about 4000 pg/mL, +/−5%, 10%, 15%, 20%, 25%, or 30%. In some embodiments, the composition comprising plasma and platelet derived proteins comprises EGF at a concentration of about 4000 to about 6000 pg/mL, +/−5%, 10%, 15%, 20%, 25%, or 30%.

In some embodiments, the composition comprising plasma and platelet derived proteins comprises FGF at a concentration of about 100 to about 3000 pg/mL. In some embodiments, the composition comprising plasma and platelet derived proteins comprises FGF at a concentration of about 100 to about 300 pg/mL. In some embodiments, the composition comprising plasma and platelet derived proteins comprises FGF at a concentration of about 300 to about 600 pg/mL. In some embodiments, the composition comprising plasma and platelet derived proteins comprises FGF at a concentration of about 600 to about 1200 pg/mL. In some embodiments, the composition comprising plasma and platelet derived proteins comprises FGF at a concentration of about 1200 to about 3000 pg/mL. In some embodiments, the composition comprising plasma and platelet derived proteins comprises FGF at a concentration of about 100 to about 3000 pg/mL, +/−5%, 10%, 15%, 20%, 25%, or 30%. In some embodiments, the composition comprising plasma and platelet derived proteins comprises FGF at a concentration of about 100 to about 300 pg/mL, +/−5%, 10%, 15%, 20%, 25%, or 30%. In some embodiments, the composition comprising plasma and platelet derived proteins comprises FGF at a concentration of about 300 to about 600 pg/mL, +/−5%, 10%, 15%, 20%, 25%, or 30%. In some embodiments, the composition comprising plasma and platelet derived proteins comprises FGF at a concentration of about 600 to about 1200 pg/mL, +/−5%, 10%, 15%, 20%, 25%, or 30%. In some embodiments, the composition comprising plasma and platelet derived proteins comprises FGF at a concentration of about 1200 to about 3000 pg/mL, +/−5%, 10%, 15%, 20%, 25%, or 30%.

In some embodiments, the composition comprising plasma and platelet derived proteins comprises HGF at a concentration of about 25 to about 2500 pg/mL. In some embodiments, the composition comprising plasma and platelet derived proteins comprises HGF at a concentration of about 25 to about 150 pg/mL. In some embodiments, the composition comprising plasma and platelet derived proteins comprises HGF at a concentration of about 150 to about 300 pg/mL. In some embodiments, the composition comprising plasma and platelet derived proteins comprises HGF at a concentration of about 300 to about 1000 pg/mL. In some embodiments, the composition comprising plasma and platelet derived proteins comprises HGF at a concentration of about 1000 to about 2500 pg/mL. In some embodiments, the composition comprising plasma and platelet derived proteins comprises HGF at a concentration of about 25 to about 2500 pg/mL, +/−5%, 10%, 15%, 20%, 25%, or 30%. In some embodiments, the composition comprising plasma and platelet derived proteins comprises HGF at a concentration of about 25 to about 150 pg/mL, +/−5%, 10%, 15%, 20%, 25%, or 30%. In some embodiments, the composition comprising plasma and platelet derived proteins comprises HGF at a concentration of about 150 to about 300 pg/mL, +/−5%, 10%, 15%, 20%, 25%, or 30%. In some embodiments, the composition comprising plasma and platelet derived proteins comprises HGF at a concentration of about 300 to about 1000 pg/mL, +/−5%, 10%, 15%, 20%, 25%, or 30%. In some embodiments, the composition comprising plasma and platelet derived proteins comprises HGF at a concentration of about 1000 to about 2500 pg/mL, +/−5%, 10%, 15%, 20%, 25%, or 30%.

In some embodiments, the composition comprises anti-inflammatory proteins. Anti-inflammatory proteins are derived from the plasma and/or platelets. In some embodiments, platelet proteins of the composition comprising plasma and platelet derived proteins comprise anti-inflammatory proteins. Anti-inflammatory proteins regulate the immune and inflammatory responses and reduce inflammation. In some embodiments, the composition comprising plasma and platelet derived proteins comprises anti-inflammatory proteins selected from interleukins (IL-1) and receptor antagonist protein (IRAP), interleukin 10 (IL-10), tissue inhibitor of metalloproteinase 1 (TIMP-1), and any combination thereof. In some embodiments, the composition comprising plasma and platelet derived proteins comprises anti-inflammatory proteins IL-1, IRAP, IL-10, and TIMP-1. In some embodiments, the composition comprising plasma and platelet derived proteins comprises anti-inflammatory proteins at a concentration of about 0.1 to about 5 mg/mL. In some embodiments, the composition comprises anti-inflammatory proteins at a concentration of about 0.1 to about 100 pg/mL. In some embodiments, the composition comprises anti-inflammatory proteins at a concentration of about 100 to about 500 pg/mL. In some embodiments, the composition comprises anti-inflammatory proteins at a concentration of about 0.1 to 100 ng/mL. In some embodiments, the composition comprises anti-inflammatory proteins at a concentration of about 100 to about 500 ng/mL. In some embodiments, the composition comprises anti-inflammatory proteins at a concentration of about 0.5 to about 1 mg/mL. In some embodiments, the composition comprises anti-inflammatory proteins at a concentration of about 1 to about 2 mg/mL. In some embodiments, the composition comprises anti-inflammatory proteins at a concentration of about 2 to about 3 mg/mL. In some embodiments, the composition comprises anti-inflammatory proteins at a concentration of about 3 to about 4 mg/mL. In some embodiments, the composition comprises anti-inflammatory proteins at a concentration of about 4 to about 5 mg/mL. In some embodiments, the composition comprises anti-inflammatory proteins at a concentration of at least 5 mg/mL. In some embodiments, the composition comprises anti-inflammatory proteins at a concentration of no more than 5 mg/mL.

In some embodiments, the composition comprises anti-oxidant proteins. Anti-oxidant proteins are derived from the plasma and/or platelets. In some embodiments, platelet proteins of the composition comprising plasma and platelet derived proteins comprise anti-oxidant proteins. Anti-oxidant proteins help prevent radical oxidation from damaging cells. In some embodiments, the composition comprising plasma and platelet derived proteins comprises anti-oxidant proteins selected from, glutathione S-transferase (GST), glutathione peroxidase-1 (GPx-1), catalase, and any combination thereof. In some embodiments, platelet proteins of the composition comprising plasma and platelet derived proteins comprise anti-oxidant proteins GST, GPx-1, and catalase. In some embodiments, the composition comprising plasma and platelet derived proteins comprises anti-oxidant proteins at a concentration of about 0.1 to about 10 μg/mL. In some embodiments, the composition comprises anti-oxidant proteins at a concentration of about 10 to about 100 μg/mL. In some embodiments, the composition comprises anti-oxidant proteins at a concentration of about 100 to about 500 pg/mL. In some embodiments, the composition comprises anti-oxidant proteins at a concentration of about 500 to about 1,000 pg/mL. In some embodiments, the composition comprises anti-oxidant proteins at a concentration of about 1 to about 500 ng/mL. In some embodiments, the composition comprises anti-oxidant proteins at a concentration of about 500 to about 1,000 ng/mL. In some embodiments, the composition comprises anti-oxidant proteins at a concentration of about 0.1 to about 5 mg/mL. In some embodiments, the composition comprises anti-oxidant proteins at a concentration of about 0.1 to about 10 pg/mL. In some embodiments, the composition comprises anti-oxidant proteins at a concentration of about 10 to about 100 pg/mL. In some embodiments, the composition comprises anti-oxidant proteins at a concentration of about 100 to about 500 pg/mL. In some embodiments, the composition comprises anti-oxidant proteins at a concentration of about 0.5 to about 1 mg/mL. In some embodiments, the composition comprises anti-oxidant proteins at a concentration of about 1 to about 5 mg/mL. In some embodiments, the composition comprises anti-oxidant proteins at a concentration of at least 5 mg/mL. In some embodiments, the composition comprises anti-oxidant proteins at a concentration of no more than 5 mg/mL.

In some embodiments, the composition comprises human plasma and platelet derived proteins comprising IFNγ, IL-5, IL-1β, IL-6, IL-1RA, IL-10, IL-13, TNFα, IL-8, IL-12p40, MCP-1, and any combination thereof. In some embodiments, the composition comprises IFN at a concentration of about 0.1 to about 0.5 pg/mL. In some embodiments, the composition comprises IL-5 at a concentration of about 0.5 to about 2.0 pg/mL. In some embodiments, the composition comprises IL-1β at a concentration of about 1.0 to about 4.0 pg/mL. In some embodiments, the composition comprises IL-6 at a concentration of about 1.0 to about 5.0 pg/mL. In some embodiments, the composition comprises IL-1Ra at a concentration of about 2.0 to about 7.0 pg/mL. In some embodiments, the composition comprises IL-1β at a composition of about 2.0 to about 10.0 pg/mL. In some embodiments, the composition comprises IL-13 at a concentration of about 1.0 to about 10.0 pg/mL. In some embodiments, the composition comprises TNFα at a concentration of about 1.0 to about 5.0 pg/mL. In some embodiments, the composition comprises IL-8 at a concentration of about 20 to about 50 pg/mL. In some embodiments, the composition comprises IL-12p40 at a concentration of about 50 to about 80 pg/mL. In some embodiments, the composition comprises MCP-1 at a concentration of about 200 to about 300 pg/mL.

In some embodiments, the composition comprises human plasma and platelet derived proteins, wherein the platelet proteins are selected from, platelet factor 4 (PF4), platelet-derived growth factor (PDGF (AB, AA, BB)), transcription growth factor-β 1 (TGFβ1), transcription growth factor-β 2 (TGFβ2), vascular endothelial growth factor (VEGF), epidermal growth factor (EGF), brain-derived neurotrophic factor (BDNF), hepatocyte growth factor (HGF), basic-fibroblast growth factor (b-FGF), insulin-like growth factor 1 (IGF-1), glia maturation factor-β (GMFB), cluster of differentiation 31 (CD31). In some embodiments, the composition comprises human plasma and platelet derived proteins, wherein the platelet proteins are selected from, platelet factor 4 (PF4), platelet-derived growth factor (PDGF (AB, AA, BB)), transcription growth factor-β 1 (TGFβ1), transcription growth factor-β 2 (TGFβ2), vascular endothelial growth factor (VEGF), epidermal growth factor (EGF), brain-derived neurotrophic factor (BDNF), hepatocyte growth factor (HGF), fibroblast growth factor (FGF), insulin-like growth factor 1 (IGF-1), glia maturation factor-β (GMFB), cluster of differentiation 31 (CD31). In some embodiments, the platelet proteins are PF4, PDGF (AB, AA, BB)), TGFβ1, TGFβ2, VEGF, EGF, BDNF, HFG, b-FGF, IGF-1, GMFB, and CD31. In some embodiments, the platelet proteins are PF4, PDGF (AB, AA, BB)), TGFβ1, TGFβ2, VEGF, EGF, HFG, FGF, IGF-1, GMFB, and CD31. In some embodiments, the platelet proteins comprise at least PDGF-AB. In some embodiments, the platelet proteins comprise at least two of PF4, PDGF (AB, AA, BB)), TGFβ 1, TGFβ2, VEGF, EGF, BDNF, HFG, FGF, IGF-1, GMFB, and CD31. In some embodiments, the platelet proteins comprise at least three of PF4, PDGF (AB, AA, BB)), TGFβ1, TGFβ2, VEGF, EGF, BDNF, HFG, FGF, IGF-1, GMFB, and CD31. In some embodiments, the platelet proteins comprise at least four of PF4, PDGF (AB, AA, BB)), TGFβ1, TGFβ2, VEGF, EGF, BDNF, HFG, FGF, IGF-1, GMFB, and CD31. In some embodiments, the platelet proteins comprise at least two of PF4, PDGF (AB, AA, BB)), TGFβ1, TGFβ2, VEGF, EGF, HFG, FGF, IGF-1, GMFB, and CD31. In some embodiments, the platelet proteins comprise at least three of PF4, PDGF (AB, AA, BB)), TGFβ 1, TGFβ2, VEGF, EGF, HFG, b-FGF, IGF-1, GMFB, and CD31. In some embodiments, the platelet proteins comprise at least four of PF4, PDGF (AB, AA, BB)), TGFβ1, TGFβ2, VEGF, EGF, HFG, FGF, IGF-1, GMFB, and CD31.

In some embodiments, the composition comprises human plasma and platelet derived proteins, wherein the platelet protein comprises PF4. In some embodiments, the composition comprises human plasma and platelet derived proteins, wherein the platelet protein comprises PDGF-AA. In some embodiments, the composition comprises human plasma and platelet derived proteins, wherein the platelet protein comprises PDGF-BB. In some embodiments, the composition comprises human plasma and platelet derived proteins, wherein the platelet protein comprises PDGF-AB. In some embodiments, the composition comprises human plasma and platelet derived proteins, wherein the platelet protein comprises TGFβ1. In some embodiments, the composition comprises human plasma and platelet derived proteins, wherein the platelet protein comprises TGFβ2. In some embodiments, the composition comprises human plasma and platelet derived proteins, wherein the platelet protein comprises VEGF In some embodiments, the composition comprises human plasma and platelet derived proteins, wherein the platelet protein comprises EGF. In some embodiments, the composition comprises human plasma and platelet derived proteins, wherein the platelet protein comprises BDNF. In some embodiments, the composition comprises human plasma and platelet derived proteins, wherein the platelet protein comprises HGF. In some embodiments, the composition comprises human plasma and platelet derived proteins, wherein the platelet protein comprises b-FGF. In some embodiments, the composition comprises human plasma and platelet derived proteins, wherein the platelet protein comprises IGF-1. In some embodiments, the composition comprises human plasma and platelet derived proteins, wherein the platelet protein comprises GMFB. In some embodiments, the composition comprises human plasma and platelet derived proteins, wherein the platelet protein comprises CD31.

In some embodiments, the composition comprises human plasma and platelet derived proteins, wherein the platelet protein comprises at least 20 µg/mL PDGF. In some embodiments, the composition comprises human plasma and platelet derived proteins, wherein the platelet protein comprises no more than 20 µg/mL PDGF. In some embodiments, the composition comprises human plasma and platelet derived proteins, wherein the platelet protein comprises 20 µg/mL PDGF. In some embodiments, the composition comprises human plasma and platelet derived proteins, wherein the platelet protein comprises between about 50 and 1,000 pg/mL PDGF-AB. In some embodiments, the composition comprises human plasma and platelet derived proteins, wherein the platelet protein comprises at least 50 pg/mL PDGF-AB. In some embodiments, the composition comprises human plasma and platelet derived proteins, wherein the platelet protein comprises no more than 50 pg/mL PDGF-AB. In some embodiments, the composition comprises human plasma and platelet derived proteins, wherein the platelet protein comprises at least 1,000 pg/mL PDGF-AB. In some embodiments, the composition comprises human plasma and platelet derived proteins, wherein the platelet protein comprises no more than 1,000 pg/mL PDGF-AB.

In some embodiments, the composition comprises human plasma and platelet derived proteins, wherein the platelet protein comprises no more than 200 ng/mL PDGF-AB. In some embodiments, the composition comprises human plasma and platelet derived proteins, wherein the platelet protein comprises about 5 ng/mL to about 200 ng/mL PDGF-AB. In some embodiments, the composition comprises human plasma and platelet derived proteins, wherein the platelet protein comprises about 10 ng/mL to about 20 ng/mL PDGF-AB. In some embodiments, the composition comprises human plasma and platelet derived proteins, wherein the platelet protein comprises about 20 ng/mL to about 40 ng/mL PDGF-AB. In some embodiments, the composition comprises human plasma and platelet derived proteins, wherein the platelet protein comprises about 40 ng/mL to about 80 ng/mL PDGF-AB. In some embodiments, the composition comprises human plasma and platelet derived proteins, wherein the platelet protein comprises about 80 ng/mL to about 160 ng/mL PDGF-AB. In some embodiments, the composition comprises human plasma and platelet derived proteins, wherein the platelet protein comprises no more than 200 ng/mL PDGF-AB. In some embodiments, the composition comprises human plasma and platelet derived proteins, wherein the platelet protein comprises 5 ng/mL to 200 ng/mL PDGF-AB. In some embodiments, the composition comprises human plasma and platelet derived proteins, wherein the platelet protein comprises 10 ng/mL to 20 ng/mL PDGF-AB. In some embodiments, the composition comprises human plasma and platelet derived proteins, wherein the platelet protein comprises 20 ng/mL to 40 ng/mL PDGF-AB. In some embodiments, the composition comprises human plasma and platelet derived proteins, wherein the platelet protein comprises 40 ng/mL to 80 ng/mL PDGF-AB. In some embodiments, the composition comprises human plasma and platelet derived proteins, wherein the platelet protein comprises 80 ng/mL to 160 ng/mL PDGF-AB.

In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the composition comprises greater than 40% w/w human serum albumin (HSA). In some embodiments, the composition comprises no more than 40% w/w HSA. In some embodiments, the composition comprises 40% w/w HSA. In some embodiments, the composition comprises about 60% to about 70% w/w HSA.

In some embodiments, the composition comprises human plasma and platelet derived proteins, wherein the plasma proteins are selected from albumin, fibrinogen, immunoglobulins, and a combination thereof, and wherein the composition comprises greater than 40% w/w human serum albumin (HSA). In some embodiments, the composition comprises no more than 40% w/w HSA. In some embodi-ments, the composition comprises 40% w/w HSA. In some embodiments, the composition comprises about 60% to about 70% w/w HSA.

In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the composition comprises greater than 20% w/w immunoglobulins. In some embodiments, the composition comprises no more than 20% w/w immuno-globulins. In some embodiments, the composition comprises 20% w/w immunoglobulins. In some embodiments, the composition comprises about 10% to about 20% w/w immu-noglobulins.

In some embodiments, the composition comprises human plasma and platelet derived proteins, wherein the plasma proteins are selected from albumin, fibrinogen, immuno-globulins, and a combination thereof, and wherein the composition comprises greater than 20% w/w immuno-globulins. In some embodiments, the composition comprises no more than 20% w/w immunoglobulins. In some embodi-ments, the composition comprises 20% w/w immunoglobu-lins. In some embodiments, the composition comprises about 10% to about 20% w/w immunoglobulins.

In some embodiments, the composition comprises human plasma and platelet derived proteins, wherein the plasma proteins are selected from albumin, fibrinogen, alpha-2-macroglobulin (A2M), immunoglobulins, and a combina-tion thereof, and wherein the composition comprises greater than 200 µg/mL A2M. In some embodiments, the compo-sition comprises no more than 200 µg/mL A2M. In some embodiments, the composition comprises 200 µg/mL A2M.

In some embodiments, the composition comprises human plasma and platelet derived proteins, wherein the plasma proteins are selected from albumin, fibrinogen, alpha-2-macroglobulin (A2M), immunoglobulins, and a combina-tion thereof, and wherein the composition comprises about 20 µg/mL to about 10 mg/mL fibrinogen. In some embodi-ments, the composition comprises 10 µg/mL to about 2 mg/mL fibrinogen. In some embodiments, the composition comprises no more than 10 mg/mL fibrinogen. In some embodiments, the composition comprises no less than 10 µg/mL fibrinogen. In some embodiments, the composition comprises no more than 10 mg/mL fibrinogen. In some embodiments, the composition comprises at least 10 mg/mL fibrinogen. In some embodiments, the composition com-prises at least 20 µg/mL fibrinogen. In some embodiments, the composition comprises no more than 20 µg/mL fibrino-gen. In some embodiments, the composition comprises about 1 mg/mL to about 5 mg/mL fibrinogen. In some embodiments, the composition comprises at least 2 mg/mL fibrinogen. In some embodiments, the composition com-prises no more than 2 mg/mL fibrinogen.

In some embodiments, the composition comprises human plasma and platelet derived proteins, wherein the plasma proteins are selected from albumin, fibrinogen, immuno-globulins, and a combination thereof, and wherein the composition comprises about 0.25 mg/mL to about 5 mg/mL fibrinogen. In some embodiments, the composition com-prises about 0.25 to about 0.5 mg/mL fibrinogen. In some embodiments, the composition comprises no more than 5 mg/mL fibrinogen. In some embodiments, the composition comprises at least 1 mg/mL fibrinogen. In some embodi-ments, the composition comprises about 1 mg/mL to about 5 mg/mL fibrinogen. In some embodiments, the composition comprises at least 2 mg/mL fibrinogen. In some embodi-ments, the composition comprises no more than 2 mg/mL fibrinogen. In some embodiments, the composition comprises about 1 mg/mL to about 2 mg/mL fibrinogen. In some embodiments, the composition comprises about 2 mg/mL to about 5 mg/mL fibrinogen. In some embodiments, the composition comprises about 0.5 mg/mL to about 1 mg/mL fibrinogen.

In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and a combination thereof. In some embodiments, the composition comprises human plasma and platelet derived proteins, wherein the plasma proteins are albumin, fibrinogen, alpha-2-macroglobulin (A2M), and immunoglobulins, and wherein the platelet proteins are PF4, PDGFAB, PDGFAA, PDGFBB, TGFβ1, TGFβ2, VEGF, EGF, BDNF, HGF, b-FGF, IGF-1, GMFB, and CD31.

In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet proteins are selected from PF4, PDGFAB, PDGFAA, PDGFBB, TGFβ1, TGFβ2, VEGF, EGF, HGF, b-FGF, IGF-1, GMFB, CD31, and a combination thereof. In some embodiments, the composition comprises human plasma and platelet derived proteins, wherein the plasma proteins are albumin, fibrinogen, alpha-2-macroglobulin (A2M), and immunoglobulins, and wherein the platelet proteins are PF4, PDGFAB, PDGFAA, PDGFBB, TGFβ1, TGFβ2, VEGF, EGF, HGF, b-FGF, IGF-1, GMFB, and CD31.

In some embodiments, the composition comprises human plasma and platelet derived proteins, wherein the plasma proteins are at least one of albumin, fibrinogen, alpha-2-macroglobulin (A2M), and immunoglobulins, and wherein the platelet proteins are at least one of PF4, PDGFAB, PDGFAA, PDGFBB, TGFβ1, TGFβ2, VEGF, EGF, HGF, FGF, IGF-1, GMFB, CD31, and a combination thereof. In some embodiments, the composition comprises human plasma and platelet derived proteins, wherein the plasma proteins are albumin, fibrinogen, alpha-2-macroglobulin (A2M), and immunoglobulins, and wherein the platelet proteins are PF4, PDGFAB, PDGFAA, PDGFBB, TGFβ1, TGFβ2, VEGF, EGF, HGF, FGF, IGF-1, GMFB, and CD31.

In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises PF4t. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises PDGF-AA. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises PDGF-BB. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises PDGF-AB. In some embodiments, the composition comprises human plasma proteins and platelet derived proteins, wherein the plasma proteins are selected from albumin, fibrinogen, alpha-2-macroglobulin (A2M), immunoglobulins, and a combination thereof, and wherein the platelet protein comprises TGF 1. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises TGFβ2. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises VEGF. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises EGF. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises BDNF. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises HGF. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises b-FGF. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises IGF-1. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises GMFB. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises CD31.

In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises at least 20 μg/mL PDGF. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises no more than 20 μg/mL PDGF. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises 20

µg/mL PDGF. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises between about 50 and 1,000 µg/mL PDGF-AB. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises at least 50 µg/mL PDGF-AB. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises no more than 50 µg/mL PDGF-AB. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises at least 1,000 µg/mL PDGF-AB. In some embodiments, the composition comprises human plasma and platelet derived proteins, wherein the plasma proteins are selected from albumin, fibrinogen, alpha-2-macroglobulin (A2M), immunoglobulins, and a combination thereof, and wherein the platelet protein comprises no more than 1,000 µg/mL PDGF-AB.

In some embodiments, the composition comprises human plasma and platelet derived proteins, wherein the plasma proteins are selected from albumin, fibrinogen, immunoglobulins, and a combination thereof, and wherein the platelet proteins are selected from PDGF (PDGF-AB, PDGF-AA, and/or PDGF-BB), TGFβ (TGFβ1 and/or TGFβ2), VEGF, EGF, FGF, HGF, and a combination thereof. In some embodiments, the composition comprises human plasma and platelet derived proteins, wherein the plasma proteins are albumin, fibrinogen, and immunoglobulins, and wherein the platelet proteins are PDGF (PDGF-AB, PDGF-AA, and/or PDGF-BB), TGFβ (TGFβ1 and/or TGFβ2), VEGF, EGF, FGF, and HGF.

In some embodiments, the composition comprises human plasma and platelet derived proteins, wherein the plasma proteins are at least one of albumin, fibrinogen, and immunoglobulins, and wherein the platelet proteins are at least one of PDGF (PDGF-AB, PDGF-AA, and/or PDGF-BB), TGFβ (TGFβ 1 and/or TGFβ2), VEGF, EGF, FGF, HGF, and a combination thereof.

In some embodiments, the composition comprises human plasma and platelet derived proteins, wherein the plasma proteins are selected from albumin, fibrinogen, immunoglobulins, and a combination thereof, and wherein the platelet protein comprises PF4t. In some embodiments, the composition comprises human plasma and platelet derived proteins, wherein the plasma proteins are selected from albumin, fibrinogen, immunoglobulins, and a combination thereof, and wherein the platelet protein comprises PDGF-AA. In some embodiments, the composition comprises human plasma and platelet derived proteins, wherein the plasma proteins are selected from albumin, fibrinogen, immunoglobulins, and a combination thereof, and wherein the platelet protein comprises PDGF-BB. In some embodiments, the composition comprises human plasma and platelet derived proteins, wherein the plasma proteins are selected from albumin, fibrinogen, immunoglobulins, and a combination thereof, and wherein the platelet protein comprises PDGF-AB. In some embodiments, the composition comprises human plasma proteins and platelet derived proteins, wherein the plasma proteins are selected from albumin, fibrinogen, immunoglobulins, and a combination thereof, and wherein the platelet protein comprises TGFβ1. In some embodiments, the composition comprises human plasma and platelet derived proteins, wherein the plasma proteins are selected from albumin, fibrinogen, immunoglobulins, and a combination thereof, and wherein the platelet protein comprises TGFβ2. In some embodiments, the composition comprises human plasma and platelet derived proteins, wherein the plasma proteins are selected from albumin, fibrinogen, immunoglobulins, and a combination thereof, and wherein the platelet protein comprises VEGF. In some embodiments, the composition comprises human plasma and platelet derived proteins, wherein the plasma proteins are selected from albumin, fibrinogen, immunoglobulins, and a combination thereof, and wherein the platelet protein comprises EGF. In some embodiments, the composition comprises human plasma and platelet derived proteins, wherein the plasma proteins are selected from albumin, fibrinogen, immunoglobulins, and a combination thereof, and wherein the platelet protein comprises BDNF. In some embodiments, the composition comprises human plasma and platelet derived proteins, wherein the plasma proteins are selected from albumin, fibrinogen, immunoglobulins, and a combination thereof, and wherein the platelet protein comprises HGF. In some embodiments, the composition comprises human plasma and platelet derived proteins, wherein the plasma proteins are selected from albumin, fibrinogen, immunoglobulins, and a combination thereof, and wherein the platelet protein comprises b-FGF. In some embodiments, the composition comprises human plasma and platelet derived proteins, wherein the plasma proteins are selected from albumin, fibrinogen, immunoglobulins, and a combination thereof, and wherein the platelet protein comprises IGF-1. In some embodiments, the composition comprises human plasma and platelet derived proteins, wherein the plasma proteins are selected from albumin, fibrinogen, immunoglobulins, and a combination thereof, and wherein the platelet protein comprises GMFB. In some embodiments, the composition comprises human plasma and platelet derived proteins, wherein the plasma proteins are selected from albumin, fibrinogen, immunoglobulins, and a combination thereof, and wherein the platelet protein comprises CD31.

In some embodiments, the composition comprises human plasma and platelet derived proteins, wherein the plasma proteins are selected from albumin, fibrinogen, immunoglobulins, and a combination thereof, and wherein the platelet protein comprises about 5 to about 200 ng/mL PDGF-AB. In some embodiments, the composition comprises human plasma and platelet derived proteins, wherein the plasma proteins are selected from albumin, fibrinogen, immunoglobulins, and a combination thereof, and wherein the platelet protein comprises at least 5 ng/mL PDGF-AB. In some embodiments, the composition comprises human plasma and platelet derived proteins, wherein the plasma proteins are selected from albumin, fibrinogen, immunoglobulins, and a combination thereof, and wherein the platelet protein comprises no more than 200 ng/mL PDGF-AB. In some embodiments, the composition comprises human plasma and platelet derived proteins, wherein the plasma proteins are selected from albumin, fibrinogen, immunoglobulins, and a combination thereof, and wherein the platelet protein comprises about 10 to about 20 ng/mL PDGF-AB. In some embodiments, the composition comprises human plasma and platelet derived proteins, wherein the plasma proteins are selected from albumin, fibrinogen, immunoglobulins, and a combination thereof, and wherein the platelet protein comprises about 20 to about 40 ng/mL PDGF-AB. In some embodiments, the composition comprises human plasma and platelet derived proteins, wherein the plasma proteins are selected from albumin, fibrinogen, immunoglobulins, and a combination thereof, and wherein the platelet protein comprises about 40 to about 80 ng/mL PDGF-AB. In some embodiments, the composition comprises human plasma and platelet derived proteins, wherein the plasma proteins are selected from albumin, fibrinogen, immunoglobulins, and a combination thereof, and wherein the platelet protein comprises about 80 to about 60 ng/mL PDGF-AB.

In some embodiments, the allogenic human plasma and platelet derived product comprises a composition with reduced concentrations of plasma proteins. In some embodiments, the allogeneic human plasma and platelet derived product comprises a composition with a reduced concentration of albumin. In some embodiments, the allogeneic human plasma and platelet derived product comprises a composition substantially of platelet proteins.

High Concentration Allogeneic Human Plasma and Platelet Derived Product

In some embodiments, the composition of the disclosure provides a high concentration allogeneic human plasma and platelet derived product. In some embodiments, the disclosure provides a composition comprising a high concentration of human plasma and platelet derived proteins. In some embodiments, the disclosure provides a composition comprising a high concentration of human plasma and platelet derived proteins, wherein the composition comprises a total protein concentration of greater than 50 mg/mL. In some embodiments, the total protein concentration is greater than 50 mg/mL and less than 500 mg/mL. In some embodiments, the total protein concentration is greater than 75 mg/mL and less than 500 mg/mL. In some embodiments, the total protein concentration is at least 75 mg/mL and less than 500 mg/mL. In some embodiments, the total protein concentration is at least 100 mg/mL and less than 500 mg/mL. In some embodiments, the total protein concentration is about 50 mg/mL to about 500 mg/mL. In some embodiments, the total protein concentration is about 75 mg/mL to about 450 mg/mL. In some embodiments, the total protein concentration is about 75 mg/mL to about 300 mg/mL. In some embodiments, the total protein concentration is about 100 mg/mL to about 300 mg/mL. In some embodiments, the total protein concentration is about 150 mg/mL to about 300 mg/mL. In some embodiments, the total protein concentration is about 100 mg/mL to about 250 mg/mL. In some embodiments, the total protein concentration is about 50 to about 60 mg/mL. In some embodiments, the total protein concentration is about 60 to about 70 mg/mL. In some embodiments, the total protein concentration is about 70 to about 80 mg/mL. In some embodiments, the total protein concentration is about 80 to about 90 mg/mL. In some embodiments, the total protein concentration is about 90 to about 100 mg/mL. In some embodiments, the total protein concentration is at least 100 mg/mL. In some embodiments, the total protein concentration is about 100 to about 200 mg/mL. In some embodiments, the total protein concentration is at least 200 mg/mL. In some embodiments, the total protein concentration is no more than 250 mg/mL.

In some embodiments, the disclosure provides a composition comprising human plasma and platelet derived proteins, wherein the composition comprises a total protein concentration of at least 20 mg/mL. In some embodiments, the total protein concentration is about 20 mg/mL to about 50 mg/mL. In some embodiments, the total protein concentration is about 20 mg/mL to about 500 mg/mL. In some embodiments, the total protein concentration is about 50 mg/mL to about 80 mg/mL. In some embodiments, the total protein concentration is about 80 mg/mL to about 160 mg/mL. In some embodiments, the total protein concentration is about 160 mg/mL to about 320 mg/mL. In some embodiments, the total protein concentration is about 30 mg/mL+/−5%, 10%, 15%, 20%, 25%, 30%, 35%, 40%, 45%, or 50%. In some embodiments, the total protein concentration is about 30 mg/mL+/−25%. In some embodiments, the total protein concentration is about 60 mg/mL+/−5%, 10%, 15%, 20%, 25%, 30%, 35%, 40%, 45%, or 50%. In some embodiments, the total protein concentration is about 60 mg/mL+/−25%. In some embodiments, the total protein concentration is about 120 mg/mL+/−5%, 10%, 15%, 20%, 25%, 30%, 35%, 40%, 45%, or 50%. In some embodiments, the total protein concentration is about 120 mg/mL+/−25%. In some embodiments, the total protein concentration is about 240 mg/mL+/−5%, 10%, 15%, 20%, 25%, 30%, 35%, 40%, 45%, or 50%. In some embodiments, the total protein concentration is about 240 mg/mL+/−25%.

In some embodiments, the disclosure provides a composition comprising a high concentration of plasma and platelet derived proteins, wherein the plasma proteins are selected from albumin, fibrinogen, A2M, immunoglobulins, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, A2M, immunoglobulins, and any combination thereof, and the total protein concentration is about 50 to about 500 mg/mL. In some embodiments, the disclosure provides a composition comprising a high concentration of plasma and platelet derived proteins, wherein the plasma proteins are selected from albumin, fibrinogen, A2M, immunoglobulins, and any combination thereof, and the total protein concentration is about 100 to about 300 mg/mL.

In some embodiments, the disclosure provides a composition comprising a high concentration of plasma and platelet derived proteins, wherein the plasma proteins are selected from albumin, fibrinogen, A2M, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, A2M, and any combination thereof, and the total protein concentration is about 50 to about 500 mg/mL. In some embodiments, the disclosure provides a composition comprising a high concentration of plasma and platelet derived proteins, wherein the plasma proteins are selected from albumin, fibrinogen, A2M, and any combination thereof, and the total protein concentration is about 100 to about 300 mg/mL.

In some embodiments, the disclosure provides a composition comprising a high concentration of plasma and platelet derived proteins, wherein the plasma proteins are albumin, fibrinogen, A2M, and immunoglobulins, and the total protein concentration is at least 50 mg/mL. In some embodiments, the disclosure provides a composition comprising a high concentration of plasma and platelet derived proteins, wherein the plasma proteins are albumin, fibrinogen, A2M, and immunoglobulins, and the total protein concentration is about 50 to about 500 mg/mL. In some embodiments, the disclosure provides a composition comprising a high concentration of plasma and platelet derived proteins, wherein the plasma proteins are albumin, fibrinogen, A2M, and immunoglobulins, and the total protein concentration is about 100 to about 300 mg/mL.

In some embodiments, the disclosure provides a composition comprising a high concentration of plasma and platelet derived proteins, wherein the plasma proteins are albumin, fibrinogen, and A2M, and the total protein concentration is at least 50 mg/mL. In some embodiments, the disclosure provides a composition comprising a high concentration of plasma and platelet derived proteins, wherein the plasma proteins are albumin, fibrinogen, and A2M, and the total protein concentration is about 50 to about 500 mg/mL. In some embodiments, the disclosure provides a composition comprising a high concentration of plasma and platelet derived proteins, wherein the plasma proteins are albumin, fibrinogen, and A2M, and the total protein concentration is about 100 to about 300 mg/mL.

In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the total protein concentration is at least 50 mg/mL. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the total protein concentration is about 50 to about 500 mg/mL. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the total protein concentration is about 100 to about 300 mg/mL.

In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, and the total protein concentration is at least 50 mg/mL. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, and the total protein concentration is about 50 to about 500 mg/mL. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, and the total protein concentration is about 100 to about 300 mg/mL.

In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the total protein concentration is about 50 to about 500 mg/mL. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the total protein concentration is about 100 to about 300 mg/mL.

In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the total protein concentration is about 50 to about 500 mg/mL. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the total protein concentration is about 100 to about 300 mg/mL.

In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, CD31, and the total protein concentration is at least 50 mg/mL. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the total protein concentration is about 50 to about 500 mg/mL. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the total protein concentration is about 100 to about 300 mg/mL.

In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, CD31, and the total protein concentration is at least 50 mg/mL. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the total protein concentration is about 50 to about 500 mg/mL. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the total protein concentration is about 100 to about 300 mg/mL.

In some embodiments, the disclosure provides a composition comprising a high concentration of plasma and platelet derived proteins, wherein the plasma proteins are selected from albumin, fibrinogen, immunoglobulins, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, immunoglobulins, and any combination thereof, and the total protein concentration is about 50 to about 500 mg/mL. In some embodiments, the disclosure provides a composition comprising a high concentration of plasma and platelet derived proteins, wherein the plasma proteins are selected from albumin, fibrinogen, immunoglobulins, and any combination thereof, and the total protein concentration is about 100 to about 300 mg/mL.

In some embodiments, the disclosure provides a composition comprising a high concentration of plasma and platelet derived proteins, wherein the plasma proteins are selected from albumin, fibrinogen, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, and any combination thereof, and the total protein concentration is about 50 to about 500 mg/mL. In some embodiments, the disclosure provides a composition comprising a high concentration of plasma and platelet derived proteins, wherein the plasma proteins are selected from albumin, fibrinogen, and any combination thereof, and the total protein concentration is about 100 to about 300 mg/mL.

In some embodiments, the disclosure provides a composition comprising a high concentration of plasma and platelet derived proteins, wherein the plasma proteins are albumin, fibrinogen, and immunoglobulins, and the total protein concentration is at least 50 mg/mL. In some embodiments, the disclosure provides a composition comprising a high concentration of plasma and platelet derived proteins, wherein the plasma proteins are albumin, fibrinogen, and immunoglobulins, and the total protein concentration is about 50 to about 500 mg/mL. In some embodiments, the disclosure provides a composition comprising a high concentration of plasma and platelet derived proteins, wherein the plasma proteins are albumin, fibrinogen, and immunoglobulins, and the total protein concentration is about 100 to about 300 mg/mL.

In some embodiments, the disclosure provides a composition comprising a high concentration of plasma and platelet derived proteins, wherein the plasma proteins are albumin and fibrinogen, and the total protein concentration is at least 50 mg/mL. In some embodiments, the disclosure provides a composition comprising a high concentration of plasma and platelet derived proteins, wherein the plasma proteins are albumin and fibrinogen, and the total protein concentration is about 50 to about 500 mg/mL. In some embodiments, the disclosure provides a composition comprising a high concentration of plasma and platelet derived proteins, wherein the plasma proteins are albumin and fibrinogen, and the total protein concentration is about 100 to about 300 mg/mL.

In some embodiments, the disclosure provides a composition comprising a high concentration of plasma and platelet derived proteins, wherein the platelet proteins are selected from PDGF-AB, PDGF-AA, PDGF-AB, TGFβ1, TGFβ2, VEGF, EGF, FGF, HGF, and any combination thereof, and the total protein concentration is at least 50 mg/mL. In some embodiments, the disclosure provides a composition comprising a high concentration of plasma and platelet derived proteins, wherein the platelet proteins are selected from PDGF-AB, PDGF-AA, PDGF-AB, TGFβ1, TGFβ2, VEGF, EGF, FGF, HGF, and any combination thereof, and the total protein concentration is about 50 to about 500 mg/mL. In some embodiments, the disclosure provides a composition comprising a high concentration of plasma and platelet derived proteins, wherein the platelet proteins are selected from PDGF-AB, PDGF-AA, PDGF-AB, TGFβ1, TGFβ2, VEGF, EGF, FGF, HGF, and any combination thereof, and the total protein concentration is about 100 to about 300 mg/mL.

In some embodiments, the disclosure provides a composition comprising a high concentration of plasma and platelet derived proteins, wherein the platelet proteins are PDGF-AB, PDGF-AA, PDGF-AB, TGFβ1, TGFβ2, VEGF, EGF, FGF, and HGF, and the total protein concentration is at least 50 mg/mL. In some embodiments, the disclosure provides a composition comprising a high concentration of plasma and platelet derived proteins, wherein the platelet proteins are PDGF-AB, PDGF-AA, PDGF-AB, TGFβ1, TGFβ2, VEGF, EGF, FGF, and HGF, and the total protein concentration is about 50 to about 500 mg/mL. In some embodiments, the disclosure provides a composition comprising a high concentration of plasma and platelet derived proteins, wherein the platelet proteins are PDGF-AB, PDGF-AA, PDGF-AB, TGFβ1, TGFβ2, VEGF, EGF, FGF, and HGF, and the total protein concentration is about 100 to about 300 mg/mL.

In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, and the total protein concentration is about 50 to about 500 mg/mL. In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, and the total protein concentration is about 100 to about 300 mg/mL.

In some embodiments, the disclosure provides a composition comprising a high concentration of plasma and platelet derived proteins, wherein the plasma proteins are selected from albumin, fibrinogen, and any combination thereof, the platelet proteins are selected from PDGF-AB, PDGF-AA, PDGF-AB, TGFβ1, TGFβ2, VEGF, EGF, FGF, HGF, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, and any combination thereof, the platelet proteins are selected from PDGF-AB, PDGF-AA, PDGF-AB, TGFβ1, TGFβ2, VEGF, EGF, FGF, HGF, and any combination thereof, and the total protein concentration is about 50 to about 500 mg/mL. In some embodiments, the disclosure provides a composition comprising a high concentration of plasma and platelet derived proteins, wherein the plasma proteins are selected from albumin, fibrinogen, and any combination thereof, the platelet proteins are selected from PDGF-AB, PDGF-AA, PDGF-AB, TGFβ1, TGFβ2, VEGF, EGF, FGF, HGF, and any combination thereof, and the total protein concentration is about 100 to about 300 mg/mL.

In some embodiments, the disclosure provides a composition comprising a high concentration of plasma and platelet derived proteins, wherein the plasma proteins are albumin, fibrinogen, and immunoglobulins, the platelet proteins are PDGF-AB, PDGF-AA, PDGF-AB, TGFβ1, TGFβ2, VEGF, EGF, FGF, and HGF, and the total protein concentration is at least 50 mg/mL. In some embodiments, the disclosure provides a composition comprising a high concentration of plasma and platelet derived proteins, wherein the plasma proteins are albumin, fibrinogen, and immunoglobulins, the platelet proteins are PDGF-AB, PDGF-AA, PDGF-AB, TGFβ1, TGFβ2, VEGF, EGF, FGF, and HGF, and the total protein concentration is about 50 to about 500 mg/mL. In some embodiments, the disclosure provides a composition comprising a high concentration of plasma and platelet derived proteins, wherein the plasma proteins are albumin, fibrinogen, and immunoglobulins, the platelet proteins are PDGF-AB, PDGF-AA, PDGF-AB, TGFβ1, TGFβ2, VEGF, EGF, FGF, and HGF, and the total protein concentration is about 100 to about 300 mg/mL.

In some embodiments, the disclosure provides a composition comprising a high concentration of plasma and platelet derived proteins, wherein the plasma proteins are albumin and fibrinogen, the platelet proteins are PDGF-AB, PDGF-AA, PDGF-AB, TGFβ1, TGFβ2, VEGF, EGF, FGF, and HGF, and the total protein concentration is at least 50 mg/mL. In some embodiments, the disclosure provides a composition comprising a high concentration of plasma and platelet derived proteins, wherein the plasma proteins are albumin and fibrinogen, the platelet proteins are PDGF-AB, PDGF-AA, PDGF-AB, TGFβ1, TGFβ2, VEGF, EGF, FGF, and HGF, and the total protein concentration is about 50 to about 500 mg/mL. In some embodiments, the disclosure provides a composition comprising a high concentration of plasma and platelet derived proteins, wherein the plasma proteins are albumin and fibrinogen, the platelet proteins are PDGF-AB, PDGF-AA, PDGF-AB, TGFβ1, TGFβ2, VEGF, EGF, FGF, and HGF, and the total protein concentration is about 100 to about 300 mg/mL.

Total protein concentration can be evaluated with any standard technique known to those with ordinary skill in the art. In some embodiments, a bicinchoninic acid assay (BCA) is used to evaluate total protein concentration. The BCA (Bicinchoninic Acid) assay, a colorimetric method of detection based on complexation of proteins with copper and BCA. The principle of the bicinchoninic acid (BCA) assay relies on the formation of a Cu2+-protein complex under alkaline conditions, followed by reduction of the Cu2+ to Cu+. The amount of reduction is proportional to the protein present. BCA forms a purple-blue complex with Cu+ in alkaline environments, thus providing a basis to monitor the reduction of alkaline Cu2+ by proteins at absorbance maximum 562 nm. In some embodiments, a Bradford assay is used to evaluate total protein concentration. In some embodiments, UV-vis/$A_{280}$ is used to evaluate total protein concentration. In some embodiments, a Lowry assay is used to evaluate total protein concentration.

Viscosity

In some embodiments, the composition comprises a viscosity that allows for localization and maintenance of the platelet and plasma proteins at the site of injection. Viscosity is a measure of the resistance of the gel to being deformed by either shear stress or tensile stress. Viscosity can be measured using any method known in the art. Suitable methods include, but are not limited to, using a viscometer or a rheometer.

In some embodiments, viscosity of the of the composition is determined at room temperature and quantified as centipoise (cP). In some embodiments, the viscosity is 1 to 50 cP. In some embodiments, the viscosity is 1 to 40 cP. In some embodiments, the viscosity is less than 40 cP. In some embodiments, the viscosity is 5 to 40 cP. In some embodiments, the viscosity is 10 to 30 cP. In some embodiments, the viscosity is 10 to 25 cP. In some embodiments, the viscosity is 10 to 15 cP. In some embodiments, the viscosity is at least 5 cP and no greater than 25 cP. In some embodiments, the viscosity is less than 50 cP. In some embodiments, the viscosity is about 1 to 2 cP. In some embodiments, the viscosity is about 3 to about 5 cP. In some embodiments, the viscosity is about 5 to about 10 cP. In some embodiments, the viscosity is about 10 to about 15 cP. In some embodiments, the viscosity is about 10 to about 20 cP. In some embodiments, the viscosity is about 20 to about 50 cP. In some embodiments, the viscosity is about 2 cP. In some embodiments, the viscosity is about 3 cP. In some embodiments, the viscosity is about 10 cP. In some embodiments, the viscosity is about 12 cP. In some embodiments, the viscosity is about 15 cP. In some embodiments, the viscosity is 20 cP. In some embodiments, the viscosity is at least 10 cP. In some embodiments, the viscosity is at least 15 cP. In some embodiments, the viscosity is no greater than 15 cP. In some embodiments, the viscosity is less than 25 cP, less than 20 cP, less than 15 cP, or less than 10 cP.

In some embodiments, viscosity of a high concentration composition comprising plasma and platelet derived proteins is reduced. In some embodiments, viscosity is reduced by dilution of the high concentration composition. In some embodiments, viscosity is reduced by using a viscosity modifier. In some embodiments, a viscosity modifier is arginine, a salt, or a hydrophobicity binder (e.g., tryptophan).

In some embodiments, the disclosure provides a composition comprising plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the viscosity is no more than 50 cP. In some embodiments, the disclosure provides a composition comprising plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the viscosity is about 1 to about 40 cP. In some embodiments, the disclosure provides a composition comprising plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the viscosity is about 10 to about 25 cP.

In some embodiments, the disclosure provides a composition comprising plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the viscosity is no more than 50 cP. In some embodiments, the disclosure provides a composition comprising plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the viscosity is about 1 to about 40 cP. In some embodiments, the disclosure provides a composition comprising plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, and the viscosity is about 10 to about 25 cP.

In some embodiments, the disclosure provides a composition comprising plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the viscosity is no more than 50 cP. In some embodiments, the disclosure provides a composition comprising plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the viscosity is about 1 to about 40 cP. In some embodiments, the disclosure provides a composition comprising plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the viscosity is about 10 to about 25 cP.

In some embodiments, the disclosure provides a composition comprising plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the viscosity is no more than 50 cP. In some embodiments, the disclosure provides a composition comprising plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the viscosity is about 1 to about 40 cP. In some embodiments, the disclosure provides a composition comprising plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, and the viscosity is about 10 to about 25 cP.

In some embodiments, the disclosure provides a composition comprising plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, and the viscosity is no more than 50 cP. In some embodiments, the disclosure provides a composition comprising plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, and the viscosity is about 1 to about 40 cP. In some embodiments, the disclosure provides a composition comprising plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, and the viscosity is about 10 to about 25 cP.

In some embodiments, the disclosure provides a composition comprising plasma and platelet derived proteins, wherein the plasma proteins are selected from albumin, fibrinogen, and any combination thereof, the platelet proteins are selected from PDGF-AB, PDGF-AA, PDGF-AB, TGFβ1, TGFβ2, VEGF, EGF, FGF, HGF, and any combination thereof, and the viscosity is no more than 50 cP. In some embodiments, the disclosure provides a composition comprising plasma and platelet derived proteins, wherein the plasma proteins are selected from albumin, fibrinogen, and any combination thereof, the platelet proteins are selected from PDGF-AB, PDGF-AA, PDGF-AB, TGFβ1, TGFβ2, VEGF, EGF, FGF, HGF, and any combination thereof, and the viscosity is about 1 to about 40 cP. In some embodiments, the disclosure provides a composition comprising plasma and platelet derived proteins, wherein the plasma proteins are selected from albumin, fibrinogen, and any combination thereof, the platelet proteins are selected from PDGF-AB, PDGF-AA, PDGF-AB, TGFβ1, TGFβ2, VEGF, EGF, FGF, HGF, and any combination thereof, and the viscosity is about 10 to about 25 cP.

In some embodiments, the disclosure provides a composition comprising plasma and platelet derived proteins, wherein the plasma proteins are albumin, fibrinogen, and immunoglobulins, the platelet proteins are PDGF-AB, PDGF-AA, PDGF-AB, TGFβ1, TGFβ2, VEGF, EGF, FGF, and HGF, and the viscosity is no more than 50 cP. In some embodiments, the disclosure provides a composition comprising plasma and platelet derived proteins, wherein the plasma proteins are albumin, fibrinogen, and immunoglobulins, the platelet proteins are PDGF-AB, PDGF-AA, PDGF-AB, TGFβ1, TGFβ2, VEGF, EGF, FGF, and HGF, and the viscosity is about 1 to about 40 cP. In some embodiments, the disclosure provides a composition comprising plasma and platelet derived proteins, wherein the plasma proteins are albumin, fibrinogen, and immunoglobulins, the platelet proteins are PDGF-AB, PDGF-AA, PDGF-AB, TGFβ1, TGFβ2, VEGF, EGF, FGF, and HGF, and the viscosity is about 10 to about 25 cP.

In some embodiments, the disclosure provides a composition comprising plasma and platelet derived proteins, wherein the plasma proteins are albumin and fibrinogen, the platelet proteins are PDGF-AB, PDGF-AA, PDGF-AB, TGFβ1, TGFβ2, VEGF, EGF, FGF, and HGF, and the viscosity is no more than 50 cP. In some embodiments, the disclosure provides a composition comprising plasma and platelet derived proteins, wherein the plasma proteins are albumin and fibrinogen, the platelet proteins are PDGF-AB, PDGF-AA, PDGF-AB, TGFβ1, TGFβ2, VEGF, EGF, FGF, and HGF, and the viscosity is about 1 to about 40 cP. In some embodiments, the disclosure provides a composition comprising plasma and platelet derived proteins, wherein the plasma proteins are albumin and fibrinogen, the platelet proteins are PDGF-AB, PDGF-AA, PDGF-AB, TGFβ1, TGFβ2, VEGF, EGF, FGF, and HGF, and the viscosity is about 10 to about 25 cP.

pH and Osmolality

In some embodiments, the composition comprising an allogeneic human plasma and platelet derived product has a pH of about 4.5 to about 8.5. In some embodiments the pH is about 5.0 to about 8.5. In some embodiments the pH is about 5.5 to about 8.5. In some embodiments the pH is about 6.0 to about 8.5. In some embodiments the pH is about 6.5 to about 8.5. In some embodiments the pH is about 7.0 to about 8.5. In some embodiments the pH is about 7.5 to about 8.5. In some embodiments, the pH is about 4.5 to about 8.0. In some embodiments, the pH is about 4.5 to about 7.5. In some embodiments, the pH is about 4.5 to about 7.0. In some embodiments, the pH is about 4.5 to about 6.5. In some embodiments, the pH is about 4.5 to about 6.0. In some embodiments, the pH is about 4.5 to about 5.5.

In some embodiments, the composition comprising an allogeneic human plasma and platelet derived product has an osmolality of about 200 to about 500 mOsmo/kg. In some embodiments, osmolality is measured via a freezing point osmometer. In some embodiments, an osmolality of about 200 to about 500 mOsmo/kg allows for proteins to remain stable. In some embodiments, an osmolality of about 200 to about 500 mOsmo/kg allows for injection into a subject.

Characterization of Composition

In some embodiments, the presence of platelet proteins and/or plasma proteins is determined by detecting protein levels. In some embodiments, the concentration of platelet and/or plasma proteins is determined by quantifying protein levels. In some embodiments, the total protein concentration of the allogeneic human plasma and platelet e derived product is determined using methods for detecting and quantifying proteins. Methods for detecting and quantifying proteins are known in the art and described herein, for example, western blot, CE-SDS, SDS-PAGE, immunosorbent assays, BCA, etc. In some embodiments, the presence of platelet proteins and/or plasma proteins is determined by SDS-PAGE. Sodium dodecyl-sulfate polyacrylamide gel electrophoresis (SDS-PAGE) is used to obtain high resolution separation of complex mixtures of proteins that comprise allogenic human platelet concentrate. This method allows protein separation by mass. Allogenic human platelet concentrate samples are diluted in a sample buffer containing SDS which denatures protein-protein interactions and mask the proteins' intrinsic charge making them similar charge-to-mass ratios. When a current is applied, all SDS-bound proteins will migrate through a gel towards the positively charged electrode. The gel is stained using an intercalating dye, visualized, and analyzed using densitometry for gross evaluation of protein composition.

In some embodiments, the presence of platelet proteins and/or plasma proteins is determined by capillary electrophoreses sodium dodecyl sulfate (CE-SDS). Protein analysis by CE-SDS relies on separation of SDS-bound protein variants by a sieving matrix (i.e. polymer) in a constant electric field. This method yields higher resolution compared to SDS-PAGE and allows for identification and purity analysis of proteins.

In some embodiments, the presence or quantity of platelet proteins and/or plasma proteins is determined by ELISA. In some embodiments, the presence or quantity of platelet proteins and/or plasma proteins is determined by quantitative sandwich enzyme immunoassay. In a quantitative sandwich enzyme immunoassay, a first antibody is coated on the surface of the multi-well plate and used as a capture antibody to facilitate the immobilization of the antigen. A second antibody can be conjugated to facilitate the detection of the antigen.

In some embodiments, the presence or quantity of platelet proteins and/or plasma proteins is determined by Meso Scale Discovery (MSD) assays. MSD relies on the same principle as ELISA but requires electrochemiluminescent signals as a detection method.

In some embodiments, the presence and/or quantity of cytokines is determined with a cytokine panel. In some embodiments, the cytokine panel is evaluated via mass spectrometry. In some embodiments, the cytokine panel is evaluated via an immunosorbent assay (e.g., ELISA, cytokine arrays). A human cytokine array is a rapid, sensitive, and economic tool to simultaneously detect multiple cytokines. Carefully selected capture antibodies are spotted in duplicate on nitrocellulose membranes. The allogeneic human platelet concentrate/antibody mixture is first diluted and incubated with the Human Cytokine Array membrane. Any cytokine/detection antibody complex present is bound by its cognate immobilized capture antibody on the membrane. Following a wash to remove unbound material, Streptavidin-HRP and chemiluminescent detection reagents are added sequentially. Light is produced at each spot in proportion to the amount of cytokine bound.

In some embodiments, the presence of A2M is determined with an enzyme linked immunosorbent assay (ELISA). In some embodiments, A2M content is determined using a commercially available sandwich ELISA. In this assay, the antibody specific for A2M is bound to the solid phase or support. A composition of interest is contacted with the solid phase or support to extract the antigen (A2M) from the sample by formation of a binary solid phase antibody: antigen complex. After a suitable incubation period, the solid support is washed to remove any unbound substances. An enzyme-linked biotinylated-polyclonal antibody specific for human A2M is then added to the wells. Following a wash to remove any unbound antibody-enzyme reagent, a substrate solution containing streptavidin-HRP is added to the wells and color develops in proportion to the amount of A2M bound in the initial step. The color development is stopped, and the intensity of the color is measured. Total A2M is determined via absorption and extrapolated from an A2M standard curve.

In some embodiments, the function of platelet proteins is determined by ELISA. In some embodiments, the function of PF4 is evaluated with a AlphaLISA kit by Revvity (Cat. No. AL398HV). In some embodiments, the function of PDGF is evaluated with a Human Platelet-Derived Growth Factor Receptor α and β (PDGFRα/β) kit by INDIGO Biosciences (Cat. No. IB23001). In some embodiments, the quantity of PDGF is determined by ELISA. In some embodiments the quantity of PDGF is evaluated with a Human Platelet-Derived Growth Factor Receptor α and β (PDGFRα/β) kit by INDIGO Biosciences (Cat. No. IB23001).

In some embodiments, the function of TFBβ is evaluated with a Human TGFβR Reporter Assay Kit by INDIGO Biosciences (Cat. NO. IB12001). In some embodiments, the quantity of TFBβ is evaluated with a Human TGFβR Reporter Assay Kit by INDIGO Biosciences (Cat. NO. IB12001). In some embodiments, the function of VEGF is evaluated with bioluminescence with a VEGF Bioassay kit by Promega (Cat. No. GA2001). In some embodiments, the quantity of VEGF is evaluated with bioluminescence with a VEGF Bioassay kit by Promega (Cat. No. GA2001). In some embodiments, the function of EGF is evaluated with a ELISA kit by Eagle Biosciences (Cat. No. EGF31-K01). In some embodiments, the quantity of EGF is evaluated with a ELISA kit by Eagle Biosciences (Cat. No. EGF31-K01). In some embodiments, the function of BDNF is evaluated with an ELISA kit by Thermo Fisher (Cat. No. EH42RB). In some embodiments, the function of HGF is evaluated with an ELISA kit by Thermo Fisher (Cat. No. KAC2211). In some embodiments, the quantity of HGF is evaluated with an ELISA kit by Thermo Fisher (Cat. No. KAC2211). In some embodiments, the function of b-FGF is evaluated with an ELISA kit by Thermo Fisher (Cat. No. EB2RB). In some embodiments, the quantity of b-FGF is evaluated with an ELISA kit by Thermo Fisher (Cat. No. EB2RB). In some embodiments, the function of IGF-1 is evaluated with an ELISA kit by Thermo Fisher (Cat. No. EH250RB). In some embodiments, the function of CD31 is evaluated with an ELISA kit by Thermo Fisher (Cat. No. BMS229). In some embodiments, the function of albumin is evaluated with an ELISA kit by Thermo Fisher (Cat. No. EHALB). In some embodiments, the function of fibrinogen is evaluated with an ELISA kit by AbCam (Cat. No. ab241383). In some embodiments, the quantity of fibrinogen is evaluated with an ELISA kit by AbCam (Cat. No. ab241383). In some embodiments, the function of A2M is evaluated with an ELISA kit by Thermo Fisher (Cat. No. EH20RB). In some embodiments, the function of IgM is evaluated with an ELISA kit by Thermo Fisher (Cat. No. BMS2098). In some embodiments, the function of IgG is evaluated with an ELISA kit by Thermo Fisher (Cat. No. BMS2091). In some embodiments, the function of IgA is evaluated with an ELISA kit by Thermo Fisher (Cat. No. BMS2096). In some embodiments, the function of IgE is evaluated with an ELISA kit by Thermo Fisher (Cat. No. BMS2097).

In some embodiments, the function of platelet proteins is determined by a cellular assay. In some embodiments, the cellular assay is a reporter assay to quantify functional activity of a protein. For example, in some embodiments, a cellular assay comprises contacting cells having a luciferase reporter gene functionally linked to a promoter responsive to a protein of interest, wherein contacting the cells with the composition indicates whether the protein of interest is functioning in the composition. In some embodiments, the cellular assay comprises stimulating a cell line with an inducer of proinflammatory cytokines and contacting the cell line with the composition to determine whether proinflammatory cytokines are reduced. In some embodiments, the function of platelet proteins. An exemplary functional assay is described by Singh, U. et al. (Clin. Chem. 2005 Dec., Vol. 51(12)2252-6) (hereby incorporated by reference in its entirety).

In some embodiments, the immunogenicity of the composition is determined. In some embodiments, immunogenicity is determined by contacting donor peripheral blood mononuclear cells (PBMCs) with the composition and quantifying levels of CD134 and/or CD137 on CD4+ T cells, as increased levels of these markers on CD4+ T cells indicates immunogenic risk of the composition. An exemplary assay for assessing immunogenicity is described in Cohen, S. et al. (MABS, 2021, Vol. 13(1): e1898831 (hereby incorporated by reference in its entirety)).

In some embodiments, the impact of the composition on cell migration and/or cell proliferation is determined. In some embodiments, cell migration and/or cell proliferation is determined by an in vitro scratch assay. In brief, a "wound" is created in a cell monolayer and then contacted with a composition described herein. Cell migration to close the "wound" is determined by capturing images over time and comparing the images to quantity the migration rate of the cells. An exemplary scratch assay is described in Rodriguez, L. et al. (Methods Mol Biol. 2005, Vol. 294: 23-9 (hereby incorporated by reference in its entirety)).

Exemplary Compositions I

In some embodiments, the disclosure provides a composition comprising a high concentration of plasma and platelet derived proteins, wherein the plasma proteins are albumin, fibrinogen, and A2M, the total protein concentration is at least 50 mg/mL, and the viscosity is about 1 to about 40 cP. In some embodiments, the disclosure provides a composition comprising a high concentration of plasma and platelet derived proteins, wherein the plasma proteins are albumin, fibrinogen, and A2M, the total protein concentration is about 50 to about 500 mg/mL, and the viscosity is about 1 to about 40 cP. In some embodiments, the disclosure provides a composition comprising a high concentration of plasma and platelet derived proteins, wherein the plasma proteins are albumin, fibrinogen, and A2M, the total protein concentration is about 100 to about 300 mg/mL, and the viscosity is about 1 to about 40 cP.

In some embodiments, the disclosure provides a composition comprising a high concentration of plasma and platelet derived proteins, wherein the plasma proteins are albumin, fibrinogen, and A2M, the total protein concentration is at least 50 mg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the total protein concentration is about 50 to about 500 mg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the total protein concentration is about 100 to about 300 mg/mL, and the viscosity is about 10 to about 25 cP.

In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, and the viscosity is about 1 to about 40 cP. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, and the viscosity is about 1 to about 40 cP. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, and the viscosity is about 1 to about 40 cP.

In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, and the viscosity is about 10 to about 25 cP. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, and the viscosity is about 10 to about 25 cP. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, and the viscosity is about 10 to about 25 cP.

In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is at least 50 mg/mL, and the viscosity is about 1 to about 40 cP. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, and the viscosity is about 1 to about 40 cP. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, and the viscosity is about 1 to about 40 cP.

In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is at least 50 mg/mL, and the viscosity is about 10 to about 25 cP. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, and the viscosity is about 10 to about 25 cP. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, and the viscosity is about 10 to about 25 cP.

In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, and the viscosity is about 1 to about 40 cP.

In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, and the viscosity is about 10 to about 25 cP.

In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, and the viscosity is about 1 to about 40 cP.

In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, and the viscosity is about 10 to about 25 cP.

In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, and the viscosity is about 1 to about 40 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, and the viscosity is about 1 to about 40 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, and the viscosity is about 1 to about 40 cP.

In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, and the viscosity is about 10 to about 25 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, and the viscosity is about 10 to about 25 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, and the viscosity is about 10 to about 25 cP.

In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, and the viscosity is about 1 to about 40 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, and the viscosity is about 1 to about 40 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, and the viscosity is about 1 to about 40 cP.

In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, and the viscosity is about 10 to about 25 cP.

In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, and the viscosity is about 1 to about 40 cP.

In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, and the viscosity is about 10 to about 25 cP.

In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is at least 50 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, and the viscosity is about 1 to about 40 cP.

In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is at least 50 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, and the viscosity is about 10 to about 25 cP.

In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, and the viscosity is about 1 to about 40 cP.

In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, and the viscosity is about 10 to about 25 cP.

In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, and the viscosity is about 1 to about 40 cP.

In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, and the viscosity is about 10 to about 25 cP.

In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, and the viscosity is about 1 to about 40 cP.

In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, and the viscosity is about 10 to about 25 cP.

In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the PDGF-AB concentration is greater than 50 pg/mL and less than 1,000 pg/mL, and the viscosity is about 1 to about 40 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, and the viscosity is about 1 to about 40 cP In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, and the viscosity is about 1 to about 40 cP.

In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, and the viscosity is about 10 to about 25 cP.

In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the fibrinogen concentration is about 1-5 mg/mL, and the viscosity is about 1 to about 40 cP.

In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the fibrinogen concentration is about 1-5 mg/mL, and the viscosity is about 10 to about 25 cP.

In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the fibrinogen concentration is about 1-5 mg/mL, and the viscosity is about 1 to about 40 cP.

In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the fibrinogen concentration is about 1-5 mg/mL, and the viscosity is about 10 to about 25 cP.

In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the fibrinogen concentration is about 1-5 mg/mL, and the viscosity is about 1 to about 40 cP.

In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the fibrinogen concentration is about 1-5 mg/mL, and the viscosity is about 10 to about 25 cP.

In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the fibrinogen concentration is about 1-5 mg/mL, and the viscosity is about 1 to about 40 cP In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the fibrinogen concentration is about 1-5 mg/mL, and the viscosity is about 1 to about 40 cP.

In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the fibrinogen concentration is about 1-5 mg/mL, and the viscosity is about 10 to about 25 cP.

In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, the fibrinogen concentration is about 1-5 mg/mL, and the viscosity is about 1 to about 40 cP.

In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, immunoglobulins, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, the fibrinogen concentration is about 1-5 mg/mL, and the viscosity is about 10 to about 25 cP.

In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, the fibrinogen concentration is about 1-5 mg/mL, and the viscosity is about 1 to about 40 cP.

In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is at least 50 mg/mL, the PDGF-AB concentration is greater than 50 pg/mL and less than 1,000 pg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 50 to about 500 mg/mL, the PDGF-AB concentration is greater than 50 pg/mL and less than 1,000 pg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are selected from albumin, fibrinogen, A2M, and any combination thereof, the platelet proteins are selected from PF4, PDGFAB, PDGFAA, PDGFBB, TGFβ1, TGFβ2, VEGF, EGF, BDNF, HGF, b-FGF, IGF-1, GMFB, CD31, and any combination thereof, the total protein concentration is about 100 to about 300 mg/mL, the PDGF-AB concentration is greater than 50 pg/mL and less than 1,000 pg/mL, the fibrinogen concentration is about 1-5 mg/mL, and the viscosity is about 10 to about 25 cP.

In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the PDGF-AB concentration is greater than 50 pg/mL and less than 1,000 pg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, the fibrinogen concentration is about 1-5 mg/mL, and the viscosity is about 1 to about 40 cP.

In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the PDGF-AB concentration is greater than 50 pg/mL and less than 1,000 pg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are albumin, fibrinogen, A2M, and immunoglobulins, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, the fibrinogen concentration is about 1-5 mg/mL, and the viscosity is about 10 to about 25 cP.

In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the PDGF-AB concentration is greater than 50 pg/mL and less than 1,000 pg/mL, the fibrinogen concentration is about 1-5 mg/mL, and the viscosity is about 1 to about 40 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ 1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, the fibrinogen concentration is about 1-5 mg/mL, and the viscosity is about 1 to about 40 cP In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, the fibrinogen concentration is about 1-5 mg/mL, and the viscosity is about 1 to about 40 cP.

In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, CD31, the total protein concentration is at least 50 mg/mL, the PDGF-AB concentration is greater than 50 pg/mL and less than 1,000 pg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 50 to about 500 mg/mL, the PDGF-AB concentration is greater than 50 pg/mL and less than 1,000 pg/mL, the fibrinogen concentration is about 1-5 mg/mL, and the viscosity is about 10 to about 25 cP. In some embodiments, the disclosure provides a composition comprising a high concentration of plasma and platelet derived proteins, wherein the plasma proteins are albumin, fibrinogen, and A2M, the platelet proteins are PF4, PDGFAB, PDGFAA, PDGFBB, TGFβ1, TGFβ2, VEGF, EGF, BDNF, HGF, b-FGF, IGF-1, GMFB, and CD31, the total protein concentration is about 100 to about 300 mg/mL, the PDGF-AB concentration is greater than 50 pg/mL and less than 1,000 pg/mL, the fibrinogen concentration is about 1-5 mg/mL, and the viscosity is about 10 to about 25 cP.

In some embodiments, the allogeneic human plasma and platelet derived product comprises a composition summarized in Table 1.

TABLE 1

| Exemplary Composition 1 Comprising Allogeneic Human Plasma and Platelet Derived Product | |
| --- | --- |
| Proteins | Concentration |
| Plasma Proteins | |
| Albumin | 0.1 ng/mL to 500 mg/mL |
| Fibrinogen | 1 ng/mL to 50 mg/mL |
| Alpha-2 Macroglobulin | 1 ng/mL to 50 mg/mL |
| Immunoglobulins | 2 to 100 mg/mL |
| Cholesterol | 0.1 ng/mL to 100 mg/mL |
| Triglycerides | 0.1 ng/mL to 100 mg/mL |
| Platelet Proteins | |
| PF4 | |
| PDGF-AA | 0.1 ng/mL to 5 mg/mL |
| PDGF-AB | 0.1 ng/mL to 5 mg/mL |
| PDGF-BB | 0.1 ng/mL to 5 mg/mL |
| CD31 | 0.1 ng/mL to 5 mg/mL |
| TGF | 0.1 ng/mL to 5 mg/mL |
| VEGF | 0.1 ng/mL to 5 mg/mL |
| EGF | 0.1 ng/mL to 5 mg/mL |
| BNDF | 0.1 ng/mL to 5 mg/mL |
| HGF | 0.1 ng/mL to 5 mg/mL |
| b-FGF | 0.1 ng/mL to 5 mg/mL |
| GMFB | 0.1 ng/mL to 5 mg/mL |
| IGF-1 | 0.1 ng/mL to 5 mg/mL |
| Interleukins | 0.1 ng/mL to 5 mg/mL |
| IRAP | 0.1 ng/mL to 5 mg/mL |
| Glutathione S-Transferase | 0.1 μg/mL to 5 mg/mL |
| Glutathione Peroxide | 0.1 μg/mL to 5 mg/mL |

In some embodiments, the allogeneic human Plasma and Platelet derived product comprises a composition summarized in Table 2.

TABLE 2

| Exemplary Composition 2 Comprising Allogeneic Human Plasma and Platelet Derived Product | |
| --- | --- |
| Proteins | Concentration |
| Plasma Proteins | |
| Albumin | 0.1 ng/mL to 500 mg/mL |
| Fibrinogen | 1 ng/mL to 50 mg/mL |
| Alpha-2 Macroglobulin | 1 ng/mL to 50 mg/mL |
| Immunoglobulins | 2 to 100 mg/mL |
| Cholesterol | 0.1 ng/mL to 100 mg/mL |
| Triglycerides | 0.1 ng/mL to 100 mg/mL |
| Platelet Proteins | |
| PF4 | |
| PDGF-AA | 1 pg/mL to 5 mg/mL |
| PDGF-AB | 1 pg/mL to 5 mg/mL |
| PDGF-BB | 1 pg/mL to 5 mg/mL |
| CD31 | 1 pg/mL to 5 mg/mL |
| TGF | 1 pg/mL to 5 mg/mL |
| VEGF | 1 pg/mL to 5 mg/mL |
| EGF | 1 pg/mL to 5 mg/mL |
| BDNF | 1 pg/mL to 5 mg/mL |
| HGF | 1 pg/mL to 5 mg/mL |
| FGF | 1 pg/mL to 5 mg/mL |
| GMFB | 1 pg/mL to 5 mg/mL |
| IGF-1 | 1 pg/mL to 5 mg/mL |
| Interleukins | 1 pg/mL to 5 mg/mL |
| IRAP | 1 pg/mL to 5 mg/mL |
| Glutathione S-Transferase | 1 pg/mL to 5 mg/mL |
| Glutathione Peroxide | 1 pg/mL to 5 mg/mL |

In some embodiments, the allogeneic human plasma and platelet derived product comprises a composition summarized in Table 3.

TABLE 3

| Exemplary Composition 3 Comprising Allogeneic Human Plasma and Platelet Derived Product | |
| --- | --- |
| Proteins | Concentration |
| Plasma Proteins | |
| Albumin | 4 to 200 mg/mL |
| Fibrinogen | 20 µg/mL to 10 mg/mL |
| Alpha-2 Macroglobulin | 100 to 1400 µg/mL |
| Immunoglobulins | 2 to 100 mg/mL |
| Cholesterol | 0.1 ng/mL to 100 mg/mL |
| Triglycerides | 0.1 ng/mL to 100 mg/mL |
| Platelet Proteins | |
| PF4 | |
| PDGF-AA | At least 5 µg/mL |
| PDGF-AB | At least 200 pg/mL |
| PDGF-BB | At least 5 µg/mL |
| CD31 | 0.1 ng/mL to 5 mg/mL |
| TGF | 0.1 ng/mL to 5 mg/mL |
| VEGF | 0.1 ng/mL to 5 mg/mL |
| EGF | 0.1 ng/mL to 5 mg/mL |
| BDNF | 0.1 ng/mL to 5 mg/mL |
| HGF | 0.1 ng/mL to 5 mg/mL |
| b-FGF | 0.1 ng/mL to 5 mg/mL |
| GMFB | 0.1 ng/mL to 5 mg/mL |
| IGF-1 | 0.1 ng/mL to 5 mg/mL |
| Interleukins | 0.1 ng/mL to 5 mg/mL |
| IRAP | 0.1 ng/mL to 5 mg/mL |
| Glutathione S-Transferase | 0.1 µg/mL to 5 mg/mL |
| Glutathione Peroxide | 0.1 µg/mL to 5 mg/mL |

In some embodiments, the allogeneic human plasma and platelet derived product comprises a composition summarized in Table 4.

TABLE 4

| Exemplary Composition 4 Comprising Allogeneic Human Plasma and Platelet Derived Product | |
| --- | --- |
| Proteins | Concentration |
| Plasma Proteins | |
| Albumin | 4 to 200 mg/mL |
| Fibrinogen | 20 µg/mL to 10 mg/mL |
| Alpha-2 Macroglobulin | 100 to 1400 µg/mL |
| Immunoglobulins | 2 to 100 mg/mL |
| Cholesterol | 0.1 ng/mL to 100 mg/mL |
| Triglycerides | 0.1 ng/mL to 100 mg/mL |
| Platelet Proteins | |
| PF4 | |
| PDGF-AA | At least 5 µg/mL |
| PDGF-AB | At least 200 pg/mL |
| PDGF-BB | At least 5 µg/mL |
| CD31 | 1 pg/mL to 5 mg/mL |
| TGF | 1 pg/mL to 5 mg/mL |
| VEGF | 1 pg/mL to 5 mg/mL |
| EGF | 1 pg/mL to 5 mg/mL |
| BDNF | 1 pg/mL to 5 mg/mL |
| HGF | 1 pg/mL to 5 mg/mL |
| FGF | 1 pg/mL to 5 mg/mL |
| GMFB | 1 pg/mL to 5 mg/mL |
| IGF-1 | 1 pg/mL to 5 mg/mL |
| Interleukins | 1 pg/mL to 5 mg/mL |
| IRAP | 1 pg/mL to 5 mg/mL |
| Glutathione S-Transferase | 1 pg/mL to 5 mg/mL |
| Glutathione Peroxide | 1 pg/mL to 5 mg/mL |

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, and PDGF at a concentration of about 20 µg/mL. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL and PDGF at a concentration of about 20 µg/mL.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, and a total protein concentration of at least 50 mg/mL. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, and a total protein concentration of at least 50 mg/mL.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, and a total protein concentration of about 50 mg/mL to about 500 mg/mL. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, and a total protein concentration of about 50 mg/mL to about 500 mg/mL.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, and a total protein concentration of about 100 mg/mL to about 300 mg/mL. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, and a total protein concentration of about 100 mg/mL to about 300 mg/mL.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, and a viscosity of about 10 to about 25 cP. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, and a viscosity of about 10 to about 25 cP.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, a total protein concentration of at least 50 mg/mL, and a viscosity of about 10 to about 25 cP. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, a total protein concentration of at least 50 mg/mL, and a viscosity of about 10 to about 25 cP.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, a total protein concentration of about 50 mg/mL to about 500 mg/mL, and a viscosity of about 10 to about 25 cP. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, a total protein concentration of about 50 mg/mL to about 500 mg/mL, and a viscosity of about 10 to about 25 cP.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, a total protein concentration of about 100 mg/mL to about 300 mg/mL, and a viscosity of about 10 to about 25 cP. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, a total protein concentration of about 100 mg/mL to about 300 mg/mL, and a viscosity of about 10 to about 25 cP.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, and a viscosity of about 1 to about 40 cP. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, and a viscosity of about 1 to about 40 cP.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, a total protein concentration of at least 50 mg/mL, and a viscosity of about 1 to about 40 cP. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, a total protein concentration of at least 50 mg/mL, and a viscosity of about 1 to about 40 cP.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, a total protein concentration of about 50 mg/mL to about 500 mg/mL, and a viscosity of about 1 to about 40 cP. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 µg/mL, a total protein concentration of about 50 mg/mL to about 500 mg/mL, and a viscosity of about 1 to about 40 cP.

In some embodiments, the composition comprising plasma and platelet derived proteins comprises albumin at concentration of about 100 to 1,400 µg/mL, fibrinogen at a concentration of about 20 µg/mL to about 10 mg/mL, immunoglobulins at a concentration of about 20% w/w, α-2-macroglobulin (A2M) at a concentration of about 200 µg/mL, PDGF at a concentration of about 20 µg/mL, a total protein concentration of about 100 mg/mL to about 300 mg/mL, and a viscosity of about 1 to about 40 cP. In some embodiments, the composition comprising plasma and platelet derived proteins comprises albumin at concentration of about 100 to 1,400 µg/mL, fibrinogen at a concentration of about 20 µg/mL to about 2 mg/mL, immunoglobulins at a concentration of about 20% w/w, A2M at a concentration of about 200 µg/mL, PDGF at a concentration of about 20 pg/mL, a total protein concentration of about 100 mg/mL to about 300 mg/mL, and a viscosity of about 1 to about 40 cP.

Exemplary Compositions II

In some embodiments, the disclosure provides a composition comprising a high concentration of plasma and platelet derived proteins, wherein the plasma proteins are selected from albumin, fibrinogen, immunoglobulin, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, immunoglobulin, and any combination thereof and the total protein concentration is about 50 to about 500 mg/mL. In some embodiments, the disclosure provides a composition comprising a high concentration of plasma and platelet derived proteins, wherein the plasma proteins are selected from albumin, fibrinogen, immunoglobulin, and any combination thereof, and the total protein concentration is about 100 to about 300 mg/mL.

In some embodiments, the disclosure provides a composition comprising a high concentration of plasma and platelet derived proteins, wherein the platelet proteins are selected from PDGF-AB, PDGF-AA, PDGF-AB, TGFβ1, TGFβ2, VEGF, EGF, FGF, HGF, and any combination thereof, and the total protein concentration is at least 50 mg/mL. In some embodiments, the disclosure provides a composition comprising a high concentration of plasma and platelet derived proteins, wherein the platelet proteins are selected from PDGF-AB, PDGF-AA, PDGF-AB, TGFβ1, TGFβ2, VEGF, EGF, FGF, HGF, and any combination thereof, and the total protein concentration is about 50 to about 500 mg/mL. In some embodiments, the disclosure provides a composition comprising a high concentration of plasma and platelet derived proteins, wherein the platelet proteins are selected from PDGF-AB, PDGF-AA, PDGF-AB, TGFβ1, TGFβ2, VEGF, EGF, FGF, HGF, and any combination thereof, and the total protein concentration is about 100 to about 300 mg/mL In some embodiments, the disclosure provides a composition comprising a high concentration of plasma and platelet derived proteins, wherein the platelet proteins are PDGF-AB, PDGF-AA, PDGF-AB, TGFβ1, TGFβ2, VEGF, EGF, FGF, and HGF, and the total protein concentration is at least 50 mg/mL. In some embodiments, the disclosure provides a composition comprising a high concentration of plasma and platelet derived proteins, wherein the platelet proteins are PDGF-AB, PDGF-AA, PDGF-AB, TGFβ1, TGFβ2, VEGF, EGF, FGF, and HGF, and the total protein concentration is about 50 to about 500 mg/mL. In some embodiments, the disclosure provides a composition comprising a high concentration of plasma and platelet derived proteins, wherein the platelet proteins are PDGF-AB, PDGF-AA, PDGF-AB, TGFβ1, TGFβ2, VEGF, EGF, FGF, and HGF, and the total protein concentration is about 100 to about 300 mg/mL.

In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, and the total protein concentration is at least 50 mg/mL. In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, and the total protein concentration is about 50 to about 500 mg/mL. In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, and the total protein concentration is about 100 to about 300 mg/mL.

In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, the total protein concentration is at least 50 mg/mL, and the PDGF-AB concentration is about 5 ng/mL to about 200 ng/mL. In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, the total protein concentration is about 50 to about 500 mg/mL, and the PDGF-AB concentration is about 5 ng/mL to about 200 ng/mL. In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, the total protein concentration is about 100 to about 300 mg/mL, and the PDGF-AB concentration is about 5 ng/mL to about 200 ng/mL.

In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, the total protein concentration is at least 50 mg/mL, and the fibrinogen concentration is about 1-5 mg/mL. In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ 1, TGFβ2, VEGF, EGF, FGF, HGF, and any combination thereof, the total protein concentration is about 50 to about 500 mg/mL, and the fibrinogen concentration is about 1-5 mg/mL. In some embodiments, the disclosure provides a composition comprising a high concentration of plasma and platelet derived proteins, wherein the plasma proteins are selected from albumin, fibrinogen, PDGF-AB, PDGF-AA, PDGF-AB, TGFβ1, TGFβ2, VEGF, EGF, FGF, HGF, and any combination thereof, the total protein concentration is about 100 to about 300 mg/mL, and the fibrinogen concentration is about 1-5 mg/mL.

In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, the total protein concentration is at least 50 mg/mL, the PDGF-AB concentration is about 5 ng/mL to about 200 ng/mL, and the fibrinogen concentration is about 1-5 mg/mL In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, the total protein concentration is about 50 to about 500 mg/mL, the PDGF-AB concentration is about 5 ng/mL to about 200 ng/mL, and the fibrinogen concentration is about 1-5 mg/mL. In some embodiments, the disclosure provides a composition comprising a high concentration of plasma and platelet derived proteins, wherein the plasma proteins are selected from albumin, fibrinogen, immunoglobulins, and any combination thereof, the platelet proteins are selected from PDGF-AB, PDGF-AA, PDGF-AB, TGFβ1, TGFβ2, VEGF, EGF, FGF, HGF, and any combination thereof, the total protein concentration is about 100 to about 300 mg/mL, the PDGF-AB concentration is about 5 ng/mL to about 200 ng/mL, and the fibrinogen concentration is about 1-5 mg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is greater than 50 mg/mL and less than or about 500 mg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is greater than 50 mg/mL and less than or about 500 mg/mL, the fibrinogen concentration is 0.25-5.0 mg/mL, and the PDGF-AB concentration is 5-200 ng/mL.

In some embodiments, a composition of the disclosure comprising the allogeneic human plasma and platelet derived product comprises (a) human plasma proteins comprising fibrinogen, albumin and immunoglobulin, and (b) human platelet proteins comprising PDGF-AB, TGFβ, VEGF, EGF, FGF, HGF, or any combination thereof, wherein the total protein concentration of the composition is greater than 50 mg/mL and less than or about 500 mg/mL.

In some embodiments, a composition of the disclosure comprising the allogeneic human plasma and platelet derived product comprises (a) human plasma proteins comprising fibrinogen, albumin and immunoglobulin, and (b) human platelet proteins comprising PDGF-AB, TGFβ, VEGF, EGF, FGF, HGF, or any combination thereof, wherein the total protein concentration of the composition is greater than 50 mg/mL and less than or about 500 mg/mL, the fibrinogen concentration is 0.25-5.0 mg/mL, and the PDGF-AB concentration is 5-200 ng/mL.

In some embodiments, a composition of the disclosure comprising the allogeneic human plasma and platelet derived product comprises (a) human plasma proteins comprising fibrinogen, albumin and immunoglobulin, and (b) human platelet proteins comprising PDGF-AB, TGFβ, VEGF, EGF, FGF, HGF, or any combination thereof, wherein the total protein concentration of the composition is greater than 50 mg/mL and less than or about 500 mg/mL, the fibrinogen concentration is 0.25-5.0 mg/mL, albumin is 60-70% w/w total protein, immunoglobulin is 10-20% w/w total protein, the PDGF-AB concentration is 5-200 ng/mL, the TGFβ concentration is 50-1000 ng/mL, the VEGF concentration is 50-1500 pg/mL, the EGF concentration is 100-5000 pg/mL, the FGF concentration is 100-3000 pg/mL, and the HGF concentration is 25-2500 pg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 20 mg/mL to about 50 mg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 20 mg/mL to about 50 mg/mL, the fibrinogen concentration is 0.25-0.5 mg/mL, and the PDGF-AB concentration is 10-20 ng/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 30 mg/mL+/−25%, the fibrinogen concentration is 0.25-0.5 mg/mL, and the PDGF-AB concentration is 10-20 ng/mL.

In some embodiments, a composition of the disclosure comprising the allogeneic human plasma and platelet derived product comprises (a) human plasma proteins comprising fibrinogen, albumin and immunoglobulin, and (b) human platelet proteins comprising PDGF-AB, TGFβ, VEGF, EGF, FGF, HGF, or any combination thereof, wherein the total protein concentration of the composition is about 20 mg/mL to about 50 mg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 20 mg/mL to about 50 mg/mL, the fibrinogen concentration is 0.25-0.5 mg/mL, and the PDGF-AB concentration is 10-20 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 30 mg/mL+/−25%, the fibrinogen concentration is 0.25-0.5 mg/mL, and the PDGF-AB concentration is 10-20 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 20 mg/mL to about 50 mg/mL, the fibrinogen concentration is 0.25-0.5 mg/mL, albumin is 60-70% w/w total protein, immunoglobulin is 10-20% w/w total protein, the PDGF-AB concentration is about 10 to about 20 ng/mL, the TGF-β concentration is about 50 ng/mL to about 150 ng/mL, the VEGF concentration is about 50 pg/mL to about 200 pg/mL, the EGF concentration is about 100 pg/mL to about 1000 pg/mL, the FGF concentration is about 100 pg/mL to about 300 pg/mL, and the HGF concentration is about 25 pg/mL to about 150 pg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 30 mg/mL+/−25%, the fibrinogen concentration is 0.25-0.5 mg/mL, albumin is 60-70% w/w total protein, immunoglobulin is 10-20% w/w total protein, the PDGF-AB concentration is about 10 to about 20 ng/mL, the TGF-β concentration is about 50 ng/mL to about 150 ng/mL, the VEGF concentration is about 50 pg/mL to about 200 pg/mL, the EGF concentration is about 100 pg/mL to about 1000 pg/mL, the FGF concentration is about 100 pg/mL to about 300 pg/mL, and the HGF concentration is about 25 pg/mL to about 150 pg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 50 mg/mL to about 80 mg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 60 mg/mL+/−25%.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 60 mg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 50 mg/mL to about 80 mg/mL, the fibrinogen concentration is 0.5-1.0 mg/mL, and the PDGF-AB concentration is 20-40 ng/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 60 mg/mL+/−25%, the fibrinogen concentration is 0.5-1.0 mg/mL, and the PDGF-AB concentration is 20-40 ng/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 60 mg/mL, the fibrinogen concentration is 0.5-1.0 mg/mL, and the PDGF-AB concentration is 20-40 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 50 mg/mL to about 80 mg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 60 mg/mL+/−25%.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 60 mg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 50 mg/mL to about 80 mg/mL, the fibrinogen concentration is 0.5-1.0 mg/mL, and the PDGF-AB concentration is 20-40 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 60 mg/mL+/−25%, the fibrinogen concentration is 0.5-1.0 mg/mL, and the PDGF-AB concentration is 20-40 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 60 mg/mL, the fibrinogen concentration is 0.5-1.0 mg/mL, and the PDGF-AB concentration is 20-40 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 50 mg/mL to about 80 mg/mL, the fibrinogen concentration is 0.5-1.0 mg/mL, albumin is 60-70% w/w total protein, immunoglobulin is 10-20% w/w total protein, the PDGF-AB concentration is about 20 to about 40 ng/mL, the TGF-β concentration is about 150 ng/mL to about 300 ng/mL, the VEGF concentration is about 200 pg/mL to about 400 pg/mL, the EGF concentration is about 1000 pg/mL to about 2000 pg/mL, the FGF concentration is about 300 pg/mL to about 600 pg/mL, and the HGF concentration is about 150 pg/mL to about 300 pg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 60 mg/mL+/−25%, the fibrinogen concentration is 0.5-1.0 mg/mL, albumin is 60-70% w/w total protein, immunoglobulin is 10-20% w/w total protein, the PDGF-AB concentration is about 20 to about 40 ng/mL, the TGF-β concentration is about 150 ng/mL to about 300 ng/mL, the VEGF concentration is about 200 pg/mL to about 400 pg/mL, the EGF concentration is about 1000 pg/mL to about 2000 pg/mL, the FGF concentration is about 300 pg/mL to about 600 pg/mL, and the HGF concentration is about 150 pg/mL to about 300 pg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 60 mg/mL, the fibrinogen concentration is 0.5-1.0 mg/mL, albumin is 60-70% w/w total protein, immunoglobulin is 10-20% w/w total protein, the PDGF-AB concentration is about 20 to about 40 ng/mL, the TGF-β concentration is about 150 ng/mL to about 300 ng/mL, the VEGF concentration is about 200 pg/mL to about 400 pg/mL, the EGF concentration is about 1000 pg/mL to about 2000 pg/mL, the FGF concentration is about 300 pg/mL to about 600 pg/mL, and the HGF concentration is about 150 pg/mL to about 300 pg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 80 mg/mL to about 160 mg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 120 mg/mL+/−25%.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 120 mg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 80 mg/mL to about 160 mg/mL, the fibrinogen concentration is 1.0-2.0 mg/mL, and the PDGF-AB concentration is 40-80 ng/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 120 mg/mL+/−25%, the fibrinogen concentration is 1.0-2.0 mg/mL, and the PDGF-AB concentration is 40-80 ng/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 120 mg/mL, the fibrinogen concentration is 1.0-2.0 mg/mL, and the PDGF-AB concentration is 40-80 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 80 mg/mL to about 160 mg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 120 mg/mL+/−25%.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 120 mg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 80 mg/mL to about 160 mg/mL, the fibrinogen concentration is 1.0-2.0 mg/mL, and the PDGF-AB concentration is 40-80 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 120 mg/mL+/−25%, the fibrinogen concentration is 1.0-2.0 mg/mL, and the PDGF-AB concentration is 40-80 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 120 mg/mL, the fibrinogen concentration is 1.0-2.0 mg/mL, and the PDGF-AB concentration is 40-80 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 80 mg/mL to about 160 mg/mL, the fibrinogen concentration is 1.0-2.0 mg/mL, albumin is 60-70% w/w total protein, immunoglobulin is 10-20% w/w total protein, the PDGF-AB concentration is about 40 to about 80 ng/mL, the TGF-β concentration is about 350 ng/mL to about 450 ng/mL, the VEGF concentration is about 400 pg/mL to about 800 pg/mL, the EGF concentration is about 2000 pg/mL to about 4000 pg/mL, the FGF concentration is about 600 pg/mL to about 1200 pg/mL, and the HGF concentration is about 300 pg/mL to about 1000 pg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 120 mg/mL+/−25%, the fibrinogen concentration is 1.0-2.0 mg/mL, albumin is 60-70% w/w total protein, immunoglobulin is 10-20% w/w total protein, the PDGF-AB concentration is about 40 to about 80 ng/mL, the TGF-β concentration is about 350 ng/mL to about 450 ng/mL, the VEGF concentration is about 400 pg/mL to about 800 pg/mL, the EGF concentration is about 2000 pg/mL to about 4000 pg/mL, the FGF concentration is about 600 pg/mL to about 1200 pg/mL, and the HGF concentration is about 300 pg/mL to about 1000 pg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 120 mg/mL, the fibrinogen concentration is 1.0-2.0 mg/mL, albumin is 60-70% w/w total protein, immunoglobulin is 10-20% w/w total protein, the PDGF-AB concentration is about 40 to about 80 ng/mL, the TGF-β concentration is about 350 ng/mL to about 450 ng/mL, the VEGF concentration is about 400 pg/mL to about 800 pg/mL, the EGF concentration is about 2000 pg/mL to about 4000 pg/mL, the FGF concentration is about 600 pg/mL to about 1200 pg/mL, and the HGF concentration is about 300 pg/mL to about 1000 pg/mL In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 160 mg/mL to about 320 mg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 240 mg/mL+/−25%.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 240 mg/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 160 mg/mL to about 320 mg/mL, the fibrinogen concentration is 2.0-5.0 mg/mL, and the PDGF-AB concentration is 80-160 ng/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 240 mg/mL+/−25%, the fibrinogen concentration is 2.0-5.0 mg/mL, and the PDGF-AB concentration is 80-160 ng/mL.

In some embodiments, a composition of the disclosure comprising the allogeneic human plasma and platelet derived product comprises (a) human plasma proteins comprising fibrinogen, and (b) human platelet proteins comprising PDGF-AB, wherein the total protein concentration of the composition is about 240 mg/mL, the fibrinogen concentration is 2.0-5.0 mg/mL, and the PDGF-AB concentration is 80-160 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 160 mg/mL to about 320 mg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 240 mg/mL+/−25%.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 240 mg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 160 mg/mL to about 320 mg/mL, the fibrinogen concentration is 2.0-5.0 mg/mL, and the PDGF-AB concentration is 80-160 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 240 mg/mL+/−25%, the fibrinogen concentration is 2.0-5.0 mg/mL, and the PDGF-AB concentration is 80-160 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 240 mg/mL, the fibrinogen concentration is 2.0-5.0 mg/mL, and the PDGF-AB concentration is 80-160 ng/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 160 mg/mL to about 320 mg/mL, the fibrinogen concentration is 2.0-5.0 mg/mL, albumin is 60-70% w/w total protein, immunoglobulin is 10-20% w/w total protein, the PDGF-AB concentration is about 80 ng/mL to about 160 ng/mL, the TGF-β concentration is about 500 ng/mL to about 1000 ng/mL, the VEGF concentration is about 800 pg/mL to about 1500 pg/mL, the EGF concentration is about 4000 pg/mL to about 6000 pg/mL, the FGF concentration is about 1200 pg/mL to about 3000 pg/mL, and the HGF concentration is about 1000 pg/mL to about 2500 pg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 240 mg/mL+/−25%, the fibrinogen concentration is 2.0-5.0 mg/mL, albumin is 60-70% w/w total protein, immunoglobulin is 10-20% w/w total protein, the PDGF-AB concentration is about 80 ng/mL to about 160 ng/mL, the TGF-β concentration is about 500 ng/mL to about 1000 ng/mL, the VEGF concentration is about 800 pg/mL to about 1500 pg/mL, the EGF concentration is about 4000 pg/mL to about 6000 pg/mL, the FGF concentration is about 1200 pg/mL to about 3000 pg/mL, and the HGF concentration is about 1000 pg/mL to about 2500 pg/mL.

In some embodiments, a composition of the disclosure comprising the allogeneic human plasma and platelet derived product comprises (a) human plasma proteins comprising fibrinogen, albumin, and immunoglobulin, and (b) human platelet proteins comprising PDGF-AB, TGFβ, VEGF, EGF, FGF, HGF, or any combination thereof, wherein the total protein concentration of the composition is about 240 mg/mL, the fibrinogen concentration is 2.0-5.0 mg/mL, albumin is 60-70% w/w total protein, immunoglobulin is 10-20% w/w total protein, the PDGF-AB concentration is about 80 ng/mL to about 160 ng/mL, the TGF-β concentration is about 500 ng/mL to about 1000 ng/mL, the VEGF concentration is about 800 pg/mL to about 1500 pg/mL, the EGF concentration is about 4000 pg/mL to about 6000 pg/mL, the FGF concentration is about 1200 pg/mL to about 3000 pg/mL, and the HGF concentration is about 1000 pg/mL to about 2500 pg/mL.

In some embodiments, the allogeneic human plasma and platelet derived product comprises a composition set forth in Example 31 produced by the method set forth in Example 31.

In some embodiments, the allogeneic human plasma and platelet derived product comprises a composition summarized in Table 5.

TABLE 5

| Exemplary Compositions 4-8 Comprising Allogeneic Human Plasma and Platelet Derived Product | | | | |
| --- | --- | --- | --- | --- |
| Exemplary Composition 4 | Exemplary Composition 5 | Exemplary Composition 6 | Exemplary Composition 7 | Exemplary Composition 8 |
| Total Protein Concentration | 20-50 mg/mL | 50-80 mg/mL | 80-160 mg/mL | 160-320 mg/mL | 50-500 mg/mL |
| Fibrinogen Concentration | 0.25-0.5 mg/mL | 0.5-1.0 mg/mL | 1-2 mg/mL | 2-5 mg/mL | 0.25-5 mg/mL |
| PDGF-AB Concentration | 10-20 ng/mL | 20-40 ng/mL | 40-80 ng/mL | 80-160 ng/mL | 5-200 ng/mL |

In some embodiments, the allogeneic human Plasma and Platelet derived product comprises a composition summarized in Table 6.

TABLE 6

| Exemplary Compositions 9-13 Comprising Allogeneic Human Plasma and Platelet Derived Product | | | | |
| --- | --- | --- | --- | --- |
| Exemplary Composition 9 | Exemplary Composition 10 | Exemplary Composition 11 | Exemplary Composition 12 | Exemplary Composition 13 |
| Total Protein Concentration | 20-50 mg/mL | 50-80 mg/mL | 80-160 mg/mL | 160-300 mg/mL | 50-500 mg/mL |
| Fibrinogen Concentration | 0.25-0.5 mg/mL | 0.5-1.0 mg/mL | 1-2 mg/mL | 2-5 mg/mL | 0.25-5 mg/mL |
| Albumin Amount | 60-70% w/w total protein | 60-70% w/w total protein | 60-70% w/w total protein | 60-70% w/w total protein | 60-70% w/w total protein |
| Immunoglobulin Amount | 10-20% w/w total protein | 10-20% w/w total protein | 10-20% w/w total protein | 10-20% w/w total protein | 10-20% w/w total protein |
| PDGF-AB Concentration | 10-20 ng/mL | 20-40 ng/mL | 40-80 ng/mL | 80-160 ng/mL | 5-200 ng/mL |

TABLE 6-continued

| | Exemplary Compositions 9-13 Comprising Allogeneic Human Plasma and Platelet Derived Product | | | | |
| --- | --- | --- | --- | --- | --- |
| | Exemplary Composition 9 | Exemplary Composition 10 | Exemplary Composition 11 | Exemplary Composition 12 | Exemplary Composition 13 |
| TGFβ Concentration | 50-150 ng/mL | 150-300 ng/mL | 300-500 ng/mL | 500-100 ng/mL | 50-1000 ng/mL |
| VEGF Concentration | 50-200 pg/mL | 200-400 pg/mL | 400-800 pg/mL | 800-1500 pg/mL | 50-1500 pg/mL |
| EGF Concentration | 100-1000 pg/mL | 1000-2000 pg/mL | 2000-4000 pg/mL | 4000-6000 pg/mL | 100-6000 pg/mL |
| FGF Concentration | 100-300 pg/mL | 300-600 pg/mL | 600-1200 pg/mL | 1200-3000 pg/mL | 100-3000 pg/mL |
| HGF Concentration | 25-150 pg/mL | 150-300 pg/mL | 300-1000 pg/mL | 1000-2500 pg/mL | 25-2500 pg/mL |

Method of Making Compositions

In some aspects, the disclosure provides methods for making compositions comprising an allogeneic human plasma and platelet derived product. In some embodiments, the methods described herein provide a highly concentrated and highly viscous composition comprising plasma and platelet derived proteins as described herein. In some embodiments, the method comprises providing a platelet suspension from one or more donors, lysing the platelets in the platelet suspension to release platelet proteins and generate a platelet extract comprising plasma proteins and platelet proteins, removing cell debris from the platelet extract to generate a purified platelet extract, and concentrating the platelet extract to generate the allogeneic human plasma and platelet derived product. In some embodiments, the method comprises removal of red blood cells and white blood cells.

Illustrative methods are described below. In some embodiments, a method for preparing a pharmaceutical composition comprising an allogenic human plasma and platelet derived product comprises thawing platelet suspensions, pooling platelet suspensions from at least 2 human donors, diluting and filtering platelet suspensions, extracting platelet proteins and inactivating viruses, removing debris and viruses, concentrating the platelet extract, and diluting the allogeneic human plasma and platelet derived product as set forth in FIG. 1.

Figure 2:
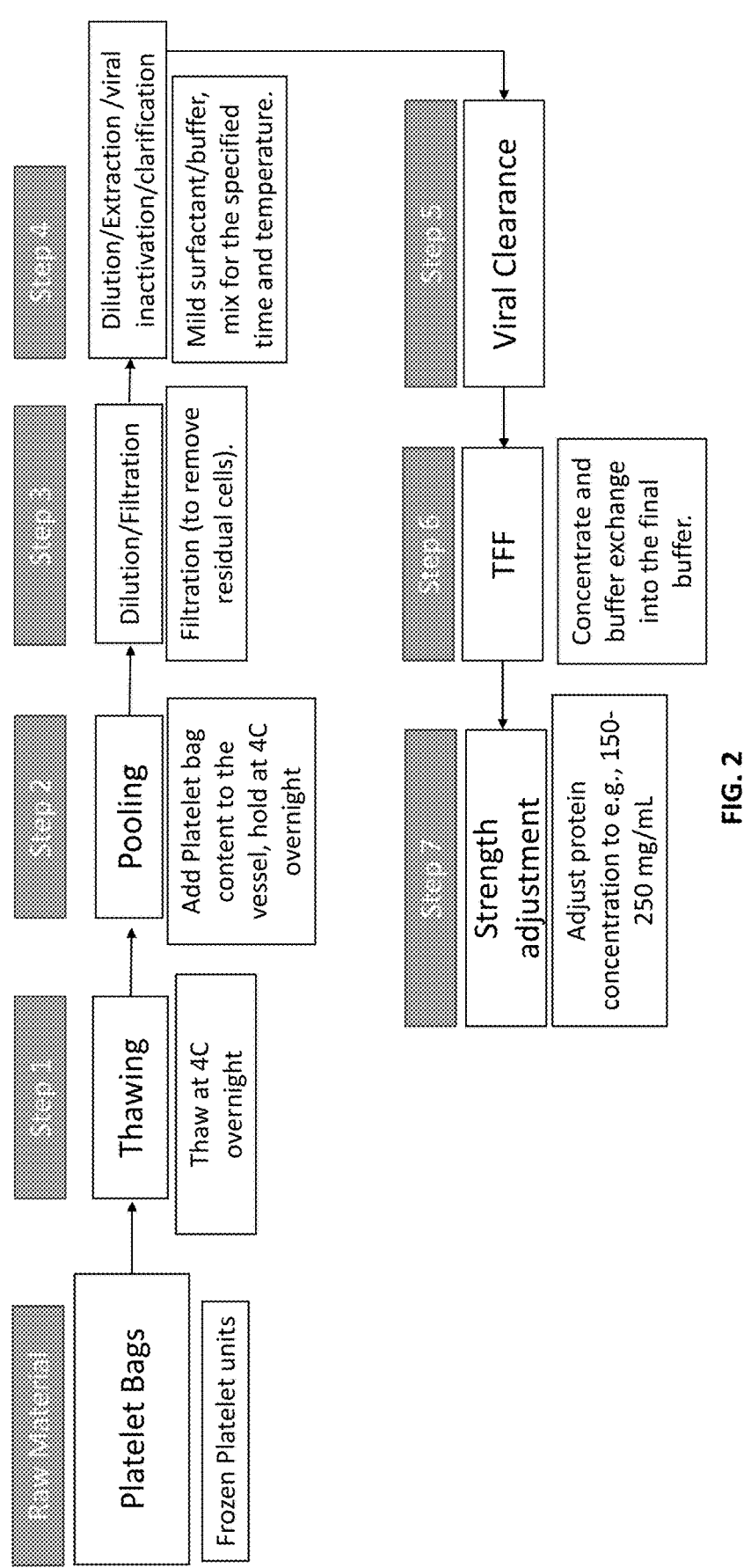

In some embodiments, a method for preparing a pharmaceutical composition comprising an allogenic human plasma and platelet derived product comprises, thawing platelet suspensions, pooling platelet suspensions from at least 2 human donors, diluting and filtering platelet suspensions, extracting platelet proteins, inactivating viruses, and diluting the platelet extract, removing debris and viruses, concentrating the platelet extract, and diluting the allogeneic human plasma and platelet derived product as set forth in FIG. 2.

Figure 3:
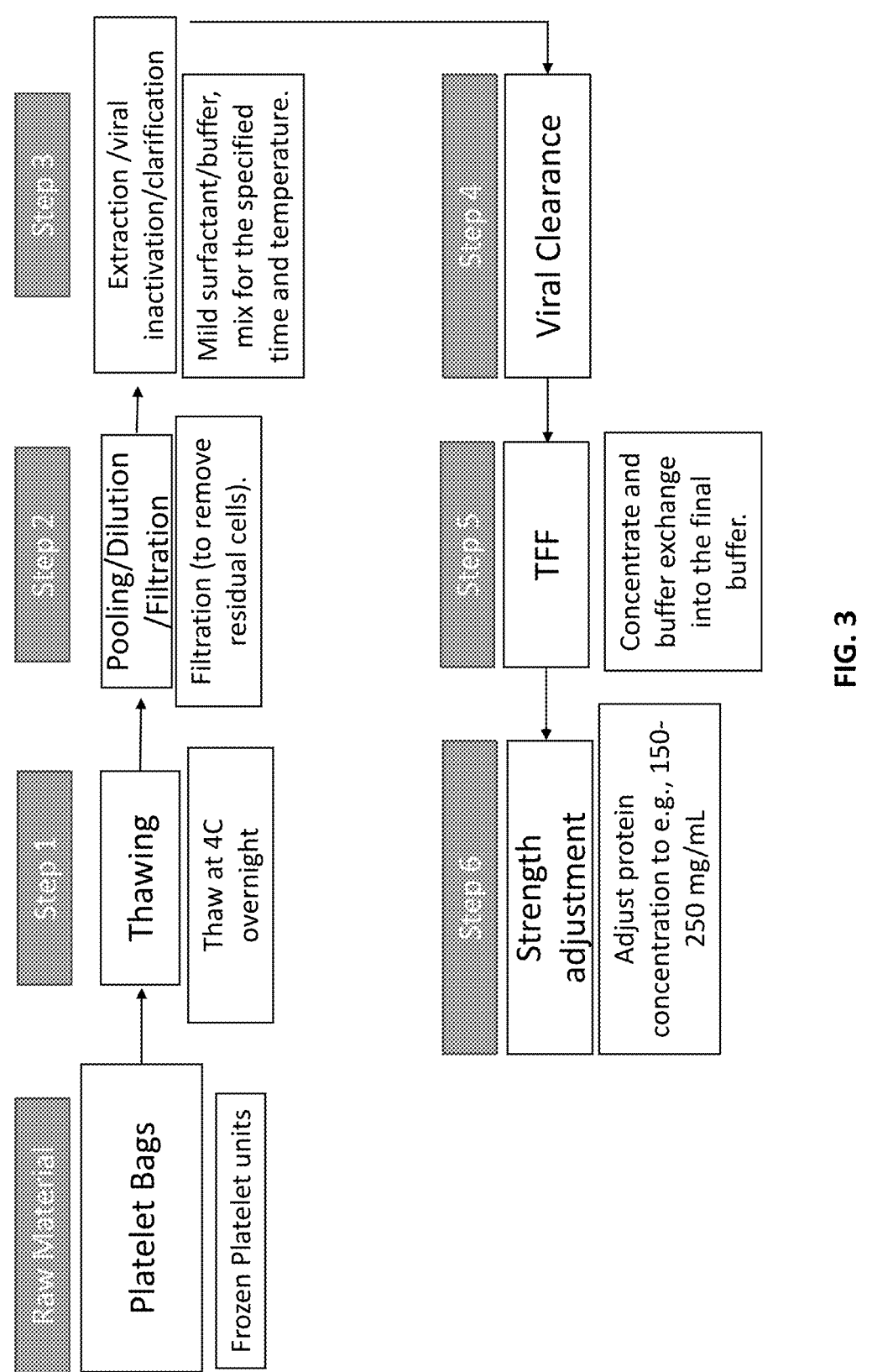

In some embodiments, a method for preparing a pharmaceutical composition comprising an allogenic human plasma and platelet derived product comprises thawing platelet suspensions, pooling platelet suspensions from at least 2 human donors, diluting, and filtering the platelet suspensions, extracting platelet proteins and inactivating viruses, removing debris and viruses, concentrating the platelet extract, and diluting the allogeneic human plasma and platelet derived product as set forth in FIG. 3.

Figure 4:
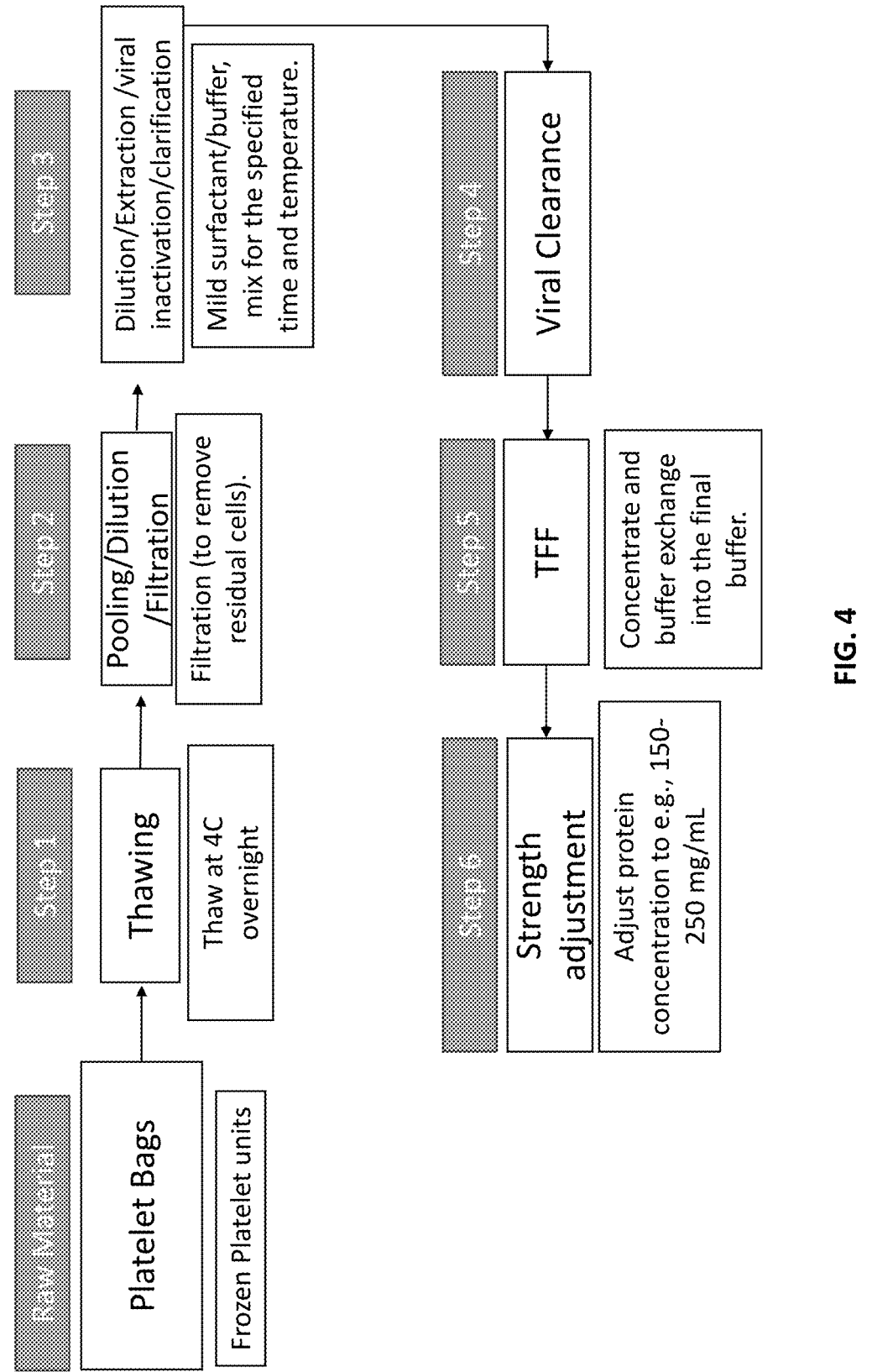

In some embodiments, a method for preparing a pharmaceutical composition comprising an allogenic human plasma and platelet derived product comprises thawing platelet suspensions, pooling platelet suspensions from at least 2 human donors, diluting, and filtering the platelet suspensions, extracting platelet proteins, inactivating viruses, and diluting, removing debris and viruses, concentrating the platelet extract, and diluting the allogenic human plasma and platelet derived product as set forth in FIG. 4.

Figure 5:
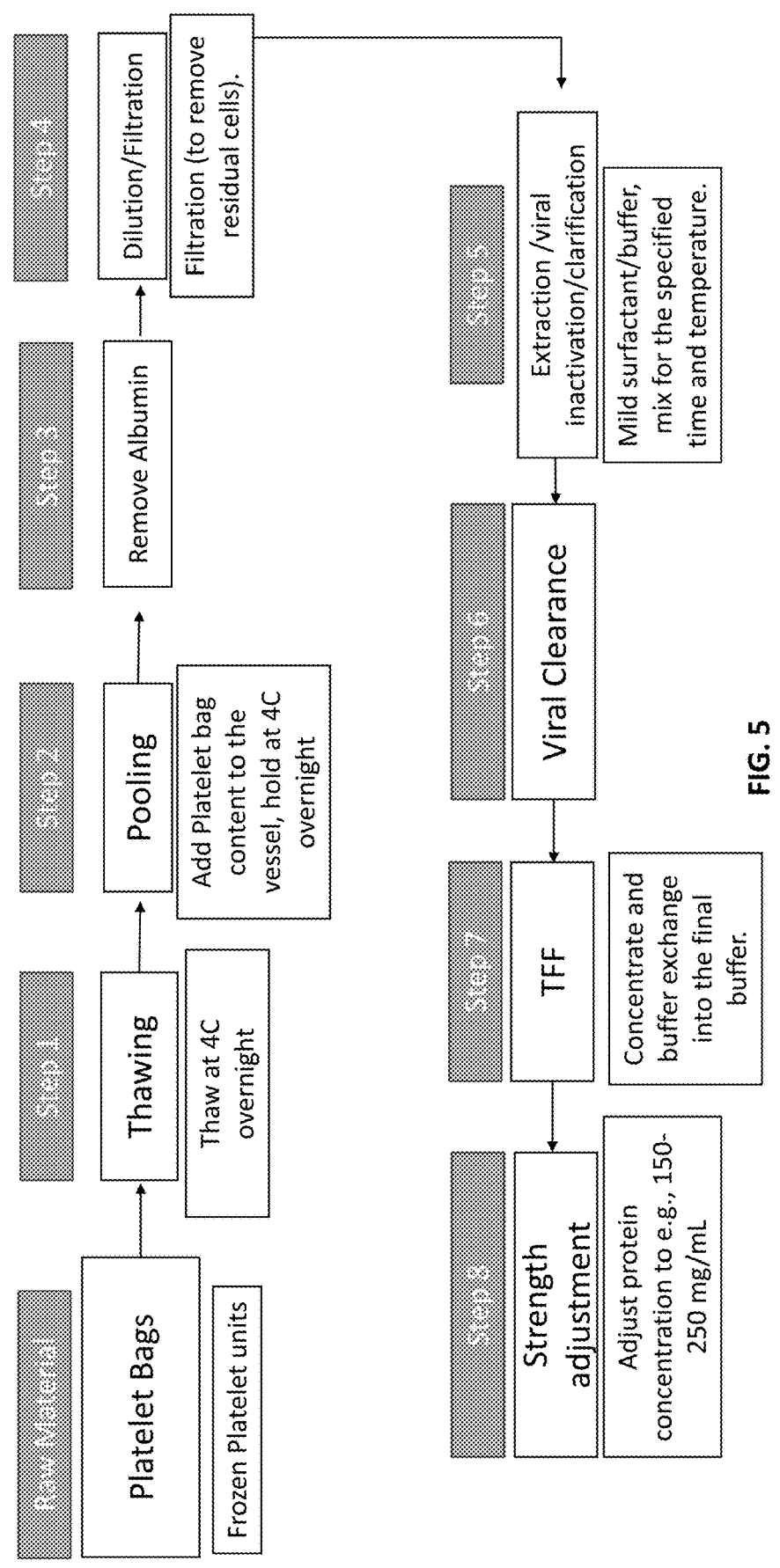

In some embodiments, a method for preparing a pharmaceutical composition comprising an allogenic human plasma and platelet derived product comprises thawing platelet suspensions, pooling platelet suspensions from at least 2 human donors, removing albumin, diluting and filtering the platelet suspensions, extracting platelet proteins and inactivating viruses, removing debris and viruses, concentrating the platelet extract, and diluting the allogenic human plasma and platelet derived product as set forth in FIG. 5.

Figure 6:
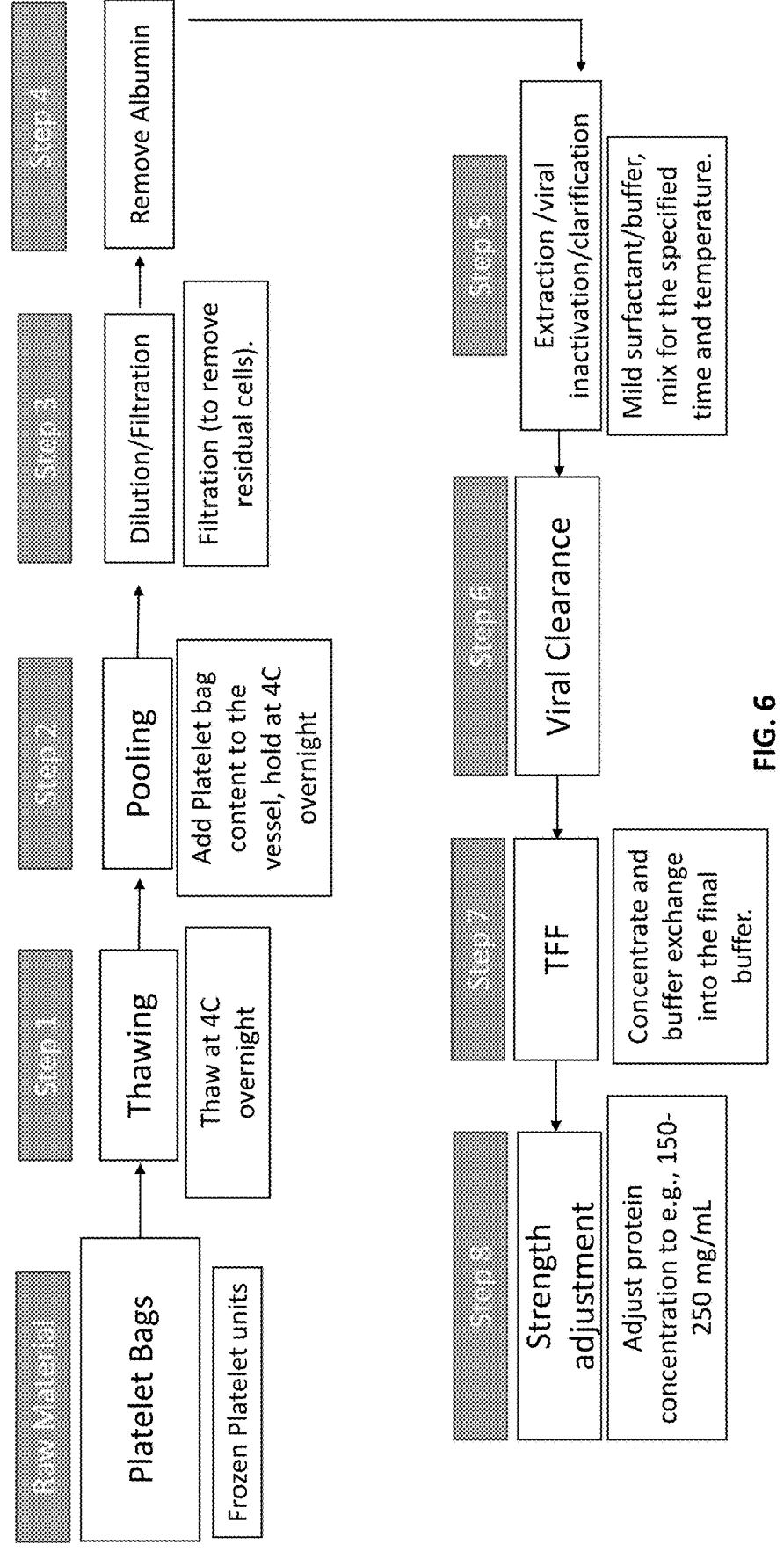

In some embodiments, a method for preparing a pharmaceutical composition comprising an allogenic human plasma and platelet derived product comprises thawing platelet suspensions, pooling platelet suspensions from at least 2 human donors, diluting and filtering the platelet suspensions, removing albumin, extracting platelet proteins and inactivating viruses, removing debris and viruses, concentrating the platelet extract, and diluting the allogeneic human plasma and platelet derived product as set forth in FIG. 6.

Figure 7:
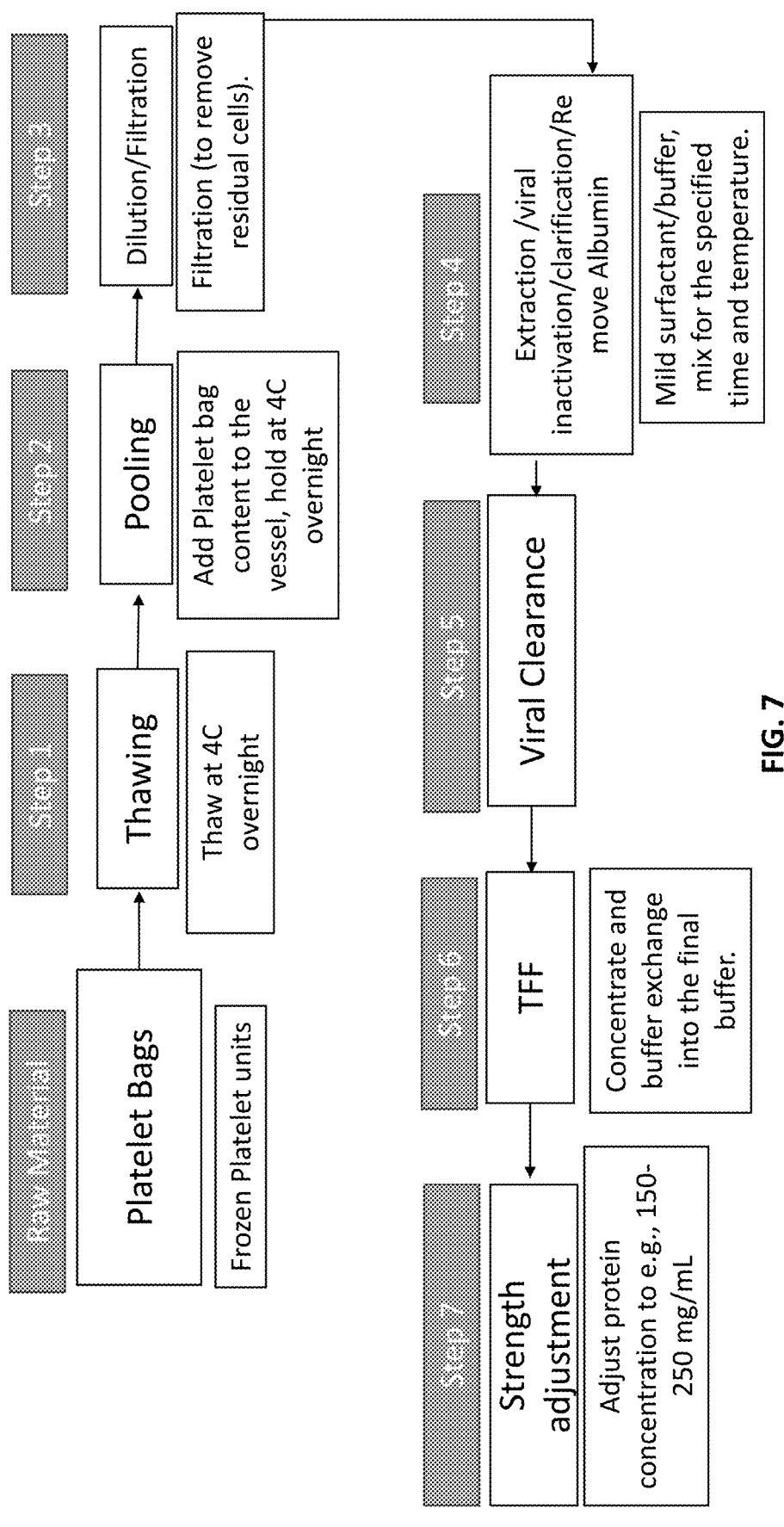

In some embodiments, a method for preparing a pharmaceutical composition comprising an allogenic human plasma and platelet derived product comprises thawing platelet suspensions, pooling platelet suspensions from at least 2 human donors, diluting and filtering the platelet suspensions, extracting platelet proteins, inactivating viruses, and removing albumin, removing debris and viruses, concentrating the platelet extract, and diluting the allogeneic human plasma and platelet derived product as set forth in FIG. 7.

Figure 8:
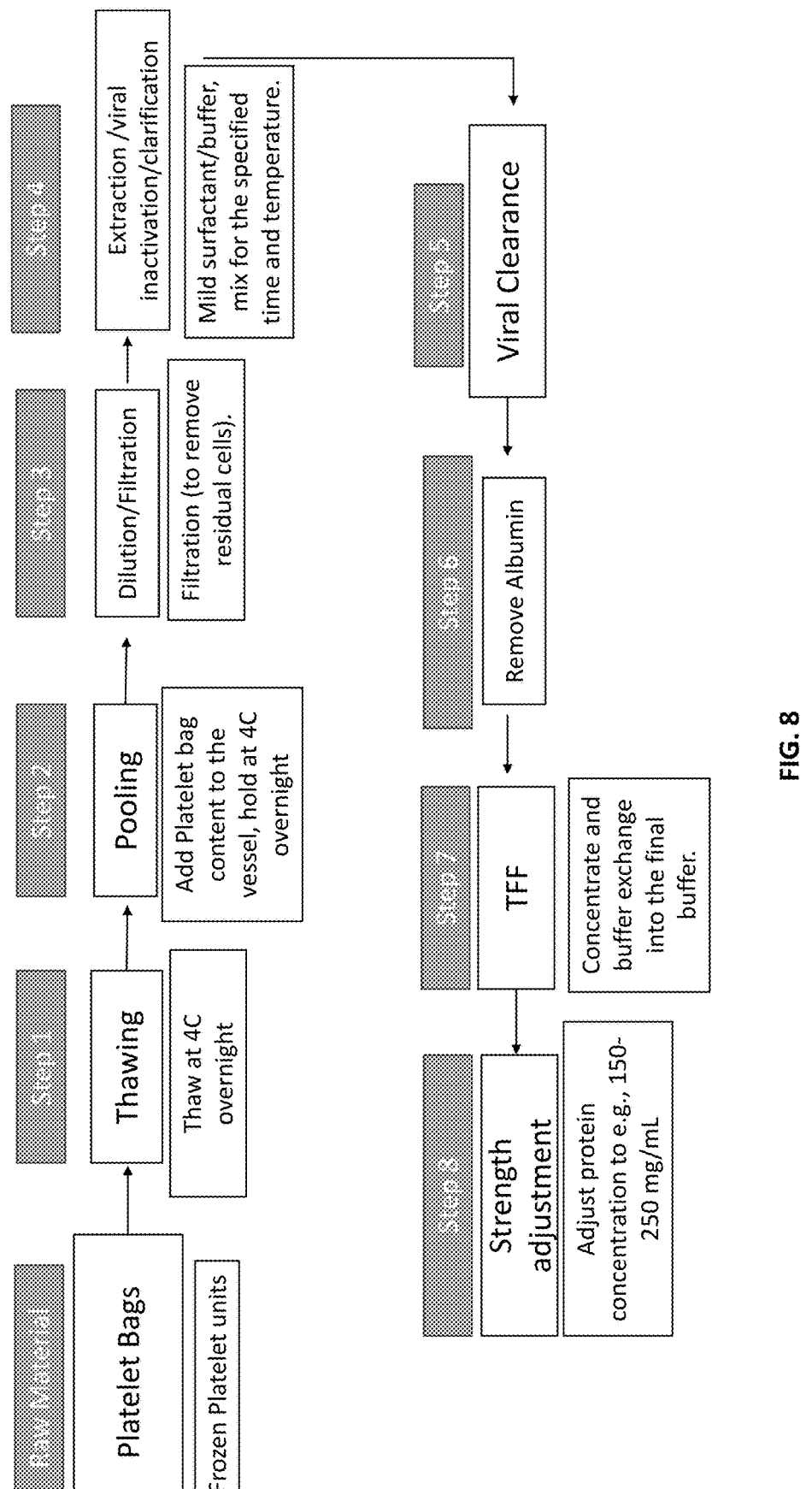

In some embodiments, a method for preparing a pharmaceutical composition comprising an allogenic human plasma and platelet derived product comprises thawing platelet suspensions, pooling platelet suspensions from at least 2 human donors, diluting and filtering the platelet suspensions, extracting platelet proteins and inactivating viruses, removing debris and viruses, removing albumin, concentrating the platelet extract, and diluting the allogenic human plasma and platelet derived product as set forth in FIG. 8.

Figure 9:
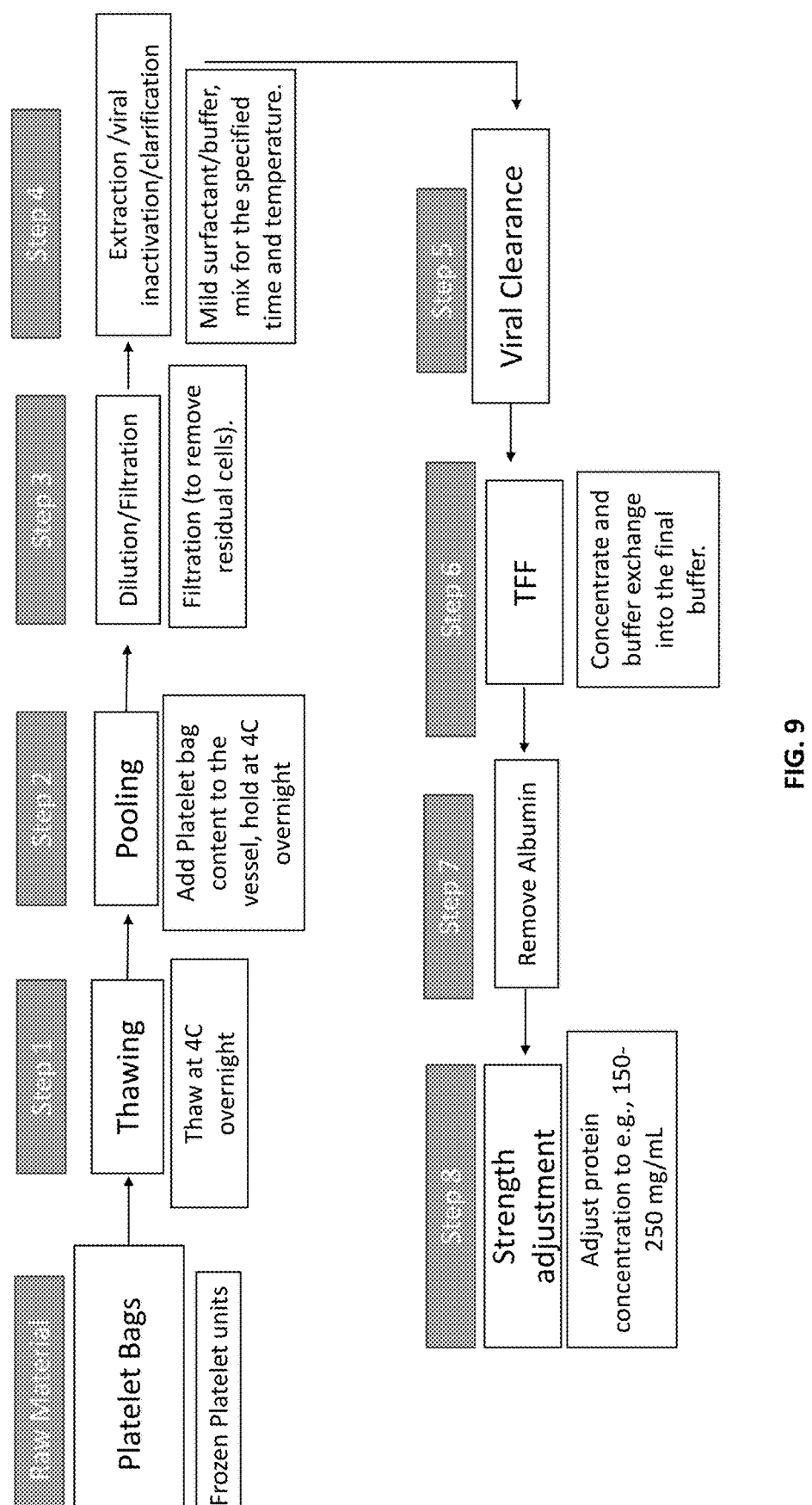

In some embodiments, a method for preparing a pharmaceutical composition comprising an allogenic human plasma and platelet derived product comprises thawing platelet suspensions, pooling platelet suspensions from at least 2 human donors, diluting and filtering the platelet suspensions, extracting platelet proteins and inactivating viruses, removing debris and viruses, concentrating the platelet extract, removing albumin, and diluting the allogenic human plasma and platelet derived product as set forth in FIG. 9.

Figure 26:
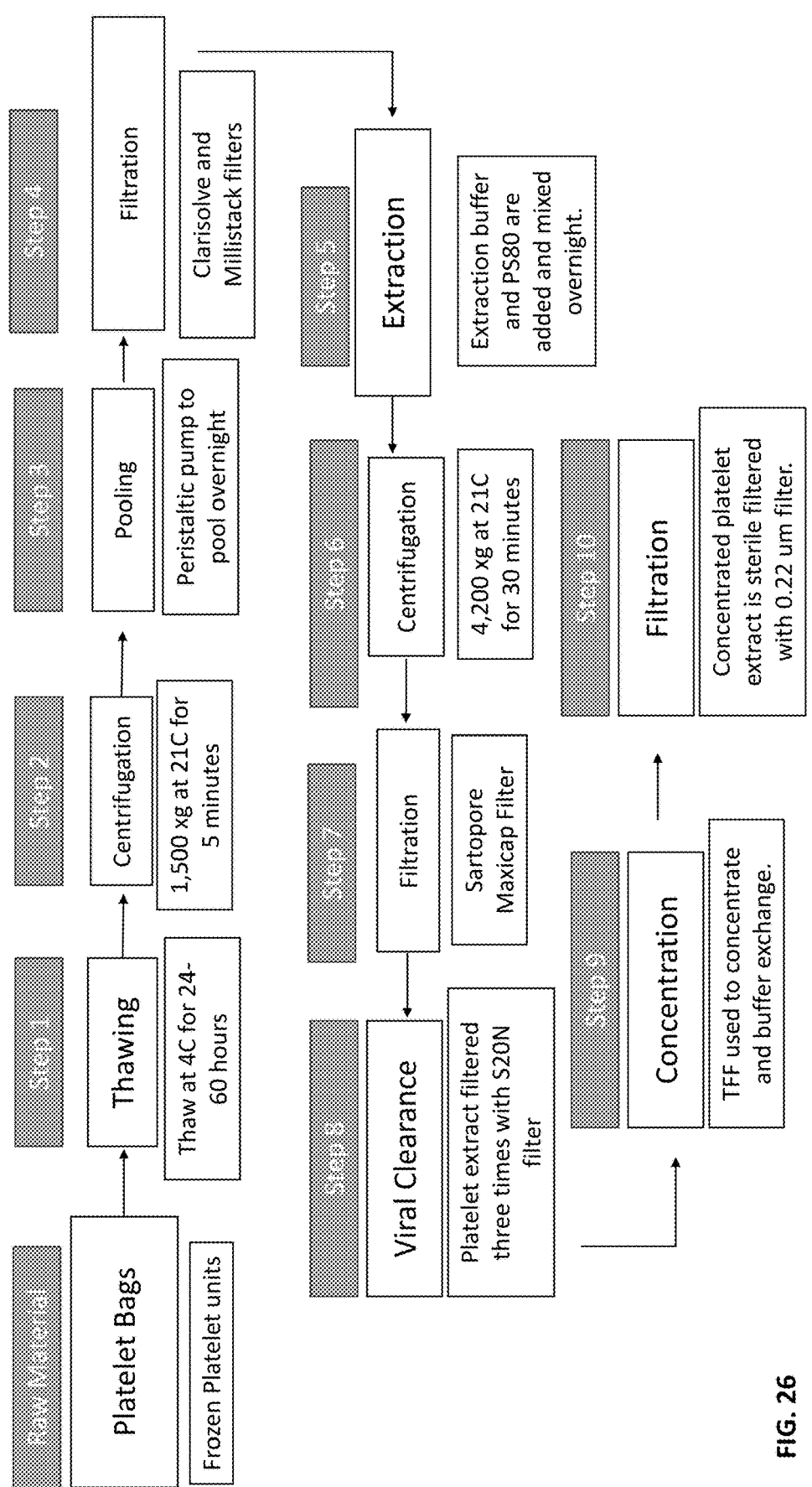
FIG. 26 provides an exemplary process for producing allogeneic human plasma and platelet derived products (AHPPDP).

In some embodiments, a method for preparing a pharmaceutical composition comprising an allogeneic human plasma and platelet derived product comprises thawing platelet suspensions, centrifuging the platelet suspensions, pooling the platelet suspensions, filtering the platelet suspensions, extracting platelet proteins, centrifuging the platelet extract, filtering the platelet extract, removing viruses, concentrating the platelet extract, and filtering the allogeneic human plasma and platelet derived product as set forth in FIG. 26.

Platelet Suspension Source

In some aspects, the compositions of the disclosure are obtained from processing of allogeneic human donor platelet suspensions from human whole blood or apheresis. In some embodiments, a platelet suspension comprises plasma and platelet cells. In some embodiments, platelet suspensions are obtained from whole blood. In some embodiments, platelets are obtained from whole blood using the buffy coat or platelet-rich plasma (PRP) technique. In the "PRP method", anticoagulated whole blood is centrifuged using a soft spin under conditions validated to segregate red blood cells (RBC) from the upper half containing a platelet and plasma mixture, so called PRP. Platelets are then concentrated by hard spin centrifugation with validated acceleration and deceleration curves. The platelet suspension is left stationary at room temperature and then the concentrate is resuspended in plasma. In the "buffy coat" method, anticoagulated whole blood is centrifuged using a hard spin with validated acceleration and deceleration curves to separate "cell-free" plasma on the top layer, a middle layer called buffy coat (BC) and a red blood cells (RBC) bottom layer. The BC layer is transferred to a satellite bag. A small quantity of plasma is returned to the BC layer and gently mixed before again being subjected to light spinning centrifugation with validated acceleration and deceleration curves.

In some embodiments, platelet suspensions are obtained from apheresis. In some embodiments, apheresis comprises an extracorporeal medical device used in blood donation that separates the platelets and returns other portions of the blood to the donor. In some embodiments, apheresis comprises centrifugation to separate out platelets.

In some embodiments, the platelet suspensions are transfusable quality platelets. In some embodiments, platelet suspensions are tested under the Food and Drug Administration (FDA) Code of Federal Regulations (CFR) requirements. In some embodiments, the platelet suspensions are tested for adventitious agents. In some embodiments, the platelet suspensions are tested for sterility. In some embodiments, the platelet suspensions are tested for infections including, but not limited to, human immunodeficiency virus (HIV), Hepatitis B virus (HBV), Hepatitis C virus (HCV), syphilis, West Nile virus, and Chagas disease. In some embodiments, platelet suspensions are tested for bacterial infections.

In some embodiments, platelet suspensions are used immediately after being obtained. In some embodiments, platelet suspensions are stored at room temperature for future use. In some embodiments, platelet suspensions are stored at about 2 to about 8° C. In some embodiments, platelet suspensions are frozen at about −80° C. In some embodiments, platelet suspensions are stored in bags for future use. In some embodiments, platelet suspensions are stored for up to one year. In some embodiments, platelet suspensions are stored for up to 6 months.

In some embodiments, platelet suspensions are obtained from platelet bags. In some embodiments, the platelet bags are thawed at about 4 to about 25° C. In some embodiments, platelet bags are thawed at about 2 to about 8° C. In some embodiments, platelet bags are thawed at 4° C. In some embodiments, thawing occurs overnight. In some embodiments, thawing occurs in a refrigerator. In some embodiments, platelet bags are gently agitated in a refrigerator to thaw. In some embodiments, thawing occurs in a water bath. In some embodiments, platelet bags are gently agitated in a water bath to thaw. In some embodiments, platelet bags are subjecting to radiation to thaw. In some embodiments, platelet bags are gently agitated and subjected to radiation to thaw. In some embodiments, platelet bags are subjected to electromagnetic waves to thaw. In some embodiments, platelet bags are gently agitated and subjected to electromagnetic waves to thaw. In some embodiments, platelet bags are visually inspected for leakage prior to thawing. In some embodiments, platelet bags are visually inspected for leakage following thawing. In some embodiments, platelet bags are visually inspected before and after thawing.

In some embodiments, total protein concentration of the whole blood or platelet concentrate is evaluated. In some embodiments, a proteomics screen is used to evaluate functional serum proteins which include, but are not limited to, human serum albumin (©), fibrinogen, and alpha-2-macroglobulin. In some embodiments, a proteomics screen is used to evaluate functional platelet proteins which include but are not limited to basic fibroblast growth factor (bFGF), epidermal growth factor (EGF), hepatocyte growth factor (HGF), platelet-derived growth factor subunit A (PDGF-AA), platelet-derived growth factor subunit A and subunit B (PDGF-AB), platelet-derived growth factor subunit B (PDGF-BB), vascular endothelial growth factor (VEGF), transcription growth factor-β (TGF-β), interleukin 10 (IL-10), and interleukin 4 (IL-4). Methods for detecting and/or quantifying proteins are described herein.

In some embodiments, an anti-coagulant is included in the platelet suspension. In some embodiments, the anti-coagulant is an acid-citrate-dextrose solution. In some embodiments, the anti-coagulant is citrate. In some embodiments, the anti-coagulant is heparin.

In some embodiments, a clotting agent is not included in the platelet suspension. In some embodiments, a clotting agent is not utilized in the methods described herein.

Donor Demographics

In some aspects, methods for making the compositions described herein comprise obtaining platelet suspension from one or more donors. In some embodiments, the methods comprise pooling platelet suspension from two or more donors. In some embodiments, the methods comprising pooling platelet suspensions from about 10 to about 50 donors. In some embodiments, the methods comprising pooling platelet suspensions from about 50 to about 100 donors. In some embodiments, the methods comprise pooling platelet suspensions from about 100 to about 200 donors. In some embodiments, the methods comprise pooling platelet suspensions from at least 100 donors. In some embodiments, the methods comprise pooling platelet suspensions from at least 200 donors. In some embodiments, the methods comprise pooling platelet suspensions from 200 to 300 donors.

In some embodiments, a donor is an adult, e.g. 16-65 years old. In some embodiments, a donor is a young adult, e.g., 16-35 years old. In some embodiments, a donor is 16-40 years old. In some embodiments, a donor is at least 35 years old. In some embodiments, a donor is no more than 35 years old. Without wishing to be bound by theory, platelet suspensions from a young adult is expected to have a higher concentration of proteins of interest and a lower concentration of proinflammatory proteins relative to an older adult (e.g., over 35 years old). In some embodiments, a donor is 36-45 years old. In some embodiments, a donor is at least 45 years old. In some embodiments, a donor is older over 45 years old. In some embodiments, the donor is less than 65 years old. In some embodiments, platelet suspensions from two or more donors comprises at least one platelet suspension from a donor 16-35 years old, and at least one platelet suspension from a donor over 35 years old.

In some embodiments, a donor population comprises males. In some embodiments, a donor population comprises females. In some embodiments, a donor population comprises males and females.

In some embodiments, a donor is healthy as determined by a physician. In some embodiments, a donor does not have a disease or disorder. In some embodiments, a donor does not have a history of a disease or disorder. In some embodiments, a donor does not have a predisposition to a disease or disorder. In some embodiments, a donor does not have a family history of a disease or disorder. In some embodiments, a donor does not have genetic predisposition to a disease or disorder.

Pooling Platelet Suspensions

In some embodiments, platelet suspensions from more than one human subject donor are pooled. In some embodiments, platelet suspension from the same human subject donor are pooled. In some embodiments, platelet suspension from different human subject donors are pooled. As used herein, "pooling" refers to combining or accumulating two or more components (e.g., platelet suspensions) into one or more containers or vessels. In some embodiments, platelet suspensions are pooled before platelet proteins are extracted. In some embodiments, platelet suspensions are pooled before being diluted. In some embodiments, platelet suspensions are pooled while being diluted. In some embodiments, platelet suspensions are pooled before albumin is removed.

In some embodiments, the platelet suspension is pooled with a multi-head peristaltic pump. In some embodiments, the multi-head peristaltic pump is selected from, Masterflex®, Ismatec®, and BT100-1L. In some embodiments the platelet suspension is pooled with a single-use jacketed mixer with scale. In some embodiments, the single-use jacketed mixer is selected from, Xcellerex and Mobius. In some embodiments, the platelet suspension is pooled at a temperature of about 2 to about 25° C. In some embodiments, the platelet suspension is pooled at a temperature of about 2 to about 8° C. In some embodiments, the platelet suspension is pooled at a temperature of at least 2° C. In some embodiments, the platelet suspension is pooled at a temperature of at least 8° C. In some embodiments, the platelet suspension is pooled at temperature of at least 25° C. In some embodiments, the platelet suspension is pooled at a temperature no higher than 2° C. In some embodiments, the platelet suspension is pooled at a temperature no higher than 8° C. In some embodiments, the platelet suspension is pooled at temperature no higher than 25° C.

In some embodiments, the platelet suspensions are pooled prior to WBC and RBC removal. In some embodiments, a single-use jacketed mixer with scale is used to pool platelet suspensions. In some embodiments, a single-use jacketed mixer is selected from Xcellerex and Mobius.

Diluting and Blood Cell Removal

In some embodiments, methods for preparing an allogeneic human plasma and platelet derived product comprises removing white blood cells (WBCs) and red blood cells (RBCs). In some embodiments, to remove blood cells, the platelet suspension from whole blood or apheresis is diluted. Without wishing to be bound by theory, diluting the platelet suspension prevents clogging during removal of blood cells and reduces the loss of platelets and plasma proteins. In some embodiments, the platelet suspension is diluted prior to blood cell removal. In some embodiments, the platelet suspension is diluted during blood cell removal. In some embodiments the platelet suspension is diluted after blood cell removal.

In some embodiments, the platelet suspension is diluted in a suitable buffer. Suitable buffers include, but are not limited to, phosphate, citrate, EDTA, NaCl, KCl, $MgCl_2$, $CaCl_2$), sucrose, glucose, trehalose, and PS20/80. In some embodiments, the buffer comprises phosphate at a concentration of about 20 to about 200 mM. In some embodiments, the buffer comprises phosphate at a concentration no greater than 20 mM. In some embodiments, the buffer comprises citrate at a concentration of about 15 to about 200 mM. In some embodiments, the buffer comprises citrate at a concentration no greater than 15 mM. In some embodiments, the buffer comprises EDTA at a concentration of about 0.3 to about 200 mM. In some embodiments, the buffer comprises EDTA at a concentration no greater than 0.3 mM. In some embodiments, the buffer comprises NaCl at a concentration of about 150 to about 200 mM. In some embodiments, the buffer comprises NaCl at a concentration no greater than 150 mM. In some embodiments, the buffer comprises KCl at a concentration of about 1 to about 200 mM. In some embodiments, the buffer comprises KCl at a concentration no greater than 1 mM. In some embodiments, the buffer comprises $MgCl_2$ at a concentration of about 1.3 to about 200 mM. In some embodiments, the buffer comprises $MgCl_2$ at a concentration no greater than 1.3 mM. In some embodiments, the buffer comprises $CaCl_2$) at a concentration of about 2.4 to about 200 mM. In some embodiments, the buffer comprises $CaCl_2$) at a concentration no greater than 200 mM. In some embodiments, the buffer comprises sucrose at a concentration of about 10 to about 200 mM. In some embodiments, the buffer comprises sucrose at a concentration no greater than 10 mM. In some embodiments, the buffer comprises glucose at a concentration of about 10 to about 200 mM. In some embodiments, the buffer comprises glucose at a concentration no greater than 10 mM. In some embodiments, the buffer comprises trehalose at a concentration of about 10 to about 200 mM. In some embodiments, the buffer comprises trehalose at a concentration no greater than 10 mM. In embodiments, the buffer comprises Polysorbate (PS20/80 at a concentration of about 0.025 to about 10%. In some embodiments, the buffer comprises PS20/80 at a concentration no greater than 0.025%. In some embodiments, the buffer pH is between about 4.0 and about 9.0. In some embodiments, the buffer pH is at least 4.0. In some embodiments, the buffer pH is at least 9.0. In some embodiments, the buffer pH is no higher than 4.0. In some embodiments, the buffer pH is no higher than 9.0.

In some embodiments, blood cell removal comprises filtering the platelet concentrate with a suitable filter. In some embodiments, a filter is made of polyvinylidene fluoride (PVDF), nylon, polyether sulfone (PES), polysulfone (PS), regenerated cellulose (RC), or Glass Fiber (GF). In some embodiments, a depth-filter is used to remove WBCs and RBCs. In some embodiments, a depth-filter is selected from, 3M:05SP01A, Sartoclear DL60, and Profile Star A030. In some embodiments, tangential flow filtration (TFF) is used to remove WBCs and RBCs. In some embodiments, the filter pore size is between about 0.1 μm and 50.0 μm. In some embodiments, the filter pore size is at least 0.1 μm. In some embodiments, the filter pore size is 0.1 μm. In some embodiments, the filter pore size is no bigger than 0.1 μm. In some embodiments, the filter pore size is at least 50.0 μm. In some embodiments, the filter pore size is 50.0 μm. In some embodiments, the filter pore size is no bigger than 50.0 μm. In some embodiments, the filter pore size is about 0.1 μm to about 5.0 μm. In some embodiments, the filter pore size is about 5 μm to about 10 μm. In some embodiments, the filter pore size is about 10 μm to about 20 μm. In some embodiments, the filter pore size is 10 μm to 25 μm. In some embodiments, the filter pore size is 25 μm to 50 μm. In some embodiments, the filter pore size is 30 μm to 40 μm. In some embodiments, the filter pore size is 35 μm to 50 μm.

WBCs exhibit different levels of rigidity at various temperatures. Specifically, WBCs are more rigid at cooler temperatures (e.g. 2-8° C.). Without wishing to be bound by theory, higher rigidity allows for more efficient filtration. Accordingly, in some embodiments, filtration occurs at 2-8° C. In some embodiments, filtration occurs at a temperature greater than 2° C. In some embodiments, filtration occurs at 2° C. In some embodiments, filtration occurs at 4° C. In some embodiments, filtration occurs at 10-20° C. In some embodiments, filtration occurs at 25-37° C. In some embodiments filtration occurs at 25° C. In some embodiments, filtration occurs at a temperature greater than 25° C. In some embodiments, filtration occurs at a temperature no greater than 37° C. In some embodiments, filtration occurs at 25-37° C. In some embodiments, filtration occurs at 30° C.

In some embodiments, the levels of WBCs and RBCs are quantified to validate that the blood cells have been removed or reduced from the platelet suspension. In some embodiments, cell count is used to determine WBCs and RBCs have been removed or reduced. In some embodiments, hemoglobin quantification is used to determine WBCs and RBCs have been removed or reduced. In some embodiments, DNA testing is used to determine WBCs have been removed. In some embodiments, RBC removal will be used to indicate removal of WBC. In some embodiments, RBC removal is determined by the amount of hemoglobin present.

In some embodiments, after filtering to remove blood cells, there is a 5-6 log reduction in white blood cell count. In some embodiments, the filtered platelet concentrate comprises $10^1$ to $10^2$ white blood cells.

Platelet Protein Extraction

Various methods known to those with ordinary skill in the art can be used to extract platelet proteins from platelets in a platelet suspension. In some aspects, the disclosure provides methods of extracting platelet proteins from platelets. In some embodiments, the platelet suspension is maintained under conditions sufficient to lyse the platelets to release platelet proteins and generate a platelet extract comprising plasma proteins and platelet proteins. In some embodiments, the platelet suspension is maintained under conditions sufficient to extract platelet proteins from the platelets and generate a platelet extract comprising plasma proteins and platelet proteins. In some embodiments, the platelet extract is stored at −80° C. until further processing to generate the compositions described herein.

Freeze-Thaw

In some embodiments, platelet proteins are extracted via freeze-thaw. In some embodiments, the platelet suspension is subjected to one freeze-thaw cycle to extract the platelet proteins. In some embodiments, the platelet suspension is subjected to two freeze-thaw cycles to extract the platelet proteins. In some embodiments, the platelet suspension is subjected to three freeze-thaw cycles to extract the platelet proteins. In some embodiments, the platelet suspension is subjected to at least two freeze-thaw cycles to extract the platelet proteins. In some embodiments, the platelet suspension is subjected to at least three freeze-thaw cycles to extract the platelet proteins.

In some embodiments, the platelet suspension is centrifuged to pelletize the platelets prior to the freeze-thaw cycle(s). In some embodiments, the platelet suspension is centrifuged at 3,000×g for 30 minutes at 22° C. In some embodiments, the platelet suspension is centrifuged a temperature of about 4 to 10° C. In some embodiments, the platelet suspension is centrifuged at a temperature of about 10 to 30° C. In some embodiments, the platelet suspension is centrifuged at a temperature of about 20 to 30° C. In some embodiments, the platelet suspension is centrifuged for about 10 to 20 minutes. In some embodiments, the platelet suspension is centrifuged for about 20 to 30 minutes. In some embodiments, the platelet suspension is centrifuged for at least 30 minutes. In some embodiments, the platelet suspension is centrifuged for no longer than 30 minutes. In some embodiments, the platelet suspension is centrifuged at 3000×g. In some embodiments, the platelet suspension is centrifuged at a speed no faster than 3,000×g. In some embodiments, the platelet suspension is centrifuged at a speed at least 3,000×g. In some embodiments, the platelet suspension is centrifuged at a speed of about 1,000 to 2,000×g. In some embodiments, the platelet suspension is centrifuged at a speed of about 2,000 to 3,000×g. In some embodiments, the platelet suspension is centrifuged at 3,000×g at a temperature of about 4 to 10° C. for about 10 to 20 minutes. In some embodiments, the platelet suspension is centrifuged at 3,000×g at a temperature of about 10 to 30° C. for about 10 to 20 minutes. In some embodiments, the platelet suspension is centrifuged at 3,000×g at a temperature of about 20 to 30° C. for about 10 to 20 minutes. In some embodiments, the platelet suspension is centrifuged at 3,000×g at a temperature of about 4 to 10° C. for about 20 to 30 minutes. In some embodiments, the platelet suspension is centrifuged at 3,000×g at a temperature of about 10 to 30° C. for about 20 to 30 minutes. In some embodiments, the platelet suspension is centrifuged at 3,000×g at a temperature of about 20 to 30° C. for about 20 to 30 minutes. In some embodiments, the platelet suspension is centrifuged at a speed no higher than 3,000×g at a temperature of about 4 to 10° C. for about 10 to 20 minutes. In some embodiments, the platelet suspension is centrifuged at a speed no higher than 3,000×g at a temperature of about 10 to 30° C. for about 10 to 20 minutes. In some embodiments, the platelet suspension is centrifuged at a speed no higher than 3,000×g at a temperature of about 20 to 30° C. for about 10 to 20 minutes. In some embodiments, the platelet suspension is centrifuged at a speed no higher than 3,000×g at a temperature of about 4 to 10° C. for about 20 to 30 minutes. In some embodiments, the platelet suspension is centrifuged at a speed no higher than 3,000×g at a temperature of about 10 to 30° C. for about 20 to 30 minutes. In some embodiments, the platelet suspension is centrifuged at a speed no higher than 3,000×g at a temperature of about 20 to 30° C. for about 20 to 30 minutes. In some embodiments, the platelet suspension is centrifuged at a speed of at least 3,000×g at a temperature of about 4 to 10° C. for about 10 to 20 minutes. In some embodiments, the platelet suspension is centrifuged at a speed of at least 3,000×g at a temperature of about 10 to 30° C. for about 10 to 20 minutes. In some embodiments, the platelet suspension is centrifuged at a speed of at least 3,000×g at a temperature of about 20 to 30° C. for about 10 to 20 minutes. In some embodiments, the platelet suspension is centrifuged at a speed of at least than 3,000×g at a temperature of about 4 to 10° C. for about 20 to 30 minutes. In some embodiments, the platelet suspension is centrifuged at a speed of at least 3,000×g at a temperature of about 10 to 30° C. for about 20 to 30 minutes. In some embodiments, the platelet suspension is centrifuged at a speed of at least 3,000×g at a temperature of about 20 to 30° C. for about 20 to 30 minutes.

In some embodiments, after centrifugation the supernatant is removed, leaving a platelet pellet. In some embodiments, the platelet pellet is washed with a suitable buffer, e.g., phosphate-buffered saline (PBS). In some embodiments, the platelet pellet is concentrated to approximately one-tenth of the starting volume of platelets in the platelet suspension. In some embodiments, the freeze-thaw cycle comprises freezing at –80° C. In some embodiments, freezing occurs at –20° C. In some embodiments, freezing occurs at about –20 to about –196° C. In some embodiments, freezing occurs at a temperature of about –60 to –80° C. In some embodiments, freezing occurs at a temperature of about –40 to –80° C. In some embodiments, freezing occurs at a temperature of about –20 to –40° C. In some embodiments, freezing occurs at a temperature of at least –80° C. In some embodiments, freezing occurs at temperature no less than –80° C. In some embodiments, freezing occurs at a temperature of at least –20° C. In some embodiments, freezing occurs at a temperature no less than –20° C. In some embodiments, freezing occurs at a temperature lower than or equal to about –20° C., lower than or equal to about –79° C., lower than or equal to about –80° C., lower than or equal to about –81° C., lower than or equal to about –82° C., lower than or equal to about –83° C., lower than or equal to about –84° C., lower than or equal to about –85° C., lower than or equal to about –86° C., lower than or equal to about –87° C., lower than or equal to about –88° C., lower than or equal to about –89° C., lower than or equal to about –90° C., lower than or equal to about –100° C., lower than or equal to about –110° C., lower than or equal to about –120° C., lower than or equal to about –130° C., lower than or equal to about –140° C., lower than or equal to about –150° C., lower than or equal to about –160° C., lower than or equal to about –170° C., lower than or equal to about –180° C., lower than or equal to about –190° C. or about –196° C. In some embodiments, liquid nitrogen is used as a cryogenic means in each freeze cycle. In some embodiments, freezing with liquid nitrogen occurs at about –210° C.

In some embodiments, freezing occurs for about 30 minutes. In some embodiments, freezing occurs for no more than 30 minutes. In some embodiments, freezing occurs for no more than 1 hour. In some embodiments, freezing occurs for about 30 minutes to about 3 hours. In some embodiments, freezing occurs for about 1 to about 3 hours. In some embodiments, freezing occurs overnight.

In some embodiments, the freeze-thaw cycle comprises thawing at a temperature of about 2 to about 50° C. In some embodiments, the freeze-thaw cycle comprises thawing at about 2 to about 25° C. In some embodiments, the freeze-thaw cycle comprises thawing at about 25 to about 50° C. In some embodiments, the freeze-thaw cycle comprises thawing at 37±1° C. In some embodiments, thawing occurs in a dry bath. In some embodiments, thawing occurs in a water bath.

In some embodiments, after the last thaw, the platelet suspension is centrifuged at 4,500×g for 30 minutes at 20±1° C. In some embodiments, the platelet suspension is placed at 56±1° C. for 30 minutes and immediately cooled for at least 5 minutes on ice. In some embodiments, the platelet suspension is then centrifuged at 104×g for 15 minutes at 4±2° C. to eliminate precipitate.

In some embodiments, thawing occurs for about 5 minutes to about 24 hours. In some embodiments, thawing occurs for about 5 minutes. In some embodiments, thawing occurs for at least 30 minutes. In some embodiments, thawing occurs for about 6 hours. In some embodiments, thawing occurs overnight. In some embodiments, thawing occurs for about 16 hours. In some embodiments, thawing occurs for about 24 hours. In some embodiments, freezing occurs for no more than 30 minutes. In some embodiments, freezing occurs for about 30 minutes to about 3 hours.

Detergent-Buffer

In some embodiments, platelet proteins are extracted from platelets via incubation of the platelet suspension in one or more detergents. In some embodiments, the detergent is an anionic detergent. An exemplary anionic detergent includes sodium dodecyl sulphate (SDS). In some embodiments, an anionic detergent is SDS. In some embodiments, the detergent is a non-ionic detergent. Exemplary non-ionic detergents include Triton X-45, Triton X-100, Triton X-114, NP-40, Tween 20, and Tween 80. In some embodiments, a non-ionic detergent is Triton X-45. In some embodiments, a non-ionic detergent is Triton X-100. In some embodiments, a non-ionic detergent is Triton X-114. In some embodiments, a non-ionic detergent is NP-40. In some embodiments, a non-ionic detergent is Tween 20. In some embodiments, a non-ionic detergent is Tween 80. In some embodiments, the detergent is a zwitterionic detergent. Exemplary zwitterionic detergents include CHAPS and CHAPSO. In some embodiments, a zwitterionic detergent is CHAPS. In some embodiments, a zwitterionic detergent is CHAPSO. In some embodiments, a detergent is non-denaturing. Exemplary non-denaturing detergents include Triton X-45, Triton X-100, Triton X-114, and NP-40. In some embodiments, a detergent denatures proteins. In some embodiments, a detergent is a mild lysis agent. Exemplary mild lysis agents include Tween 20, Tween 80, CHAPS and CHAPSO. In some embodiments, a detergent is a strong lysis agent. An exemplary strong lysis agent is SDS. In some embodiments, the detergent is selected from SDS, Triton X-45, Triton X-100, Triton X-114, NP-40, Tween 20, Tween 80, CHAPS, and CHAPSO. In some embodiments, the detergent is SDS. In some embodiments, the detergent is Triton X-45. In some embodiments, the detergent is Triton X-100. In some embodiments, the detergent is Triton X-114. In some embodiments, the detergent is NP-40. In some embodiments, the detergent is Tween 20. In some embodiments, the detergent is Tween 80. In some embodiments, the detergent is CHAPS. In some embodiments, the detergent is CHAPSO. In some embodiments, the detergent is a cationic detergent. In some embodiments, the cationic detergent is ethyl trimethyl ammonium bromide.

In some embodiments, the detergent solution comprises sodium citrate. In some embodiments, the detergent solution comprises a chelating agent. In some embodiments, the chelating agent is EDTA. In some embodiments, the detergent solution comprises polysorbate 80 (PS80). In some embodiments, the detergent solution comprises sodium citrate, EDTA, and PS80.

In some embodiments, the platelet suspension is gently rocked in detergent. In some embodiments, the platelet suspension is incubated in the detergent for about 10 minutes to about 24 hours. In some embodiments, the platelet suspension is incubated in the detergent for about 10 minutes to about 1 hour. In some embodiments, the platelet suspension is incubated in the detergent for about 1 hour to about 6 hours. In some embodiments, the platelet suspension is incubated in the detergent for about 8 to about 10 hours. In some embodiments, the platelet suspension is incubated in the detergent overnight. In some embodiments, the platelet suspension is incubated in the detergent for about 12 hours to about 24 hours. In some embodiments, the platelet suspension is incubated in the detergent for no less than 10 minutes. In some embodiments, the platelet suspension is incubated in the detergent for no more than 24 hours.

In some embodiments, the platelet suspension is incubated in the detergent at a temperature of about 2 to about 40° C. In some embodiments, the platelet suspension is incubated in the detergent at a temperature of about 2 to about 8° C. In some embodiments, the platelet suspension is incubated in the detergent at a temperature of about 20 to about 30° C. In some embodiments, the platelet suspension is incubated in the detergent at a temperature of about 30 to about 40° C. In some embodiments, the platelet suspension is incubated in the detergent at a temperature no less than 2° C. In some embodiments, the platelet suspension is incubated in the detergent at a temperature no greater than 50° C.

In some embodiments, the platelet suspension is gently rocked in detergent for about 10 minutes to about 24 hours at a temperature of about 2 to 40° C. In some embodiments, the platelet suspension is gently rocked in detergent for about 10 minutes to about 1 hour at a temperature of about 2 to 40° C. In some embodiments, the platelet suspension is gently rocked in detergent for about 1 hour to about 6 hours at a temperature of about 2 to about 40° C. In some embodiments, the platelet suspension is gently rocked in detergent for about 8 hours to about 10 hours at a temperature of about 4 to about 40° C. In some embodiments, the platelet suspension is gently rocked in detergent for about 12 to about 24 hours at a temperature of about 4 to about 40° C.

In some embodiments, the platelet suspension is gently rocked in detergent for about 10 minutes to about 24 hours at a temperature of about 2 to 8° C. In some embodiments, the platelet suspension is gently rocked in detergent for about 10 minutes to about 1 hour at a temperature of about 2 to 8° C. In some embodiments, the platelet suspension is gently rocked in detergent for about 1 hour to about 6 hours at a temperature of about 2 to about 8° C. In some embodiments, the platelet suspension is gently rocked in detergent for about 8 hours to about 10 hours at a temperature of about 2 to about 8° C. In some embodiments, the platelet suspension is gently rocked in detergent for about 12 to about 24 hours at a temperature of about 2 to about 8° C.

In some embodiments, the platelet suspension is gently rocked in detergent for about 10 minutes to about 24 hours at a temperature of about 20 to 30° C. In some embodiments, the platelet suspension is gently rocked in detergent for about 10 minutes to about 1 hour at a temperature of about 20 to 30° C. In some embodiments, the platelet suspension is gently rocked in detergent for about 1 hour to about 6 hours at a temperature of about 20 to about 30° C. In some embodiments, the platelet suspension is gently rocked in detergent for about 8 hours to about 10 hours at a temperature of about 20 to about 30° C. In some embodiments, the platelet suspension is gently rocked in detergent for about 12 to about 24 hours at a temperature of about 20 to about 30° C.

In some embodiments, the platelet suspension is gently rocked in detergent for about 10 minutes to about 24 hours at a temperature of about 30 to 40° C. In some embodiments, the platelet suspension is gently rocked in detergent for about 10 minutes to about 1 hour at a temperature of about 30 to 40° C. In some embodiments, the platelet suspension is gently rocked in detergent for about 1 hour to about 6 hours at a temperature of about 30 to about 40° C. In some embodiments, the platelet suspension is gently rocked in detergent for about 8 hours to about 10 hours at a temperature of about 30 to about 40° C. In some embodiments, the platelet suspension is gently rocked in detergent for about 12 to about 24 hours at a temperature of about 30 to about 40° C.

Osmotic Pressure

In some embodiments, platelet proteins are extracted from platelets by decreasing or increasing the osmolality of the surrounding fluid in the platelet suspension. In some embodiments, the osmolality of the surrounding fluid is decreased. In some embodiments, pl the osmolality of the surrounding fluid is increased. In some embodiments, salts are used to vary the osmolality of the surrounding fluid. In some embodiments, water is used to vary the osmolality of the surrounding fluid. In some embodiments, sugars are used to vary the osmolality of the surrounding fluid. In some embodiments, buffers are used to vary the osmolality of the surrounding fluid. In some embodiments, citrate is used to lower or increase the osmolality of the surrounding fluid. In some embodiments, the concentration of citrate is about 1 to about 200 mM. In some embodiments, the concentration of citrate is about 1 mM. In some embodiments, the concentration of citrate is about 20 mM. In some embodiments, the concentration of citrate is about 200 mM. In some embodiments, the concentration of citrate is at least 1 mM. In some embodiments, the concentration of citrate is no more than 1 mM. In some embodiments, the concentration of citrate is at least 20 mM. In some embodiments, the concentration of citrate is no more than 20 mM. In some embodiments, the concentration of citrate is at least 100 mM. In some embodiments, the concentration of citrate is no more than 100 mM. In some embodiments, the concentration of citrate is at least 200 mM. In some embodiments, the concentration of citrate is no more than 200 mM. In some embodiments, water is used to lower or increase the osmolality of the surrounding fluid. In some embodiments, citrate and water are used to lower or increase the osmolality of the surrounding fluid.

In some embodiments, the platelet suspension is diluted to lower the osmolality of the surrounding fluid. In some embodiments, the platelet concentrate is diluted 2-fold. In some embodiments, the platelet suspension is diluted 4-fold. In some embodiments, the platelet suspension is diluted 8-fold. In some embodiments, the platelet suspension is diluted at least 2-fold. In some embodiments, the platelet concentrate is diluted at least 8-fold.

In some embodiments, the osmolality ranges from about 0.01 to about 1,000 mOsm/kg. In some embodiments, the osmolality ranges from 0.01 to 5 mOsm/kg. In some embodiments, the osmolality ranges from 10 to 50 mOsm/kg. In some embodiments, the osmolality ranges from 100 to 250 mOsm/kg. In some embodiments, the osmolality ranges from 500 to 750 mOsm/kg. In some embodiments, the osmolality ranges from 750 to 1,000 mOsm/kg.

Sonication

In some embodiments, platelet proteins are extracted from platelets via sonication. In some embodiments, sonication comprises an ultrasonic bath to deliver high-frequency sound waves. In some embodiments, sonication comprises an ultrasonic probe to deliver high-frequency sound waves. In some embodiments, the high-frequency sound waves are at least 10 kHz. In some embodiments, the high-frequency sound waves are no greater than 10 kHz. In some embodiments, the high-frequency sound waves are at least 20 kHz.
Electroporation In some embodiments, platelet proteins are extracted from platelets via electroporation in which a high-voltage electrical pulse is delivered. In some embodiments, the electric pulse ranges in magnitude from about 0.1 to about 10 kV. In some embodiments, the electric pulse ranges in magnitude from about 0.1 to about 5 kV. In some embodiments, the electric pulse ranges in magnitude from about 5 to about 10 kV. In some embodiments, the electric pulse ranges in resistance from about 1 to about 300Ω. In some embodiments, the electric pulse ranges in resistance from about 1 to about 50Ω. In some embodiments, the electric pulse ranges in resistance from about 50 to about 100Ω. In some embodiments, the electric pulse ranges in resistance from about 100 to about 200Ω. In some embodiments, the electric pulse ranges in resistance from about 200 to about 300Ω. In some embodiments, the electric pulse ranges in capacitance from about 1 to about 100 μF. In some embodiments, the electric pulse ranges in capacitance from about 1 to about 50 μF. In some embodiments, the electric pulse ranges in capacitance from about 50 to about 100 μF. In some embodiments, the electric pulse is administered for about 1 to about 20 milliseconds. In some embodiments, the electric pulse is administered for about 1 to about 10 milliseconds. In some embodiments, the electric pulse is administered for about 10 to about 20 milliseconds.

In some embodiments, an electric pulse with a magnitude of about 0.1 to about 10 kV is delivered for about 1 to about 20 milliseconds. In some embodiments, an electric pulse with a magnitude of about 0.1 to about 5 kV is delivered for about 1 to about 20 milliseconds. In embodiments, an electric pulse with a magnitude of about 5 to about 10 kV is delivered for about 1 to about 20 milliseconds. In some embodiments, an electric pulse with a magnitude of about 0.1 to about 10 kV is delivered for about 1 to about 10 milliseconds. In some embodiments, an electric pulse with a magnitude of about 0.1 to about 5 kV is delivered for about 1 to about 10 milliseconds. In embodiments, an electric pulse with a magnitude of about 5 to about 10 kV is delivered for about 1 to about 10 milliseconds. In some embodiments, an electric pulse with a magnitude of about 0.1 to about 10 kV is delivered for about 10 to about 20 milliseconds. In some embodiments, an electric pulse with a magnitude of about 0.1 to about 5 kV is delivered for about 10 to about 20 milliseconds. In embodiments, an electric pulse with a magnitude of about 5 to about 10 kV is delivered for about 10 to about 20 milliseconds.
Microfluidics In some embodiments, platelet proteins are extracted from platelets via microfluidics in which platelets are passed through a microchannel at high pressure. In some embodiments, platelet proteins are extracted by one pass of the platelets through a microchannel. In some embodiments, platelet protein are extracted by at least one pass of the platelets through a microchannel. In some embodiments, platelets are subjected to pressure ranging from about 10,000 to about 50,000 PSI. In some embodiments, platelets are subjected to pressure ranging 10,000 to about 25,000 PSI. In some embodiments, platelets are subjected to pressure ranging from about 25,000 to about 50,000 PSI. In some embodiments, platelets are passed through a microchannel once at a pressure of about 10,000 to about 50,000 PSI. In some embodiments, platelets are passed through a microchannel once at a pressure of about 10,000 to about 25,000 PSI. In some embodiments, platelets are passed through a microchannel once at a pressure of about 25,000 to about 50,000 PSI. In some embodiments, platelets are passed through a microchannel at least once at a pressure of about 10,000 to about 50,000 PSI. In some embodiments, platelets are passed through a microchannel at least once at a pressure of about 10,000 to about 25,000 PSI. In some embodiments, platelets are passed through a microchannel at least once at a pressure of about 25,000 to about 50,000 PSI.
Combinatorial Approach to Platelet Protein Extraction In some embodiments, a combinatorial approach is used to extract platelet proteins. In some embodiments, the combinatorial approach comprises methods selected from, but not limited to, freeze-thaw, buffer-detergent, osmotic pressure, sonication, electroporation, and microfluidics. In some embodiments, the combinatorial approach comprises at least two methods. In some embodiments, the combinatorial approach comprises at least three methods. In some embodiments, the combinatorial approach comprises at least four methods.

In some embodiments, freeze-thaw and detergent-buffer are used to extract platelet proteins. In some embodiments, osmotic pressure and detergent-buffer are used to extract platelet proteins. In some embodiments, sonication and detergent-buffer are used to extract platelet proteins. In some embodiments, electroporation and detergent-buffer are used to extract platelet proteins. In some embodiments, microfluidics and detergent-buffer are used to extract platelet proteins.

In some embodiments, freeze-thaw, detergent-buffer, and osmotic pressure are used to extract platelet proteins. In some embodiments, freeze-thaw, detergent-buffer, and sonication are used to extract platelet proteins. In some embodiments, freeze-thaw, detergent-buffer, and electroporation are used to extract platelet proteins. In some embodiments, freeze-thaw, detergent-buffer, and microfluidics are used to extract platelet proteins.
Purification In some embodiments, after platelet proteins have been extracted from the platelets, thereby generating a platelet extract, the platelet extract is separated from cell debris and aggregates to generate a purified platelet extract. In some embodiments, cell debris is removed before and after extraction of platelet proteins. Removal of cell debris and aggregates can be performed with any standard technique known to those with ordinary skill in the art and described herein.
Micro-Filtration In some embodiments, cell debris and aggregates are removed from the platelet extract via micro-filtration, in which the extract is passed through a filter at a defined flow rate. In some embodiments, a filter membrane is selected from polyvinylidene fluoride (PVDF), nylon, polyether sulfone (PES), polysulfone (PS), regenerated cellulose (RC), and glass fiber. In some embodiments, a filter pore size is 0.2 μm. In some embodiments, a filter pore size is at least 0.2 μm. In some embodiments, a filter pore size is no larger than 2 μm. In some embodiments, a filter pore size is between 0.2 and 2 μm. In some embodiments, the flow rate is between about 0.1 to about 50 L/hour. In some embodiments, the flow rate is between about 0.1 and about 5 L/hour. In some embodiments, the flow rate is between about 10 and about 25 L/hour. In some embodiments, the flow rate is between about 25 and about 50 L/hour.

In some embodiments, the extract is passed through a filter with a pore size of about 0.2 to about 2 μm at a flow rate of about 0.1 to about 50 L/hour. In some embodiments, the extract is passed through a filter with a pore size of 0.2 to about 2 μm at a flow rate of about 0.1 to about 5 L/hour. In some embodiments, the extract is passed through a filter with a pore size of 0.2 to about 2 μm at a flow rate of about 10 to about 25 L/hour. In some embodiments, the extract is passed through a filter with a pore size of 0.2 to about 2 μm at a low rate of about 25 to about 50 L/hour. In some embodiments, the extract is passed through a filter with a pore size of 0.2 μm at a flow rate of about 0.1 to about 50 L/hour. In some embodiments, the extract is passed through a filter with a pore size of 0.2 μm at a flow rate of about 0.1 to about 5 L/hour. In some embodiments, the extract is passed through a filter with a pore size of 0.2 μm at a flow rate of about 10 to about 25 L/hour. In some embodiments, the extract is passed through a filter with a pore size of 0.2 μm at a low rate of about 25 to about 50 L/hour. In some embodiments, the extract is passed through a filter with a pore size of 2 μm at a flow rate of about 0.1 to about 50 L/hour. In some embodiments, the extract is passed through a filter with a pore size of 2 μm at a flow rate of about 0.1 to about 5 L/hour. In some embodiments, the extract is passed through a filter with a pore size of 2 μm at a flow rate of about 10 to about 25 L/hour. In some embodiments, the extract is passed through a filter with a pore size of 2 μm at a low rate of about 25 to about 50 L/hour.

In some embodiments, micro-filtration comprises at least two cycles of filtration. Without wishing to be bound by theory, filtering with a larger pore size following by filtering with a smaller pore size will help prevent clogging and increase recovery. In some embodiments, micro-filtration comprises at least three cycles of filtration. In some embodiments, micro-filtration comprises filtering with a 2 μm filter followed by filtering with a 0.2 μm filter.

Depth-Filtration

In some embodiments, cell debris and aggregates are removed from the platelet extract via depth-filtration in which the extract is passed through a filtration medium at a defined flow rate. In some embodiments, a filtration medium is selected from cellulose, polypropylene, diatomaceous earth (DE), and non-DE in stacked disks. In some embodiments, a filtration medium is cellulose. In some embodiments, a filtration medium is polypropylene. In some embodiments, a filtration medium is DE. In some embodiments, a filtration medium is non-DE in stacked disks. In some embodiments, the flow rate is between about 0.1 to about 50 L/hour. In some embodiments, the flow rate is between about 0.1 and about 5 L/hour. In some embodiments, the flow rate is between about 10 and about 25 L/hour. In some embodiments, the flow rate is between about 25 and about 50 L/hour.

In some embodiments, the platelet extract is flowed over a cellulose filter at about 0.1 to about 5 L/hour. In some embodiments, the platelet extract is flowed over a cellulose filter at about 10 to about 25 L/hour. In some embodiments, the platelet extract is flowed over a cellulose filter at about 25 to about 50 L/hour. In some embodiments, the platelet extract is flowed over a polypropylene filter at about 0.1 to about 5 L/hour. In some embodiments, the platelet extract is flowed over a polypropylene filter at about 10 to about 25 L/hour. In some embodiments, the platelet extract is flowed over a polypropylene filter at about 25 to about 50 L/hour. In some embodiments, the platelet extract is flowed over a DE filter at about 0.1 to about 5 L/hour. In some embodiments, the platelet extract is flowed over a DE filter at about 10 to about 25 L/hour. In some embodiments, the platelet extract is flowed over a DE filter at about 25 to about 50 L/hour. In some embodiments, the platelet extract is flowed over a non-DE filter at about 0.1 to about 5 L/hour. In some embodiments, the platelet extract is flowed over a non-DE filter at about 10 to about 25 L/hour. In some embodiments, the platelet extract is flowed over a non-DE filter at about 25 to about 50 L/hour.

Centrifugation

In some embodiments, cell debris and aggregates are removed from the platelet extract via centrifugal force for a defined amount of time. In some embodiments, the platelet extract is centrifuged at about 50 to about 50,000×g. In some embodiments, the platelet extract is centrifuged at about 10 to about 10,000×g. In some embodiments, the platelet extract is centrifuged at about 10,000 to about 25,000×g. In some embodiments, the platelet extract is centrifuged at about 25,000 to about 50,000×g. In some embodiments, the platelet extract is centrifuged for about 1 to about 100 minutes. In some embodiments, the platelet extract is centrifuged for about 1 to about 60 minutes. In some embodiments, the platelet extract is centrifuged for about 60 to about 100 minutes. In some embodiments, the platelet extract is centrifuged at about 50 to about 50,000×g for about 1 to about 100 minutes. In some embodiments, the platelet extract is centrifuged at about 50 to about 50,000×g for about 1 to about 60 minutes. In some embodiments, the platelet extract is centrifuged at about 50 to about 50,000×g for about 60 to about 100 minutes. In some embodiments, the platelet extract is centrifuged at about 10 to about 10,000×g for about 1 to about 100 minutes. In some embodiments, the platelet extract is centrifuged at about 10 to about 10,000×g for about 1 to about 60 minutes. In some embodiments, the platelet extract is centrifuged at about 10 to about 10,000×g for about 60 to about 100 minutes. In some embodiments, the platelet extract is centrifuged at about 10,000 to about 25,000×g for about 1 to about 100 minutes. In some embodiments, the platelet extract is centrifuged at about 10,000 to about 25,000×g for about 1 to about 60 minutes. In some embodiments, the platelet extract is centrifuged at about 10,000 to about 25,000×g for about 60 to about 100 minutes. In some embodiments, the platelet extract is centrifuged at about 25,000 to about 50,000×g for about 1 to about 100 minutes. In some embodiments, the platelet extract is centrifuged at about 25,000 to about 50,000×g for about 1 to about 60 minutes. In some embodiments, the platelet extract is centrifuged at about 25,000 to about 50,000×g for about 60 to about 100 minutes.

Viral Inactivation and Removal

In some embodiments, a method for preparing the allogeneic human plasma and platelet derived product described herein comprises viral inactivation and/or viral removal.

The term "viral inactivation" refers to maintenance of viruses in the platelet suspension or platelet extract, but the viruses are rendered non-viable e.g. by dissolving their lipid coat or by destroying their virion structure. The term "virus removal" refers to removal of viruses from the platelet suspension or platelet extract.

In some embodiments, viral inactivation occurs before removal of blood cells. In some embodiments, viral inactivation occurs after removal of blood cells. In some embodiments, viral inactivation occurs during removal of blood cells. In some embodiments, viral inactivation occurs during lysis of the platelets. In some embodiments, viral inactivation occurs during lysis of the platelets via buffer-detergent methods as described above. In some embodiments, viral inactivation occurs after platelet lysis. In some embodiments, viral inactivation occurs before dilution of the platelet suspension or platelet extract. In some embodiments, viral inactivation occurs after dilution of the platelet suspension or platelet extract. In some embodiments, viral inactivation occurs during dilution of the platelet suspension or platelet extract. In some embodiments, viral inactivation occurs before removal of cell debris and aggregates from the platelet extract. In some embodiments, viral inactivation occurs after removal of cell debris and aggregates from the platelet extract. In some embodiments, viral inactivation occurs during removal of cell debris and aggregates from the platelet extract.

In some embodiments, viral inactivation occurs with heat treatment. In some embodiments, heat inactivation is performed at a temperature of at least 45° C. In some embodiments, heat inactivation is performed at a temperature of no higher than 45° C. In some embodiments, heat inactivation is performed at a temperature of 45° C. In some embodiments, heat inactivation is performed for 1 hour. In some embodiments, heat inactivation is performed for at least 1 hour. In some embodiments, heat inactivation is performed at a temperature no higher than 45° C. for 1 hour. In some embodiments, heat inactivation is performed at a temperature of no higher than 45° C. for at least 1 hour. In some embodiments, heat inactivation is performed at a temperature of at least 45° C. for 1 hour. In some embodiments, heat inactivation is performed at a temperature of at least 45° C. for at least 1 hour. In some embodiments, heat inactivation is performed at a temperature of 45° C. for 1 hour. In some embodiments, heat inactivation is performed at a temperature of 45° C. for at least 1 hour. In some embodiments, a stabilizer can be added to platelet lysate to stabilize platelet proteins. In some embodiments, the stabilizer is sucrose. In some embodiments, the stabilizer is glycine. In some embodiments, the stabilizer is a combination of sucrose and glycine.

In some embodiments, viral inactivation occurs by varying pH. In some embodiments, the pH is lowered to inactivate viruses. In some embodiments, the pH is raised to inactivate viruses. In some embodiments, the pH is lowered to about 4. In some embodiments, the pH is lowered to about 3 to about 5. In some embodiments, the pH change lasts for about 6 to about 24 hours. In some embodiments, the pH change lasts for about 6 to about 16 hours. In some embodiments, the pH change lasts for about 16 to about 24 hours. In some embodiments, the pH is lowered to about 4 for about 6 to about 24 hours. In some embodiments, the pH is lowered to about 4 for about 6 to about 16 hours. In some embodiments, the pH is lowered to about 4 for about 16 to about 24 hours. In some embodiments, the pH is lowered to about 3 to about 5 for about 6 to about 24 hours. In some embodiments, the pH is lowered to about 3 to about 5 for about 6 to about 16 hours. In some embodiments, the pH is lowered to about 3 to about 5 for about 16 to about 24 hours.

In some embodiments, viral inactivation occurs with UV. In some embodiments, viral inactivation occurs with UV and riboflavin. In some embodiments, viral inactivation occurs with UV and riboflavin. In some embodiments, viral inactivation occurs with gamma radiation. In some embodiments, viral inactivation occurs with chemical treatment. Chemicals that can inactivate viruses include, but are not limited to, b-propiolactone, riboflavin, sulfites, and caprylate.

In some embodiments, viral removal occurs with nanofiltration. In some embodiments, the nanometer-scale filters can be any one of the following, Planova BioEX, Viresolve, Ultipore, Pegasus, or Virosart. In some embodiments, the nanometer-scale filter is a Planova S20N filter. In some embodiments, the nanofilter has a pore size of about 15 to about 75 nm. In some embodiments, the nanofilter has a pore size of less than 75 nm. In some embodiments, the nanofilter has a pore size of about 15 nm. In some embodiments, the nanofilter has a pore size of about 20 nm. In some embodiments, the nanofilter has a pore size of about 35 nm. In some embodiments, the nanofilter has a pore size of about 75 nm.

In some embodiments, viral removal occurs with filtration through a hollow fiber. In some embodiments, viral removal occurs with ion exchange chromatography. In some embodiments, viral removal occurs with affinity chromatography.

In some embodiments, viral removal occurs before removal of blood cells. In some embodiments, viral removal occurs after removal of blood cells. In some embodiments, viral removal occurs during removal of blood cells. In some embodiments, viral removal occurs during lysis of the platelets. In some embodiments, viral removal occurs during lysis of the platelets via buffer-detergent methods as described above. In some embodiments, viral removal occurs after platelet lysis. In some embodiments, viral removal occurs before dilution of the platelet suspension or platelet extract. In some embodiments, viral removal occurs after dilution of the platelet suspension or platelet extract. In some embodiments, viral removal occurs during dilution of the platelet suspension or platelet extract. In some embodiments, viral removal occurs before removal of cell debris and aggregates from the platelet extract. In some embodiments, viral removal occurs after removal of cell debris and aggregates from the platelet extract. In some embodiments, viral removal occurs during removal of cell debris and aggregates from the platelet extract.

In some embodiments, successful viral removal is determined by RT-qPCR. In some embodiments, RT-qPCR is used to detect viral nucleic acids.

Concentration

In some embodiments, the purified platelet extract described above is concentrated to generate the allogeneic human plasma and platelet derived product. In some embodiments, the platelet proteins and plasma proteins of the purified platelet extract are concentrated. Methods for concentrating proteins are known to those of skill in the art and described herein.

In some embodiments, concentration of the purified platelet extract occurs via buffer exchange and concentration. In some embodiments, buffer exchange removes components used throughout the method to maintain proteins in solution. In some embodiments, buffer exchanges removes components used during extraction of platelet proteins. In some embodiments, buffer exchange and concentration is carried out via a tangential flow filtration (TFF) system. In TFF, the solution of interest (e.g., purified platelet extract) is flowed over a membrane held by a module. In some embodiments, the module is selected from cassettes, hollow fiber, and ceramic. In some embodiments, the membrane is selected from modified polyethersulfone (mPES), regenerated cellulose, mixed cellulose ester, stabilized cellulose, phosphatidylserine (PS), and polyethersulfone (PES). In some embodiments, membranes are assembled into a filter assembly. In some embodiments, the membrane molecular weight cut off is between 1 kDa and 1,000 Kda. In some embodiments, the molecular weight cut off is between 500 kDa and 1,000 kDa. In some embodiments, the molecular weight cut off is between 750 kDa and 1,000 kDa. In some embodiments, the membrane molecular weight cut off is between 1 kDa and 500 kDa. In some embodiments, the molecular weight cut off is between 1 kDa and 30 kDa. In some embodiments, the molecular weight cut off is between 30 kDa and 60 kDa. In some embodiments, the molecular cut off weight is between 100 and 200 kDa. In some embodiments, the molecular cut off weight is between 250 and 500 kDa.

In some embodiments, the solution of interest is flowed over at least two filter assemblies. In some embodiments, the solution of interest is flowed over at least three filter assemblies. In some embodiments, the solution of interest is flowed over at least four filter assemblies. In some embodiments, the molecular weight cut off of a first filter assembly is different from the molecular weight cut off of a second filter assembly. In some embodiments, the molecular weight cut offs of every filter assembly is different.

The TFF system is conditioned with buffer prior to use. In some embodiments, conditioning with buffer wets the membrane. In some embodiments, conditions with buffer removes preservatives and storage solutions that may be present. Following conditioning, the solution of interest is introduced into the TFF system. A pump generates a tangential flow across the membrane, allowing solvent to pass through while the target molecules (e.g., purified platelet concentrate) is retained. As the feed solution flows across the membrane, water is driven through the membrane, creating a concentrated retentate on one side of the membrane. In some embodiments the flow rate is about 1 to about 50 L/hour. In some embodiments, the flow rate is at least 1 L/hour. In some embodiments, the flow rate is no more than 1 L/hour. In some embodiments, the flow rate is at least 50 L/hour. In some embodiments, the flow rate is no more than 50 L/hour. In some embodiments, the flow rate is about 1 to about 10 L/hour. In some embodiments, the flow rate is at about 10 to about 20 L/hour. In some embodiments, the flow rate is about 20 to about 30 L/hour. In some embodiments, the flow rate is about 30 to about 40 L/hour. In some embodiments, the flow rate is about 40 to about 50 L/hour. The retentate contains the concentrated target molecules, while the permeate (filtrate) contains the removed impurities and excess solvent/buffer. In some embodiments, TFF solvents and buffers are selected from phosphate, citrate, EDTA, NaCl, KCl, $MgCl_2$, $CaCl_2$), sucrose, glucose, trehalose, polysorbate 20 (PS20) and polysorbate 80 (PS80). In some embodiments, the buffer comprises phosphate at a concentration of about 20 to about 200 mM. In some embodiments, the buffer comprises phosphate at a concentration no greater than 20 mM. In some embodiments, the buffer comprises citrate at a concentration of about 15 to about 200 mM. In some embodiments, the buffer comprises citrate at a concentration no greater than 15 mM. In some embodiments, the buffer comprises EDTA at a concentration of about 0.3 to about 200 mM. In some embodiments, the buffer comprises EDTA at a concentration no greater than 0.3 mM. In some embodiments, the buffer comprises NaCl at a concentration of about 150 to about 200 mM. In some embodiments, the buffer comprises NaCl at a concentration no greater than 150 mM. In some embodiments, the buffer comprises KCl at a concentration of about 1 to about 200 mM. In some embodiments, the buffer comprises KCl at a concentration no greater than 1 mM. In some embodiments, the buffer comprises $MgCl_2$ at a concentration of about 1.3 to about 200 mM. In some embodiments, the buffer comprises $MgCl_2$ at a concentration no greater than 1.3 mM. In some embodiments, the buffer comprises $CaCl_2$ at a concentration of about 2.4 to about 200 mM. In some embodiments, the buffer comprises $CaCl_2$ at a concentration no greater than 200 mM. In some embodiments, the buffer comprises sucrose at a concentration of about 10 to about 200 mM. In some embodiments, the buffer comprises sucrose at a concentration no greater than 10 mM. In some embodiments, the buffer comprises glucose at a concentration of about 10 to about 200 mM. In some embodiments, the buffer comprises glucose at a concentration no greater than 10 mM. In some embodiments, the buffer comprises trehalose at a concentration of about 10 to about 200 mM. In some embodiments, the buffer comprises trehalose at a concentration no greater than 10 mM. In embodiments, the buffer comprises PS20 at a concentration of about 0.025 to about 10%. In some embodiments, the buffer comprises PS20 at a concentration no greater than 0.025%. In embodiments, the buffer comprises PS80 at a concentration of about 0.025 to about 10%. In some embodiments, the buffer comprises PS80 at a concentration no greater than 0.025%.

In some embodiments, the buffer can be exchanged using a protein stabilizing buffer. In some embodiments, protein stabilizing buffers are selected from, phosphate, acetate, citrate, sulphate, glutamate, lactate, histidine, succinate, aspartic acid, tromethamine, and 2-(N-morpholino)ethanesulfonic acid (MES). In some embodiments, the protein stabilizing buffers include buffers that stabilize proteins and adjust tonicity and osmolarity. In some embodiments, protein stabilizing buffers comprise sucrose, dextrose, trehalose, sorbitol, mannitol, maltose, sodium chloride, potassium chloride, calcium chloride, magnesium chloride, or any combination thereof.

The concentrated and diafiltrated target molecules are collected as the final retentate. The product can then be further processed or formulated for the subsequent downstream processing steps.

Removing Plasma Proteins

In some embodiments, plasma proteins are removed from the allogeneic human plasma and platelet derived product. In some embodiments, the plasma proteins are removed after pooling. In some embodiments, plasma proteins are removed before platelet protein extraction. In some embodiments, plasma proteins are removed after platelet protein extraction. In some embodiments, plasma proteins are removed before concentration. In some embodiments, plasma proteins are removed after concentration.

In some embodiments, albumin is removed. In some embodiments, immunoglobulins are removed. In some embodiments, albumin and immunoglobulins are removed. In some embodiments, albumin and immunoglobulins are removed simultaneously. In some embodiments, the same affinity column is used to remove albumin and immunoglobulins. In some embodiments, different affinity columns are used in parallel to remove albumin and immunoglobulins.

Concentration Adjustment and Sterile Filtration

In some embodiments, the allogeneic human plasma and platelet derived product is sterile filtered. Filtration can be performed with any standard technique known to those with ordinary skill in the art. In some aspects, the disclosure provides methods of sterile filtering concentrated platelet lysate.

In some embodiments, the allogeneic human plasma and platelet derived product is diluted to a desired concentration. In some embodiments, the allogeneic human plasma and platelet derived product is concentrated to a desired concentration. In some embodiments, the desired concentration is about 20 to about 500 mg/mL. In some embodiments, the desired concentration is about 50 to about 500 mg/mL. In some embodiments, the desired concentration is greater than 50 mg/mL and less than or about 500 mg/mL. In some embodiments, the desired concentration is about 50 to about 80 mg/mL. In some embodiments, the desired concentration is about 80 to about 160 mg/mL. In some embodiments, the desired concentration is about 160 to about 320 mg/mL. In some embodiments, the desired concentration is about 70 to about 250 mg/mL. In some embodiments, the desired concentration is about 70 to about 150 mg/mL. In some embodiments, the desired concentration is about 150 to about 250 mg/mL. In some embodiments, the desired concentration is about 150 to about 200 mg/mL. In some embodiments, the desired concentration is at least 150 mg/mL. In some embodiments, the desired concentration is at least 200 mg/mL. In some embodiments, the desired concentration is less than about 500 mg/mL. in some embodiments, the desired concentration is greater than 50 mg/mL.

In some embodiments, the allogeneic human plasma and platelet derived product is passed through a filter with a pore size of about 0.1 to about 0.22 µm. In some embodiments, the filter pore size is no bigger than 0.22 µm. In some embodiments, the filter pore size is at least 0.1 µm. In some embodiments, the filter pore size is about 0.1 to about 0.2 µm. In some embodiments, the filter material is selected from polyvinylidene fluoride (PVDF), nylon, polyether sulfone (PES), polysulfone (PS), regenerated cellulose (RC), and glass fiber.

Lyophilization

In some embodiments, the allogeneic human plasma and platelet derived product is lyophilized. Lyophilization is advantageous at least because the resulting substance is easier to store, can be kept in a small place, is easier to handle, can be applied in a formulation (e.g., in a dry powder, an ointment, a suspension, a solution, a gel, a cream or a biocompatible, synthetic or natural solid matrix) chosen according to the circumstances, can be administered at an optimal dose, normally has a longer shelf life, and can easily be screened for the most active preparation.

In some embodiments, lyophilization comprises freezing the allogeneic human plasma and platelet derived product. In some embodiments, freezing occurs at a temperature lower than −10° C. In some embodiments, freezing occurs at a temperature lower than −20° C. In some embodiments, freezing occurs at a temperature lower than −60° C. In some embodiments, freezing occurs at a temperature lower than 80° C. In some embodiments, freezing occurs for at least 30 minutes. In some embodiments, freezing occurs for about 1 to about 3 hours. In some embodiments, freezing occurs for about 6 to about 12 hours. In some embodiments, freezing occurs overnight. In some embodiments, freezing occurs for no more than 24 hours.

In some embodiments, lyophilization comprises drying the allogeneic human plasma and platelet derived product. In some embodiments, a drying is facilitated by a vacuum. In some embodiments, lyophilization comprises reducing the water concentration of the allogeneic human plasma and platelet derived product. In some embodiments, reducing the water concentration prevents biological or chemical reactions.

Exemplary Methods of Making the Compositions

In some embodiments, a method for preparing a pharmaceutical composition comprising an allogenic human plasma and platelet derived product comprises (a) extracting platelet proteins from plasma and platelets from one or more human donor subjects, thereby generating a platelet extract, (b) removing cell debris and aggregates from the platelet extract, thereby generating a purified platelet extract, and (c) concentrating the purified platelet extract. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, and (c) concentrating the purified platelet extract. In some embodiments, the method comprises (a) extracting platelet proteins from plasma and platelets from one or more human donor subjects with a buffer-detergent, thereby generating a platelet extract, (b) removing cell debris and aggregates from the platelet extract, thereby generating a purified platelet extract, and (c) concentrating the purified platelet extract. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, and (c) concentrating the purified platelet extract.

In some embodiments, the method comprises (a) extracting platelet proteins from plasma and platelets from one or more human donor subjects, thereby generating platelet extract, (b) removing cell debris and aggregates from the platelet extract, thereby generating a purified platelet extract, and (c) concentrating the purified platelet extract via tangential flow filtration (TFF). In some embodiments, the method comprises (a) extracting platelet proteins from plasma and platelets from one or more human donor subjects, (b) removing cell debris and aggregates from the platelet extract, thereby generating purified platelet extract, and (c) concentrating the purified platelet extract via spin filters.

In some embodiments, the method comprises (a) extracting platelet proteins from plasma and platelets from one or more human donor subjects via freeze-thaw, thereby generating platelet extract, (b) removing cell debris and aggregates from the platelet extract, thereby generating a purified platelet extract, and (c) concentrating the purified platelet extract via TFF. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, and (c) concentrating the purified platelet extract via spin filters.

In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, and (c) concentrating the purified platelet extract via TFF. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, and (c) concentrating the purified platelet extract via spin filters.

In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, and (c) concentrating the purified platelet extract via TFF. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, and (c) concentrating the purified platelet extract via spin filters.

In some embodiments, the methods comprise (a) extracting platelet proteins from plasma and platelets from one or more human donor subjects, thereby generating a platelet extract, (b) removing cell debris and aggregates from the platelet extract via centrifugation, thereby generating a purified platelet extract, and (c) concentrating the purified platelet extract. In some embodiments, the method comprises extracting platelet proteins from plasma and platelets from one or more human donor subjects via freeze-thaw, thereby generating a platelet extract, (b) removing cell debris and aggregates from the platelet extract via centrifugation, thereby generating a purified platelet extract, and (c) concentrating the purified platelet extract. In some embodiments, the method comprises (a) extracting platelet proteins from plasma and platelets from one or more human donor subjects via buffer-detergent, thereby generating a platelet extract, (b) removing cell debris and aggregates from the platelet extract via centrifugation, thereby generating a purified platelet extract, and (c) concentrating the purified platelet extract. In some embodiments, the method comprises (a) extracting platelet proteins from plasma and platelets from one or more human donor subjects via osmotic pressure, thereby generating a platelet extract, (b) removing cell debris and aggregates from the platelet extract via centrifugation, thereby generating a purified platelet extract, and (c) concentrating the purified platelet extract.

In some embodiments, the method comprises (a) extracting platelet proteins from plasma and platelets from one or more human donor subjects, thereby generating a platelet extract, (b) removing cell debris and aggregates from the platelet extract via centrifugation, thereby generating a purified platelet extract, and (c) concentrating purified platelet extract via TFF. In some embodiments, the method comprises (a) extracting platelet proteins from plasma and platelets from one or more human donor subjects, thereby generating a platelet extract, (b) removing cell debris and aggregates from the platelet extract via centrifugation, generating a purified platelet extract, and (c) concentrating the purified platelet extract via spin filters.

In some embodiments, the method comprises (a) extracting platelet proteins from plasma and platelets from one or more human donors via freeze-thaw, thereby generating a platelet extract (b) removing cell debris and aggregates from the platelet extract via centrifugation, thereby generating a purified platelet extract, and (c) concentrating the purified platelet extract via TFF. In some embodiments, the method comprises (a) extracting platelet proteins from plasma and platelets from one or more human donor subjects via freeze-thaw, thereby generating a platelet extract, (b) removing cell debris and aggregates from the platelet extract via centrifugation, thereby generating a purified platelet extract, and (c) concentrating the purified platelet extract via spin filters.

In some embodiments, the method comprises (a) extracting platelet proteins from plasma and platelets from one or more human donor subjects via buffer-detergent, thereby generating a platelet extract, (b) removing cell debris and aggregates from the platelet extract via centrifugation, thereby generating a purified platelet extract, and (c) concentrating the purified platelet extract via TFF. In some embodiments, the method comprises (a) extracting platelet proteins from plasma and platelets from one or more human donor subjects via buffer-detergent, thereby generating a platelet extract, (b) removing cell debris and aggregates via centrifugation, thereby generating a purified platelet extract, and (c) concentrating the purified platelet extract via spin filters.

In some embodiments, the method comprises (a) extracting platelet proteins from plasma and platelets from one or more human donor subjects via osmotic pressure, thereby generating a platelet extract, (b) removing cell debris and aggregates from the platelet extract via centrifugation, thereby generating a purified platelet extract, and (c) concentrating the purified platelet extract via TFF. In some embodiments, the method comprises (a) extracting platelet proteins from plasma and platelets from one or more human donor subjects via osmotic pressure, thereby generating a platelet extract, (b) removing cell debris and aggregates from the platelet extract via centrifugation, thereby generating a purified platelet extract, and (c) concentrating the purified platelet extract via spin filters.

In some embodiments, the methods comprise (a) extracting platelet proteins from plasma and platelets from one or more human donor subjects, thereby generating a platelet extract, (b) removing cell debris and aggregates from the platelet extract via filtration, thereby generating a purified platelet extract, and (c) concentrating the purified platelet extract. In some embodiments, the method comprises extracting platelet proteins from plasma and platelets from one or more human donors via freeze-thaw, thereby generating a platelet extract (b) removing cell debris and aggregates from the platelet extract via filtration, thereby generating a purified platelet extract, and (c) concentrating the purified platelet extract. In some embodiments, the method comprises (a) extracting platelet proteins from plasma and platelets from one or more human donor subjects via buffer-detergent, thereby generating a platelet extract, (b) removing cell debris and aggregates from the platelet extract via filtration, thereby generating a purified platelet extract, and (c) concentrating the purified platelet extract. In some embodiments, the method comprises (a) extracting platelet proteins from plasma and platelets from one or more human donor subjects via osmotic pressure, thereby generating a platelet extract, (b) removing cell debris and aggregates from the platelet extract via filtration, thereby generating a purified platelet extract, and (c) concentrating the purified platelet extract.

In some embodiments, the method comprises (a) extracting platelet proteins from plasma and platelets from one or more human donor subjects, thereby generating a platelet extract, (b) removing cell debris and aggregates via filtration, thereby generating a purified platelet extract, and (c) concentrating the purified platelet extract via TFF. In some embodiments, the method comprises (a) extracting platelet proteins from plasma and platelets from one or more human donor subjects, thereby generating a platelet extract, (b) removing cell debris and aggregates from the platelet extract via filtration, thereby generating a purified platelet extract, and (c) concentrating the purified platelet extract via spin filters.

In some embodiments, the method comprises (a) extracting platelet proteins from plasma and platelets from one or more human donor subjects via freeze-thaw, thereby generating a platelet extract, (b) removing cell debris and aggregates from the platelet extract via filtration, thereby generating a purified platelet extract, and (c) concentrating the purified platelet extract via TFF. In some embodiments, the method comprises (a) extracting platelet proteins from plasma and platelets from one or more human donor subjects via freeze-thaw, thereby generating a platelet extract (b) removing cell debris and aggregates from the platelet extract via filtration, thereby generating a purified platelet extract, and (c) concentrating the purified platelet extract via spin filters.

In some embodiments, the method comprises (a) extracting platelet proteins from plasma and platelets from one or more human donor subjects via buffer-detergent, thereby generating a platelet extract (b) removing cell debris and aggregates from the platelet extract via filtration, thereby generating a purified platelet extract, and (c) concentrating the purified platelet extract via TFF. In some embodiments, the method comprises (a) extracting platelet proteins from plasma and platelets from one or more human donor subjects via buffer-detergent, thereby generating a platelet extract, (b) removing cell debris and aggregates from the platelet extract via filtration, thereby generating a purified platelet extract, and (c) concentrating the purified platelet extract via spin filters.

In some embodiments, the method comprises (a) extracting platelet proteins from plasma and platelets from one or more human donor subjects via osmotic pressure, thereby generating a platelet extract, (b) removing cell debris and aggregates from the platelet extract via filtration, thereby generating a purified platelet extract, and (c) concentrating the purified platelet extract via TFF. In some embodiments, the method comprises (a) extracting platelet proteins from plasma and platelets from one or more human donor subjects via osmotic pressure, thereby generating a platelet extract, (b) removing the cell debris and aggregates from the platelet extract via filtration, thereby generating a purified platelet extract, and (c) concentrating the purified platelet extract via spin filters.

In some embodiments, the methods comprise (a) extracting platelet proteins from plasma and platelets from one or more human donor subjects, thereby generating a platelet extract, (b) removing the cell debris and aggregates from the platelet extract via centrifugation and filtration, thereby generating a purified platelet extract, and (c) concentrating the purified platelet extract. In some embodiments, the method comprises extracting platelet proteins from plasma and platelets from one or more human donor subjects via freeze-thaw, thereby generating a platelet extract, (b) removing cell debris and aggregates from the platelet extract via centrifugation and filtration, thereby generating a purified platelet extract, and (c) concentrating the purified platelet extract. In some embodiments, the method comprises (a) extracting platelet proteins from plasma and platelets from one or more human donor subjects via buffer-detergent, thereby generating a platelet extract, (b) removing cell debris and aggregates from the platelet extract via centrifugation and filtration, thereby generating a purified platelet extract, and (c) concentrating the purified platelet extract. In some embodiments, the method comprises (a) extracting platelet proteins from plasma and platelets from one or more human donor subjects via osmotic pressure, thereby generating a platelet extract, (b) removing cell debris and aggregates from the platelet extract via centrifugation and filtration, thereby generating a purified platelet extract, and (c) concentrating the purified platelet extract.

In some embodiments, the method comprises (a) extracting platelet proteins from plasma and platelets from one or more human donor subjects, thereby generating a platelet extract (b) removing cell debris and aggregates from the platelet extract via centrifugation and filtration, thereby generating a purified platelet extract, and (c) concentrating the purified platelet extract via TFF. In some embodiments, the method comprises (a) extracting platelet proteins from plasma and platelets from one or more human donor subjects, thereby generating a platelet extract, (b) removing cell debris and aggregates from the platelet extract via centrifugation and filtration, thereby generating a purified platelet extract, and (c) concentrating the purified platelet extract via spin filters.

In some embodiments, the method comprises (a) extracting platelet proteins from plasma and platelets from one or more human donor subjects via freeze-thaw, thereby generating a platelet extract, (b) removing cell debris and aggregates from the platelet extract via centrifugation and filtration, thereby generating a purified platelet extract, and (c) concentrating the purified platelet extract via TFF. In some embodiments, the method comprises (a) extracting platelet proteins from plasma and platelets from one or more human donor subjects via freeze-thaw, thereby generating a platelet extract, (b) removing the cell debris and aggregates from the platelet extract via centrifugation and filtration, thereby generating a purified platelet extract, and (c) concentrating the purified platelet extract via spin filters.

In some embodiments, the method comprises (a) extracting platelet proteins from plasma and platelets from one or more human donor subjects via buffer-detergent, thereby generating a platelet extract (b) removing cell debris and aggregates from the platelet extract via centrifugation and filtration, thereby generating a purified platelet extract, and (c) concentrating the purified platelet extract via TFF. In some embodiments, the method comprises (a) extracting platelet proteins from plasma and platelets from one or more human donor subjects via buffer-detergent, thereby generating a platelet extract, (b) removing cell debris and aggregates from the platelet extract via centrifugation and filtration, thereby generating a purified platelet extract, and (c) concentrating the purified platelet extract via spin filters.

In some embodiments, the method comprises (a) extracting platelet proteins from plasma and platelets from one or more human donor subjects via osmotic pressure, thereby generating a platelet extract (b) removing cell debris and aggregates from the platelet extract via centrifugation and filtration, thereby generating a purified platelet extract, and (c) concentrating the purified platelet extract via TFF. In some embodiments, the method comprises (a) extracting platelet proteins from plasma and platelets from one or more human donor subjects via osmotic pressure, thereby generating a platelet extract, (b) removing the cell debris and aggregates from the platelet extract via centrifugation and filtration, thereby generating a purified platelet extract and (c) concentrating the purified platelet extract via spin filters.

In some embodiments, the method comprises (a) obtaining a platelet suspension from whole blood or apheresis, (b) extracting the platelet proteins from plasma and platelets from one or more human donor subjects, thereby generating a platelet extract (c) removing cell debris and aggregates from the platelet extract, thereby generating a purified platelet extract, and (d) concentrating the purified platelet extract. In some embodiments, the method comprises (a) obtaining a platelet suspension from whole blood or apheresis, (b) extracting the platelet proteins from plasma and platelets from one or more human donor subjects via freeze-thaw, thereby generating a platelet extract, (c) removing cell debris and aggregates from the platelet extract, thereby generating a purified platelet extract, and (d) concentrating the purified platelet extract. In some embodiments, the method comprises (a) obtaining a platelet suspension from whole blood or apheresis, (b) extracting the platelet proteins from plasma and platelets from one or more human donor subjects via detergent-buffer, thereby generating a platelet extract, (c) removing cell debris and aggregates from the platelet extract, thereby generating a purified platelet extract, and (d) concentrating the purified platelet extract. In some embodiments, the method comprises (a) obtaining a platelet suspension from whole blood or apheresis, (b) extracting the platelet proteins from plasma and platelets from one or more human donor subjects via osmotic pressure, thereby generating a platelet extract, (c) removing cell debris and aggregates from the platelet extract, thereby generating a purified platelet extract and (d) concentrating the purified platelet extract.

In some embodiments, the method comprises (a) obtaining a platelet suspension from whole blood or apheresis, (b) extracting the platelet proteins from plasma and platelets from one or more human donor subjects, thereby generating a platelet extract, (c) removing cell debris and aggregates from the platelet extract, thereby generating a purified platelet extract, and (d) concentrating the purified platelet extract via TFF. In some embodiments, the method comprises (a) obtaining a platelet suspension from whole blood or apheresis, (b) extracting the platelet proteins from plasma and platelets from one or more human donor subjects, thereby generating a platelet extract, (c) removing cell debris and aggregates from the platelet extract, thereby generating a purified platelet extract, and (d) concentrating the purified platelet extract via spin filters.

In some embodiments, the method comprises (a) obtaining a platelet suspension from whole blood or apheresis, (b) extracting the platelet proteins from plasma and platelets from one or more human donor subjects via freeze-thaw, thereby generating a platelet extract, (c) removing cell debris and aggregates from the platelet extract, thereby generating a purified platelet extract, and (d) concentrating the purified platelet extract via TFF. In some embodiments, the method comprises (a) obtaining a platelet suspension from whole blood or apheresis, (b) extracting the platelet proteins from plasma and platelets from one or more human donor subjects via freeze-thaw, thereby generating a platelet extract, (c) removing cell debris and aggregates from the platelet extract, thereby generating a purified platelet extract, and (d) concentrating the purified platelet extract via spin filters.

In some embodiments, the method comprises (a) obtaining a platelet suspension from whole blood or apheresis, (b) extracting the platelet proteins from plasma and platelets from one or more human donor subjects via buffer-detergent, thereby generating a platelet extract, (c) removing cell debris and aggregates from the platelet extract, thereby generating a purified platelet extract, and (d) concentrating the purified platelet extract via TFF. In some embodiments, the method comprises (a) obtaining a platelet suspension from whole blood or apheresis, (b) extracting the platelet proteins from plasma and platelets from one or more human donor subjects via buffer-detergent, thereby generating a platelet extract, (c) removing cell debris and aggregates from the platelet extract, thereby generating a purified platelet extract, and (d) concentrating the purified platelet extract via spin filters.

In some embodiments, the method comprises (a) obtaining a platelet suspension from whole blood or apheresis, (b) extracting the platelet proteins from plasma and platelets from one or more human donor subjects via osmotic pressure, thereby generating a platelet extract, (c) removing cell debris and aggregates from the platelet extract, thereby generating a purified platelet extract, and (d) concentrating the purified platelet extract via TFF. In some embodiments, the method comprises (a) obtaining a platelet suspension from whole blood or apheresis, (b) extracting the platelet proteins from plasma and platelets from one or more human donor subjects via osmotic pressure, thereby generating a platelet extract (c) removing cell debris and aggregates from the platelet extract, thereby generating a purified platelet extract, and (d) concentrating the purified platelet extract via spin filters.

In some embodiments, the method comprises (a) obtaining and diluting a platelet suspension from whole blood or apheresis, (b) extracting the platelet proteins from plasma and platelets from one or more human donor subjects, thereby generating a platelet extract (c) removing cell debris and aggregates from the platelet extract, thereby generating a purified platelet extract, and (d) concentrating the purified platelet extract. In some embodiments, the method comprises (a) obtaining and diluting a platelet suspension from whole blood or apheresis via dilution, (b) extracting the platelet proteins from plasma and platelets from one or more human donor subjects via freeze-thaw, thereby generating a platelet extract, (c) removing cell debris and aggregates from the platelet extract, thereby generating a purified platelet extract, and (d) concentrating the purified platelet extract. In some embodiments, the method comprises (a) obtaining and diluting a platelet suspension from whole blood or apheresis, (b) extracting the platelet proteins from plasma and platelets from one or more human donor subjects via detergent-buffer, thereby generating a platelet extract, (c) removing cell debris and aggregates from the platelet extract, thereby generating a purified platelet extract, and (d) concentrating the purified platelet extract. In some embodiments, the method comprises (a) obtaining and diluting a platelet suspension from whole blood or apheresis, (b) extracting the platelet proteins from plasma and platelets from one or more human donor subjects via osmotic pressure, thereby generating a platelet extract, (c) removing cell debris and aggregates from the platelet extract, thereby generating a purified platelet extract, and (d) concentrating the purified platelet extract.

In some embodiments, the method comprises (a) obtaining and diluting a platelet suspension from whole blood or apheresis, (b) extracting the platelet proteins from plasma and platelets from one or more human donor subjects, thereby generating a platelet extract, (c) removing cell debris and aggregates from the platelet extract, thereby generating a purified platelet extract, and (d) concentrating the purified platelet extract via TFF. In some embodiments, the method comprises (a) obtaining and diluting a platelet suspension from whole blood or apheresis, (b) extracting the platelet proteins from plasma and platelets from one or more human donor subjects, thereby generating a platelet extract, (c) removing cell debris and aggregates from the platelet extract, thereby generating a purified platelet extract, and (d) concentrating the purified platelet extract via spin filters.

In some embodiments, the method comprises (a) obtaining and diluting a platelet suspension from whole blood or apheresis, (b) extracting the platelet proteins from plasma and platelets from one or more human donor subjects via freeze-thaw, thereby generating a platelet extract, (c) removing cell debris and aggregates from the platelet extract, thereby generating a purified platelet extract, and (d) concentrating the purified platelet extract via TFF. In some embodiments, the method comprises (a) obtaining and diluting a platelet suspension from whole blood or apheresis, (b) extracting the platelet proteins from plasma and platelets from one or more human donor subjects via freeze-thaw, thereby generating a platelet extract, (c) removing cell debris and aggregates from the platelet extract, thereby generating a purified platelet extract and (d) concentrating the purified platelet extract via spin filters.

In some embodiments, the method comprises (a) obtaining and diluting a platelet suspension from whole blood or apheresis, (b) extracting the platelet proteins from plasma and platelets from one or more human donor subjects via buffer-detergent, thereby generating a platelet extract, (c) removing cell debris and aggregates from the platelet extract, thereby generating a purified platelet extract and (d) concentrating the purified platelet extract via TFF. In some embodiments, the method comprises (a) obtaining and diluting a platelet suspension from whole blood or apheresis, (b) extracting the platelet proteins from plasma and platelets from one or more human donor subjects via buffer-detergent, thereby generating a platelet extract, (c) removing cell debris and aggregates from the platelet extract, thereby generating a purified platelet extract, and (d) concentrating the purified platelet extract via spin filters.

In some embodiments, the method comprises (a) obtaining and diluting a platelet suspension from whole blood or apheresis, (b) extracting the platelet proteins from plasma and platelets from one or more human donor subjects via osmotic pressure, thereby generating a platelet extract, (c) removing cell debris and aggregates from the platelet extract, thereby generating a purified platelet extract, and (d) concentrating the purified platelet extract via TFF. In some embodiments, the method comprises (a) obtaining and diluting a platelet suspension from whole blood or apheresis, (b) extracting the platelet proteins from plasma and platelets from one or more human donor subjects via osmotic pressure, thereby generating a platelet extract, (c) removing cell debris and aggregates from the platelet extract, thereby generating a purified platelet extract, and (d) concentrating the purified platelet extract via spin filters.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the an allogeneic human plasma and platelet derived product with a nylon filter. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract, thereby generating an allogeneic human plasma and platelet derived product and (d) sterile filtering the allogeneic human plasma and platelet derived product with a nylon filter. In some embodiments, the method comprises (a) extracting platelet proteins from plasma and platelets from one or more human donor subjects via osmotic pressure, thereby generating a platelet extract (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating purified platelet extract via spin filters, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects via buffer-detergent, thereby generating a platelet extract (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via osmotic pressure, thereby generating a platelet extract (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects, thereby generating a platelet extract (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via freeze-thaw, thereby generating a platelet extract, (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via freeze-thaw, thereby generating a platelet extract, (b) clarifying the platelet extract, thereby generating a purified platelet extract, (c) concentrating the purified platelet extract, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via osmotic pressure thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects, thereby generating a platelet extract (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects, thereby generating a platelet extract, (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product. In some embodiments, the method comprises (a) extracting platelet proteins from plasma and platelets from one or more human donor subjects via freeze-thaw, thereby generating a platelet extract, (b) removing cell debris and aggregates from the platelet extract via centrifugation, thereby generating a purified platelet extract (c) concentrating the purified platelet extract, thereby generating an allogeneic human plasma and platelet derived product, and (d) sterile filtering the allogeneic human plasma and platelet derived product.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via freeze-thaw, thereby generating a platelet extract (b) removing cell debris and aggregates from the platelet extract, thereby generating a purified platelet extract (c) concentrating the purified platelet extract, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract (c) concentrating the purified platelet extract, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract (c) concentrating the purified platelet extract via spin filters, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects, thereby generating a platelet extract (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via freeze-thaw, thereby generating a platelet extract, (b) removing cell debris and aggregates via centrifugation, thereby generating a purified platelet extract, (c) concentrating the purified platelet extract, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects, thereby generating a platelet extract (b) removing cell debris and aggregates from the platelet extract, thereby generating a purified platelet extract, (c) concentrating the purified platelet extract, generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects, thereby generating a platelet extract (b) removing cell debris and aggregates from the platelet extract, thereby generating a purified platelet extract (c) concentrating the purified platelet extract via TFF, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects, thereby generating a platelet extract, (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product with a nylon filter. In some embodiments, the method comprises (a) extracting platelet proteins from plasma and platelets from one or more human donor subjects via freeze-thaw, thereby generating a platelet extract, (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product with a nylon filter.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract (c) concentrating the purified platelet extract via spin filters, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects, thereby generating a platelet extract (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via freeze-thaw, thereby generating a platelet extract, (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract, via TFF, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a PES filter.

In some embodiments, the method comprises (a) extracting platelet from plasma and platelets from one or more human donor subjects, via buffer-detergent, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via buffer-detergent, thereby generating a platelet extract, (b) removing cell debris and aggregates from platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via TFF, thereby generating an allogeneic human plasma and platelet derived product, and (d) sterile filtering the allogeneic human plasma and platelet derived product with a PES filter. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) concentrating the purified platelet extract via spin filters, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects, thereby generating a platelet extract, (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product with a PES filter. In some embodiments, the method comprises (a)

extracting platelet proteins from plasma and platelets from one or more human donor subjects via freeze-thaw, thereby generating a platelet extract, (b) removing cell debris and aggregates from the platelet extract via centrifugation, thereby generating a purified platelet extract, (c) concentrating the purified platelet extract, thereby generating an allogeneic human plasma and platelet derived product, and (d) sterile filtering the allogeneic human plasma and platelet derived product with a PES filter.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) diluting the purified platelet extract, and (d) concentrating the purified platelet extract. In some embodiments, the method comprises (a) extracting the platelet proteins from plasma and platelets from one or more human donor subjects via freeze-thaw, thereby generating a platelet extract, (b) removing cell debris and aggregates from the platelet extract, thereby generating a purified platelet extract, (c) diluting the purified platelet extract, and (d) concentrating the purified platelet extract. In some embodiments, the method comprises (a) extracting the platelet proteins from plasma and platelets from one or more human donor subjects via buffer-detergent, thereby generating a platelet extract, (b) removing cell debris and aggregates from the platelet extract, thereby generating a purified platelet extract, (c) diluting the purified platelet extract, and (d) concentrating the purified platelet extract. In some embodiments, the method comprises (a) extracting the platelet proteins from plasma and platelets from one or more human donor subjects via osmotic pressure, thereby generating a platelet extract, (b) removing cell debris and aggregates from the platelet extract, thereby generating a purified platelet extract (c) diluting the purified platelet extract, and (d) concentrating the purified platelet extract.

In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) diluting the purified platelet extract, and (d) concentrating the purified platelet extract via TFF. In some embodiments, the method comprises (a) extracting platelet proteins from plasma and platelets from one or more human donor subjects, thereby generating a platelet extract, (b) removing cell debris and aggregates from the platelet extract, thereby generating a purified platelet extract, (c) diluting the purified platelet extract, and (d) concentrating the purified platelet extract via spin filters.

In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) diluting the purified platelet extract, and (d) concentrating the purified platelet extract via TFF. In some embodiments, the method comprises (a) extracting platelet proteins from plasma and platelets from one or more human donor subjects via freeze-thaw, thereby generating a platelet extract, (b) removing cell debris and aggregates from the platelet extract, thereby generating a purified platelet extract, (c) diluting the purified platelet extract, and (d) concentrating the purified platelet extract via spin filters.

In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) diluting the purified platelet extract, and (d) concentrating the purified platelet extract via TFF. In some embodiments, the method comprises (a) extracting platelet proteins from plasma and platelets from one or more human donor subjects via buffer-detergent, thereby generating a platelet extract, (b) removing cell debris and aggregates from the platelet extract, thereby generating a purified platelet extract, (c) diluting the purified platelet extract, and (d) concentrating the purified platelet extract via spin filters.

In some embodiments, the method comprises (a) extracting platelet proteins from plasma and platelets from one or more human donor subjects via osmotic pressure, thereby generating (b) removing cell debris and aggregates from the platelet extract, thereby generating a purified platelet extract, (c) diluting the purified platelet extract, and (d) concentrating the purified platelet extract via TFF. In some embodiments, the method comprises (a) extracting platelet proteins from plasma and platelets from one or more human donor subjects via osmotic pressure, thereby generating a platelet extract, (b) removing cell debris and aggregates from the platelet extract, thereby generating a purified platelet extract, (c) diluting the purified platelet extract, and (d) concentrating the purified platelet extract via spin filters.

In some embodiments, the method comprises (a) extracting platelet proteins from plasma and platelets from one or more human donor subjects, thereby generating a platelet extract, (b) removing cell debris and aggregates from the platelet extract via centrifugation, thereby generating a purified platelet extract, (c) diluting the purified platelet extract, and (d) concentrating the purified platelet extract. In some embodiments, the method comprises (a) extracting platelet proteins from plasma and platelets from one or more human donor subjects via freeze-thaw, thereby generating a platelet extract, (b) removing cell debris and aggregates from the platelet extract via centrifugation, thereby generating a purified platelet extract, (c) diluting the purified platelet extract, and (d) concentrating the purified platelet extract. In some embodiments, the method comprises (a) extracting platelet proteins from plasma and platelets from one or more human donor subjects via buffer-detergent, thereby generating a platelet extract, (b) removing cell debris and aggregates from the platelet extract via centrifugation, thereby generating a purified platelet extract, (c) diluting the purified platelet extract, and (d) concentrating the purified platelet extract. In some embodiments, the method comprises (a) extracting platelet proteins from plasma and platelets from one or more human donor subjects via osmotic pressure, thereby generating a platelet extract, (b) removing cell debris and aggregates from the platelet extract via centrifugation, thereby generating a purified platelet extract, (c) diluting the purified platelet extract, and (d) concentrating the purified platelet extract. In some embodiments, the method comprises (a) extracting platelet proteins from plasma and platelets from one or more human donor subjects, thereby generating a platelet extract, (b) removing cell debris and aggregates from the platelet extract via centrifugation, thereby generating a purified platelet extract, (c) diluting the purified platelet extract, and (d) concentrating the purified platelet extract via TFF.

In some embodiments, a method for preparing a pharmaceutical composition comprising an allogeneic human plasma and platelet derived product comprises (a) providing a platelet suspension from one or more donor human subjects, wherein the platelet suspension comprises plasma and platelets, and wherein plasma comprises plasma proteins, (b) maintaining the plasma and platelets under conditions appropriate to extract platelet proteins from the platelets, thereby generating a platelet extract comprising the plasma proteins and the platelet proteins, (c) separating the platelet extract from cell debris, thereby generating a purified platelet extract comprising the plasma proteins and the platelet proteins, and (d) concentrating the purified platelet extract, thereby generating the allogeneic human plasma and platelet derived product.

In some embodiments, a method for preparing a pharmaceutical composition comprising an allogeneic human plasma and platelet derived product comprises (a) providing a platelet suspension from one or more donor human subjects, wherein the platelet suspension comprises plasma and platelets, and wherein plasma comprises plasma proteins, (b) maintaining the plasma and platelets under conditions appropriate to extract platelet proteins from the platelets, wherein extracting the platelet proteins comprises freeze-thaw, thereby generating a platelet extract comprising the plasma proteins and the platelet proteins, (c) separating the platelet extract from cell debris, thereby generating a purified platelet extract comprising the plasma proteins and the platelet proteins, and (d) concentrating the purified platelet extract, thereby generating the allogeneic human plasma and platelet derived product.

In some embodiments, a method for preparing a pharmaceutical composition comprising an allogeneic human plasma and platelet derived product comprises (a) providing a platelet suspension from one or more donor human subjects, wherein the platelet suspension comprises plasma and platelets, and wherein plasma comprises plasma proteins, (b) maintaining the plasma and platelets under conditions appropriate to extract platelet proteins from the platelets, wherein extracting the platelet proteins comprises buffer-detergent, thereby generating a platelet extract comprising the plasma proteins and the platelet proteins, (c) separating the platelet extract from cell debris, thereby generating a purified platelet extract comprising the plasma proteins and the platelet proteins, and (d) concentrating the purified platelet extract, thereby generating the allogeneic human plasma and platelet derived product.

In some embodiments, a method for preparing a pharmaceutical composition comprising an allogeneic human plasma and platelet derived product comprises (a) providing a platelet suspension from one or more donor human subjects, wherein the platelet suspension comprises plasma and platelets, and wherein plasma comprises plasma proteins, (b) maintaining the plasma and platelets under conditions appropriate to extract platelet proteins from the platelets, wherein an anti-coagulant is added to the platelet suspension, thereby generating a platelet extract comprising the plasma proteins and the platelet proteins, (c) separating the platelet extract from cell debris, thereby generating a purified platelet extract comprising the plasma proteins and the platelet proteins, and (d) concentrating the purified platelet extract, thereby generating the allogeneic human plasma and platelet derived product.

In some embodiments, a method for preparing a pharmaceutical composition comprising an allogeneic human plasma and platelet derived product comprises (a) providing a platelet suspension from one or more donor human subjects, wherein the platelet suspension comprises plasma and platelets, and wherein plasma comprises plasma proteins, (b) maintaining the plasma and platelets under conditions appropriate to extract platelet proteins from the platelets, wherein an anti-coagulant is added to the platelet suspension and extracting the platelet proteins comprises buffer-detergent, thereby generating a platelet extract comprising the plasma proteins and the platelet proteins, (c) separating the platelet extract from cell debris, thereby generating a purified platelet extract comprising the plasma proteins and the platelet proteins, and (d) concentrating the purified platelet extract, thereby generating the allogeneic human plasma and platelet derived product.

In some embodiments, a method for preparing a pharmaceutical composition comprising an allogeneic human plasma and platelet derived product comprises (a) providing a platelet suspension from one or more donor human subjects, wherein the platelet suspension comprises plasma and platelets, and wherein plasma comprises plasma proteins, (b) maintaining the plasma and platelets under conditions appropriate to extract platelet proteins from the platelets, wherein an anti-coagulant is added to the platelet suspension and extracting the platelet proteins comprises buffer-detergent, thereby generating a platelet extract comprising the plasma proteins and the platelet proteins, (c) separating the platelet extract from cell debris via centrifugation and filtration, thereby generating a purified platelet extract comprising the plasma proteins and the platelet proteins, and (d) concentrating the purified platelet extract, thereby generating the allogeneic human plasma and platelet derived product.

In some embodiments, a method for preparing a pharmaceutical composition comprising an allogeneic human plasma and platelet derived product comprises (a) providing a platelet suspension from one or more donor human subjects, wherein the platelet suspension comprises plasma and platelets, and wherein plasma comprises plasma proteins, (b) maintaining the plasma and platelets under conditions appropriate to extract platelet proteins from the platelets, wherein an anti-coagulant is added to the platelet suspension and extracting the platelet proteins comprises buffer-detergent, thereby generating a platelet extract comprising the plasma proteins and the platelet proteins, (c) separating the platelet extract from cell debris via centrifugation and filtration, wherein filtration also removes viruses, thereby generating a purified platelet extract comprising the plasma proteins and the platelet proteins, and (d) concentrating the purified platelet extract, thereby generating the allogeneic human plasma and platelet derived product.

In some embodiments, a method for preparing a pharmaceutical composition comprising an allogeneic human plasma and platelet derived product comprises (a) providing a platelet suspension from one or more donor human subjects, wherein the platelet suspension comprises plasma and platelets, and wherein plasma comprises plasma proteins, (b) maintaining the plasma and platelets under conditions appropriate to extract platelet proteins from the platelets, wherein an anti-coagulant is added to the platelet suspension and extracting the platelet proteins comprises buffer-detergent, thereby generating a platelet extract comprising the plasma proteins and the platelet proteins, (c) separating the platelet extract from cell debris via centrifugation and filtration, wherein filtration also removes viruses, thereby generating a purified platelet extract comprising the plasma proteins and the platelet proteins, and (d) concentrating the purified platelet extract via TFF, thereby generating the allogeneic human plasma and platelet derived product.

In some embodiments, a method for preparing a pharmaceutical composition comprising an allogeneic human plasma and platelet derived product comprises (a) providing a platelet suspension from one or more donor human subjects, wherein the platelet suspension comprises plasma and platelets, and wherein plasma comprises plasma proteins, (b) maintaining the plasma and platelets under conditions appropriate to extract platelet proteins from the platelets, wherein an anti-coagulant is added to the platelet suspension and extracting the platelet proteins comprises buffer-detergent, thereby generating a platelet extract comprising the plasma proteins and the platelet proteins, (c) separating the platelet extract from cell debris via centrifugation and filtration, wherein filtration also removes viruses, thereby generating a purified platelet extract comprising the plasma proteins and the platelet proteins, (d) concentrating the purified platelet extract via TFF, and (e) filtering the purified platelet extract, thereby generating the allogenic human platelet and plasma derived product.

In some embodiments, a method for preparing a pharmaceutical composition comprising an allogenic human plasma and platelet derived product comprises (a) thawing platelet bags, thereby generating a platelet suspension, (b) centrifuging the platelet suspension, (c) concentrating the platelet suspension, (d) filtering the platelet suspension, (e) extracting platelet proteins from plasma and platelets, thereby generating a platelet extract, (f) centrifuging the platelet extract, (g) filtering the platelet extract, (h) inactivating and removing viruses, (i) concentrating the platelet extract, thereby generating concentrated purified platelet extract and (j) filtering the concentrated purified platelet extract, thereby generating the allogeneic human platelet and plasma derived product.

Pharmaceutical Compositions and Methods of Use

In some aspects, the disclosure provides a pharmaceutical composition comprising an allogeneic human plasma and platelet derived product described herein. In some embodiments, the pharmaceutical composition is formulated for injection. In some embodiments, the pharmaceutical composition is formulated for epidural injection. In some embodiments, the pharmaceutical composition is formulated for intraarticular injection. In some embodiments, the pharmaceutical composition is formulated for intrathecal injection. In some embodiments, the pharmaceutical composition is formulated for intravenous injection. In some embodiments, the pharmaceutical composition is formulated for intramuscular injection. In some embodiments, the pharmaceutical composition is formulated for subcutaneous administration. In some embodiments, the pharmaceutical composition is formulated for intraosseous administration. In some embodiments, the pharmaceutical composition is formulated for bursal injection. In some embodiments, the pharmaceutical composition is formulated for injection into a tendon. In some embodiments, the pharmaceutical composition is formulated for injection into a ligament. In some embodiments, the pharmaceutical composition is formulated for sub-retinal injection. In some embodiments, the pharmaceutical composition is formulated for intravitreal injection. In some embodiments, the pharmaceutical composition is formulated for suprachoroidal injection. In some embodiments, the pharmaceutical composition is formulated as an eye drop. In some embodiments, the pharmaceutical composition is formulated as a bioadhesive. In some embodiments, the pharmaceutical composition is formulated as a gel. In some embodiments, the pharmaceutical composition is formulated as a gel within a bandage. In some embodiments, the pharmaceutical composition is formulated as a hydrocolloid bandage.

In some embodiments, the pharmaceutical composition is formulated so that it is suitable for self-administration. In some embodiments, the pharmaceutical composition is formulated for administration via a vial and syringe, a prefilled syringe, or a spring-driven prefilled pen or autoinjector.

In some embodiments, the pharmaceutical composition is prepared with a physiologically acceptable carrier or diluent. Suitable carriers or excipients are, for example, water, saline, dextrose, glycerol, of the like and combinations thereof. Lyophilized compositions are typically rehydrated before therapeutic use. In some embodiments, the pharmaceutical composition comprises carriers or excipients suitable for delivery to the central nervous system. Formulation strategies for epidural or intrathecal administration are described at least by Calias, P. et al. (*Pharmacology & therapeutics* vol. 144, 2 (2014): 114-22), incorporated herein by this reference.

In some embodiments, the pharmaceutical composition forms a depot at the site of injection, such that the platelet proteins and plasma proteins are maintained at the site of injection for a period of time.

In some embodiments, the disclosure provides a method for treating pain, comprising administering a composition comprising the allogenic human plasma and platelet derived product described herein.

For injuries such as traumatic injuries or open wounds, local direct delivery of high concentration plasma and platelet protein solution holds promise in acceleration of wound healing. Autologous platelet rich plasma has been discussed in this context and its promise has been noted (Everts, Peter A et al. *International journal of molecular sciences* vol. 25, 14 7914. 19 Jul. 2024, doi:10.3390/ijms25147914 and Shariati, Aref et al. *Annals of clinical microbiology and antimicrobials* vol. 20, 1 40. 27 May 2021, doi:10.1186/s12941-021-00442-x). Without wishing to be bound by theory, the compositions described herein would provide a therapeutic option immediately available without the need to rely on the patient and the preparation of their own blood. Furthermore, when combined with formulation excipients and/or when adhered to a bandage system a high concentration plasma and platelet protein solution could also provide effective antimicrobial protection and action (Ahmadpoor, Fatemeh et al. *ACS applied bio materials* vol. 8, 1 (2025): 152-165. doi:10.1021/acsabm.4c00788).

Accordingly, in some embodiments, the disclosure provides a method for treating traumatic injury or open wounds, comprising administering a composition comprising the allogenic human plasma and platelet derived product described herein. In some embodiments, the traumatic injury or open wound is a burn injury.

Sub-retinal injection of cord blood platelet rich plasma was explored clinically for the treatment of geographic atrophy (GA) associated with dry age-related macular degeneration (d-AMD) where the results supported safety, but improved outcomes were not demonstrated in the trial (Rizzo, Stanislao et al. *Ophthalmology science* vol. 4, 6 100476. 24 Jan. 2024, doi:10.1016/j.xops.2024.100476). Furthermore, evidence from mouse models suggest that a product rich in growth factors would be beneficial for treatment of age-related macular degeneration (Anitua, Eduardo et al *Medicina (Kaunas, Lithuania)* vol. 60, 12 2036. 10 Dec. 2024, doi:10.3390/medicina60122036). In addition, autologous platelet rich plasma has shown promise in acceleration of healing in corneal defects (Alizadeh, Shaban et al. *Journal of ophthalmic & vision research* vol. 14, 2 (2019): 131-135. doi:10.4103/jovr.jovr_279_17). Without wishing to be bound by theory, the compositions described herein may provide higher doses of active proteins and lead to greater and more measurable therapeutic effects.

In some embodiments, the disclosure provides a method for treating ophthalmic indications, comprising administering a composition comprising the allogenic human plasma and platelet derived product described herein. In some embodiments, an ophthalmic indication is age-related macular degeneration. In some embodiments, an ophthalmic indication is diabetic retinopathy.

In some embodiments, the disclosure provides a method for treating an orthopedic indication, comprising administering a composition comprising the allogeneic human plasma and platelet derived product described herein. In some embodiments, the orthopedic indication is back pain. In some embodiments, the orthopedic indication is painful lumbosacral radiculopathy. In some embodiments, the orthopedic injury is a spinal cord injury. In some embodiments, an orthopedic injury is osteoarthritis. In some embodiments, an orthopedic injury is ligament laxity. In some embodiments, an orthopedic injury is a rotator cuff injury. In some embodiments, an orthopedic injury is a muscle injury. In some embodiments, the orthopedic indication is joint pain. In some embodiments, the orthopedic indication is knee pain. In some embodiments, the orthopedic indication is shoulder pain. In some embodiments, the orthopedic indication is carpal tunnel.

Exemplary Treatment Methods I

In some embodiments, the disclosure provides a method for treating painful lumbosacral radiculopathy in a subject in need thereof, comprising administering the pharmaceutical composition via epidural injection. In some embodiments, the disclosure provides a method for treating painful lumbosacral radiculopathy in a subject in need thereof, comprising administering the pharmaceutical composition via intrathecal injection.

In some embodiments, the disclosure provides a method for treating painful lumbosacral radiculopathy in a subject in need thereof, comprising administering a pharmaceutical composition via epidural injection to a subject, wherein the pharmaceutical composition comprises an allogeneic human plasma and platelet derived product comprising:
    (a) human plasma proteins comprising albumin, globulins, and fibrinogen; and
    (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF),
    wherein the total protein concentration of the composition is greater than 50 mg/mL and less than or about 500 mg/mL.

In some embodiments, the disclosure provides a method for treating painful lumbosacral radiculopathy in a subject in need thereof, comprising administering a pharmaceutical composition via epidural injection to a subject, wherein the pharmaceutical composition comprises an allogeneic human plasma and platelet derived product comprising:
    (a) human plasma proteins comprising albumin, globulins, and fibrinogen; and
    (b) human platelet proteins comprising PDGF-AB, PDGF-AA, PDGF-BB, TGFβ1, TGFβ2, BDNF, VEGF, FGF, EGF and HGF,
    wherein the concentration of PDGF-AB is greater than 50 pg/mL and less than 1,000 pg/mL.

In some embodiments, the disclosure provides a method for treating painful lumbosacral radiculopathy in a subject in need thereof, comprising administering a pharmaceutical composition via epidural injection to a subject, wherein the pharmaceutical composition comprises an allogeneic human plasma and platelet derived product comprising:
    (a) human plasma proteins comprising albumin, globulins, and fibrinogen; and
    (b) human platelet proteins comprising PDGF-AB, PDGF-AA, PDGF-BB, TGFβ1, TGFβ2, BDNF, VEGF, FGF, EGF and HGF,
    wherein the concentration of fibrinogen is about 20 μg/mL to about 10 mg/mL.

In some embodiments, the disclosure provides a method for treating painful lumbosacral radiculopathy in a subject in need thereof, comprising administering a pharmaceutical composition via epidural injection to a subject, wherein the pharmaceutical composition comprises an allogeneic human plasma and platelet derived product comprising:
    (a) human plasma proteins comprising albumin, globulins, and fibrinogen; and
    (b) human platelet proteins comprising PDGF-AB, PDGF-AA, PDGF-BB, TGFβ1, TGFβ2, BDNF, VEGF, FGF, EGF and HGF,
    wherein the viscosity of the composition is about 1 to about 40 cP.

In some embodiments, the disclosure provides a method for treating painful lumbosacral radiculopathy in a subject in need thereof, comprising administering a pharmaceutical composition via epidural injection to a subject, wherein the pharmaceutical composition comprises an allogeneic human plasma and platelet derived product comprising:
    (a) human plasma proteins comprising albumin, globulins, and fibrinogen; and
    (b) human platelet proteins comprising PDGF-AB, PDGF-AA, PDGF-BB, TGFβ1, TGFβ2, BDNF, VEGF, FGF, EGF and HGF,
    wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 pg/mL to about 10 mg/mL, and wherein the viscosity of the composition is about 1 to about 40 cP.

In some embodiments, the disclosure provides a method for treating painful lumbosacral radiculopathy in a subject in need thereof, comprising administering a pharmaceutical composition via intrathecal injection to a subject, wherein the pharmaceutical composition comprises an allogeneic human plasma and platelet derived product comprising:
    (a) human plasma proteins comprising albumin, globulins, and fibrinogen; and
    (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF),
    wherein the total protein concentration of the composition is greater than 50 mg/mL and less than or about 500 mg/mL.

In some embodiments, the disclosure provides a method for treating painful lumbosacral radiculopathy in a subject in need thereof, comprising administering a pharmaceutical composition via intrathecal injection to a subject, wherein the pharmaceutical composition comprises an allogeneic human plasma and platelet derived product comprising:
    (a) human plasma proteins comprising albumin, globulins, and fibrinogen; and (b) human platelet proteins comprising PDGF-AB, PDGF-AA, PDGF-BB, TGFβ, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating painful lumbosacral radiculopathy in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating painful lumbosacral radiculopathy in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating painful lumbosacral radiculopathy in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating back pain in a subject in need thereof, comprising administering the pharmaceutical composition via epidural injection. In some embodiments, the disclosure provides a method for treating back pain in a subject in need thereof, comprising administering the pharmaceutical composition via intrathecal injection.

In some embodiments, the disclosure provides a method for treating back pain in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating back pain in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating back pain in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating back pain in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating back pain in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating back pain in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating back pain in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating back pain in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating back pain in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating back pain in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating spinal cord injury in a subject in need thereof, comprising administering the pharmaceutical composition via epidural injection. In some embodiments, the disclosure provides a method for treating spinal cord injury in a subject in need thereof, comprising administering the pharmaceutical composition via intrathecal injection.

In some embodiments, the disclosure provides a method for treating spinal cord injury in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating spinal cord injury in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating spinal cord injury in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating spinal cord injury in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating spinal cord injury in a subject in need thereof, comprising administering a pharmaceutical composition via epidural injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating spinal cord injury in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating spinal cord injury in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating spinal cord injury in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating spinal cord injury in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating spinal cord injury in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating osteoarthritis in a subject in need thereof, comprising administering the pharmaceutical composition via intrathecal injection. In some embodiments, the disclosure provides a method for treating osteoarthritis in a subject in need thereof, comprising administering the pharmaceutical composition via intraosseous injection.

In some embodiments, the disclosure provides a method for treating osteoarthritis in a subject in need thereof, comprising administering a pharmaceutical composition via intraosseous injection to a subject, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating osteoarthritis in a subject in need thereof, comprising administering a pharmaceutical composition via intraosseous injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating osteoarthritis in a subject in need thereof, comprising administering a pharmaceutical composition via intraosseous injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating osteoarthritis in a subject in need thereof, comprising administering a pharmaceutical composition via intraosseous injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating osteoarthritis in a subject in need thereof, comprising administering a pharmaceutical composition via intraosseous injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating osteoarthritis in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating osteoarthritis in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating osteoarthritis in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating osteoarthritis in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating osteoarthritis in a subject in need thereof, comprising administering a pharmaceutical composition via intrathecal injection to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating ligament laxity in a subject in need thereof, comprising administering the pharmaceutical composition via injection into the injured ligament.

In some embodiments, the disclosure provides a method for treating ligament laxity in a subject in need thereof, comprising administering a pharmaceutical composition via injection into the injured ligament to a subject, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating ligament laxity in a subject in need thereof, comprising administering a pharmaceutical composition via injection into the injured ligament to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating ligament laxity in a subject in need thereof, comprising administering a pharmaceutical composition via injection into the injured ligament to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating ligament laxity in a subject in need thereof, comprising administering a pharmaceutical composition via injection into the injured ligament to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating ligament laxity in a subject in need thereof, comprising administering a pharmaceutical composition via injection into the injured ligament to a subject, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating rotator cuff injury in a subject in need thereof, comprising administering the pharmaceutical composition via intraarticular injection. In some embodiments, the disclosure provides a method for treating rotator cuff injury in a subject in need thereof, comprising administering the pharmaceutical composition via injection into the rotator cuff tendon. In some embodiments, the disclosure provides a method for treating rotator cuff injury in a subject in need thereof, comprising administering the pharmaceutical composition via bursal injection.

In some embodiments, the disclosure provides a method for treating rotator cuff injury in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating rotator cuff injury in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating rotator cuff injury in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating rotator cuff injury in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating rotator cuff injury in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating rotator cuff injury in a subject in need thereof, comprising administering a pharmaceutical composition via injection to the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating rotator cuff injury in a subject in need thereof, comprising administering a pharmaceutical composition via injection to the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating rotator cuff injury in a subject in need thereof, comprising administering a pharmaceutical composition via injection to the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating rotator cuff injury in a subject in need thereof, comprising administering a pharmaceutical composition via injection to the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating rotator cuff injury in a subject in need thereof, comprising administering a pharmaceutical composition via injection to the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating rotator cuff injury in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating rotator cuff injury in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating rotator cuff injury in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating rotator cuff injury in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating rotator cuff injury in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating muscle injury in a subject in need thereof, comprising administering the pharmaceutical composition via intramuscular injection. In some embodiments, the disclosure provides a method for treating muscle injury in a subject in need thereof, comprising administering the pharmaceutical composition via injection into the local muscle tear region.

In some embodiments, the disclosure provides a method for treating muscle injury in a subject in need thereof, comprising administering a pharmaceutical composition via intramuscular injection, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating muscle injury in a subject in need thereof, comprising administering a pharmaceutical composition via intramuscular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating muscle injury in a subject in need thereof, comprising administering a pharmaceutical composition via intramuscular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating muscle injury in a subject in need thereof, comprising administering a pharmaceutical composition via intramuscular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating muscle injury in a subject in need thereof, comprising administering a pharmaceutical composition via intramuscular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating muscle injury in a subject in need thereof, comprising administering a pharmaceutical composition via injection to the local muscle tear region, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating muscle injury in a subject in need thereof, comprising administering a pharmaceutical composition via injection to the local muscle tear region, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating muscle injury in a subject in need thereof, comprising administering a pharmaceutical composition via injection to the local muscle tear region, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating muscle injury in a subject in need thereof, comprising administering a pharmaceutical composition via injection to the local muscle tear region, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating muscle injury in a subject in need thereof, comprising administering a pharmaceutical composition via injection to the local muscle tear region, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating joint pain in a subject in need thereof, comprising administering the pharmaceutical composition via intraosseous injection. In some embodiments, the disclosure provides a method for treating joint pain in a subject in need thereof, comprising administering the pharmaceutical composition via intraarticular injection.

In some embodiments, the disclosure provides a method for treating joint pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating joint pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating joint pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating joint pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating joint pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating joint pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating joint pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating joint pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating joint pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating joint pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating knee pain in a subject in need thereof, comprising administering the pharmaceutical composition via intraarticular injection. In some embodiments, the disclosure provides a method for treating knee pain in a subject in need thereof, comprising administering the pharmaceutical composition via intraosseous injection.

In some embodiments, the disclosure provides a method for treating knee pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating knee pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating knee pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 µg/mL to about 10 mg/mL.

In some embodiments, the disclosure provides a method for treating knee pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating knee pain in a subject in need thereof, comprising administering a pharmaceutical composition via intraosseous injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 µg/mL to about 10 mg/mL, and wherein the viscosity of the composition is about 1 to about 40 cP.

In some embodiments, the disclosure provides a method for treating knee pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating knee pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating knee pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 µg/mL to about 10 mg/mL.

In some embodiments, the disclosure provides a method for treating knee pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating knee pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 µg/mL to about 10 mg/mL, and wherein the viscosity of the composition is about 1 to about 40 cP.

In some embodiments, the disclosure provides a method for treating shoulder pain in a subject in need thereof, comprising administering the pharmaceutical composition via intraarticular injection. In some embodiments, the disclosure provides a method for treating shoulder pain in a subject in need thereof, comprising administering the pharmaceutical composition via injection into the rotator cuff tendon. In some embodiments, the disclosure provides a method for treating shoulder pain in a subject in need thereof, comprising administering the pharmaceutical composition via bursal injection.

In some embodiments, the disclosure provides a method for treating shoulder pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating shoulder pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating shoulder pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating shoulder pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating shoulder pain in a subject in need thereof, comprising administering a pharmaceutical composition via intraarticular injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating shoulder pain in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating shoulder pain in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating shoulder pain in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating shoulder pain in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating shoulder pain in a subject in need thereof, comprising administering a pharmaceutical composition via bursal injection, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20

μg/mL to about 10 mg/mL, and wherein the viscosity of the composition is about 1 to about 40 cP.

In some embodiments, the disclosure provides a method for treating shoulder pain in a subject in need thereof, comprising administering a pharmaceutical composition via injection into the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating shoulder pain in a subject in need thereof, comprising administering a pharmaceutical composition via injection into the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating shoulder pain in a subject in need thereof, comprising administering a pharmaceutical composition via injection into the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating shoulder pain in a subject in need thereof, comprising administering a pharmaceutical composition via injection into the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating shoulder pain in a subject in need thereof, comprising administering a pharmaceutical composition via injection into the rotator cuff tendon, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating carpal tunnel in a subject in need thereof, comprising administering the pharmaceutical composition via injection into the carpal tunnel under the ligament.

In some embodiments, the disclosure provides a method for treating carpal tunnel in a subject in need thereof, comprising administering a pharmaceutical composition via injection into the carpal tunnel under the ligament, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating carpal tunnel in a subject in need thereof, comprising administering a pharmaceutical composition via injection into the carpal tunnel under the ligament, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating carpal tunnel in a subject in need thereof, comprising administering a pharmaceutical composition via injection into the carpal tunnel under the ligament, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating carpal tunnel in a subject in need thereof, comprising administering a pharmaceutical composition via injection into the carpal tunnel under the ligament, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating carpal tunnel in a subject in need thereof, comprising administering a pharmaceutical composition via injection into the carpal tunnel under the ligament, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating chemotherapy-induced peripheral neuropathy (CIPN) in a subject in need thereof, comprising administering the pharmaceutical composition via systemic administration. In some embodiments, systemic administration of the pharmaceutical composition comprises a subcutaneous injection. In some embodiments, systemic administration of the pharmaceutical composition comprises intramuscular injection. In some embodiments, systemic administration of the pharmaceutical composition comprises intravenous injection. In some embodiments, CIPN is associated with nerves in the fingers and/or toes. In some embodiments, the disclosure provides a method for treating CIPN associated with nerves in the fingers and/or toes in a subject in need thereof, comprising administering the pharmaceutical composition via intravenous administration.

In some embodiments, the disclosure provides a method for treating CIPN in a subject in need thereof, comprising administering a pharmaceutical composition via systemic administration, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating CIPN in a subject in need thereof, comprising administering a pharmaceutical composition via systemic administration, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating CIPN in a subject in need thereof, comprising administering a pharmaceutical composition via systemic administration, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating CIPN in a subject in need thereof, comprising administering a pharmaceutical composition via systemic administration, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating CIPN in a subject in need thereof, comprising administering a pharmaceutical composition via systemic administration, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

In some embodiments, the disclosure provides a method for treating CIPN in a subject in need thereof, comprising administering a pharmaceutical composition via intravenous administration, wherein the pharmaceutical composition comprises an allogeneic human plasma and platelet derived product comprising:

(a) human plasma proteins comprising albumin, globulins, and fibrinogen; and (b) human platelet proteins comprising platelet derived growth factor (PDGF)-AB, PDGF-AA, PDGF-BB, transforming growth factor beta (TGFβ1, TGFβ2), brain-derived neurotrophic factor (BDNF), vascular endothelial growth factor (VEGF), b-fibroblast growth factor (FGF), epidermal growth factor (EGF) and hepatocyte growth factor (HGF), wherein the total protein concentration of the composition is greater than 50 mg/mL and less than or about 500 mg/mL.

In some embodiments, the disclosure provides a method for treating CIPN in a subject in need thereof, comprising administering a pharmaceutical composition via intravenous administration, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of PDGF-AB is greater than 50 pg/mL and less than 1,000 pg/mL.

In some embodiments, the disclosure provides a method for treating CIPN in a subject in need thereof, comprising administering a pharmaceutical composition via intravenous administration, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the concentration of fibrinogen is about 20 μg/mL to about 10 mg/mL.

In some embodiments, the disclosure provides a method for treating CIPN in a subject in need thereof, comprising administering a pharmaceutical composition via intravenous administration, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein the viscosity of the composition is about 1 to about 40 cP.

In some embodiments, the disclosure provides a method for treating CIPN in a subject in need thereof, comprising administering a pharmaceutical composition via intravenous administration, wherein the pharmaceutical composition comprises an allogeneic human plasma and platelet derived product comprising:

(a) human plasma proteins comprising albumin, globulins, and fibrinogen; and (b) human platelet proteins comprising PDGF-AB, PDGF-AA, PDGF-BB, TGFβ1, TGFβ2, BDNF, VEGF, FGF, EGF and HGF, wherein, the total protein concentration of the composition is greater than 50 mg/mL and less than or about 500 mg/mL, wherein the concentration of PDGF-AB is greater than 50 pg/mL and less than 1,000 pg/mL, wherein the concentration of fibrinogen is about 20 μg/mL to about 10 mg/mL, and wherein the viscosity of the composition is about 1 to about 40 cP.

Exemplary Treatment Methods II

In some embodiments, the disclosure provides a method for treating pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating pain, the human plasma proteins comprise albumin and immunoglobulin, and the human platelet proteins comprise one or more of TGF-β, VEGF, EGF, FGF and HGF. In any of the foregoing embodiments related to a method for treating pain, the pharmaceutical composition is administered via injection. In any of the foregoing embodiments related to a method for treating pain, about 1 mL to about 20 mL of the pharmaceutical composition is administered via injection.

In some embodiments, the disclosure provides a method for treating painful lumbosacral radiculopathy in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating painful lumbosacral radiculopathy in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating painful lumbosacral radiculopathy in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating painful lumbosacral radiculopathy in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating painful lumbosacral radiculopathy in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating painful lumbosacral radiculopathy in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating painful lumbosacral radiculopathy, the human plasma proteins comprise albumin and immunoglobulin, and the human platelet proteins comprise one or more of TGF-β, VEGF, EGF, FGF and HGF. In any of the foregoing embodiments related to a method for treating pain, the pharmaceutical composition is administered via epidural or intrathecal injection. In any of the foregoing embodiments related to a method for treating pain, the pharmaceutical composition is administered via an x-ray guided needle. In any of the foregoing embodiments related to a method for treating pain, about 1 mL to about 20 mL, about 1 mL to about 10 mL, or about 1 mL to about 5 mL of the pharmaceutical composition is administered via an x-ray guided needle. In any of the foregoing embodiments related to a method for treating pain, about 1 mL to about 5 mL of the pharmaceutical composition is administered via an x-ray guided needle.

In some embodiments, the disclosure provides a method for treating a spinal cord injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating a spinal cord injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating a spinal cord injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating a spinal cord injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating a spinal cord injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating a spinal cord injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating a spinal cord injury, the human plasma proteins comprise albumin and immunoglobulin, and the human platelet proteins comprise one or more of TGF-β, VEGF, EGF, FGF and HGF. In any of the foregoing embodiments related to a method for treating a spinal cord injury, the pharmaceutical composition is administered via epidural or intrathecal injection. In any of the foregoing embodiments related to a method for treating a spinal cord injury, 1 mL to about 20 mL, about 1 mL to about 10 mL, or about 1 mL to about 5 mL of the pharmaceutical composition is administered via epidural or intrathecal injection. In any of the foregoing embodiments related to a method for treating a spinal cord injury, about 1 mL to about 5 mL of the pharmaceutical composition is administered via epidural or intrathecal injection.

In some embodiments, the disclosure provides a method for treating back pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating back pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating back pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating back pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating back pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating back pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating back pain, the human plasma proteins comprise albumin and immunoglobulin, and the human platelet proteins comprise one or more of TGF-β, VEGF, EGF, FGF and HGF. In any of the foregoing embodiments related to a method for treating back pain, the pharmaceutical composition is administered via epidural or intrathecal injection. In any of the foregoing embodiments related to a method for treating back pain, 1 mL to about 20 mL, about 1 mL to about 10 mL, or about 1 mL to about 5 mL of the pharmaceutical composition is administered via epidural or intrathecal injection. In any of the foregoing embodiments related to a method for treating back pain, about 1 mL to about 5 mL of the pharmaceutical composition is administered via epidural or intrathecal injection.

In some embodiments, the disclosure provides a method for treating chemotherapy-induced peripheral neuropathy (CIPN) in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating CIPN in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating CIPN in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating CIPN in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating CIPN in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating CIPN in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating CIPN, the human plasma proteins comprise albumin and immunoglobulin, and the human platelet proteins comprise one or more of TGF-β, VEGF, EGF, FGF and HGF. In any of the foregoing embodiments related to a method for treating CIPN, the pharmaceutical composition is administered via systemic or intravenous injection. In any of the foregoing embodiments related to a method for treating CIPN, about 1 mL to about 20 mL of the pharmaceutical composition is administered via systemic or intravenous injection.

In some embodiments, the disclosure provides a method for treating carpal tunnel in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating carpal tunnel in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating carpal tunnel in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating carpal tunnel in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating carpal tunnel in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating carpal tunnel in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating carpal tunnel, the human plasma proteins comprise albumin and immunoglobulin, and the human platelet proteins comprise one or more of TGF-β, VEGF, EGF, FGF and HGF. In any of the foregoing embodiments related to a method for treating carpal tunnel, the pharmaceutical composition is administered via injection into carpal tunnel under ligament. In any of the foregoing embodiments related to a method for treating carpal tunnel, about 1 mL to about 5 mL of the pharmaceutical composition is administered via injection into carpal tunnel under ligament.

In some embodiments, the disclosure provides a method for treating shoulder pain or a rotator cuff injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating shoulder pain or a rotator cuff injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating shoulder pain or a rotator cuff injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating shoulder pain or a rotator cuff injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating shoulder pain or a rotator cuff injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating shoulder pain or a rotator cuff injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating shoulder pain or a rotator cuff injury, the human plasma proteins comprise albumin and immunoglobulin, and the human platelet proteins comprise one or more of TGF-β, VEGF, EGF, FGF and HGF. In any of the foregoing embodiments related to a method for treating shoulder pain or a rotator cuff injury, the pharmaceutical composition is administered via injection into a rotator cuff tendon, bursal injection, or intaarticular injection. In any of the foregoing embodiments related to a method for treating shoulder pain or a rotator cuff injury, about 1 mL to about 20 mL of the pharmaceutical composition is administered via injection into a rotator cuff tendon, bursal injection, or intaarticular injection.

In some embodiments, the disclosure provides a method for treating joint pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating joint pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating joint pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating joint pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating joint pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating joint pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating joint pain, the human plasma proteins comprise albumin and immunoglobulin, and the human platelet proteins comprise one or more of TGF-β, VEGF, EGF, FGF and HGF. In any of the foregoing embodiments related to a method for treating joint pain, the pharmaceutical composition is administered via intraarticular injection or intraosseous injection. In any of the foregoing embodiments related to a method for treating joint pain, about 1 mL to about 20 mL of the pharmaceutical composition is administered via intraarticular injection or intraosseous injection.

In some embodiments, the disclosure provides a method for treating knee pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating knee pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating knee pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating knee pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating knee pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating knee pain in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating knee pain, the human plasma proteins comprise albumin and immunoglobulin, and the human platelet proteins comprise one or more of TGF-β, VEGF, EGF, FGF and HGF. In any of the foregoing embodiments related to a method for treating knee pain, the pharmaceutical composition is administered via intraarticular injection or intraosseous injection. In any of the foregoing embodiments related to a method for treating knee pain, about 1 mL to about 20 mL of the pharmaceutical composition is administered via intraarticular injection or intraosseous injection.

In some embodiments, the disclosure provides a method for treating a muscle injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating a muscle injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating a muscle injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating a muscle injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating a muscle injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating a muscle injury in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating a muscle injury, the human plasma proteins comprise albumin and immunoglobulin, and the human platelet proteins comprise one or more of TGF-β, VEGF, EGF, FGF and HGF. In any of the foregoing embodiments related to a method for treating a muscle injury, the pharmaceutical composition is administered via intramuscular injection or injection into local muscle tear region. In any of the foregoing embodiments related to a method for treating a muscle injury, about 1 mL to about 20 mL or about 1 mL to about 5 mL of the pharmaceutical composition is administered via intramuscular injection or injection into local muscle tear region.

In some embodiments, the disclosure provides a method for treating ligament laxity in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating ligament laxity in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating ligament laxity in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating ligament laxity in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating ligament laxity in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating ligament laxity in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating ligament laxity, the human plasma proteins comprise albumin and immunoglobulin, and the human platelet proteins comprise one or more of TGF-β, VEGF, EGF, FGF and HGF. In any of the foregoing embodiments related to a method for treating ligament laxity, the pharmaceutical composition is administered via injection into an injured ligament. In any of the foregoing embodiments related to a method for treating ligament laxity, about 1 mL to about 20 mL of the pharmaceutical composition is administered via injection into an injured ligament.

In some embodiments, the disclosure provides a method for treating osteoarthritis in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating osteoarthritis in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating osteoarthritis in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating osteoarthritis in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating osteoarthritis in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating osteoarthritis in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating osteoarthritis, the human plasma proteins comprise albumin and immunoglobulin, and the human platelet proteins comprise one or more of TGF-β, VEGF, EGF, FGF and HGF. In any of the foregoing embodiments related to a method for treating osteoarthritis, the pharmaceutical composition is administered via intraosseous injection or intraarticular injection. In any of the foregoing embodiments related to a method for treating osteoarthritis, about 1 mL to about 5 mL of the pharmaceutical composition is administered via intraosseous injection or intraarticular injection.

In some embodiments, the disclosure provides a method for treating an ophthalmic indication in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating an ophthalmic indication in a subject in need thereof, comprising administering a pharmaceutical composition comprising an allogeneic human plasma and platelet derived product comprising:

(a) human plasma proteins comprising fibrinogen; and (b) human platelet proteins comprising PDGF-AB, wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating an ophthalmic indication in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating an ophthalmic indication in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating an ophthalmic indication in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating an ophthalmic indication in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating an ophthalmic indication, the human plasma proteins comprise albumin and immunoglobulin, and the human platelet proteins comprise one or more of TGF-β, VEGF, EGF, FGF and HGF. In any of the foregoing embodiments related to a method for treating an ophthalmic indication, the pharmaceutical composition is administered via intravitreal injection, sub-retinal injection or suprachoroidal injection. In any of the foregoing embodiments related to a method for treating an ophthalmic indication, about 0.01 mL to about 2 mL of the pharmaceutical composition is administered via intravitreal injection, sub-retinal injection or suprachoroidal injection.

In some embodiments, the disclosure provides a method for treating an open, traumatic, or burn wound in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is greater than 50 mg/mL and less than or about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating an open, traumatic, or burn wound in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is about 50 mg/mL to about 500 mg/mL, the fibrinogen concentration is about 0.25 mg/mL to about 5 mg/mL, and the PDGF-AB concentration is about 5 ng/mL to about 200 ng/mL.

In some embodiments, the disclosure provides a method for treating an open, traumatic, or burn wound in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is about 20 mg/mL to about 50 mg/mL, the fibrinogen concentration is about 0.25 mg/mL to about 0.5 mg/mL, and the PDGF-AB concentration is about 10 ng/mL to about 20 ng/mL.

In some embodiments, the disclosure provides a method for treating an open, traumatic, or burn wound in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is about 50 mg/mL to about 80 mg/mL, the fibrinogen concentration is about 0.5 mg/mL to about 1 mg/mL, and the PDGF-AB concentration is about 20 ng/mL to about 40 ng/mL.

In some embodiments, the disclosure provides a method for treating an open, traumatic, or burn wound in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is about 80 mg/mL to about 160 mg/mL, the fibrinogen concentration is about 1 mg/mL to about 2 mg/mL, and the PDGF-AB concentration is about 40 ng/mL to about 80 ng/mL.

In some embodiments, the disclosure provides a method for treating an open, traumatic, or burn wound in a subject in need thereof, comprising administering a pharmaceutical composition comprising an allogeneic human plasma and platelet derived product comprising:

(a) human plasma proteins comprising fibrinogen; and
    (b) human platelet proteins comprising PDGF-AB,
    wherein the total protein concentration is about 160 mg/mL to about 320 mg/mL, the fibrinogen concentration is about 2 mg/mL to about 5 mg/mL, and the PDGF-AB concentration is about 80 ng/mL to about 160 ng/mL.

In any of the foregoing embodiments related to a method for treating an open, traumatic, or burn wound, the human plasma proteins comprise albumin and immunoglobulin, and the human platelet proteins comprise one or more of TGF-β3, VEGF, EGF, FGF and HGF. In any of the foregoing embodiments related to a method for treating an open, traumatic, or burn wound, the pharmaceutical composition is administered via local administration. In any of the foregoing embodiments related to a method for treating an open, traumatic, or burn wound, about 1 mL to about 20 mL of the pharmaceutical composition is administered via local administration.

In some embodiments, the present disclosure provides a method for treating an indication recited in Table 7 with a composition described herein. In some embodiments, the method for treating the indication comprises administering via a route of administration specified in Table 7. In some embodiments, the volume of composition administered is selected from the volumes specified in Table 7.

TABLE 7

Exemplary Indications For Treatment with a Composition Comprising an Allogeneic Human Plasma and Platelet Derived Product

| Indication(s) | Route(s) of Administration | Volume of Composition |
|---|---|---|
| Painful LSR | Epidural Injection | 1-5 mL |
| Spinal Cord Injury Back Pain | Intrathecal Injection | (1-20, 1-10, 1-5) |
| CIPN | Intravenous or systemic | 1-20 mL |
| Carpal tunnel | Injection into carpal tunnel under ligament | 1-5 mL |
| Shoulder pain Rotator cuff injury | Injection into rotator cuff tendon Bursal injection Intraarticular Injection | 1-20 mL |
| Joint pain Knee pain | Intraarticular Injection Intraosseous Injection | 1-20 mL |
| Muscle injury | Injection into local muscle tear region Intramuscular Injection | 1-20 mL, 1-5 |
| Ligament laxity | Injection into injured ligament | 1-20 mL |
| Osteoarthritis | ~~Intrathecal Injection~~ Intraosseous Injection Intraarticular Injection | 1-5 mL |
| Ophthalmic | Intravitreal Sub-retinal Injection Suprachoroidal injection | 0.01-2 mL |
| Traumatic, open or burn wounds | Local administration | 1-20 mL |

In some embodiments, the pharmaceutical composition is packaged in a single-use vial. In some embodiments, the pharmaceutical composition is packaged in a pre-filled syringe. In some embodiments, the pharmaceutical composition is packaged in a multi-use vial. In some embodiments, the pharmaceutical composition is packaged in or on a bandage.

In some embodiments, the pharmaceutical composition is administered in a hospital setting. In some embodiments, the pharmaceutical composition is administered in a sterile room. In some embodiments, the pharmaceutical composition is administered at an out-patient facility. In some embodiments, the pharmaceutical composition is administered in a radiology procedure room.

In some embodiments, administration comprises a C-arm X-ray machine. In some embodiments, a physician inserts a guide needle to image an injury area with an X-ray. In some embodiments, a contrast agent is injected for imaging. In some embodiments, the pharmaceutical composition is injected via the C-arm X-ray machine. In some embodiments, X-ray imaging is used to guide the needle into an injury site. In some embodiments, a contrast agent is injected after the pharmaceutical composition is injected. In some embodiments, a contrast agent is used to visualize localization or spreading of the pharmaceutical composition. In some embodiments, a contrast agent is injected before and after the pharmaceutical composition is injected. In some embodiments, an anesthetic is used at or around the injection site.

In some embodiments, about 1 to about 20 mL of the pharmaceutical composition are injected. In some embodiments, about 1 to about 10 mL of the pharmaceutical composition are injected. In some embodiments, about 5 to about 15 mL of the pharmaceutical composition are injected. In some embodiments, about 10 to about 20 mL of the pharmaceutical composition are injected. In some embodiments, about 1 to about 10 mL of the pharmaceutical composition are injected. In some embodiments, about 1 to about 6 mL of the pharmaceutical composition are injected. In some embodiments, about 1 to about 5 mL of the pharmaceutical composition are injected. In some embodiments, no more than 1 mL of the pharmaceutical composition is injected. In some embodiments, no more than 6 mL of the pharmaceutical composition is injected. In some embodiments, no more than 20 mL of the pharmaceutical composition is injected. In some embodiments, at least 1 mL of the pharmaceutical composition is injected. In some embodiments, at least 2 mL of the pharmaceutical composition is injected. In some embodiments, at least 3 mL of the pharmaceutical composition is injected. In some embodiments, at least 4 mL of the pharmaceutical composition is injected. In some embodiments, at least 5 mL of the pharmaceutical composition is injected. In some embodiments, at least 6 mL of the pharmaceutical composition is injected. In some embodiments, about 1 mL of the pharmaceutical composition is injected. In some embodiments, about 2 mL of the pharmaceutical composition is injected. In some embodiments, about 3 mL of the pharmaceutical composition is injected. In some embodiments, about 4 mL of the pharmaceutical composition is injected. In some embodiments, about 5 mL of the pharmaceutical composition is injected. In some embodiments, about 6 mL of the pharmaceutical composition is injected. In some embodiments, about 1 to about 3 mL of the pharmaceutical composition is injected.

In some embodiments, about 1 to about 5 mL of the pharmaceutical composition are injected with a C-arm X-ray machine. In some embodiments, no more than 1 mL of the pharmaceutical composition is injected with a C-arm X-ray machine. In some embodiments, no more than 5 mL of the pharmaceutical composition is injected with a C-arm X-ray machine. In some embodiments, at least 1 mL of the pharmaceutical composition is injected with a C-arm X-ray machine. In some embodiments, at least 5 mL of the pharmaceutical composition is injected with a C-arm X-ray machine. In some embodiments, about 1 to about 3 mL of the pharmaceutical composition is injected with a C-arm X-ray machine. In some embodiments, 1 mL of the pharmaceutical composition is injected with a C-arm X-ray machine. In some embodiments, 2 mL of the pharmaceutical composition is injected with a C-arm X-ray machine. In some embodiments, 3 mL of the pharmaceutical composition is injected with a C-arm X-ray machine.

In some embodiments, about 1 to about 5 mL of the pharmaceutical composition are epidurally injected with a C-arm X-ray machine. In some embodiments, no more than 1 mL of the pharmaceutical composition is epidurally injected with a C-arm X-ray machine. In some embodiments, no more than 5 mL of the pharmaceutical composition is epidurally injected with a C-arm X-ray machine. In some embodiments, at least 1 mL of the pharmaceutical composition is epidurally injected with a C-arm X-ray machine. In some embodiments, at least 5 mL of the pharmaceutical composition is epidurally injected with a C-arm X-ray machine. In some embodiments, about 1 to about 3 mL of the pharmaceutical composition is epidurally injected with a C-arm X-ray machine. In some embodiments, 1 mL of the pharmaceutical composition is epidurally injected with a C-arm X-ray machine. In some embodiments, 2 mL of the pharmaceutical composition is epidurally injected with a C-arm X-ray machine. In some embodiments, 3 mL of the pharmaceutical composition is epidurally injected with a C-arm X-ray machine.

Kits

In some aspects, the disclosure provides a kit comprising a container comprising a composition described herein and instructions for administering the composition to a subject in need thereof. In some embodiments, the instructions specify administering the composition via epidural injection. In some embodiments, the instructions specify administering the composition via intraarticular injection. In some embodiments the instructions specify administering the composition via intrathecal injection. In some embodiments, the composition is lyophilized and the instructions comprise sets for reconstituting the composition. In some embodiments, the kit comprises a vial, flask, bottle, syringe, or other contained in which the pharmaceutical composition can be placed. In some embodiments, the kit comprises reagents In some embodiments, the container is a single-use vial. In some embodiments, the container is a multi-use vial.

In some embodiments, a kit comprises a container comprising a composition described herein, wherein the container is suitable for self-administration. Containers and devices suitable for self-administration include vials and syringes, prefilled syringes, spring-driven prefilled pens or autoinjectors.

Definitions

For the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

The term "about" or "approximately" when immediately preceding a numerical value means a range (e.g., plus or minus 10% of that value). For example, "about 50" can mean 45 to 55, "about 25,000" can mean 22,500 to 27,500, etc., unless the context of the disclosure indicates otherwise, or is inconsistent with such an interpretation. For example, in a list of numerical values such as "about 49, about 50, about 55, . . . ", "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein. Similarly, the term "about" when preceding a series of numerical values or a range of values (e.g., "about 10, 20, 30" or "about 10-30") refers, respectively to all values in the series, or the endpoints of the range.

The terms "at least," "less than" or "more than" prior to a number or series of numbers (e.g., "at least two") is understood to include the number adjacent to the term "at least," "less than" or "more than," and all subsequent numbers or integers that could logically be included, as clear from context. When the term "at least," "less than" or "more than" is present before a series of numbers or a range, it is understood that "at least," "less than" or "more than" can modify each of the numbers in the series or range.

The term "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein, the term "subject" refers to any subject, e.g., a human or a non-human mammal, for whom diagnosis, prognosis, or therapy is desired. The term "subject" may mean a human or non-human mammal affected, likely to be affected, or suspected to be affected with a disease. In aspects, a subject is a mammal. A mammal includes primates, such as humans, monkeys, chimpanzee, and apes, and non-primates such as domestic animals, including laboratory animals (such as rabbits and rodents, e.g., guinea pig, rat, or mouse) and household pets and farm animals (e.g., cats, dogs, swine, cattle, sheep, goats, horses, rabbits), and non-domestic animals, such as wildlife, birds, reptile, fish, or the like.

As used herein, the term "pharmaceutical composition" is a formulation containing the compounds and compositions of the present disclosure in a form suitable for administration to a subject.

As used herein, the term "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

The terms "polypeptide" and "protein" are used interchangeably herein. The term "polypeptide" refers to a protein or peptide that typically contains or consists of at least 20, and preferably at least 30, such as at least 50 amino acids. The term "peptide" refers to an oligomer containing or consisting of at least 2 amino acids to about 19 amino acids.

The terms "purifying" and "purification" in all their grammatical forms relate to the act of (substantially) reducing/depleting contaminants from the desired allogeneic human plasma and platelet derived product and intermediates thereof (e.g., platelet extract).

The terms "concentrating" and "concentration" in all their grammatical forms relate to the act of (substantially) increasing the concentration of a desired protein or proteins (e.g., platelet proteins) in a composition.

Other Embodiments

In some aspects, the disclosure relates to the following embodiments. Throughout this section, the term "embodiment" is abbreviated as "E" followed by a letter and an ordinal. For example, EA1 is equivalent to Embodiment A1.

EA1. A pharmaceutical composition comprising an allogeneic human plasma and platelet derived product comprising:
  (a) human plasma proteins comprising albumin, globulins, and fibrinogen; and
  (b) human platelet proteins comprising platelet derived growth factor (PDGF)-AB, PDGF-AA, PDGF-BB, transforming growth factor beta (TGFb1, TGFb2), brain-derived neurotrophic factor (BDNF), vascular endothelial growth factor (VEGF), b-fibroblast growth factor (FGF), epidermal growth factor (EGF) and hepatocyte growth factor (HGF),
  wherein the total protein concentration of the composition is greater than 50 mg/mL and less than or about 500 mg/mL.

EA2. A pharmaceutical composition comprising an allogeneic human plasma and platelet derived product comprising:
  (a) human plasma proteins comprising albumin, globulins, and fibrinogen; and
  (b) human platelet proteins comprising PDGF-AB, PDGF-AA, PDGF-BB, TGFb1, TGFb2, BDNF, VEGF, FGF, EGF and HGF,
  wherein the concentration of PDGF-AB is greater than 50 pg/mL and less than 1,000 pg/mL.

EA3. The pharmaceutical composition of embodiment A2, wherein the total protein concentration of the composition is greater than 50 mg/mL and less than or about 500 mg/mL.

EA4. The pharmaceutical composition of embodiment A1 or A3, wherein the total protein concentration is less than or about 250 mg/mL.

EA5. The pharmaceutical composition of embodiment A1 or A3, wherein the total protein concentration is about 100 mg/mL to about 250 mg/mL.

EA6. The pharmaceutical composition of any one of embodiments A1-A5, wherein the composition has a viscosity of 50 cP or less.

EA7. The pharmaceutical composition of embodiment A6, wherein the composition comprises a viscosity of less than 25 cP, less than 20 cP, less than 15 cP, or less than 10 cP.

EA8. The pharmaceutical composition of embodiment A7, wherein the viscosity is about 1 to about 5 cP, 5 to about 10 cP, about 10 to about 15 cP, or about 15 to about 20 cP.

EA9. The pharmaceutical composition of any one of embodiments A1-A8, wherein the composition has a pH of about 4.5 to about 8.5.

EA10. The pharmaceutical composition of any one of embodiments A1-A9, wherein the composition has an osmolality of about 200 to about 500 mOsmo/kg.

EA11. The pharmaceutical composition of any one of embodiments A1-A10, wherein the concentration of albumin is about 100 to about 1,400 mg/mL.

EA12. The pharmaceutical composition of any one of embodiments A1-A11, wherein the concentration of albumin is greater than or about 40% w/w.

EA13. The pharmaceutical composition of any one of embodiments A1-A12, wherein albumin is human serum albumin.

EA14. The pharmaceutical composition of any one of embodiments A1-A13, wherein the concentration of fibrinogen is about 20 μg/mL to about 10 mg/mL, or about 1 mg/mL to about 5 mg/mL.

EA15. The pharmaceutical composition of any one of embodiments A1-A14, wherein the globulins comprise immunoglobulins.

EA16. The pharmaceutical composition of embodiment A15, wherein the concentration of immunoglobulins is greater than or about 20% w/w.

EA17. The pharmaceutical composition of any one of embodiments A1-A16, wherein the globulins comprise alpha-2-macroglobulin (A2M).

EA18. The pharmaceutical composition of embodiment A17, wherein the concentration of A2M is greater than or about 200 mg/mL.

EA19. The pharmaceutical composition of any one of embodiments A1-A18, wherein the platelet proteins comprise an anti-inflammatory protein.

EA20. The pharmaceutical composition of embodiment A19, wherein the anti-inflammatory protein is selected from interleukin 1 (IL-1), receptor antagonist protein (IRAP), IL-10, TIMP-1, and any combination thereof.

EA21. The pharmaceutical composition of any one of embodiments A1-A20, wherein the platelet proteins comprise an antioxidant protein.

EA22. The pharmaceutical composition of embodiment A21, wherein the antioxidant protein is selected from glutathione S-transferase, glutathione peroxidase, catalase, and any combination thereof.

EA23. The pharmaceutical composition of any one of embodiments A1-A22, comprising a buffer which maintains plasma proteins in solution.

EA24. The pharmaceutical composition of embodiment A23, wherein the buffer comprises citrate or phosphate buffer comprising NaCl.

EA25. The pharmaceutical composition of any one of embodiments A1-A27, wherein the composition forms a depot at a site of injection.

EA26. The pharmaceutical composition of any one of embodiments A1-A25, wherein the composition is formulated for epidural injection.

EA27. The pharmaceutical composition of any one of embodiments A1-A25, wherein the composition is formulated for intraarticular injection.

EA28. The pharmaceutical composition of any one of embodiments A1-A25, wherein the composition is formulated for intrathecal injection.

EA29. The pharmaceutical composition of any one of embodiments A1-A25, wherein the composition is formulated for intramuscular injection.

EA30. A method for treating an orthopedic indication or injury in a subject, comprising administering to the subject the pharmaceutical composition of any one of embodiments A1-A29.

EA31. The method of embodiment A30, wherein the orthopedic indication or injury is selected from painful lumbar radiculopathy, a spinal cord injury, osteoarthritis, ligament laxity, a rotator cuff injury, and a muscle injury.

EA32. The method of embodiment A30 or A31, wherein the pharmaceutical composition is administered locally.

EA33. The method of embodiment A32, wherein local administration is epidural, intrathecal, intra-articular, intramuscular, direct injection into a tendon, or direction injection into a ligament.

EA34. A method for treating painful lumbar radiculopathy in a subject, comprising administering to the subject the pharmaceutical composition of embodiment A26.

EA35. The method of embodiment A34, comprising x-ray guided needle injection.

EA36. A method for treating a spinal cord injury in a subject, comprising administering to the subject the pharmaceutical composition of embodiment A28.

EA37. A method for treating osteoarthritis in a subject, comprising administering to the subject the pharmaceutical composition of embodiment A27.

EA38. The method of any one of embodiments A30-A37, comprising diluting the pharmaceutical composition to a desired dose.

EA39. A method for treating chemotherapy-induced peripheral neuropathy (CIPN), comprising administering to the subject the pharmaceutical composition of any one of embodiments A1-A24.

EA40. The method of embodiment A39, wherein administering is systemic administration, optionally intravenous administration.

EA41. Use of the pharmaceutical composition of any one of embodiments A1-A29 for treating an orthopedic indication or injury in a subject.

EA42. The use of embodiment A41, wherein the orthopedic indication or injury is selected from painful lumbar radiculopathy, a spinal cord injury, osteoarthritis, ligament laxity, a rotator cuff injury, and a muscle injury.

EA43. The use of embodiment A41 or A42, wherein the pharmaceutical composition is formulated for local administration.

EA44. The use of embodiment A43, wherein local administration is epidural, intrathecal, intra-articular, intramuscular, direct injection into a tendon, or direction injection into a ligament.

EA45. Use of the pharmaceutical composition of embodiment A26 for treating painful lumbar radiculopathy in a subject.

EA46. The use of embodiment A45, comprising x-ray guided needle injection.

EA47. Use of the pharmaceutical composition of embodiment A28 for treating a spinal cord injury in a subject.

EA48. Use of the pharmaceutical composition of embodiment A27 for treating osteoarthritis in a subject.

EA49. A kit comprising a container comprising the pharmaceutical composition of any one of embodiments A1-A29 and instructions for treating a subject with an orthopedic indication or injury.

EA50. The kit of embodiment A49, wherein the orthopedic indication or injury is selected from painful lumbar radiculopathy, a spinal cord injury, osteoarthritis, ligament laxity, a rotator cuff injury, and a muscle injury.

EA51. The kit of embodiment A49 or A50, wherein the instructions comprise diluting the pharmaceutical composition to an appropriate dose.

EA52. The kit of any one of embodiments A49-A51, wherein the instructions comprise injecting the pharmaceutical composition into a site appropriate for the orthopedic indication or injury.

EA53. Use of the pharmaceutical composition of any one of embodiments A1-A24 for treating CIPN in a subject.

EA54. The use of embodiment A53, wherein the pharmaceutical composition is formulated for systemic administration, optionally intravenous administration.

EA55. A pharmaceutical composition comprising an allogeneic human plasma and platelet derived product comprising:
(a) human plasma proteins comprising fibrinogen; and
(b) human platelet proteins comprising PDGF-AB,
wherein the total protein concentration of the composition is greater than 50 mg/mL and less than or about 500 mg/mL.

EA56. A pharmaceutical composition comprising an allogeneic human plasma and platelet derived product comprising:
(a) human plasma proteins comprising fibrinogen; and
(b) human platelet proteins comprising PDGF-AB,
wherein the concentration of PDGF-AB is greater than 50 pg/mL and less than 1,000 pg/mL.

EA57. The pharmaceutical composition of embodiment A55 or A56, wherein human plasm proteins further comprise albumin and/or immunoglobulins.

EA58. The pharmaceutical composition of any one of embodiments A55-A57, wherein human platelet proteins further comprise PDGF-AA, PDGF-BB, TGFb1, TGFb2, VEGF, FGF, EGF, HGF, or any combination thereof.

EB1. A method for preparing a pharmaceutical composition comprising an allogeneic human plasma and platelet derived product, wherein the method comprises:
(a) providing a platelet suspension from one or more donor human subjects, wherein the platelet suspension comprises plasma and platelets, and wherein plasma comprises plasma proteins;
(b) maintaining the plasma and platelets under conditions appropriate to extract platelet proteins from the platelets, thereby generating a platelet extract comprising the plasma proteins and the platelet proteins;
(c) separating the platelet extract from cell debris, thereby generating a purified platelet extract comprising the plasma proteins and the platelet proteins, wherein:
(i) the plasma proteins comprise albumin, globulins, and fibrinogen; and
(ii) the platelet proteins comprise PDGF-AB, PDGF-AA, PDGF-BB, TGFb1, TGFb2, BDNF, VEGF, b-FGF, EGF and HGF,
(d) concentrating the purified platelet extract, thereby generating the allogeneic human plasma and platelet derived product.

EB2. The method of embodiment B1, wherein the platelet suspension is from one or more donor human subjects at an age of 16 to 65 years old.

EB3. The method of embodiment B1, wherein the platelet suspension is from one or more donor human subjects at an age of 16 to 35 years old.

EB4. The method of any one of embodiments B1-B3, wherein the platelet suspension is from 10 or more donor human subjects.

EB5. The method of any one of embodiments B1-B4, wherein the platelet suspension is from whole-blood.

EB6. The method of any one of embodiments B1-B4, wherein the platelet suspension is from apheresis.

EB7. The method of any one of embodiments B1-B6, wherein the platelet suspension has been treated with an anti-coagulant, optionally wherein the anti-coagulant is selected from an acid-citrate-dextrose solution, citrate, and heparin.

EB8. The method of any one of embodiments B1-B7, wherein step (b) comprises (i) applying at least one freeze-thaw cycle, (ii) contacting the platelet suspension with a detergent, (iii) applying osmotic pressure, (iv) sonication, (v) electroporation, (vi) high pressure microfluidics, or (vii) any combination of (i)-(vi).

EB9. The method of any one of embodiments B1-B7, wherein step (b) comprises applying at least one freeze-thaw cycle to the platelet suspension.

EB10. The method of embodiment B9, wherein the at least one freeze-thaw cycle comprises freezing the source at about –2100 C to about –800 C and thawing the platelet suspension at about 2-80 C, 15-250 C, or up to 370 C.

EB11. The method of any one of embodiments B8-B10, wherein the at least one freeze-thaw cycle is three freeze-thaw cycles.

EB12. The method of any one of embodiments B1-B11, wherein step (b) comprises contacting the platelet suspension with a detergent to extract platelet proteins from platelets.

EB13. The method of embodiment B12, wherein the detergent is an anionic detergent, a non-ionic detergent, a cationic detergent, or a zwitterionic detergent.

EB14. The method of embodiment B12 or B13, wherein the detergent is non-denaturing, a mild lysis agent, or a strong lysis agent.

EB15. The method of any one of embodiments B12-B14, wherein the detergent is sodium dodecyl sulphate (SDS), ethyl trimethyl ammonium bromide, Triton X-45, Triton X-100, Triton X-114, NP-40, Tween 20, Tween 80, CHAPS, or CHAPSO.

EB16. The method of any one of embodiments B12-B15, wherein the platelet suspension is incubated with the detergent under continuous mixing or gentle rocking for about 10 minutes to about 24 hours, optionally at a temperature of about 40 C to about 400 C.

EB17. The method of any one of embodiments B1-B16, wherein step (b) comprises applying osmotic pressure to the platelet suspension.

EB18. The method of embodiment B17, wherein osmotic pressure is increased by salts, sugars, and/or buffers.

EB19. The method of embodiment B17, wherein osmotic pressure is decreased by water, salts, sugars, and/or buffers.

EB20. The method of any one of embodiments B17-B19, wherein osmotic pressure is from about 0.01 to about 1,000 mOsm/kg.

EB21. The method of any one of embodiments B1-B20, further comprising, inactivating and/or removing or reducing viruses.

EB22. The method of embodiment B21, wherein inactivating and/or removing or reducing viruses occurs in step (b), wherein conditions appropriate to extract platelet proteins inactivate viruses.

EB23. The method of embodiment B21, wherein inactivating and/or removing or reducing viruses occurs after step (b).

EB24. The method of embodiment B23, wherein inactivating viruses comprises heat-inactivation, ultraviolet radiation, chemical treatment, or low pH treatment.

EB25. The method of embodiment B23 or B24, wherein removing or reducing viruses comprises nanofiltration or chromatography.

EB26. The method of any one of embodiments B1-B25, wherein step (b) occurs in the absence of a clotting agent.

EB27. The method of any one of embodiments B1-B26, wherein step (b) does not include removing a clot.

EB28. The method of any one of embodiments B1-B27, wherein step (c) comprises micro-filtration, depth-filtration, or centrifugation.

EB29. The method of any one of embodiments B1-B28, wherein step (d) comprises tangential flow filtration of the purified platelet extract, optionally wherein a membrane for tangential flow filtration has a size of about 1 KDa to about 500 KDa.

EB30. The method of any one of embodiments B1-B28, wherein step (d) comprises using spin filters to concentrate the purified platelet extract.

EB31. The method of any one of embodiments B1-B30, wherein the platelet suspension is diluted in a solution prior to step (b).

EB32. The method of any one of embodiments B1-B31, wherein the purified platelet extract is diluted in a solution prior to step (d).

EB33. The method of embodiment B31 or B32, wherein the solution is a buffer, optionally phosphate buffered saline (PBS) or a buffer comprising citrate.

EB34. The method of any one of embodiments B1-B33, further comprising step (e) sterile filtering the allogeneic human plasma and platelet derived product.

EB35. The method of embodiment B34, wherein step (e) comprises passing the allogeneic human plasma and platelet derived product through a filter of about 0.1 mm to about 0.22 mm.

EB36. The method of any one of embodiments B1-B35, comprising reducing or removing blood cells from the platelet suspension prior to step (b).

EB37. The method of embodiment B36, wherein blood cells comprise red blood cells and white blood cells.

EB38. The method of embodiment B37, wherein white blood cells are reduced by about a 5-6 log reduction.

EB39. The method of any one of embodiments B36-B38, comprising passing the platelet suspension through a filter at a temperature of about 20 C to about 80 C.

EB40. The method of embodiment B39, wherein the filter is about 0.1 mm to about 40 mm.

EB41. The method of any one of embodiments B1-B40, wherein step (b) comprises maintaining the platelet suspension in conditions sufficient to maintain plasma proteins in solution.

EB42. The method of any one of embodiments B1-B41, wherein the human allogeneic plasma and platelet derived product is diluted to a dosage form.

EB43. The method of embodiment B42, wherein the dosage form is for epidural injection, intramuscular injection, intrathecal injection, intraarticular injection, direct injection to a tendon, or direct injection to a ligament.

EB44. The method of any one of embodiments B1-B43, wherein the total protein concentration of the pharmaceutical composition is greater than 50 mg/mL and less than or about 500 mg/mL.

EB45. The method of embodiment B44, wherein the total protein concentration is less than or about 250 mg/mL.

EB46. The method of embodiment B44 or B45, wherein the total protein concentration is about 100 mg/mL to about 250 mg/mL.

EB47. The method of any one of embodiments B1-B46, wherein the pharmaceutical composition has a viscosity of 50 cP or less.

EB48. The method of embodiment B47, wherein the pharmaceutical composition comprises a viscosity of less than 25 cP, less than 20 cP, less than 15 cP, or less than 10 cP.

EB49. The method of embodiment B48, wherein the viscosity is about 1 to about 5 cP, 5 to about 10 cP, about 10 to about 15 cP, or about 15 to about 20 cP.

EB50. The method of any one of embodiments B1-B49, wherein the pharmaceutical composition has a pH of about 4.5 to about 8.5.

EB51. The method of any one of embodiments B1-B50, wherein the composition has an osmolality of about 200 to about 500 mOsmo/kg.

EB52. The method of any one of embodiments B1-B51, wherein the concentration of albumin is about 100 to about 1,400 mg/mL.

EB53. The method of any one of embodiments B1-B52, wherein the concentration of albumin is greater than or about 40% w/w.

EB54. The method of any one of embodiments B1-B53, wherein albumin is human serum albumin.

EB55. The method of any one of embodiments B1-B54, wherein the concentration of fibrinogen is about 20 μg/mL to about 10 mg/mL, or about 1 mg/mL to about 5 mg/mL.

EB56. The method of any one of embodiments B1-B55, wherein the globulins comprise immunoglobulins.

EB57. The method of embodiment B56, wherein the concentration of immunoglobulins is greater than or about 20% w/w.

EB58. The method of any one of embodiments B1-B57, wherein the globulins comprise alpha-2-macroglobulin (A2M).

EB59. The method of embodiment B58, wherein the concentration of A2M is greater than or about 200 mg/mL.

EB60. The method of any one of embodiments B1-B59, wherein the concentration of PDGF-AB is greater than 50 pg/mL and less than 1,000 pg/mL.

EB61. The method of any one of embodiments B1-B61, wherein the platelet proteins comprise an anti-inflammatory protein.

EB62. The method of embodiment B61, wherein the anti-inflammatory protein is selected from interleukin 1 (IL-1), receptor antagonist protein (IRAP), IL-10, TIMP-1, and any combination thereof.

EB63. The method of any one of embodiments B1-B62, wherein the platelet proteins comprise an antioxidant protein.

EB64. The method of embodiment B63, wherein the antioxidant protein is selected from glutathione S-transferase, glutathione peroxidase, catalase, and any combination thereof.

EB65. A pharmaceutical composition comprising an allogeneic human plasma and platelet derived product produced by the method of any one of embodiments B1-B64.

EB66. The pharmaceutical composition of embodiment B65, wherein the composition forms a depot at a site of injection.

EB67. The pharmaceutical composition of any one of embodiments B65-B66 wherein the composition is formulated for epidural injection.

EB68. The pharmaceutical composition of any one of embodiments B65-B66, wherein the composition is formulated for intraarticular injection.

EB69. The pharmaceutical composition of any one of embodiments B65-B66, wherein the composition is formulated for intrathecal injection.

EB70. The pharmaceutical composition of any one of embodiments B65-B66, wherein the composition is formulated for intramuscular injection.

EB71. A method for treating an orthopedic indication or injury in a subject, comprising administering to the subject the pharmaceutical composition of any one of embodiments B65-B70.

EB72. The method of embodiment B71, wherein the orthopedic indication or injury is selected from painful lumbar radiculopathy, a spinal cord injury, osteoarthritis, ligament laxity, a rotator cuff injury, and a muscle injury.

EB73. The method of embodiment B71 or B72, wherein the pharmaceutical composition is administered locally.

EB74. The method of embodiment B73, wherein local administration is epidural, intrathecal, intra-articular, intramuscular, direct injection into a tendon, or direction injection into a ligament.

EB75. A method for treating painful lumbar radiculopathy in a subject, comprising administering to the subject the pharmaceutical composition of embodiment B67.

EB76. The method of embodiment B75, comprising x-ray guided needle injection.

EB77. A method for treating a spinal cord injury in a subject, comprising administering to the subject the pharmaceutical composition of embodiment B69.

EB78. A method for treating osteoarthritis in a subject, comprising administering to the subject the pharmaceutical composition of embodiment B68.

EB79. The method of any one of embodiments B71-B78, comprising diluting the pharmaceutical composition to a desired dose.

EB80. Use of the pharmaceutical composition of any one of embodiments B65-B70, for treating an orthopedic indication or injury in a subject.

EB81. The use of embodiment B80, wherein the orthopedic indication or injury is selected from painful lumbar radiculopathy, a spinal cord injury, osteoarthritis, ligament laxity, a rotator cuff injury, and a muscle injury.

EB82. The use of embodiment B80 or B81, wherein the pharmaceutical composition is formulated for local administration.

EB83. The use of embodiment B82, wherein local administration is epidural, intrathecal, intra-articular, intramuscular, direct injection into a tendon, or direction injection into a ligament.

EB84. Use of the pharmaceutical composition of embodiment B67, for treating painful lumbar radiculopathy in a subject.

EB85. The use of embodiment B84, comprising x-ray guided needle injection.

EB86. Use of the pharmaceutical composition of embodiment B69, for treating a spinal cord injury in a subject.

EB87. Use of the pharmaceutical composition of embodiment B68, for treating osteoarthritis in a subject.

EB88. A kit comprising a container comprising the pharmaceutical composition of any one of embodiments B65-B70, and instructions for treating a subject with an orthopedic indication or injury.

EB89. The kit of embodiment B88, wherein the orthopedic indication or injury is selected from painful lumbar radiculopathy, a spinal cord injury, osteoarthritis, ligament laxity, a rotator cuff injury, and a muscle injury.

EB90. The kit of embodiment B88 or B90, wherein the instructions comprise diluting the pharmaceutical composition to an appropriate dose.

EB91. The kit of any one of embodiments B88-B90, wherein the instructions comprise injecting the pharmaceutical composition into a site appropriate for the orthopedic indication or injury.

EB92. A method for treating CIPN in a subject, comprising administering the pharmaceutical composition of embodiment B65 to the subject.

EB93. The method of embodiment B92, wherein administering comprises systemic administration, optionally intravenous administration.

EB94. Use of the pharmaceutical composition of embodiment B65 for treating CIPN in a subject.

EB95. The use of embodiment B94, wherein the pharmaceutical composition is formulated for systemic administration, optionally intravenous administration.

EB96. A method for preparing a pharmaceutical composition comprising an allogeneic human plasma and platelet derived product, wherein the method comprises:

(a) providing a platelet suspension from one or more donor human subjects, wherein the platelet suspension comprises plasma and platelets, and wherein plasma comprises plasma proteins;

(b) maintaining the plasma and platelets under conditions appropriate to extract platelet proteins from the platelets, thereby generating a platelet extract comprising the plasma proteins and the platelet proteins;

(c) separating the platelet extract from cell debris, thereby generating a purified platelet extract comprising the plasma proteins and the platelet proteins, wherein:

(i) the plasma proteins comprise fibrinogen; and (ii) the platelet proteins comprise PDGF-AB, (d) concentrating the purified platelet extract, thereby generating the allogeneic human plasma and platelet derived product.

EB97. The method of embodiment B96, wherein human plasm proteins further comprise albumin and/or immunoglobulins.

EB98. The method of embodiment B96 or B97, wherein human platelet proteins further comprise PDGF-AA, PDGF-BB, TGFb1, TGFb2, VEGF, FGF, EGF, HGF, or any combination thereof.

EXAMPLES

Example 1. Preparing Allogeneic Plasma and Platelet Derived Products

To prepare a composition comprising an allogeneic human plasma and platelet derived product, a method is utilized, wherein the method comprises obtaining platelet suspension (i.e., plasma and platelets) from one or more human donor subjects, extracting platelet proteins from the platelets to generate a platelet extract comprising plasma proteins and platelet proteins, purifying the platelet extract by separating cell debris from the platelet extract, and concentrating the purified platelet extract. Exemplary and optional steps in the method are described below, and exemplary methods are provided in Examples 2-9 and 31.

Obtaining Platelet Suspensions

Platelet suspensions are obtained from one or more human donor subjects e.g., 16-35 years old. Alternatively, platelet suspensions are obtained from one or more human donor subjects, e.g., 35-65 years old. Platelet suspensions are obtained from whole blood units, blood fractions, and/or plasma fractions. Alternatively, platelet suspensions are obtained from transfusable quality platelets. The platelets can be separated from whole blood using apheresis or appropriate centrifuge procedures. Whole blood or platelets are treated with suitable anti-coagulant (Sodium citrate, EDTA, phosphate).

Filtering

The white blood cells and red blood cells are removed from the platelet suspensions via filtration. The platelet suspensions are passed through a suitable filter included, but not limited to, polyvinylidene fluoride (PVDF), nylon, polyether sulfone (PES), polysulfone (PS), regenerated cellulose (RC), or Glass Fiber (GF) filters. The size of the filter ranges from 0.1 μm to 40 μm and occurs at temperatures between 1 and 37° C. The plasma and platelets can be diluted prior to filtration to prevent clogging.

Extracting Platelet Proteins

To extract platelet proteins from the platelets, the platelet suspensions are maintained under appropriate conditions. The platelet suspensions can be diluted before or during extraction. Exemplary methods for extracting platelet proteins are provided below. For each method, several parameters will be evaluated including, but not limited to, total protein concentration, quantity of gross particulates, osmolality, and the quantities of functional platelet and serum proteins.

Freeze-Thaw

An exemplary method for extracting platelet proteins is subjecting the platelet suspensions to at least one freeze-thaw cycle. A freeze-thaw cycle includes maintaining the platelet suspensions at about −80° C. and then about 37° C. Alternatively, a freeze-thaw cycle includes maintaining platelet suspensions at about −80° C. and then about 25° C. The resulting platelet extract can be stored at −80° C. until further processing.

Detergent-Buffer

An exemplary method for extracting platelet proteins is maintaining the plasma and platelets in a sufficient detergent-buffer. The platelet suspensions are incubated with one or more detergents under continuous mixing or rocking for between 10 minutes and 24 hours. Incubation temperatures range from 4 to 40° C. Exemplary detergent include, but are not limited to, Sodium dodecyl sulphate (SDS), Triton X-45, Triton X-100, Triton X-114, NP-40, Tween 20, Tween 80, CHAPS, and CHAPSO.

Osmosis

An exemplary method for extracting platelet proteins is maintaining the platelet suspensions under hyperosmotic or hypoosmotic conditions. Specifically, the osmolality in the surrounding fluid can be increased or decreased. The osmolality ranges from 0.01 to 1000 mOsm/kg. Salts, sugars, and buffers that are compatible with platelet suspensions are added to increase osmosis. The change in osmolality can drive water into the platelets, breaking the platelet membrane. Conversely, the change in osmolality can draw water out of platelets, shrinking the platelets so they release proteins.

Sonication

An exemplary method for extracting platelet proteins is subjecting the platelet suspensions to sonication. Specifically, the platelet suspensions are pulsed with high-frequency sound waves via ultrasonic bath or probe. The frequency is 5 to 30 kHz, the temperature is 2-8° C., the pulse time is 1-30 seconds, and the rest time is 10-60 seconds. The conditions are optimized to prevent protein degradation.

Electroporation

An exemplary method for extracting platelet proteins is subjecting the plasma and platelets to electroporation. Specifically, the platelet suspensions are pulsed with a high-voltage electrical pulse with defined magnitude and lengths ranging from 0.1-10 kV, 1-300Ω, and 1-100 F. Electrical pulsing occurs from about 1 to about 20 milliseconds. Salts, sugars, cationic polymers, anionic polymers, surfactants, and buffers compatible with the platelet suspensions will be used.

High Pressure/Microfluidics

An exemplary method for extracting platelet proteins is subjecting the platelet suspensions to high pressure. For example, platelet suspensions can be subjected to high pressure using microchannels at pressures ranging from 10,000 to 50,000 PSI. The platelet suspensions can be passed through the microchannels one or more times.

Purifying the Platelet Extract

After extracting the platelet proteins to generate a platelet extract, cell debris and aggregates are removed from the platelet extract to generate a purified platelet extract. Several methods can be used to purify the platelet extract including, but not limited to, micro-filtration, depth-filtration, and centrifugation. Exemplary methods are described below. For each method, the extract will be inspected for total protein concentration and successful removal of debris and aggregates.

Micro-Filtration

An exemplary method for purifying the platelet extract is micro-filtration. Specifically, the platelet extract is passed through a filter with a 0.2 μm or larger pore size at a flow rate ranging from 0.1 to 50 L/hour. Suitable filters include, but are not limited to, polyvinylidene fluoride (PVDF), nylon, polyether sulfone (PES), polysulfone (PS), regenerated cellulose (RC), or Glass Fiber (GF) filters.

Depth-Filtration

An exemplary method for purifying the platelet extract is depth-filtration. Specifically, the platelet extract is passed through a filter at a flow rate of between 0.1 to 50 L/hour. Suitable filters include, but are not limited to, cellulose, polypropylene, Diatomaceous earth (DE), or non-DE in stacked disks.

Centrifugation

An exemplary method for purifying the platelet extract is centrifugation. Specifically, the platelet extract is centrifuged at 50 to 50,000×g for about 1 to about 100 minutes at about 2 to about 25° C.

Viral Inactivation and Removal

Viruses are inactivated and removed from the platelet suspension, platelet extract or purified platelet extract. Viral inactivation and removal can occur before extraction, after extraction, during extraction, or before concentration. Viruses can be inactivated via known techniques including, but not limited to, heat treatment, pH treatment, UV treatment, and chemical treatment. Chemicals suitable for viral inactivation include b-propiolactone, riboflavin, sulfites, and caprylate. Known techniques to remove viruses include, but are not limited to, filtration, affinity chromatography, and ion exchange chromatography.

Concentrating the Platelet Proteins

After removal of cell debris and aggregates, the purified platelet extract is concentrated to generate the allogeneic human plasma and platelet derived product. Exemplary methods for concentrating the purified platelet extract are provided below.

Tangential Flow Filtration

An exemplary method for concentrating the purified platelet extract is tangential flow filtration (TFF). Specifically, the purified platelet extract is subjected to TFF to concentrate the platelet proteins with TFF modules that include, but are not limited to, cassettes, hollow fiber, and ceramic, mPES membranes, regenerated cellulose, mixed cellulose ester, stabilized cellulose, polysulfone (PS), polyethersulfone (PES), and low-protein binding membranes. The membranes have a molecular weight cutoff between 1 kDa and 60 kDa. Alternatively, the membranes have a molecule weight cutoff between 1 kDa and 1,000 kDa. The TFF system is conditioned with a suitable buffer to ensure proper wetting of the membrane and to remove any preservatives or storage solutions that may be present. The product mix feed is introduced into the TFF system. The pump generates a tangential flow across the membrane, allowing the solvent to pass through while retaining the target molecules. The flow rate ranges from 1 to 50 L/hour. As the feed solution flows across the membrane, water is driven through the membrane, creating a concentrated retentate on one side of the membrane. The retentate contains the concentrated target product, while the permeate (filtrate) contains the removed impurities and excess solvent/buffer. The TFF process is closely monitored for transmembrane pressure, flow rates, and concentration factors. These parameters are controlled to optimize concentration and prevent membrane fouling or clogging. The concentrated and dia-filtrated product is collected as the final retentate. The product can then be further processed or formulated for the subsequent downstream processing steps. Several parameters will be evaluated including, but not limited to, total protein concentration, quantity of gross particulates, osmolality, and the quantities of functional platelet and serum proteins.

Centrifugal Filters

An exemplary method of concentrating the purified platelet extract is use of a centrifugal filter. A suitable filter includes, but is not limited to, regenerated cellulose. The filter has a molecular weight cut off is 10 kDa. The platelet extract is centrifuged at 3.000×g for 15 minutes.

Removal of Plasma Proteins

The method described herein can include removal of plasma proteins. The plasma proteins are removed resulting in concentrated platelet proteins with higher purity. Plasma proteins include, but are not limited to, albumin, immunoglobulin, and fibrinogen. Methods to remove plasma proteins include, but are not limited to, affinity columns, size exclusion columns, fibrinogen clotting with $CaCl_2$), and ion exchange chromatography. Plasma proteins can be removed before extraction, after extraction, before cell debris and aggregate removal, after cell debris and aggregate removal, before concentration, or after concentration.

Sterile Filtration

After obtaining the allogeneic human plasma and platelet derived product, the product can be sterile filtered. The product is filtered with sterilization-grade filters sized 0.22 μm or less. Suitable filters include, but is not limited to, polyvinylidene fluoride (PVDF), nylon, polyether sulfone (PES), polysulfone (PS), regenerated cellulose (RC), or Glass Fiber (GF) filters. If desired, the product can be filled in a suitable container and kept frozen or refrigerated, liquid or solid (e.g., lyophilized for long-term storage or used as a powder).

Example 2: Process Option 1 for Preparing Allogeneic Plasma and Platelet Derived Products An exemplary method to prepare a composition comprising an allogeneic human plasma and platelet derived product as described herein is depicted in FIG. 1 and described below:

Thawing: Platelet suspensions are obtained from one or more human donors are thawed at about 2 to about 8° C. for about 24 to about 72 hours.

Pooling: Thawed platelet suspensions from at least 2 human donors are added to a pooling vessel.

Dilution and Filtration: Platelet suspensions are placed in an extraction vessel diluted in a buffer comprising, citrate, phosphate, polysorbate 80, and EDTA at a pH of about 4.0 to about 9.0. Depth-filtration or tangential flow filtration (TFF) can be used to remove blood cells. Depth-filters are selected from, 3M:05SP01A, Sartoclear DL60, Profile Star A030, among others.

Extraction and Viral Inactivation: Platelet proteins are extracted via freeze-thaw, buffer/detergent, or osmotic pressure. Viral inactivation is achieved with heat, ultraviolet-C treatment, detergent treatment, or pH treatment, among other techniques. Cell debris and aggregates are removed from the plasma and platelets via filtration via spin centrifugation or a pump filtration system.

Viral Clearance: Filtration or chromatography is used to remove viruses. Filtration can comprise nanometer-scale filters selected from Planova BioEX, Viresolve, Ultipore, Pegasus, or Virosart, among others. Other Planova filters may also be suitable, including S20N filters.

Concentration: The platelet extract is concentrated with 10 MWCO spin filters and buffer exchanged to the formulation buffer. TFF can be used to concentrate and buffer exchange the platelet proteins.

Strength Adjustment: Concentrated platelet extract is diluted to a concentration of 150-250 mg/mL. Alternatively, concentrated platelet extract is diluted to a concentration of 70 to 250 mg/mL. The platelet proteins are then sterile filtered with a 0.22 μm filter.

Example 3: Process Option 2 for Preparing Allogeneic Plasma and Platelet Derived Products A method to prepare a composition comprising an allogeneic human plasma and platelet derived product is depicted in FIG. 2 and described below:

Thawing: Platelet suspensions obtained from one or more human donors are thawed at about 2 to about 8° C. for about 24 to about 72 hours.

Pooling: Thawed platelet suspensions from at least 2 human donors are added to a pooling vessel.

Dilution and Filtration: Platelet suspensions are placed in an extraction vessel and diluted in a buffer comprising, citrate, phosphate, polysorbate 80, and EDTA at a pH of about 4.0 to about 9.0. Depth-filtration or tangential flow filtration (TFF) can be used to remove blood cells. Depth-filters are selected from, 3M:05SP01A, Sartoclear DL60, Profile Star A030, among others.

Extraction, Viral Inactivation, and Dilution: Platelet proteins are extracted via freeze-thaw, buffer/detergent, or osmotic pressure. Viral inactivation is achieved with heat, ultraviolet-C treatment, detergent treatment, or pH treatment, among other techniques. Platelet extracts are diluted. Cell debris and aggregates are removed from the plasma and platelets via filtration via spin centrifugation or a pump filtration system.

Viral Clearance: Filtration or chromatography is used to remove viruses. Filtration can comprise nanometer-scale filters selected from Planova BioEX, Viresolve, Ultipore, Pegasus, or Virosart, among others. Other Planova filters may also be suitable, including S20N filters.

Concentration: The platelet extract is concentrated with 10 MWCO spin filters and buffer exchanged to the formulation buffer. TFF can be used to concentrate and buffer exchange the platelet proteins.

Strength Adjustment: Concentrated platelet extract is diluted to a dose of 150-250 mg/mL. Alternatively, concentrated platelet extract is diluted to a concentration of 70 to 250 mg/mL. The platelet proteins are then sterile filtered with a 0.22 μm filter.

Example 4: Process Option 3 for Preparing Allogeneic Plasma and Platelet Derived Products A method to prepare a composition comprising an allogeneic human plasma and platelet derived product is depicted in FIG. 3 and described below:

Thawing: Platelet suspensions obtained from one or more human donors are thawed at about 2 to about 8° C. for about 24 to about 72 hours Pooling, Dilution, and Filtration: Platelet suspensions from at least 2 human donors are placed in an extraction vessel. Depth-filtration or tangential flow filtration (TFF) can be used to remove blood cells. Depth-filters are selected from, 3M:05SP01A, Sartoclear DL60, Profile Star A030, among others. Platelet suspensions are filtered into dilution buffer bags.

Extraction and Viral Inactivation: Platelet proteins are extracted via freeze-thaw, buffer/detergent, or osmotic pressure. Viral inactivation is achieved with heat, ultraviolet-C treatment, detergent treatment, or pH treatment, among other techniques. Cell debris and aggregates are removed from the plasma and platelets via filtration via spin centrifugation or a pump filtration system.

Viral Clearance: Filtration or chromatography is used to remove viruses. Filtration can comprise nanometer-scale filters selected from Planova BioEX, Viresolve, Ultipore, Pegasus, or Virosart, among others. Other Planova filters may also be suitable, including S20N filters.

Concentration: The platelet extract is concentrated with 10 MWCO spin filters and buffer exchanged to the formulation buffer. TFF can be used to concentrate and buffer exchange the platelet proteins.

Strength Adjustment: Concentrated platelet extract is diluted to a dose of 150-250 mg/mL. Alternatively, concentrated platelet extract is diluted to a concentration of 70 to 250 mg/mL. The platelet proteins are then sterile filtered with a 0.22 μm filter.

Example 5: Process Option 4 for Preparing Allogeneic Plasma and Platelet Derived Products A method to prepare a composition comprising an allogeneic human plasma and platelet derived product is depicted in FIG. 4 and described below:

Thawing: Platelet suspensions obtained from one or more human donors are thawed at about 2 to about 8° C. for about 24 to about 72 hours.

Pooling, Dilution, and Filtration: Platelet suspensions from at least 2 human donors are placed in an extraction vessel. Depth-filtration or tangential flow filtration (TFF) can be used to remove blood cells. Depth-filters are selected from, 3M:05SP01A, Sartoclear DL60, Profile Star A030, among others. Platelet suspensions are filtered into dilution buffer bags.

Extraction and Viral Inactivation: Platelet proteins are extracted via freeze-thaw, buffer/detergent, or osmotic pressure. Viral inactivation is achieved with heat, ultraviolet-C treatment, detergent treatment, or pH treatment, among other techniques. Platelet proteins are diluted. Platelet proteins are clarified with filtration via spin centrifugation or a pump filtration system.

Viral Clearance: Platelet proteins are diluted. Filtration or chromatography is used to remove viruses. Filtration can comprise nanometer-scale filters selected from Planova BioEX, Viresolve, Ultipore, Pegasus, or Virosart, among others. Other Planova filters may also be suitable, including S20N filters.

Concentration: Platelet proteins are concentrated with 10 MWCO spin filters and buffer exchanged to the formulation buffer. TFF can be used to concentrate and buffer exchange the platelet proteins.

Strength Adjustment: Concentrated platelet proteins are diluted to an optimal dose of 150-250 mg/mL. Alternatively, concentrated platelet extract is diluted to a concentration of 70 to 250 mg/mL. The platelet proteins are then sterile filtered with a 0.22 μm filter.

Example 6: Process Option 5 for Preparing Allogeneic Human Plasma and Platelet Derived Product A method to prepare a composition comprising an allogeneic human plasma and platelet derived product is depicted in FIG. 5 and described below:

Thawing: Platelet suspensions obtained from one or more human donors are thawed at about 2 to about 8° C. for about 24 to about 72 hours.

Pooling: Thawed platelet suspensions from at least 2 human donor subjects are added to a pooling vessel.

Remove Albumin: Albumin is removed with affinity chromatography.

Dilution and Filtration: Platelet suspensions are placed in an extraction vessel and diluted in a buffer comprising, citrate, phosphate, polysorbate 80, and EDTA at a pH of about 4.0 to about 9.0. Depth-filtration or tangential flow filtration (TFF) can be used to remove blood cells. Depth-filters are selected from, 3M:05SP01A, Sartoclear DL60, Profile Star A030, among others.

Extraction and Viral Inactivation: Platelet proteins are extracted via freeze-thaw, buffer/detergent, or osmotic pressure. Viral inactivation is achieved with heat, ultraviolet-C treatment, detergent treatment, or pH treatment, among other techniques. Cell debris and aggregates are removed from the plasma and platelets via filtration via spin centrifugation or a pump filtration system. TFF can be used to clarify platelet extracts.

Viral Clearance: Filtration or chromatography is used to remove viruses. Filtration can comprise nanometer-scale filters selected from Planova BioEX, Viresolve, Ultipore, Pegasus, or Virosart, among others. Other Planova filters may also be suitable, including S20N filters.

Concentration: The platelet extract is concentrated with 10 MWCO spin filters and buffer exchanged to the formulation buffer. TFF can be used to concentrate and buffer exchange the platelet proteins.

Strength Adjustment: Concentrated platelet extract is diluted to a dose of 150-250 mg/mL. Alternatively, concentrated platelet extract is diluted to a concentration of 70 to 250 mg/mL. The platelet proteins are then sterile filtered with a 0.22 μm filter.

Example 7: Process Option 6 for Preparing Allogeneic Human Plasma and Platelet Derived Product A method to prepare a composition comprising an allogeneic human plasma and platelet derived product is depicted in FIG. 6 and described below:

Thawing: Platelet suspensions obtained from one or more human donors are thawed at about 2 to about 8° C. for about 24 to about 72 hours.

Pooling: Thawed platelet suspensions from at least 2 human donors are added to a pooling vessel.

Dilution and Filtration: Platelet suspensions are placed in an extraction vessel and diluted in a buffer comprising, citrate, phosphate, polysorbate 80, and EDTA at a pH of about 4.0 to about 9.0. Depth-filtration or tangential flow filtration (TFF) can be used to remove blood cells. Depth-filters are selected from, 3M:05SP01A, Sartoclear DL60, Profile Star A030, among others.

Remove Albumin: Albumin is removed with affinity chromatography.

Extraction and Viral Inactivation: Platelet proteins are extracted via freeze-thaw, buffer/detergent, or osmotic pressure. Viral inactivation is achieved with heat, ultraviolet-C treatment, detergent treatment, or pH treatment, among other techniques. Cell debris and aggregates are removed from the plasma and platelets via filtration via spin centrifugation or a pump filtration system.

Viral Clearance: Filtration or chromatography is used to remove viruses. Filtration can comprise nanometer-scale filters selected from Planova BioEX, Viresolve, Ultipore, Pegasus, or Virosart, among others. Other Planova filters may also be suitable, including S20N filters.

Concentration: The platelet extract is concentrated with 10 MWCO spin filters and buffer exchanged to the formulation buffer. TFF can be used to concentrate and buffer exchange the platelet proteins.

Strength Adjustment: Concentrated platelet extract is diluted to a dose of 150-250 mg/mL. Alternatively, concentrated platelet extract is diluted to a concentration of 70 to 250 mg/mL. The platelet proteins are then sterile filtered with a 0.22 μm filter.

Example 8: Process Option 7 for Preparing
Allogeneic Human Plasma and Platelet Derived
Product A method to prepare a composition comprising an allogeneic human plasma and platelet derived product is
depicted in FIG. 7 and described below:

Thawing: Platelet suspensions obtained from one or more
human donors are thawed at about 2 to about 8° C. for
about 24 to about 72 hours.

Pooling: Thawed platelet suspensions from at least 2
human donors are added to a pooling vessel.

Dilution and Filtration: Platelet suspensions are placed in
an extraction vessel and diluted in a buffer comprising,
citrate, phosphate, polysorbate 80, and EDTA at a pH of
about 4.0 to about 9.0. Depth-filtration or tangential
flow filtration (TFF) can be used to remove blood cells.
Depth-filters are selected from, 3M:05SP01A, Sarto-
clear DL60, Profile Star A030, among others.

Extraction, Viral Inactivation, and Remove Albumin:
Platelet proteins are extracted via freeze-thaw, buffer/
detergent, or osmotic pressure. Viral inactivation is
achieved with heat, ultraviolet-C treatment, detergent
treatment, or pH treatment, among other techniques.
Cell debris and aggregates are removed from the
plasma and platelets via filtration via spin centrifuga-
tion or a pump filtration system. Albumin is removed
with affinity chromatography.

Viral Clearance: Filtration or chromatography is used to
remove viruses. Filtration can comprise nanometer-scale filters selected from Planova BioEX, Viresolve,
Ultipore, Pegasus, or Virosart, among others. Other
Planova filters may also be suitable, including S20N
filters.

Concentration: The platelet extract is concentrated with
10 MWCO spin filters and buffer exchanged to the
formulation buffer. TFF can be used to concentrate and
buffer exchange the platelet proteins.

Strength Adjustment: Concentrated platelet extract is
diluted to a dose of 150-250 mg/mL. Alternatively,
concentrated platelet extract is diluted to a concentra-
tion of 70 to 250 mg/mL. The platelet proteins are then
sterile filtered with a 0.22 μm filter.

Example 9: Process Option 8 for Preparing
Allogeneic Human Plasma and Platelet Derived
Product A method to prepare a composition comprising an allo-
geneic human plasma and platelet derived product is
depicted in FIG. 8 and described below:

Thawing: Platelet suspensions obtained from one or more
human donors are thawed at about 2 to about 8° C. for
about 24 to about 72 hours.

Pooling: Thawed platelet suspensions from at least 2 human donors are added to a pooling vessel.

Dilution and Filtration: Platelet suspensions are placed in
an extraction vessel and diluted in a buffer comprising,
citrate, phosphate, polysorbate 80, and EDTA at a pH of
about 4.0 to about 9.0. Depth-filtration or tangential
flow filtration (TFF) can be used to remove blood cells.
Depth-filters are selected from, 3M:05SP01A, Sarto-
clear DL60, Profile Star A030, among others.

Extraction, Viral Inactivation: Platelet proteins are
extracted via freeze-thaw, buffer/detergent, or osmotic
pressure. Viral inactivation is achieved with heat, ultra-
violet-C treatment, detergent treatment, or pH treatment, among other techniques. Cell debris and aggre-
gates are removed from the plasma and platelets via
filtration via spin centrifugation or a pump filtration
system.

Viral Clearance: Filtration or chromatography is used to
remove viruses. Filtration can comprise nanometer-
scale filters selected from Planova BioEX, Viresolve,
Ultipore, Pegasus, or Virosart, among others. Other
Planova filters may also be suitable, including S20N
filters.

Remove Albumin: Albumin is removed with affinity chro-
matography.

Concentration: The platelet extract is concentrated with
10 MWCO spin filters and buffer exchanged to the
formulation buffer. TFF can be used to concentrate and
buffer exchange the platelet proteins.

Strength Adjustment: Concentrated platelet extract is
diluted to a dose of 150-250 mg/mL. Alternatively,
concentrated platelet extract is diluted to a concentra-
tion of 70 to 250 mg/mL. The platelet proteins are then
sterile filtered with a 0.22 μm filter.

Example 10: Process Option 9 for Preparing
Allogeneic Human Plasma and Platelet Derived
Product A method to prepare a composition comprising an allo-
geneic human plasma and platelet derived product is
depicted in FIG. 9 and described below:

Thawing: Platelet suspensions obtained from one or more
human donors are thawed at about 2 to about 8° C. for
about 24 to about 72 hours.

Pooling: Thawed platelet suspensions from at least 2
human donors are added to a pooling vessel.

Dilution and Filtration: Platelet suspensions are placed in
an extraction vessel and diluted in a buffer comprising,
citrate, phosphate, polysorbate 80, and EDTA at a pH of
about 4.0 to about 9.0. Depth-filtration or tangential
flow filtration (TFF) can be used to remove blood cells.
Depth-filters are selected from, 3M:05SP01A, Sarto-
clear DL60, Profile Star A030, among others.

Extraction, Viral Inactivation: Platelet proteins are
extracted via freeze-thaw, buffer/detergent, or osmotic
pressure. Viral inactivation is achieved with heat, ultra-
violet-C treatment, detergent buffer, or pH treatment,
among other techniques. Cell debris and aggregates are
removed from the plasma and platelets via filtration via
spin centrifugation or a pump filtration system.

Viral Clearance: Filtration or chromatography is used to
remove viruses. Filtration can comprise nanometer-
scale filters selected from Planova BioEX, Viresolve,
Ultipore, Pegasus, or Virosart, among others. Other
Planova filters may also be suitable, including S20N
filters.

Concentration: The platelet extract is concentrated with
10 MWCO spin filters and buffer exchanged to the
formulation buffer. TFF can be used to concentrate and
buffer exchange the platelet proteins.

Remove Albumin: Albumin is removed with affinity chro-
matography.

Strength Adjustment: Concentrated platelet extract is
diluted to a dose of 150-250 mg/mL. Alternatively,
concentrated platelet extract is diluted to a concentra-
tion of 70 to 250 mg/mL. The platelet proteins are then
sterile filtered with a 0.22 μm filter.

Example 11: Evaluation of Platelet Protein Extraction Methods for Generating Allogeneic Human Plasma and Platelet Derived Product To evaluate methods of extracting platelet proteins from platelets, frozen bags of plasma and platelets were utilized. Three extraction methods were evaluated: (1) osmotic pressure, (2) detergent-buffer, and (3) freeze-thaw. Prior to extraction, the bags of plasma and platelets were thawed at 37° C. for 1-2 hours.

Osmotic Pressure

The thawed platelets were subjected to both hypo-osmotic and hyper-osmotic conditions. Three different hypo-osmotic conditions were evaluated, as detailed in Table 8. To subject platelets to hyper-osmotic conditions, 100 mM of citrate (pH 7.5) was added.

TABLE 8

Hypo-osmotic Conditions Used to Extract Platelet Proteins

| Condition | Platelet Bag | 20 mM Citrate pH 7.5 | Water |
|---|---|---|---|
| 1 | 1 | 1 | 0 |
| 2 | 1 | 1 | 2 |
| 3 | 1 | 1 | 6 |

Detergent 0.6% Tween 20 (Polysorbate 20) was used to evaluate platelet extraction via detergent. The thawed platelets were diluted in a buffer comprising 100 mM citrate (pH 7.5) and 0.6% Tween 20.

Freeze/Thaw

A standard protocol was used to lyse platelets with freeze-thaw. Briefly, platelets were centrifuged at 3,000×g for 30 minutes at 22° C., and the supernatant was decanted. The platelet pellets were washed with phosphate-buffered saline (PBS) and concentrated to one-tenth of the initial volume. The concentrated platelet pellets were frozen at −70° C. for at least 1 hour and thawed at 37° C. for 30 minutes. Complete freezing and thawing was evaluated via visual inspection. A total of three cycles of freeze-thaw were performed. The platelets were then centrifuged at 4,500×g for 30 minutes at 20° C. The platelet pellets were heated at 56° C. for 30 minutes in a dry bath and immediately frozen at −70° C. for at least one hour. The platelets were centrifuged at 104×g for 15 minutes at 4° C. to eliminate precipitates.

Evaluating Soluble Protein Concentration

To evaluate the impact of the extraction conditions on soluble protein concentration, total protein was quantified using a bicinchoninic acid assay (BCA). The total protein concentration for each extraction method is outlined in Table 9.

TABLE 9

Total Protein Concentration of Various Extraction Conditions

| Sample | Protein Concentration (mg/mL) |
|---|---|
| Hypo-osmotic 1 | 74.1 |
| Hypo-osmotic 2 | 69.5 |
| Hypo-osmotic 3 | 62.1 |
| Hyper-osmotic | 64.2 |
| Detergent | 67.7 |
| Freeze-Thaw | 66.5 |
| Initial Material | 66.5 |

Figure 10:
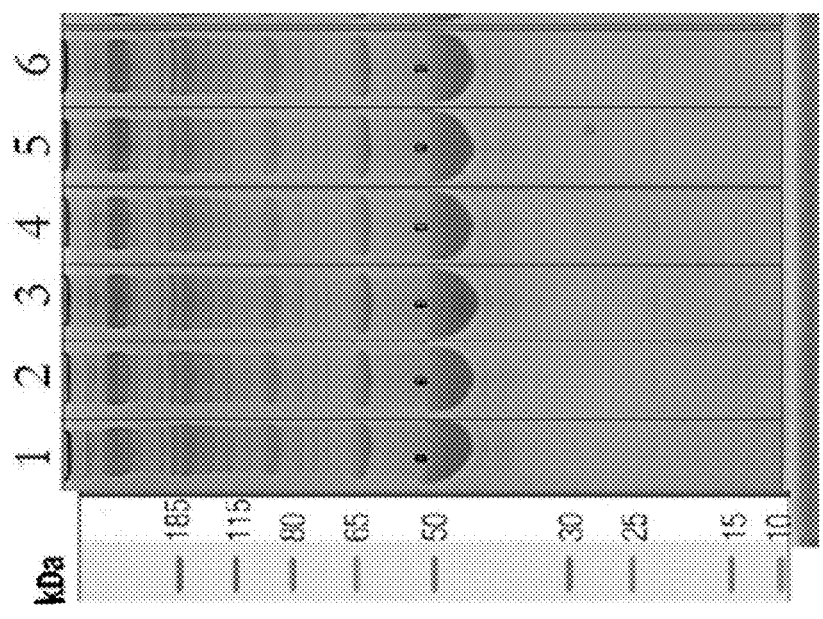
FIG. 10 provides a sodium dodecyl sulfate-polyacrylamide gel electrophoreses (SDS-PAGE) gel of soluble protein following extraction of platelet proteins via different extraction methods. Lane 1 shows total soluble protein following extraction via hypo-osmotic 1 conditions. Lane 2 shows total soluble protein following extraction via hypo-osmotic 2 conditions. Lane 3 shows total soluble protein following extraction via hypo-osmotic 3 conditions. Lane 4 shows total soluble protein following extraction via hyper-osmotic conditions. Lane 5 shows total soluble protein following extraction via detergent. Lane 6 shows total soluble protein following extraction via 3 freeze-thaw cycles.

Sodium dodecyl sulfate-polyacrylamide gel electrophoreses (SDS-PAGE) was performed to further evaluate the effects of extraction conditions on total soluble protein (Table 9, FIG. 10). diluted protein sample were mixed with 1:4 with sample loading buffer (Invitrogen) and heated at 70° C. for 10 min. Samples were then loaded (5-25 g total protein load) into precast NuPAGE 4-12% Bis-Tris 1.0 mm Minigel (Invitrogen). Then, 5 μL of Pre-stained SDS-PAGE Standards (Bio-Rad) were loaded in each gel run. Human serum albumin and immunoglobulin control were included as protein specific molecular mass control. Electrophoresis was performed at room temperature for approximately 45 min using a constant voltage (200V) in 1× solution of NuPAGE MES SDS running buffer (Invitrogen) until the dye front reached the end of the gel. The gel is stained with Simply Blue Stain (Invitrogen) for approximately 30 minutes and washed overnight prior to imaging. Using densitometry, human serum albumin and immunoglobulin composition is determined by weight by weight percentage. All of the extraction conditions resulted in comparable protein concentrations and compositions.

Example 12: Assessing PDGF Quantity and Function in Allogeneic Human Plasma and Platelet Derived Product To assess the allogeneic human plasma and platelet derived product produced by the foregoing methods, i.e., Process 1 without viral clearance and formulated in sodium citrate and salt, PDGF content and function was determined in a low-concentration and a high-concentration product. The low-concentration product is the high-concentration product diluted in 100 mM citrate and 5 mM EDTA. PDGF content was also determined in the starting material of platelet suspension and purified platelet extract (i.e., before concentration). Specifically, the amount of PDGF was quantified using a commercially available sandwich enzyme linked immunosorbent assay (ELISA) from R&D Systems. The antibody specific for PDGF-BB was bound to the solid phase or support. Diluted allogenic human plasma and platelet derived product was used to extract the antigen (PDGF) from the sample by formation of a binary solid phase antibody:antigen complex. After a suitable incubation period, the solid support was washed to remove any unbound substances. An enzyme-linked polyclonal antibody specific for human PDGF-AA was then added to the wells. Following a wash to remove any unbound antibody-enzyme reagent, a substrate solution was added to the wells and color develops in proportion to the amount of PDGF-AB bound in the initial step. The color development was stopped, and the intensity of the color was measured. Total PDGF-AB was determined via absorption and extrapolated from a PDGF-AB standard curve. The concentrations of PDGF are outlined in Table 10. These results indicate PDGF-AB concentration is increased after extracting platelet proteins from platelets (purified platelet extract) and after concentration of the purified platelet extract, indicating the methods described herein concentrate platelet proteins such as PDGF-AB.

TABLE 10

| | | PDGF-AB (pg/mg) Total Protein | PDGF-AB Average Concentration (μg/mL) |
|---|---|---|---|
| Sample | Total Protein (mg/mL) | | |
| Platelet Suspension | 77 | 48 | 3.7 |
| Purified platelet extract | 79.9 | 201 | 16 |
| Low Concentration Product | 54 | 394 | 21 |
| High Concentration Product | 156.3 | 427 | 67 |

Figure 11:
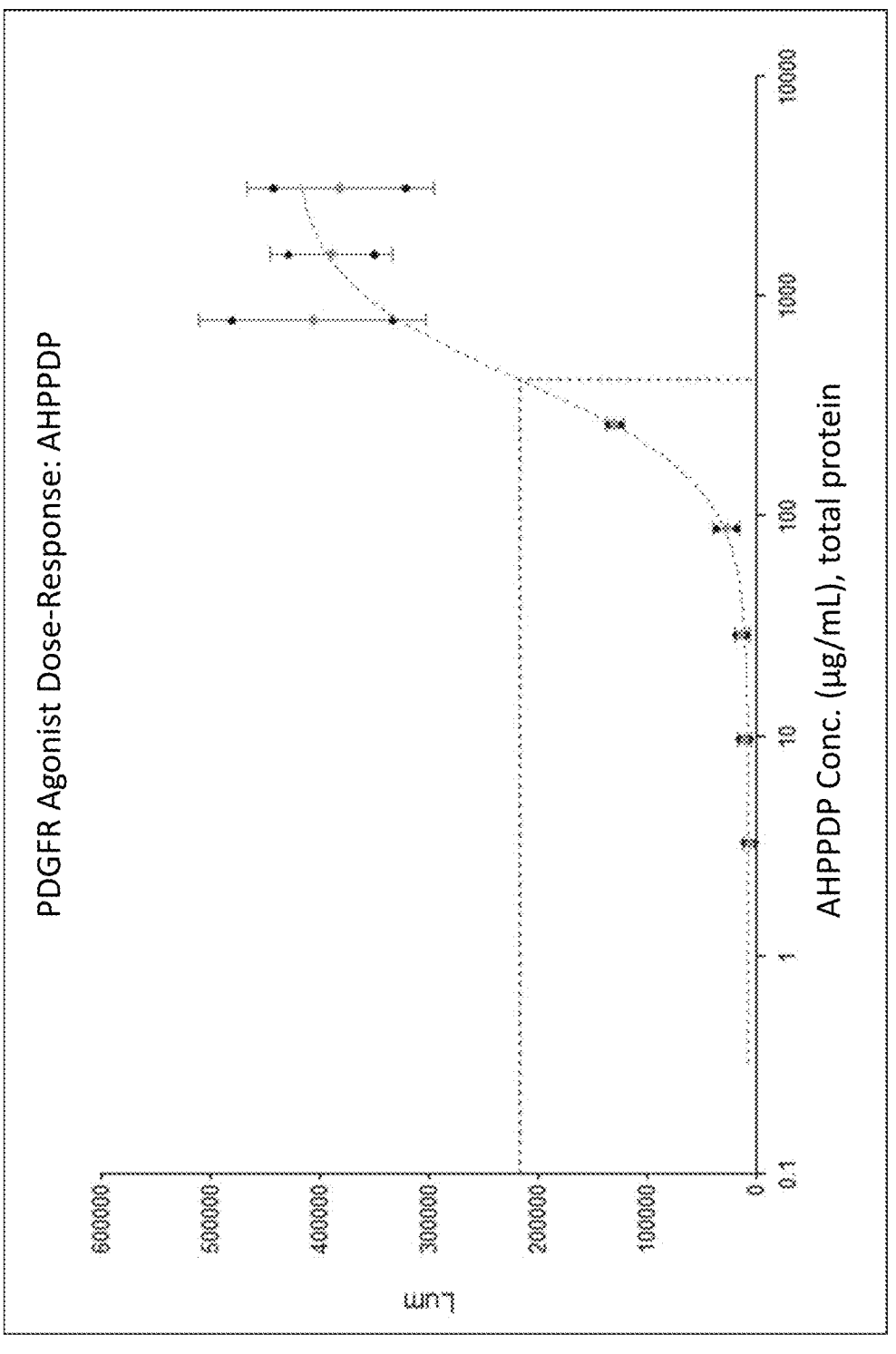
FIG. 11 provides a graph showing the activity of PDGF in allogenic human plasma and platelet derived product in a reporter cell assay.

To evaluate the functional activity of allogeneic human plasma and platelet derived product, the activity of PDGF was assessed. Reporter cell lines were contacted with concentrated allogeneic human plasma and platelet derived product and the levels of PDGF were quantified with the Platelet-Derived Growth Factor Receptors a and R Reporter Assay System (Indigo Biosciences). The activity of PDGF is summarized in FIG. 11. These results indicate the function of PDGF was maintained during the process described herein for generating the allogeneic human plasma and platelet derived product.

Example 13: Assessing A2M Quantity in Allogeneic Human Plasma and Platelet Derived Product To assess the allogeneic human plasma and platelet derived product produced by the foregoing methods, i.e., Process 1 without viral clearance and formulated in sodium citrate and salt, alpha-2-macroglobulin (A2M) content was determined using a commercially available sandwich enzyme linked immunosorbent assay (ELISA; Invitrogen). In this assay, the antibody specific for A2M was bound to the solid phase or support. Diluted allogenic human plasma and platelet derived product was diluted in 100 mM citrate and 5 mM EDTA and contacted with the support to extract the antigen (A2M) from the sample by formation of a binary solid phase antibody:antigen complex. After a suitable incubation period, the solid support was washed to remove any unbound substances. An enzyme-linked biotinylated-polyclonal antibody specific for human A2M was then added to the wells. Following a wash to remove any unbound antibody-enzyme reagent, a substrate solution containing streptavidin-HRP was added to the wells and color develops in proportion to the amount of A2M bound in the initial step. The color development was stopped, and the intensity of the color was measured. Total A2M was determined via absorption and extrapolated from an A2M standard curve. The concentrations of A2M are summarized in Table 11.

TABLE 11

A2M Levels in Allogeneic Human Plasma and Platelet Derived Product

| Sample | Dilution Factor | A2M (μg/mL) |
|---|---|---|
| 1 | 1500 | 272 |
| 2 | 3000 | 287 |
| 3 | 6000 | 285 |

Example 14: Analysis of Fibrinogen in Allogenic Human Plasma and Platelet Derived Product To assess the allogeneic human plasma and platelet derived product produced by the foregoing methods, i.e., Process 1 without viral clearance and formulated in sodium citrate and salt, fibrinogen content was determined using a commercially available sandwich enzyme linked immunosorbent assay (ELISA; LSBio). A high concentration allogeneic human plasma and platelet derived product (i.e., ~150 mg/mL total protein concentration) was used to evaluate fibrinogen content. The high concentration allogeneic human plasma and platelet derived product was prepared via extracting platelet proteins from platelet suspensions via freeze-thaw and concentrated via spin filters.

In the ELISA assay, the antibody specific for fibrinogen was bound to the solid phase or support. Allogenic human plasma and platelet derived product was diluted in buffer provided by the ELISA kit and contacted with the support to extract the antigen (fibrinogen) from the sample by formation of a binary solid phase antibody:antigen complex. After a suitable incubation period, the solid support was washed to remove any unbound substances. An enzyme-linked biotinylated-polyclonal antibody specific for human fibrinogen was then added to the wells. Following a wash to remove any unbound antibody-enzyme reagent, a substrate solution containing streptavidin-HRP was added to the wells and color develops in proportion to the amount of fibrinogen bound in the initial step. The color development was stopped, and the intensity of the color was measured. Total fibrinogen was determined via absorption and extrapolated from a fibrinogen standard curve. The concentrations of fibrinogen are summarized in Table 12. Specifically, the amount of fibrinogen was determined for the starting material, i.e., a platelet suspension, and the allogeneic human plasma and platelet derived product produced by the methods described herein. These data show not only that fibrinogen is maintained in the allogeneic human plasma and platelet derived product, but that concentration is increased.

TABLE 12

Fibrinogen Levels in Allogeneic Human Plasma and Platelet Derived Product

| Sample | Formulation | Fibrinogen mg/mL |
|---|---|---|
| Platelet suspension | PBS | 0.778 |
| Allogeneic Human Plasma and Platelet Derived Product | 100 mM Citrate, 5 mM EDTA | 1.765 |

Example 15: Analysis of Cytokines in Allogeneic Human Plasma and Platelet Derived Product To assess the allogeneic human plasma and platelet derived product produced by the foregoing methods, i.e., Process 1 without viral clearance and formulated in sodium citrate and salt, cytokine content was determined. The human cytokine array (R&D Systems) is a rapid, sensitive, and economic tool to simultaneously detect 105 cytokines. Carefully selected capture antibodies have been spotted in duplicate on nitrocellulose membranes. The allogeneic human plasma and platelet derived product and antibody mixture was first diluted and incubated with the Human Cytokine Array membrane. Any cytokine/detection antibody complex present was bound by its cognate immobilized capture antibody on the membrane. Following a wash to remove unbound material, Streptavidin-HRP and chemiluminescent detection reagents were added sequentially. Light was produced at each spot in proportion to the amount of cytokine bound.

Of the 105 cytokines assessed, the following 96 were detected in allogeneic human plasma platelet protein samples (cytokines in bold align with expected composition): Adiponectin/Acrp30, IFN-gamma, CCL2/MCP-1, Angiogenin, IGFBP-2, CCL7/MCP-3, Angiopoietin-1, IGFBP-3 M-CSF, Angiopoietin-2, IL-1 alpha/IL-1F1, MIF, Apolipoprotein A1, IL-1 beta/IL-1F2, BAFF/BLyS/TNFSF13B, IL-1ra/IL-1F3, CCL3/CCL4, BDNF, IL-2, CCL20/MIP-3 alpha, CD14, IL-3, CCL19/MIP-3 beta, CD30, IL-4, MMP-9, CD31/PECAM-1, IL-5, Myeloperoxidase, CD40 Ligand/TNFSF5, IL-6, Osteopontin (OPN), Chitinase 3-like, IL-8, PDGF-AA, Complement Component C5/C5a, IL-10, PDGF-AB/BB, Complement Factor D, IL-11, Pentraxin 3/TSF-14, C-Reactive Protein/CRP, IL-12 p70, CXCL4/PF4, Cripto-1, IL-13, RAGE, Cystatin C, IL-15, CCL5/RANTES, Dkk-1, IL-16, RBP4, DPPIV/CD26, IL-17A, Relaxin-2, EGF, IL-18 BPa, Resistin, CXCL5/ENA-78, IL-19, CXCL12/SDF-1 alpha, Endoglin/CD105, IL-22, Serpin E1/PAI-1, EMMPRIN, SHBG, Fas Ligand, ST2/IL1, R4, FGF basic, IL-27, CCL17/TARC, KGF/FGF-7, IL-31, TFF3, FGF-19, IL-32 alpha/beta/gamma, TfR, Flt-3 Ligand, TGF-alpha, G-CSF, Thrombospondin-1, GDF-15, CXCL10/IP-10, TIM-1, GM-CSF, CXCL11/I-TAC, CXCL1/GRO alpha, Kallikrein 3/PSA, uPAR, Growth Hormone (GH), Leptin, VCAM-1, HGF, VEGF, ICAM-1/CD54, Lipocalin-2/NGAL, and Vitamin D BP.

Example 16: Concentration of Platelet Proteins to Generate Allogeneic Human Plasma and Platelet Derived Product To assess the step of concentrating platelet extract in the method of producing an allogeneic human plasma and platelet derived product, 1 bag of plasma platelets was split into 4 samples. The bags were initially thawed and then subjected to three cycles of freeze-thaw. Specifically, platelets were frozen for over an hour at about −60 to −80° C. To thaw, the platelets were placed in a 37° C. bath for 30 minutes. The platelets were centrifuged for 15 minutes at 3,000×g. The platelets were then sterile filtered with a 0.2 μm polyethersulfone (PES) vacuum filter. One sample was diluted 2-fold in 100 mM citrate buffer at pH 7.5. One sample was diluted 2-fold in in Dulbecco's phosphate buffered saline (DPBS). Two samples remained undiluted ("water"). The platelets were then concentrated with 10 kDa MWCO Amicon spin filters. The concentration of total soluble protein was quantified via BCA and viscosity was quantified via a capillary viscometer. The total soluble protein and viscosity are outlined in Table 13. Without being bound by theory, compositions with higher viscosity allow for localized injection and positive pressure to accelerate healing.

TABLE 13

Summary of Viscosity and Protein Concentration After Extraction and Concentration

| Buffer | Viscosity (cP) | Conc.(mg/mL) |
|---|---|---|
| t0 | 1.43* | — |
| Cit-1$^{st}$ spin | 1.43 | 51 |
| PBS-1$^{st}$ spin | 1.44 | 52 |
| water 1-1$^{st}$ spin | 1.87 | 91 |
| water 2-1$^{st}$ spin | 1.67 | 87 |
| Cit-2$^{nd}$ spin | 2.67 | 118 |
| PBS-2$^{nd}$ spin | 2.65 | 128 |
| water 1-2$^{nd}$ spin | 2.59 | 135 |
| water 2-2$^{nd}$ spin | 3.68 | 167 |
| Cit-3$^{rd}$ spin | 9.76 | 225 |
| PBS-3$^{rd}$ spin | 12.2 | 261 |
| water 1-3$^{rd}$ spin | 11.7 | 259 |
| water 2-3$^{rd}$ spin | 7.42 | 248 |

Example 17: Sterile Filtering Concentrated Platelet Proteins

Figure 12:
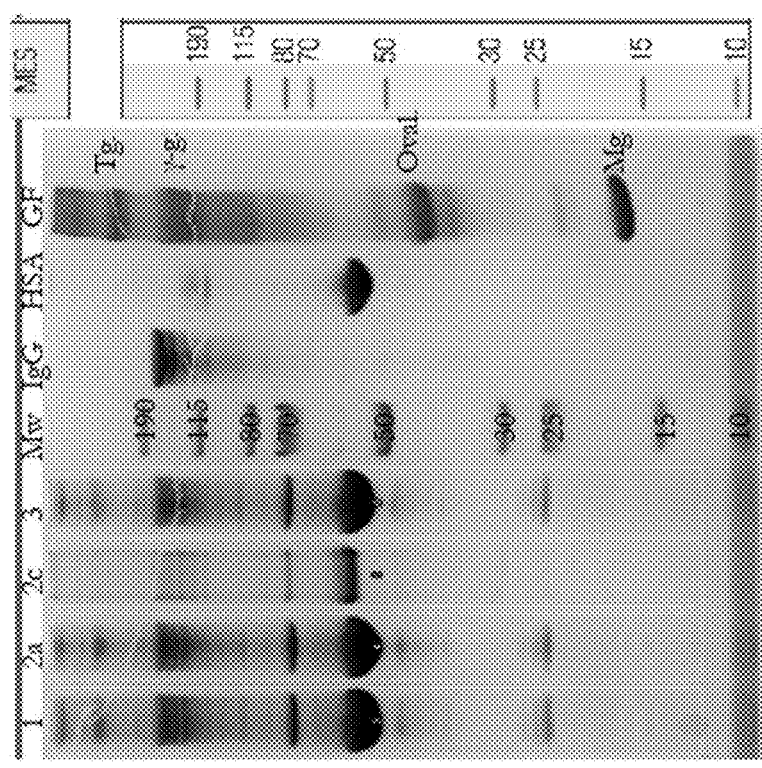
FIG. 12 provides an SDS-PAGE gel showing protein of sterile filtered platelet extract samples. Lane 1 shows extracted platelet proteins before sterile filtration. Lane 2a shows protein in the soluble layer after centrifugation at 15,000×g. Lane 2c shows protein in the cell pellet after centrifugation at 15,000×g. Lane 3 shows soluble protein after centrifugation at 15,000×g and sterile filtration with a 0.2 μm polyethansulfone (PES) filter. Lane Mw depicts the molecular weight ladder. Lane IgG depicts a representative monoclonal antibody for IgG at 1 mg/mL. Lane HSA depicts 1 mg/mL pure human serum albumin. Lane GF depicts 1 mg/mL gel filtration standard (Bio-Rad).

To evaluate the effects of sterile filtration on total soluble protein, platelets were lysed via freeze-thaw as described in Example 3. The platelet proteins were filtered with 0.2 μm nylon and polyethersulfone (PES) filters. The total soluble protein of two samples filtered with nylon filters was quantified via BCA (Table 14). To evaluate total protein of samples filtered with PES filters, SDS-PAGE was run (FIG. 12). Samples were taken after extraction and after sterile filtration. Samples were compared to pure IgG and human serum albumin to evaluate the major proteins within the soluble fraction.

TABLE 14

Protein Concentration after Extraction and Sterile Filtration

| Sample | Protein Concentration after filtration (mg/mL) |
|---|---|
| 1 | 57.6 |
| 2 | 57.1 |

Example 18: Analysis of Immunogenicity of Allogeneic Human Plasma and Platelet Derived Product To evaluate the immunogenicity of an allogeneic human plasma and platelet derived product, an in vitro screen is used (see Cohen, S. et al., (2021). Immunogenicity risk assessment for biotherapeutics through in vitro detection of CD134 and CD137 on T helper cells. Briefly, donor peripheral blood mononuclear cells (PBMCs) are incubated with AHPPDP or KLH (keyhole limpet hemocyanin) and cultured for 42-48 hours. The PBMCs are washed and analyzed by fluorescence-activated cell sorting (FACS). The CD4+ T cell fraction of the PBMCs is evaluated for expression of CD134 and CD137. Enhanced levels of CD134 and/or CD137 indicate high immunogenic potential. KLH represents a positive control for the assay.

To assess the potential immunogenicity of AHPPDP, an in vitro assay was used to compare the CD4+ T cell response of human donor peripheral blood mononuclear cells (PBMC) to AHPPDP, keyhole limpet hemocyanin (KLH), and commercially available intravenous immunoglobulin (IVIg; Gammagard®). In the assay KLH was used as a positive control, and IVIg was chosen as an allogenic blood product to compare against AHPPDP as it had the potential for similar contaminants. The AHPPDP composition utilized in this assay (CUR-2401-6L-SEP24) was generated by the method set forth in Example 31, FIG. 26, including concentration of platelet proteins through buffer exchange including removal of citrate and formulating in a suitable buffer. The stimulation index (SI) was calculated for each compound (Table 15), which is defined as the ability of the biotherapeutic to increase the fraction of live CD4+ cells that were positive for either CD134 or CD137 compared to the fraction of cells positive for these markers in formulation buffer samples.

TABLE 15

| Equation used to generate stimulation index. | |
| --- | --- |
| Equation 1: Stimulation Index (SI) | % of (Live CD4+CD134+, Live CD4+CD137+, Live CD4+CD134+CD137+) in AHPPDP, IVIg, KLH treated samples % of (Live CD4+CD134+, Live CD4+CD137+, Live CD4+CD134+CD137+) in formulation buffer samples |

Figure 20:
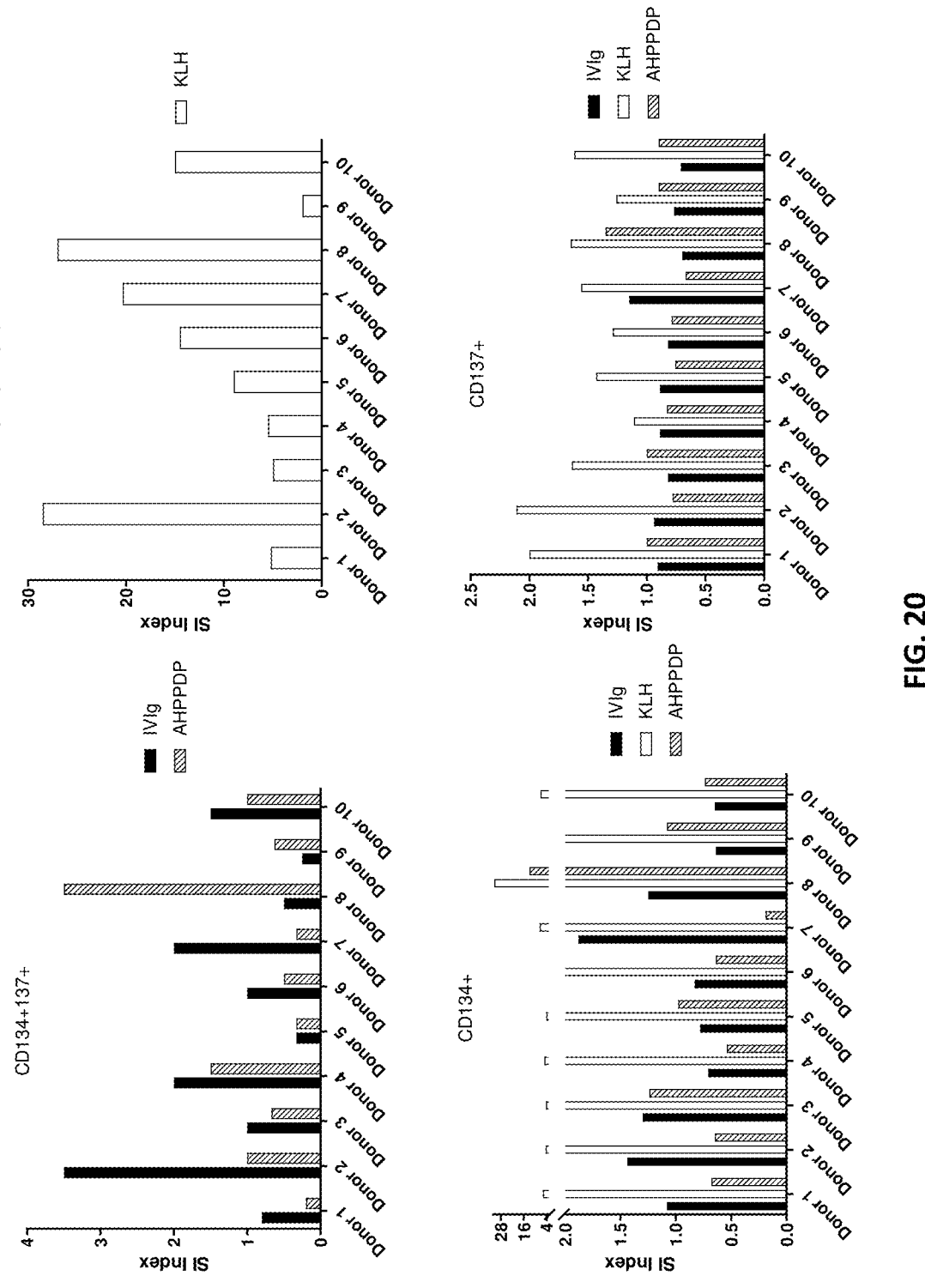
FIG. 20 provides graphs depicting CD4+ T cell response of human donor peripheral blood mononuclear cells (PBMC) after treatment with AHPPDP, keyhole limpet hemocyanin (KLH), or immunoglobulin (IVIg).

In this assay, AHPPDP was tested against 10 healthy donor samples (including Rh positive and negative, and O, A, and AB blood types). The results, provided in FIG. 20, demonstrate KLH elicited the highest SI score, as expected for a strongly immunogenic protein commonly used as a positive control in immunoassays. For 9 of 10 donors tested, AHPPDP had a similar or lower SI score than IVIg. Only Donor 8 had a higher response to AHPPDP than IVIg and had an extremely high response to KLH. Donor 2 had a very strong response to KLH and IVIg, and lower response to AHPPDP.

The results indicate the immunogenicity of AHPPDP may be similar to other blood-derived products, such as IVIg, and does not strongly activate T-cells.

Example 19: Activity of Growth Factors in Allogeneic Human Plasma and Platelet Derived Product To evaluate the functional activity of allogeneic human plasma and platelet derived product, growth factors are assessed. Reporter cell lines are contacted with the allogeneic human plasma and platelet derived product and the levels of growth factors are quantified. Growth factors are assessed with commercially available kits. For example, EGFR (e.g., Human EGFR1 Report Assay Kit, Indigo Biosciences), TGF-β (e.g., Human Transforming Growth Factors Beta Receptors I/II Report Assay System, Indigo Biosciences), VEGF (e.g., VEGF Bioassay, Promega), and PDGF (e.g., Platelet-Derived Growth Factor Receptors a and R Reporter Assay System, Indigo Biosciences) are evaluated.

Example 20: Induction of Anti-Inflammatory Response by Allogeneic Human Plasma and Platelet Derived Product To evaluate whether the allogeneic human plasma and platelet derived product induces an anti-inflammatory response, an in vitro screen is used (see Singh, U., et al., 2005). Development of an in vitro screening assay to test the anti-inflammatory properties of dietary supplements and pharmacologic agents. Clinical chemistry, 51(12), 2252-2256.). Briefly, the monocytic cell line, THP-1, which is known to produce proinflammatory cytokines in response to lipopolysaccharide (LPS) stimulation, is utilized. THP-1 cells are grown in RPMI supplemented with fetal bovine serum (FBS) until they reach 70% confluency. THP-1 cells are pre-treated with allogeneic human plasma and platelet derived product for 1 hour. The cells are then contacted with 50 μg/L LPS for 4 hours. The supernatants are harvested and IL-1β, TNF-α, and IL-6 levels are quantified via enzyme-linked immunosorbent assays (ELISAs) and reported as pg/mg.

Example 21: Epidural Dosing of Allogeneic Human Plasma and Platelet Derived Product To investigate the feasibility and tolerability of epidural dosing of the allogeneic human plasma and platelet derived product, Sprague-Dawley rats is evaluated. On Day 1, 4-6 hours prior to treatment, the rats is observed. Each animal is administered a dose of vehicle (control) or the allogeneic human plasma and platelet derived product via a single epidural administration on Day 1. The animals are evaluated daily following treatment until euthanasia. Body weights are recorded prior to treatment and on Days 2, 3, 4, and prior to euthanasia. Interim blood is collected on Day 2 via tail vein/saphenous. 300 μL of blood samples is processed to serum and stored at nominally −70° C. until pharmacokinetic analysis.

Animals are euthanized via $CO_2$. A maximum obtainable volume (MOV) of whole blood samples is collected. At least 200 μL of whole blood is collected into EDTA tube and stored cold until CBC and coagulation analysis. The remaining blood sample is processed to serum and stored in aliquots. Aliquots are stored at nominally −70° C. until comprehensive chemical analysis. Whole blood and serum is evaluated.

Following exsanguination, animals undergo cardiac perfusion with saline. In brief, whole body intracardiac perfusion is performed by inserting 23/21-gauge needle (or appropriate) attached to 10 mL syringe (or appropriate) containing saline set into the lumen of the left ventricle for perfusion. The right atrium is incised to provide a drainage outlet for perfusate. Gentle and steady pressure is applied to the plunger to perfuse the animal after the needle is positioned in the heart. Adequate flow of the flushing solution is ensured when the exiting perfusate flows clear (free of visible blood) indicating that the flushing solution has saturated the body, and the procedure is complete.

Example 22: Amelioration of Pain In Vivo with Allogeneic Human Plasma and Platelet Derived Product To investigate the effect of an allogeneic human plasma and platelet derived product on neuropath pain, an in vivo mouse model is used. Neuropathic pain is characterized by abnormal sensitivity to stimuli. Chemotherapy Induced Neuropathic Pain (CINP) is induced in mice by treating mice with paclitaxel for 5 days. Allogeneic human plasma and platelet derived product or control is injected into mice on Day 6 and 7. Response to cool allodynia is assessed prior to treatment with paclitaxel and prior to and after treatment with AHPPDP or control. Cytokine levels, neurofilament light chain and histological markers of inflammation are assessed during treatment and after necropsy on Day 14.

Example 23. Efficacy of Repeat Dosing of AHPPDP in Arthritis

To investigate the efficacy of allogenic human platelet and plasma derived product (AHPPDP) on arthritis in knees, Sprague Dawley rats were used. Arthritis was induced by a single intra-articular (IA) injection of complete Freund's adjuvant (CFA) as previously described (Noh A S M, et al. PLoS One. 2021 Dec. 8; 16(12):e0260423. doi: 10.1371/journal.pone.0260423). Specifically, CFA was injected into the right knee of adult male Sprague Dawley rats (n=4/group). A composition comprising AHPPDP, referred to as "Composition E26h" was prepared based on the methods disclosed herein. Specifically, Composition E26h was prepared as outlined in Process 1 above (Example 2, FIG. 1), without Step 5 (viral clearance). Further the platelet proteins were concentrated through buffer exchange including removal of citrate and formulating in a suitable buffer. Composition E26h was injected into the IA space of the right knee on Days −3, −1, and 2 relative to CFA injection. Buffer as used as the vehicle. Protein concentrations of Composition E26h and vehicle are set forth in Table 16.

TABLE 16

| Test Articles | |
| --- | --- |
| Test Article | Concentration [a] (mg/mL) |
| Vehicle | 0 |
| AHPPDP (Composition E26h) | 123 |

[a] Total protein concentration.

On Day 1, while under light isoflurane anesthesia, all rats received either 50 or 100 μg (50 and 100 μL, respectively) of CFA by a single IA injection into the right knee according to Table 17. Body weights were recorded prior to CFA induction on Day −3 and daily thereafter until study termination on Day 7. Detailed clinical observations were conducted beginning on Day −3 prior to treatment and once daily thereafter until the end of study on Day 7. Both left and right knees were measured using calipers performed prior to CFA induction on Day −3 and daily thereafter. All rats were terminated on Day 7.

TABLE 17

| | | | Experimental Design | | |
| --- | --- | --- | --- | --- | --- |
| Group No. | Animal No. | Induction | Treatment on Days −3, −1, and 2 via IA injection | Dose Level[a] (mg/knee) | Dose Volume (μL/knee) |
| 1 | 4 | 100 μL CFA injection on Day 1 (Rt knee via IA) | Vehicle | 0 | 50 |
| 2 | 4 | | AHPPDP (Composition E26h) | 6.2 | 50 |
| 3 | 4 | 50 μL CFA injection on Day 1 (Rt knee via IA) | Vehicle | 0 | 50 |
| 4 | 4 | | AHPPDP (Composition E26h) | 6.2 | 50 |

Abbreviations: CFA = complete Freund's adjuvant; IA = intra-articular; No. = number; ROA = route of administration; Rt = right.
[a] AHPPDP dose refers to the total protein concentration.

Following euthanasia, rats underwent cardiac perfusion with saline. In brief, whole-body intracardiac perfusion was performed by inserting 23/21-gauge needle attached to 10/20/50 mL syringe containing saline set into the lumen of the left ventricle for perfusion. The right atrium was incised to provide a drainage outlet for perfusate. Gentle and steady pressure was applied to the plunger to perfuse the rat after the needle was positioned in the heart. Adequate flow of the flushing solution was ensured when the exiting perfusate flowed clear (free of visible blood) indicating that the flushing solution saturated the body, and the procedure was complete.

Right knees from all rats and one left knee from one animal per group were decalcified, embedded in paraffin, sectioned, and stained with hematoxylin and eosin (H&E) to observe inflammation and Saf-O to evaluate proteoglycan and cartilage at the articular surface.

Figure 13A:
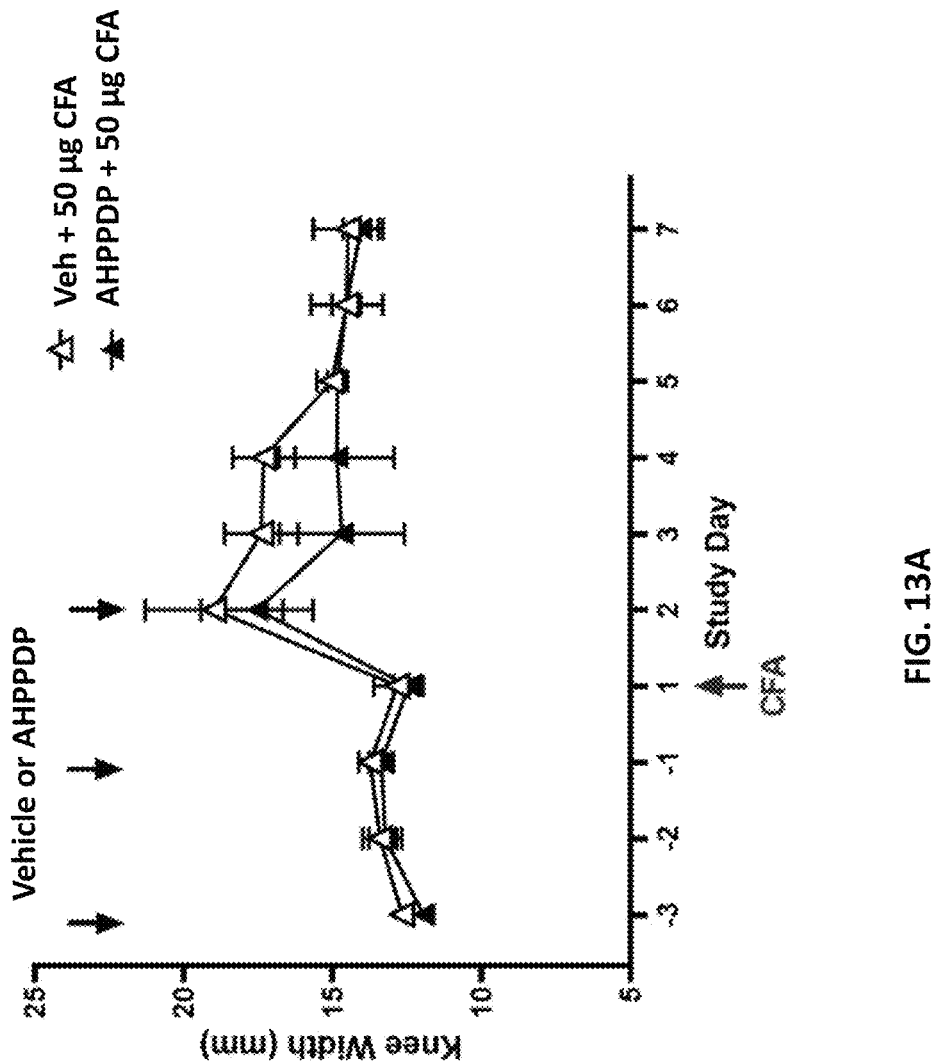
FIG. 13A shows a graph depicting knee width (mm) of an arthritis rat model. 50 μg complete Freund's adjuvant (CFA) was injected in the intra-articular (IA) space of the right knee of Sprague Dawley rats to induce arthritis on Day 1 (bottom arrow). On Days −3, −1, and 2 relative CFA injection (top arrows), rats were injected with a composition comprising AHPPDP (Composition E26h) or vehicle set forth in Table 16.
Figure 13B:
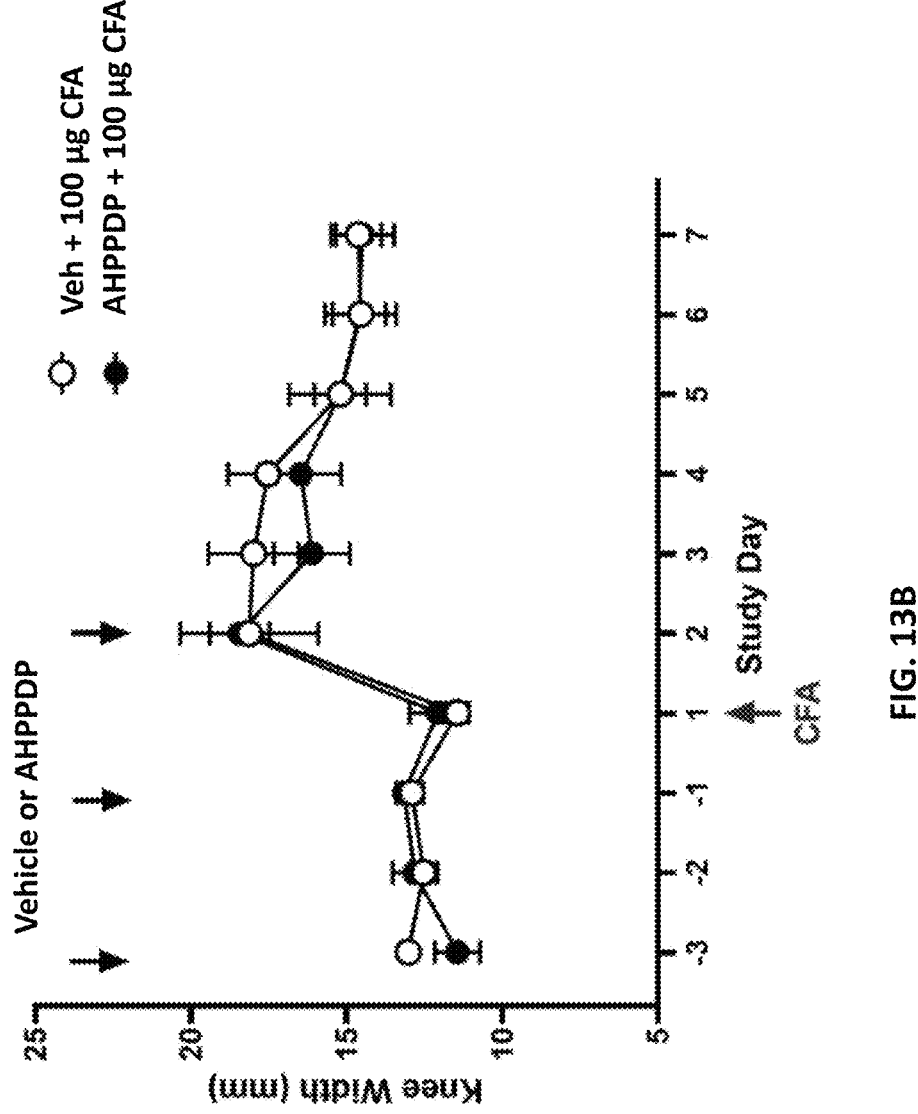
FIG. 13B shows a graph depicting knee width (mm) of an arthritis rat model. 100 pg complete Freund's adjuvant (CFA) was injected in the intra-articular (IA) space of the right knee of Sprague Dawley rats to induce arthritis on Day 1 (bottom arrow). On Days −3, −1, and 2 relative CFA injection (top arrows), rats were injected with Composition E26h or vehicle set forth in Table 16.

Body weight changes were generally comparable across treatment groups. Minimal (<5%) or no decrease was observed in group means across treatment groups, and decreases were generally more apparent on the day following CFA induction. One rat in Group 1 lost between 10-15% body weight on Days 5-7. There were no abnormal observations for Groups 1-4. Knee widths were similar across all groups prior to CFA induction on Day −3 to Day 1. On Day 2 following CFA induction, knee widths substantially increased in all groups indicating swelling. Rats were observed to not bear weight on the swollen right hind limb. On Days 3 and 4, groups treated with vehicle and 50 or 100 μg CFA had larger knee widths than groups treated with Composition E26h and 50 or 100 μg CFA. Knee widths for the group administered Composition E26h and 100 μg CFA had greater widths than the group administered the same dose of Composition E26h and 50 μg CFA. The group administered Composition E26h and 50 μg CFA had the lowest knee widths than all other groups. By Day 5, no differences in knee widths were observed across treatment groups (FIG. 13A-13B).

Intra-articular injection of 50 or 100 μg CFA into the right knee of Sprague Dawley rats induced marked inflammation 24 hours after injection, which persisted for 3 days, and then subsided to baseline levels by Day 5 as assessed by knee width measurements. Repeated intraarticular injection of Composition E26h appeared to have reduced knee widths relative to vehicle during the period of marked CFA-induced knee inflammation. On Day 2 there were no apparent differences in inflammation between groups treated with vehicle or Composition E26h On Day 3, there was a reduction in the swelling in the AHPPDP-treated groups relative to the vehicle groups. These results show, intra-articular injection of a composition comprising AHPPDP reduces inflammation and treats symptoms of arthritis in the knee.

Example 24. Efficacy of AHPPDP on Acute Paclitaxel-Induced Peripheral Neuropathy The purpose of this study was to evaluate the effect of a composition comprising AHPPDP on cool allodynia in an acute chemotherapy-induced mouse model of paclitaxel-induced peripheral neuropathy (PIPN). A composition comprising AHPPDP was prepared as described in Example 23. A low dose (Composition F20f) and a high dose (Composition F20d) were prepared.

Figure 14:
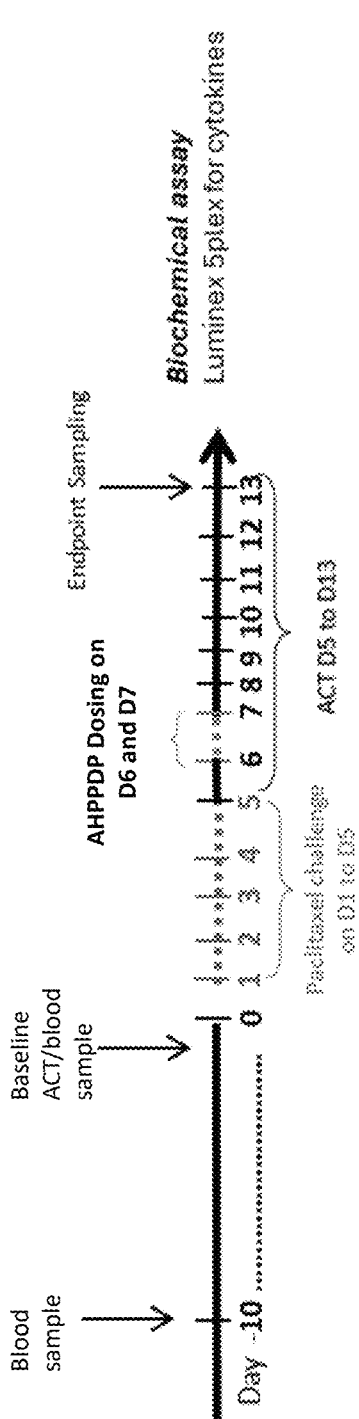
FIG. 14 shows a schematic of a study design for acute paclitaxel-induced peripheral neuropathy. 15 mg/kg/day paclitaxel was administered intraperitoneally (IP) once daily to animals for 5 days. A composition comprising AHPPDP at either a low dose (~300 mg/kg; Composition F20f) or a high dose (~600 mg/kg; Composition F20d) was administered intravenously (IV) once on Day 6 and Day 7.

Adult male C57BL6/J mice were administered vehicle (n=10) or Composition F20f/F20d (n=15/dose group) intravenously (IV) under isoflurane anesthesia once on Day 6 and on Day 7 according to the experimental design presented in FIG. 14. Protein concentrations of the compositions and vehicle are set forth in Table 18.

TABLE 18

| Test Articles | |
| --- | --- |
| Test Article | Concentration (mg/mL)[a] |
| Vehicle | NA |
| Composition F20f | 61.2 |
| Composition F20d | 116.4 |

[a]Total protein concentration.

Paclitaxel 15 mg/kg/day was administered intraperitoneally (IP) once daily to mice in Groups 2, 3, and 4 for 5 consecutive days (Table 19 and FIG. 14). Group 1 received an IP injection of the paclitaxel vehicle as the control.

TABLE 19

| | | | Paclitaxel | |
| | Group | | Dose/ | AHPPDP Dose/ |
| | size | | Injection | Injection |
| Group | (n) | Chemotherapy | (mg/kg, IP) | (mg/kg, IV) |
| --- | --- | --- | --- | --- |
| 1 | 10 | Vehicle (for paclitaxel) | — | 0 (vehicle) |
| 2 | 15 | Paclitaxel | 15 | 0 (vehicle) |
| 3 | 15 | Paclitaxel | 15 | ~300 (Composition F20f) |
| 4 | 15 | Paclitaxel | 15 | ~600 (Compoisition F20d) |

Abbreviations: Conc. = concentration; IP = intraperitoneal(ly); IV = intravenous(ly); No. = number; ROA = route of administration.
Note:
Paclitaxel or vehicle was administered in a volume of 10 mL/kg; AHPPDP or vehicle was administered in a volume of 5 mL/kg.

Body weights were assessed prior to group assignment and daily during administration of the test articles set forth in Table 18. The welfare of the animals was checked at least daily by trained personnel and supervised by a veterinarian when warranted by clinical signs or other welfare-related changes.

Acetone Cooling Test for Allodynia:

Before subjecting the mice to the baseline acetone cooling test (ACT), they were pre-handled for 2 minutes on two consecutive days in their maintenance room with the purpose of decreasing false oversensitivity. Prior to testing, mice were allowed to acclimate to the testing room for 30-60 minutes.

The ACT was conducted by first placing the mice into individual Plexiglas chambers (i.e., von Frey chambers). The animals were allowed to acclimate in the test chambers for approximately an additional 30 minutes (±15 minutes, depending on their behavior). Test chamber habituation was deemed sufficient when the mice have explored the surroundings, groomed, and settled down. Testing was not performed while the animal was grooming, sleeping, urinating or defecating.

To produce a cooling sensation, a 10-15 µL of acetone spray was applied onto the medial area of the plantar hind paw using 0.5 mL syringes. Acetone application was done from close distance to the paw without touching the skin.

Responses of each animal to acetone were monitored for 20 seconds, and the score was given based on the following four-point scale:

0=Short response to acetone, but doesn't stay scared after the first reaction OR reacts once more after acetone reaction.

1=Two to three quick withdrawals, flicks, licks or stamps of the paw. Duration of the reaction is either 1 sec/reaction OR only one, but prolonged reaction (e.g. tremor) or it's duration is 3-5 sec.

2=Repeated (4-5) short withdrawals, flicks, licks or stamps of the paw. Duration of the reaction is either 1 sec/reaction OR only one, but prolonged reaction, maximum of 10 sec.

3=Notably prolonged or continuous (>5) withdrawals, flicks or licks of the stimulated paw. Duration of the reaction is either 1 sec/reaction OR only one, but prolonged reaction, minimum of 10 sec.

During each 20-second trial, the responses were tallied, and the score (0-3 points) given after the trial. A total of 3 trials (altogether 60 seconds) were performed on each paw with a minimum interval of 5 minutes between trials. The obtained three individual scores were added to obtain a single score over a cumulative period of 60 seconds. Thus, for one test, the minimum score of one paw was 0, while the maximum possible score was 9. To accomplish a result value for a mouse at a certain test timepoint, the total scores obtained for the left and right paws were averaged.

Blood Collection for Cytokine Analysis:

Blood (up to 100 µL) was collected on Day 5 (2 hours following paclitaxel and ACT) and Day 8 (following ACT) from the saphenous vein and processed to plasma. Plasma was analyzed using a Luminex multiplex assay for IL-6, IL1-β, IL-10, TNF-α, and IFN-7 for Groups 2 and 4 only.

Terminal Procedures:

Mice were euthanized with 180 mg/kg pentobarbital followed by exsanguination and transcardiac perfusion with ice cold heparinized (heparin 2.5 IU/mL) saline following with 4% paraformaldehyde. The cervical, thoracic, and lumbar segments of the spinal cord and left sciatic nerve were collected and fixed 24 hours in 4% paraformaldehyde at 4° C., then embedded in paraffin. Processed samples were held for potential future analysis.

Results:

Mice administered paclitaxel (Groups 2, 3, and 4) showed body weight loss concurrent with the onset of paclitaxel dosing and began weight gain on study Day 10. Mean group weights were significantly lower in Groups 2, 3, and 4 on Days 5 through 13 when compared to Group 1, which received paclitaxel vehicle on Days 1 through 5 and AHPPDP vehicle on Day 6 and 7.

Some mice in Groups 2, 3, and 4 showed transient clinical signs after treatment including piloerection, unkempt coat, and/or hunched posture following vehicle or AHPPDP. These observations were more severe in the vehicle group. With the exception of mortality described below, clinical observations recovered in all other animals.

Three mice in Group 2 (paclitaxel+vehicle) were found dead or humanely euthanized. No mortality was observed in groups administered AHPPDP.

Figure 15:
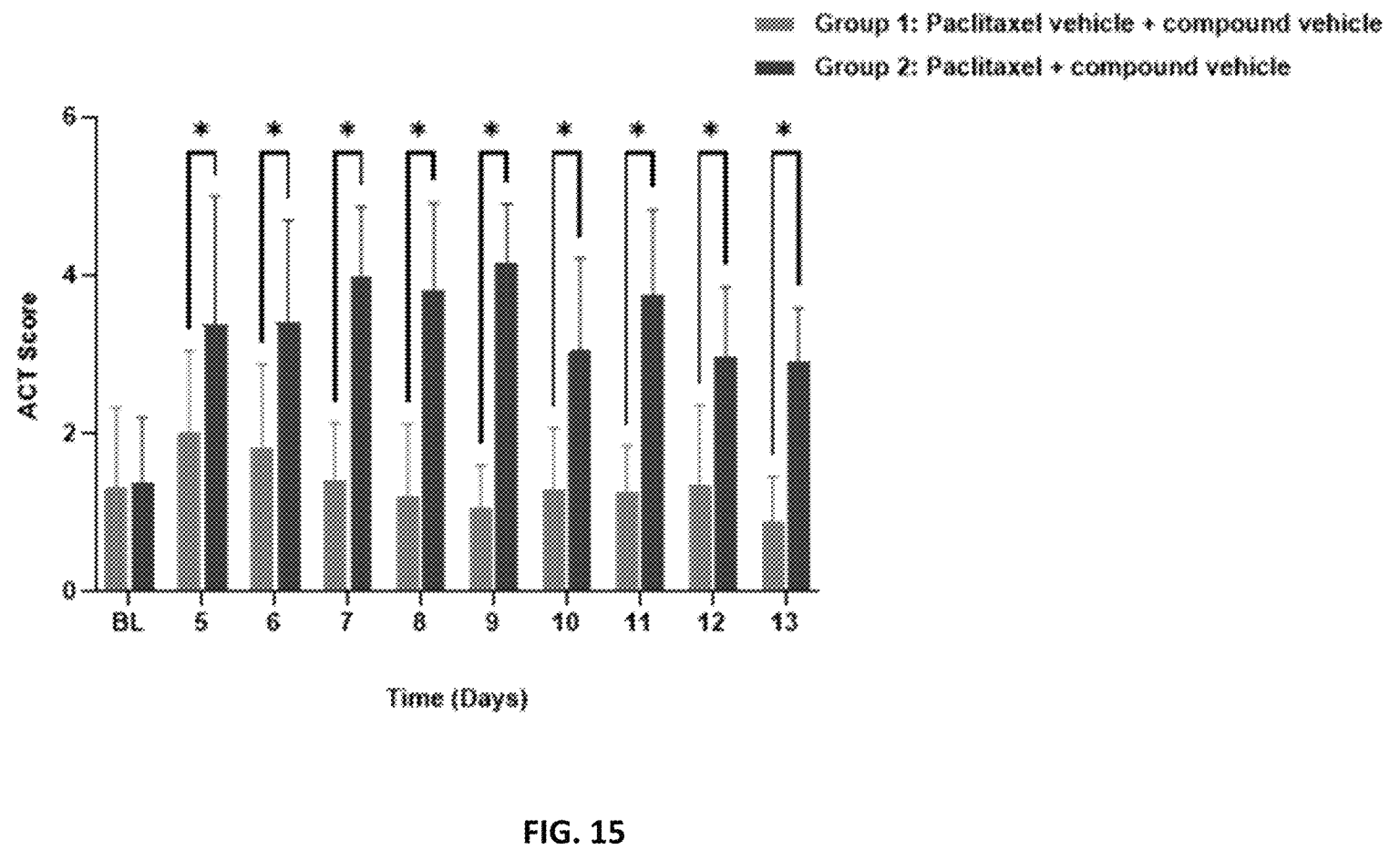

Paclitaxel induced allodynia on all Day 5 through 13 test days as defined by ACT score relative to vehicle (FIG. 15). Statistically significant differences were observed between the vehicle+vehicle group (Group 1) compared to paclitaxel+vehicle (Group 2) on all testing days.

Figure 16:
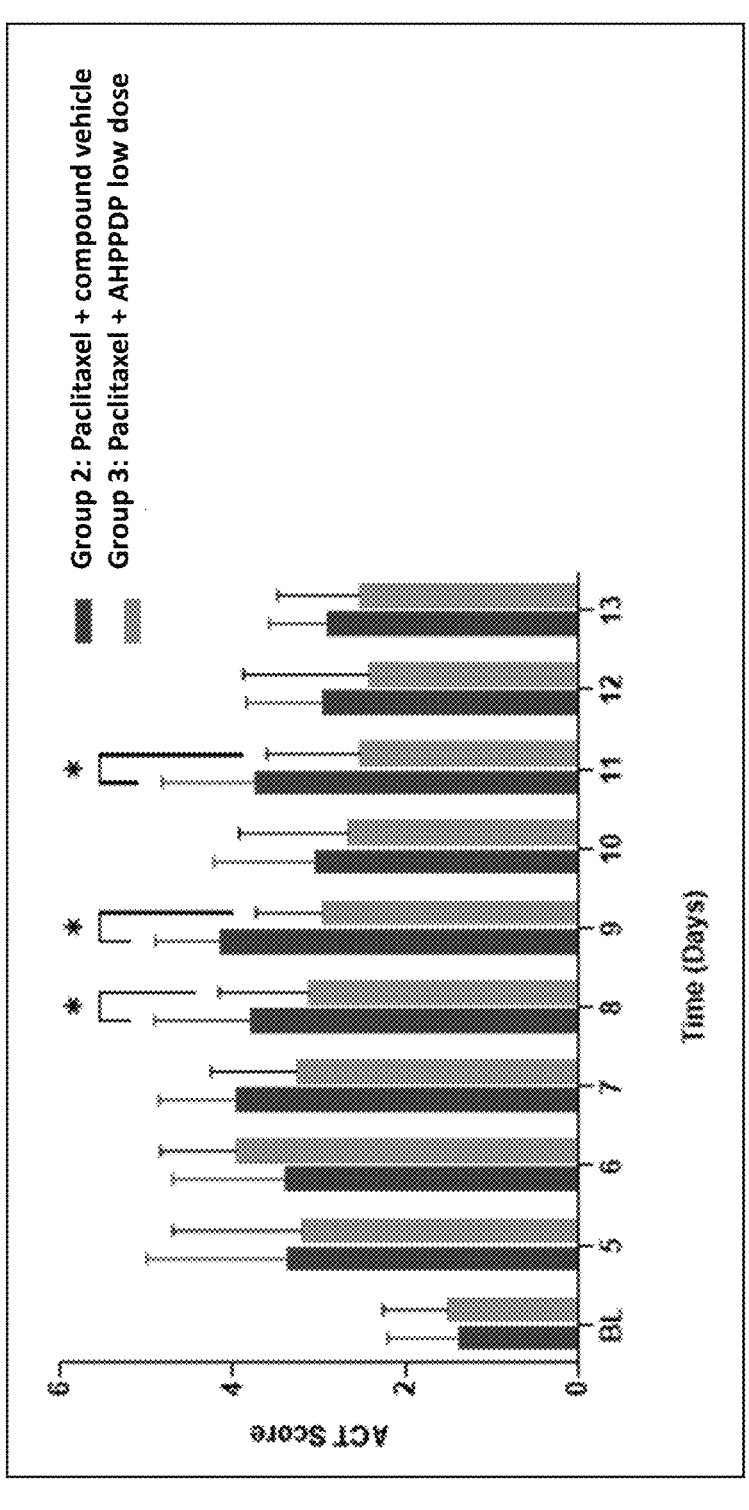
FIG. 16 is a graph showing paclitaxel-induced allodynia quantified by an ACT score following intravenous administration of Composition F20f or vehicle set forth in Table 18. Data are presented as Mean±SEM; Group 1, n=10 and Group 2, n=15. Group 3 vs Group 2: *p<0.05 (Mann-Whitney test).
Figure 17:
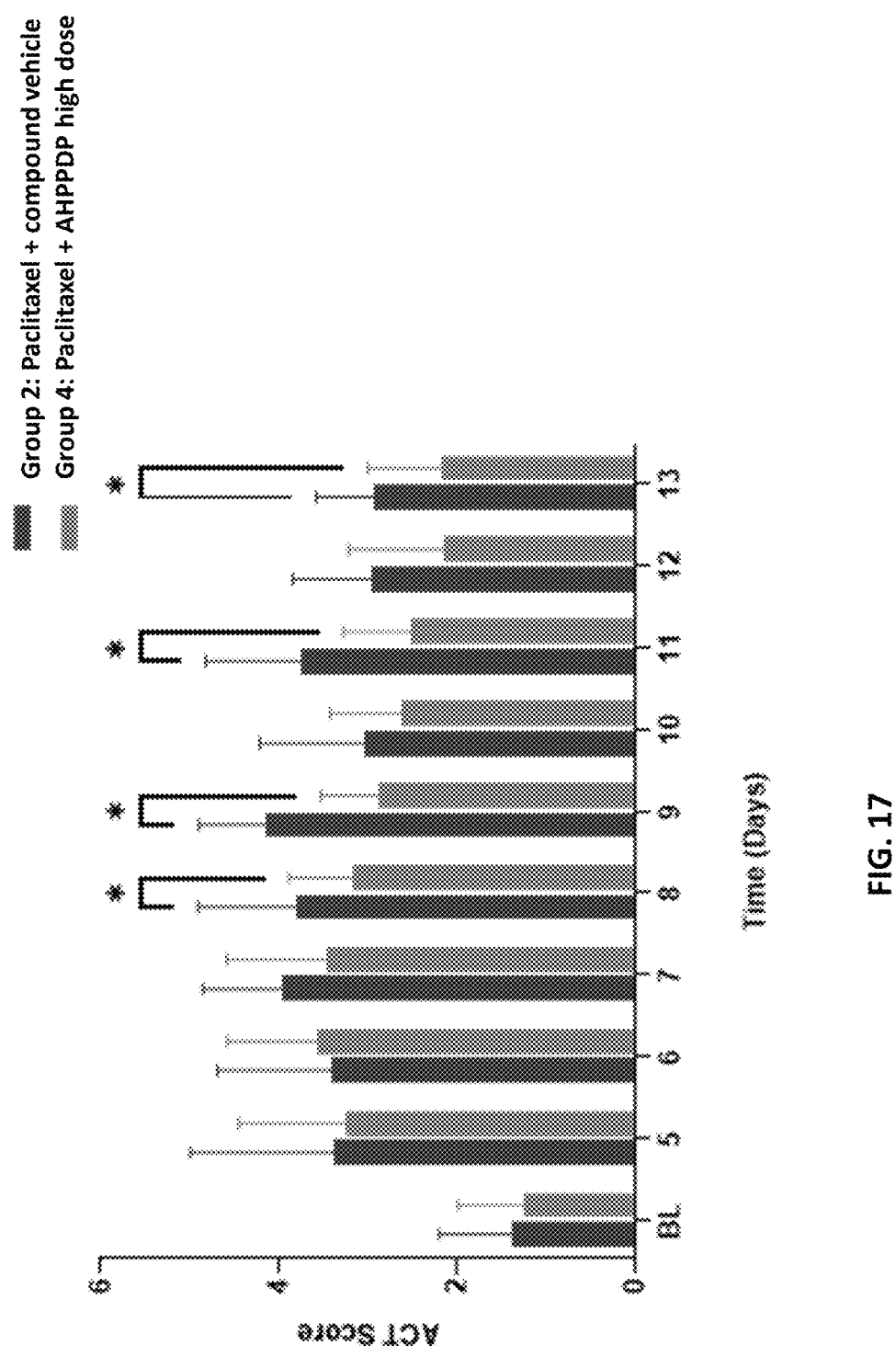
FIG. 17 is a graph showing paclitaxel-induced allodynia quantified by an ACT score following intravenous administration of Composition F20d or vehicle set forth in Table 18. Data are presented as Mean±SEM; Group 1, n=10 and Group 2, n=15. Group 4 vs Group 2: *p<0.05 (Mann-Whitney test).

Following intravenous administration of AHPPDP for 2 consecutive days, both low (~300 mg/kg) and high (~600 mg/kg) doses of AHPPDP reduced paclitaxel-induced allodynia relative to vehicle on multiple test days as shown in FIG. 16 and FIG. 17, respectively. Both dose levels reduced allodynia on Days 8, 9, and 11; the high dose additionally reduced allodynia on Day 13. There were no statistically significant differences in ACT score between the AHPPDP low and high dose groups. Systemic administration of AHPPDP significantly reduced paclitaxel-induced cool allodynia, which is a functional observation of peripheral neuropathy.

Figure 19:
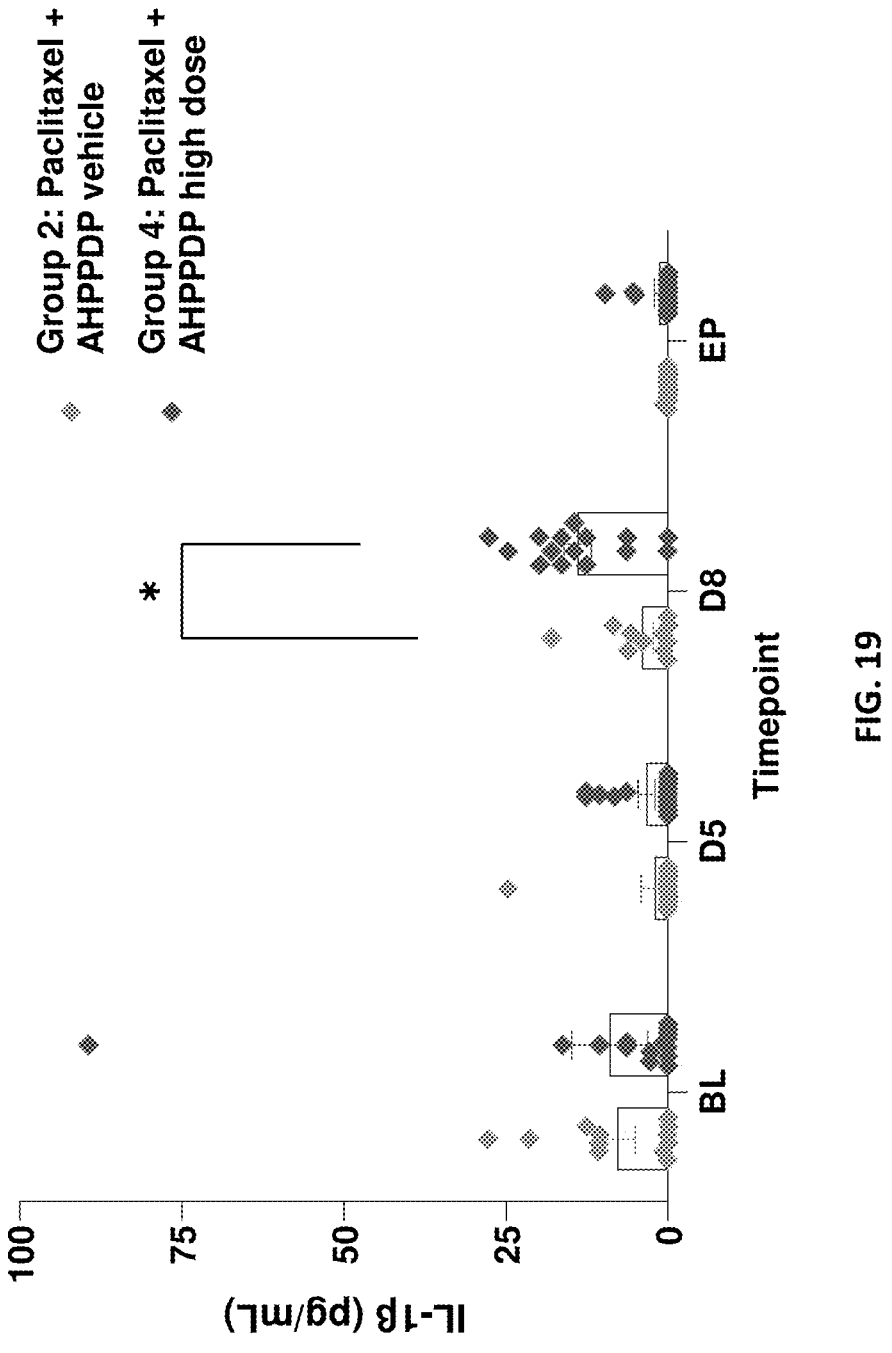
FIG. 19 provides graphs depicting levels of IL-1β cytokine levels in mouse plasma following treatment with paclitaxel or paclitaxel and either low dose AHPPDP (F20f) or high dose AHPPDP (F20d). BL=baseline; D5=Day 5; D8=Day 8; EP=end of study. Statistical analysis: *p<0.05 (Mann-Whitney test)

Cytokine analysis revealed no apparent differences between Groups 2 and 4 for any cytokine except for IL-1β. IL-1β was statistically significantly higher in the AHPPDP-treated group on Day 8, after receiving 2 doses of AHPPDP, and returned to low levels by the end of study (FIG. 19). IL-1β is crucial for both cellular defense and tissue repair, and has a complex role in response to CNS injury.

These results indicate a composition comprising AHPPDP is useful for treating symptoms of neuropathy.

Example 25. In Vitro Effects of AHPPDP on LPS-Induced Inflammation in THP-1 Cells The purpose of this study was to evaluate anti-inflammatory effects of AHPPDP on lipopolysaccharide (LPS) induced inflammation as demonstrated by changes in IL 1 beta, IL-6, and TNF alpha cytokine production in THP-1 cells. A composition comprising AHPPDP was prepared as described in Example 23 and sterile filtered, referred to as Composition E26f. 300,000 THP-1 cells were plated per well. Control wells included media only. Cells were contacted with LPS and test articles as outlined in Tables 20 and 21. For a positive control, cells were administered 1.0 μg/mL Candesartan. Candesartan is a statin and known to reduce the production of cytokines. Specifically, candesartan is an angiotensin receptor subtype 1 inhibitor and was utilized as a positive control. The cells were incubated for 1 hour.

TABLE 20

Test Articles

| Test Article | Concentration (mg/mL)[a] |
| --- | --- |
| Composition E26f | 145.8 |
| Vehicle 3 | 0 |
| Vehicle 1 | 0 |

[a]Total protein concentration via BCA.

TABLE 21

LPS Stimulation

| Treatment | LPS Stimulation |
| --- | --- |
| Cells Only | No LPS<br>LPS, 500 ng/mL<br>LPS, 5 μg/mL) |
| Candesartan (1 μg/mL) | LPS, 500 ng/mL<br>LPS, 5 μg/mL) |
| IVIG (1 mg/mL) | No LPS<br>LPS, 500 ng/mL<br>LPS, 5 μg/mL) |
| AHPPDP high concentration<br>(76 mg/mL; Composition E26f) | No LPS<br>LPS, 500 ng/mL<br>LPS, 5 μg/mL) |

TABLE 21-continued

LPS Stimulation

| Treatment | LPS Stimulation |
| --- | --- |
| AHPPDP low concentration<br>(19 mg/mL; Composition E26f) | No LPS<br>LPS, 500 ng/mL<br>LPS, 5 μg/mL) |

Abbreviations:
Conc. = concentration;
LPS = lipopolysaccharide

The cells were incubated, and samples of the supernatant were collected at 4 hours and 24 hours. The remaining cells were collected and analyzed for total cell count and percent viability. The Meso Scale Discovery (MSD; Rockville, MS) V-PLEX kit (4-PLEX) with IL-1b, IL-6, IL-8, and TNF-α were used to analyze the cytokines in the media at 4 and 24 hours after LPS stimulation.

Figure 18:
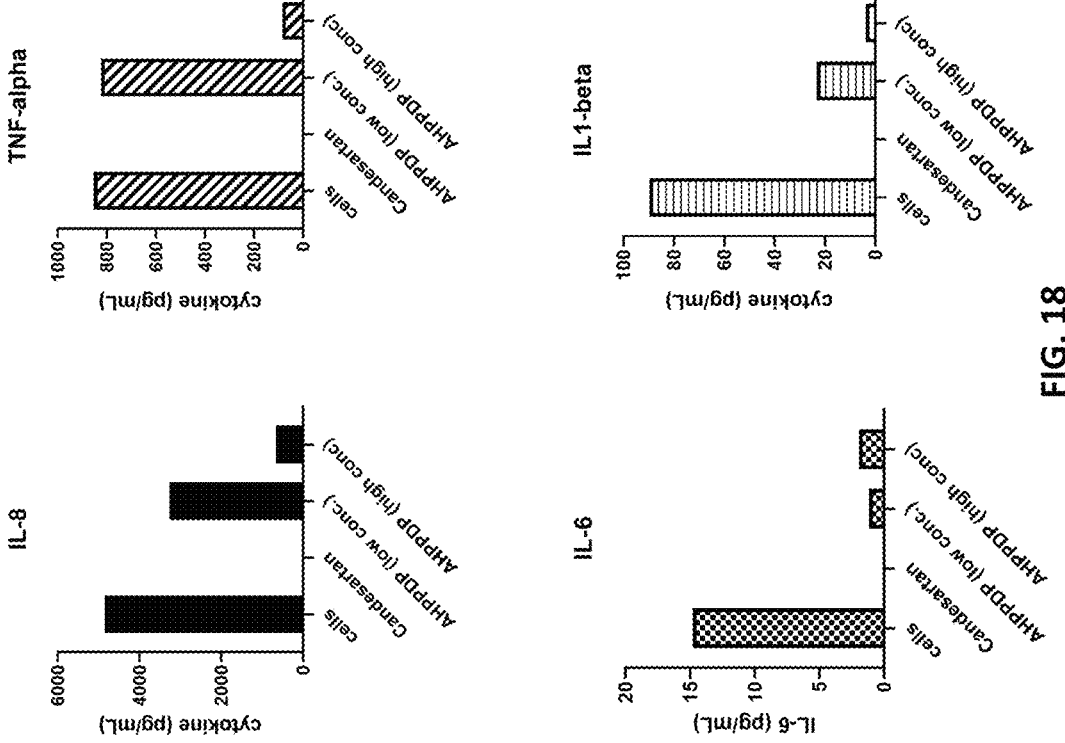
FIG. 18 provides graphs depicting reduction of cytokine levels in THP-1 cells after induction of inflammation by lipopolysaccharide and treatment with a composition comprising AHPPDP (Composition E26f).

AHPPDP reduced LPS-induced cytokine production in THP-1 cells in a concentration-dependent manner (Table 22, FIG. 18). The positive control, Candesartan, performed as expected, fully reducing the production of cytokines.

TABLE 22

Cytokine Production Following Treatment
with Candesartan or AHPPDP

| Condition<br>(500 ng LPS); 24 hours | IL-6<br>(pg/mL) | TNF-alpha<br>(pg/mL) | IL-8<br>(pg/mL) | IL1-beta<br>(pg/mL) |
| --- | --- | --- | --- | --- |
| Cells | 14.8 | 854 | 4856 | 89.7 |
| Candesartan | 0 | 0 | 1.44 | 0 |
| AHPPDP (19 mg/mL) | 1.15 | 823 | 3270 | 23.3 |
| AHPPDP (76 mg/mL) | 1.96 | 85.1 | 664 | 3.88 |

These results indicate AHPPDP has anti-inflammatory properties.

Example 26. Activity of Growth Factors in Allogeneic Human Plasma and Platelet Derived Product To evaluate the functional activity of AHPPDP, activation of PDGF receptor α/β (PDGFR α/β) and EGF receptors (EGFR), were assessed. The AHPPDP composition utilized (CUR-001-20L-SEP24) was generated by the method set forth in Example 31, FIG. 26, including concentration of platelet proteins through buffer exchange including removal of citrate and formulating in a suitable buffer.

The PDGFRα/β assay is a commercially available cell-based reporter assay kit that utilizes proprietary human cells that have been engineered to provide constitutive expression of the human PDGFR α/β. To evaluate PDGF, cells were used which constitutively express both platelet derived growth factor receptors alpha and beta (PDGFRα and PDGFRβ). Agonism of the receptor leads to activation of the Ca$^{+2}$ calcineurin nuclear factor of activated T-cells (NFAT) cascade. The NFAT response elements were linked to luciferase. Thus, the presence of functional PDGF would result in increased levels of luciferase. The specificity of signal was confirmed by depleting PDGF in AHPPDP (composition E27f; data not shown).

The EGFR1 assay is a commercially available cell-based reporter assay kit that utilizes proprietary human cells that provide constitutive expression of the Human Type 1 epidermal growth factor receptor. The reporter cells contain the luciferase reporter gene functionally linked to an upstream minimal promoter and tandem signal transducer and activator of transcription 3 (STAT3) genetic response element sequences. Signaling via EGFR1 activates STAT3, resulting in a dose-dependent luminescent signal.

AHPPDP contained quantifiable levels of PDGF (FIG. 21A) with a half maximal effective PDGF concentration (EC50) of 0.856 ng/mL. AHPPDP showed functional agonist activity in PDGF receptor activation (FIG. 21B). Matrix effects were present at the higher concentrations of both curves, creating a gel-like reaction in the assay plate. This interference resulted in lower signals at the top end of the curves and limited the ability to see the full agonist activity of AHPPDP.

Figure 21D:
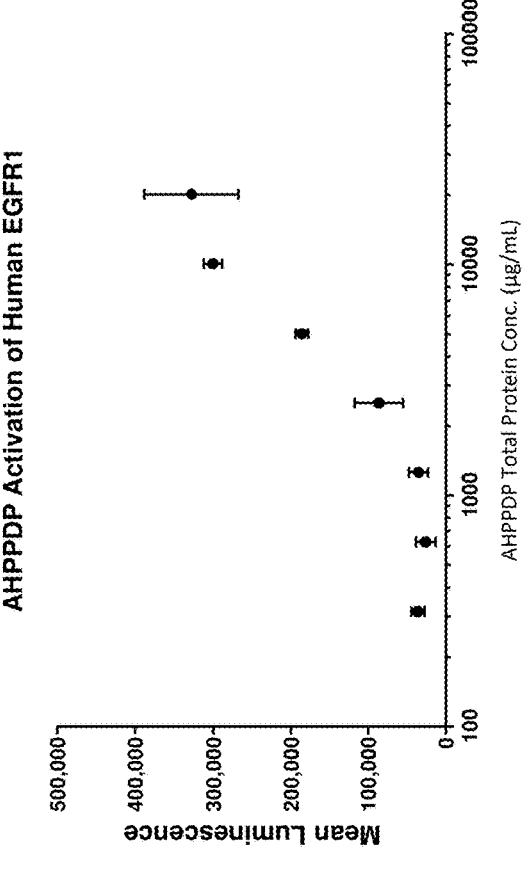
Figure 21C:
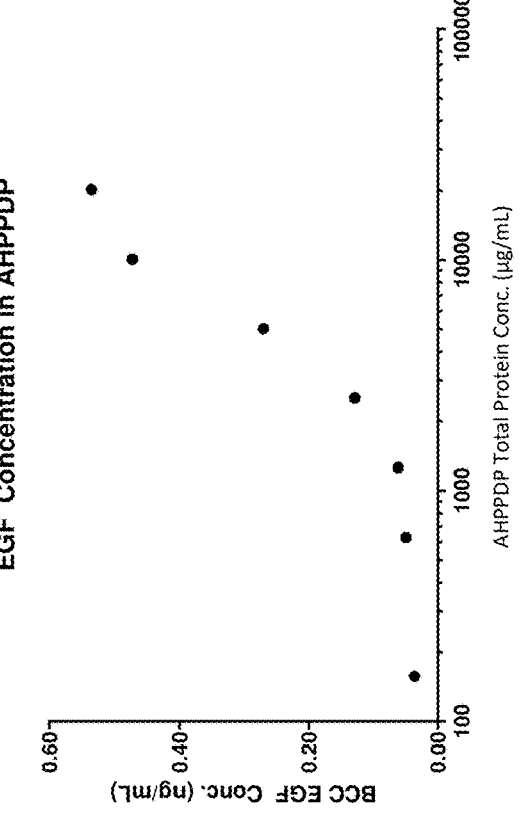

AHPPDP contained quantifiable levels of EGF (FIG. 21C) with an EC50 of 0.812 ng/mL. AHPPDP showed functional agonist in EGFR1 receptor activation (FIG. 21D).

Example 27: Induction of Anti-Inflammatory Response by Allogeneic Human Plasma and Platelet Derived Product An in vitro cytokine release assay was developed to characterize the anti-inflammatory potential of AHPPDP (see Singh, U., et al., 2005). Briefly, a Tohoku Hospital Pediatrics-1 (THP-1) human monocytic cell line was stimulated with lipopolysaccharide (LPS) to elicit cytokine secretion. AHPPDP (CUR-2401-6L-SEP24) was prepared as described in Example 31, FIG. 26 including concentration of platelet proteins through buffer exchange including removal of citrate and formulating in a suitable buffer. The AHPPDP was added to the cells prior to LPS stimulation to assess if the amount of cytokines are able to be reduced. Candesartan, an angiotensin receptor subtype 1 inhibitor previously shown to reduce cytokine levels, was utilized and confirmed as a positive control. THP-1 cells were pre-incubated with media, vehicle, candesartan at 1 μg/mL or AHPPDP at 10 or 20 mg/mL. The maximum concentration of AHPPDP that could be tested in this assay was 20 mg/mL, due to gelling observed in wells. The cells were then incubated with 500 ng/mL of LPS and cytokine secretion (IL-1, IL-6, IL-8, and TNF-α) was assessed at 4 and 24 hours.

Figure 22:
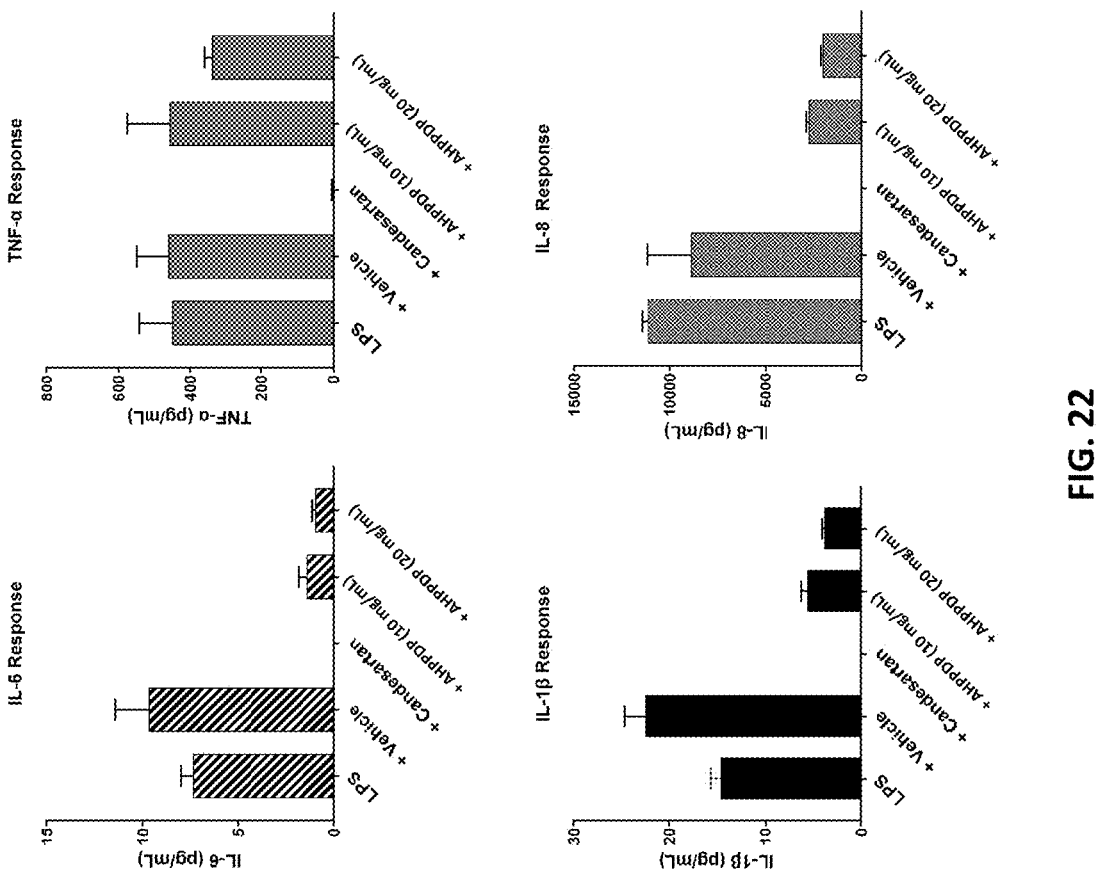
FIG. 22 provides graphs depicting reduction of cytokine levels in THP-1 cells after induction of inflammation by lipopolysaccharide and treatment with a composition comprising AHPPDP (Composition CUR-2401-6L-SEP24).

Results of this assay demonstrate the anti-inflammatory potential of AHPPDP. AHPPDP reduced the levels of cytokine in the media, demonstrating anti-inflammatory activity, as shown in FIG. 22. Levels of IL-6 were reduced over 80% by 10 and 20 mg/mL AHPPDP; IL-13 was reduced 62% by 10 mg/mL AHPPDP, and 74% by 20 mg/mL AHPPDP.

Levels of IL-8 were reduced by over 75% by 10 and 20 mg/mL AHPPDP. More modest reductions were observed in TNF-α, with only 25% reduction with 20 mg/mL of AHPPDP. All cytokines were inhibited by 1 μg/mL candesartan. There were either no or negligible cytokine responses when cells were incubated with either concentration of AHPPDP alone (data not shown).

These studies demonstrate the broad anti-inflammatory activity of AHPPDP in an in vitro assay.

Example 28: In Vivo Tolerability of Formulated Allogeneic Human Plasma and Platelet Derived Product To investigate the in vivo tolerability of allogeneic human plasma and platelet derived product (AHPPDP, PLS-RPT2007-A-50) formulated in sodium citrate as generated by the foregoing methods, Briefly, platelet suspensions underwent three freeze-thaw cycles, were clarified via centrifugation and filtration, and then buffer exchanged and concentrated. Sprague Dawley rats were utilized. Specifically, adult male rats were administered the test articles set forth in Table 23.

TABLE 23

| Test Articles | | |
| --- | --- | --- |
| Test Article | Formulation | Concentration (mg/mL) |
| PLS-RPT2007-A-50 [a] | 100 mM sodium citrate, | 54 [b] |
| Vehicle (Sodium citrate) | 5 mM EDTA, pH 7.5 | NA |
| PBS | Phosphate buffered saline | NA |

[a] PLS-RPT2007-A-50 derived from human origin was tested and found non-reactive for HIV-1 RNA, HCV RNA, HBsAg, HBV DNA, WNV RNA, ZIKV-RNA, and negative for syphilis by serological test.
[b] Total protein concentration.

Sprague Dawley rats (n=1-2/group) were administered AHPPDP, vehicle, or PBS via subcutaneous (SC) or epidural/intrathecal (Epi/IT) injection on Day 1 under light isoflurane anesthesia according to the study design set forth in Table 24 below. The intended route of administration to the rats is epidural, but as the injection was not performed using fluoroscopy (or other) imaging-guided technique the possibility of intrathecal administration cannot be excluded; therefore, the route is called epidural/intrathecal.

TABLE 24

| Experimental Design | | | | | | |
| --- | --- | --- | --- | --- | --- | --- |
| Group No. | Animal No. (ID No.) | Treatment | Dose Level (mg/animal) | Dose Conc. (mg/mL)[a] | Dose Volume (μL/animal) | ROA |
| 1 | 3 (1-3) | Vehicle (PBS) | 0 | 0 | 75 | Epi/IT |
| 2 | 1 (10) | AHPPDP | 4.1 | 54 | 75 | Epi/IT |
| 3 | 2 (4, 5) | Vehicle (Sodium Citrate) | 0 | 0 | 75[b], 25[c] | Epi/IT |
| 4 | 2 (6, 7) | Vehicle (Sodium Citrate) | 0 | 0 | 75 | SC |
| 5 | 2 (8, 9) | AHPPDP | 4.1 | 54 | 75 | SC |

Abbreviations: Conc. = concentration; epi/IT = epidural/intrathecal; ID = animal identification; No. = number; PBS = phosphate buffered saline; ROA = route of administration; SC = subcutaneous.
[a] AHPPDP concentration is the total protein concentration.
[b] Animal No. 5 received 75 μL of sodium citrate buffer.
[c] Animal No. 4 received 25 μL of sodium citrate buffer.

Body weights of the rats were recorded prior to administration of AHPPDP or vehicle, and daily over a 7-day period. Clinical observations were conducted on Day 1 prior to dosing, at 2-6 hours following dosing, and daily thereafter. Blood samples (~300 μL) were collected via tail/saphenous or jugular veins on Day 2 for complete blood count analysis. Rats were terminated via $CO_2$ asphyxiation on Day 8.

A single SC injection of AHPPDP or vehicle-containing sodium citrate was well tolerated, and no abnormal clinical observations were noted over the 7-day period. Conversely, all rats administered either AHPPDP (n=1) or vehicle containing sodium citrate (n=2) via epi/IT injection displayed potentially adverse responses within an hour of administration, indicating the epi/IT injection of sodium citrate-containing formulation was not well tolerated. As a result of this response, these animals were humanely euthanized within an hour and not replaced.

Modest decreases (less than 10% change from baseline) in body weights were observed beginning on Day 2 in remaining animals that was followed by partial recovery in body weight by Day 8. The results show single subcutaneous injections of AHPPDP and vehicle formulations containing 100 mM sodium citrate were well tolerated in Sprague Dawley rats, whereas a single epi/IT administration of formulations containing 100 mM sodium citrate was not tolerated.

Example 29. In Vivo Immune Response to Repeat Subcutaneous Injection of Formulated Allogeneic Human Plasma and Platelet Derived Product To investigate the potential immune response of repeat administration of AHPPDP (PLS-RPT2007-A-150) formulated in 100 mM sodium citrate, Sprague Dawley rats were utilized. Briefly, platelet suspensions underwent three freeze-thaw cycles, were clarified via centrifugation and filtration, and then buffer exchanged and concentrated. Adult male and female rats were administered the test articles set forth in Table 25.

TABLE 25

| Test Articles | | |
| --- | --- | --- |
| Test Article | Formulation | Concentration (mg/mL) |
| PLS-RPT2007-A-150[a] | 100 mM sodium citrate, 5 mM EDTA, pH 7.5 | 156[b] |
| Vehicle (Sodium citrate) | | NA |

[a]PLS-RPT2007-A-150 derived from human origin was tested and found non-reactive for HIV-1 RNA, HCV RNA, HBsAg, HBV DNA, WNV RNA, ZIKV-RNA, and negative for syphilis by serological test.
[b]Total protein concentration.

Sprague Dawley rats (6-7 weeks old; n=3/sex/group) were administered vehicle or AHPPDP via SC injection on Days 1, 15, and 29 according to the study design set forth in Table 26 below.

TABLE 26

| | | | Experimental Design | | | |
| --- | --- | --- | --- | --- | --- | --- |
| Group No. | Animal No. (ID No.) | Treatment | Dose Level (mg/animal) | Dose Conc. (mg/mL)[a] | Dose Volume (μL/animal) | ROA |
| 1 | 3/sex (1-6) | Vehicle (Sodium Citrate) | 0 | 0 | 100 | SC |
| 2 | 3/sex (7-12) | AHPPDP | 15.6 | 156 | 100 | SC |

Abbreviations: Conc. = concentration; ID = animal identification; No. = number; ROA = route of administration; SC = subcutaneous.

[a]AHPPDP concentration is the total protein concentration.

Body weights were recorded prior to dosing and weekly until termination. Detailed clinical observations were conducted prior to dosing and once daily thereafter. Additional observations were conducted approximately 4 hours post dose on dosing days. Blood samples (~150 µL) was collected via tail/saphenous or jugular veins on Day 16 for comprehensive complete blood count (CBC) analysis. On Day 30, terminal whole blood samples were collected for hematology, serum chemistry, and enzyme-linked immunosorbent assay (ELISA) for quantitation of HSA. Detection and quantitation of HSA was performed using a commercially available human albumin ELISA kit (#ab227933, ABCAM® [Cambridge, UK]) with colorimetric detection. Part of the whole blood was placed in EDTA tubes for CBC and the remainder processed for serum for serum chemistry and ELISA. All rats were terminated on Day 30 via C02 asphyxiation.

Clinical observations of the rats were performed over the study period. No abnormal clinical observations were noted indicating repeated SC injection of AHPPDP or vehicle containing sodium citrate was well tolerated. Further, there were no apparent differences in intergroup means for hematology parameters vehicle control and AHPPDP group means on Day 15 or Day 30, and no differences in intragroup means for each treatment on Day 15 compared to Day 30. There were no apparent differences in serum chemistry parameters for rats administered vehicle control compared to rats administered AHPPDP on Day 30.

Human serum albumin (HSA) levels were higher in rats treated with AHPPDP. Specifically, HSA levels on Day 30 were detected in all but one rat administered AHPPDP (Mean±standard error: 5.25E+07±1.64E+07 µg/mL). All rats administered the vehicle control had serum levels below 1.6E+07 µg/mL.

Following termination, a necropsy was performed on all the rats. No gross pathological changes were observed in animals administered vehicle. Among animals administered AHPPDP, some findings were observed in the heart and/or kidneys, but the relation of these gross observations to the test article is unknown.

The results indicate that repeated subcutaneous injections of AHPPDP and vehicle formulations containing 100 mM sodium citrate were well tolerated in male and female Sprague Dawley rats. There were no apparent signs of immune response following single or repeated administration of AHPPDP.

Example 30. Impact of Depth Filter Materials on PDGF-AB Concentration

To investigate the impact of depth filter materials on PDGF-AB concentration of AHPPDP, five bags of platelets were thawed at 5° C. for 24 hours and then pooled. The pooled blood was split into two samples. One sample did not have buffer added. A buffer consisting of 100 mM sodium citrate and 5 mM EDTA was added to the second sample. Both samples were centrifuged at 3,000×g for 15 minutes. Polysorbate 80 was spiked into the samples at a final concentration of 0.2%, and the samples were incubated overnight at 5° C. The samples were filtered via depth-filtration using either polyacrylic fiber and silica, diatomaceous earth (DE) and cellulose, or cellulose. The resulting filtrate was labeled "Main". An additional rinse of the filter was performed to recover any remaining protein and was labeled "Rinse".

Figure 23:
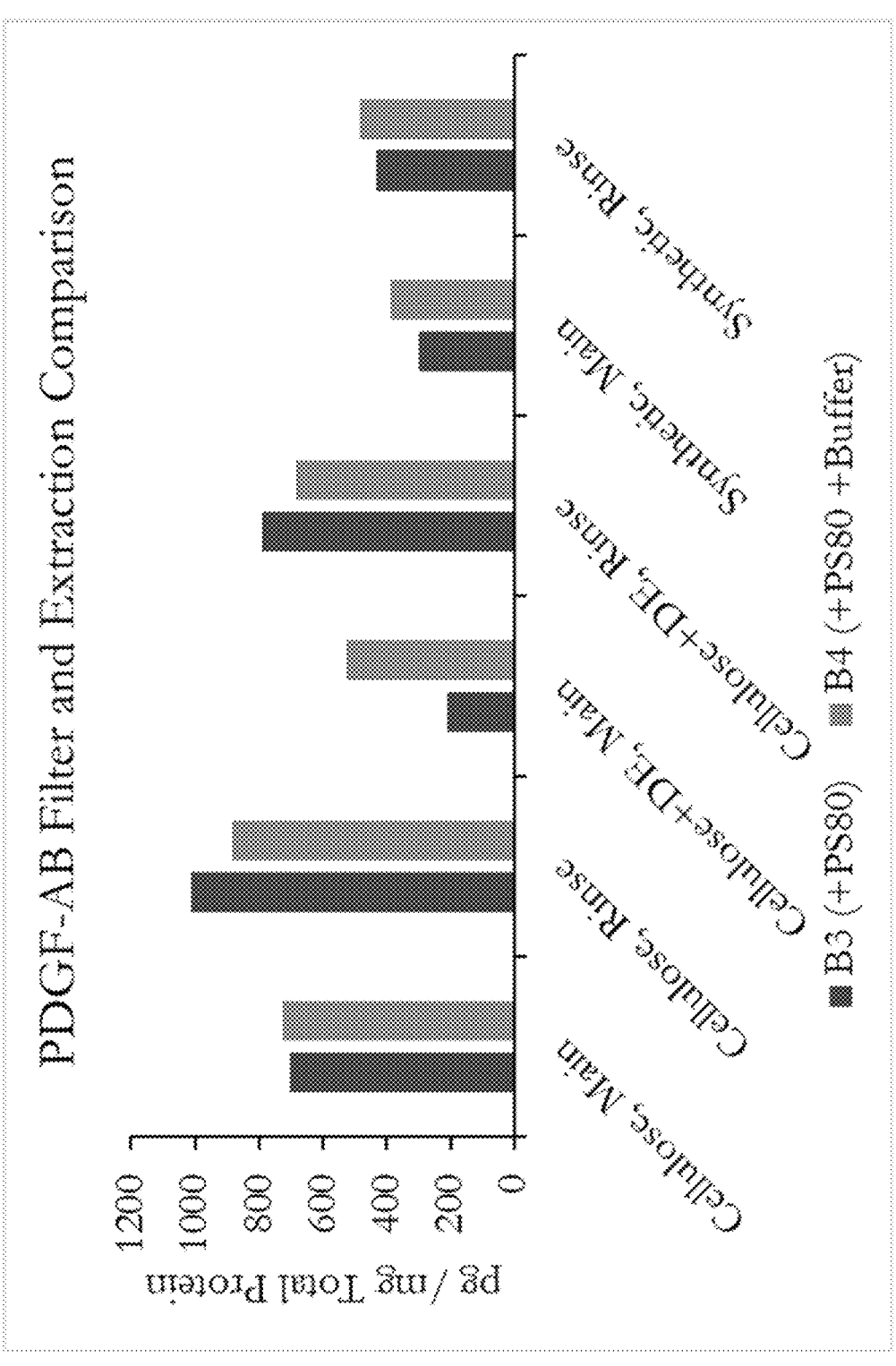
FIG. 23 provides a graph of total protein concentration of pooled whole blood following depth filtration with a polyacrylic fiber and silica, diatomaceous earth (DE) and cellulose, or cellulose filter.
Figure 24:
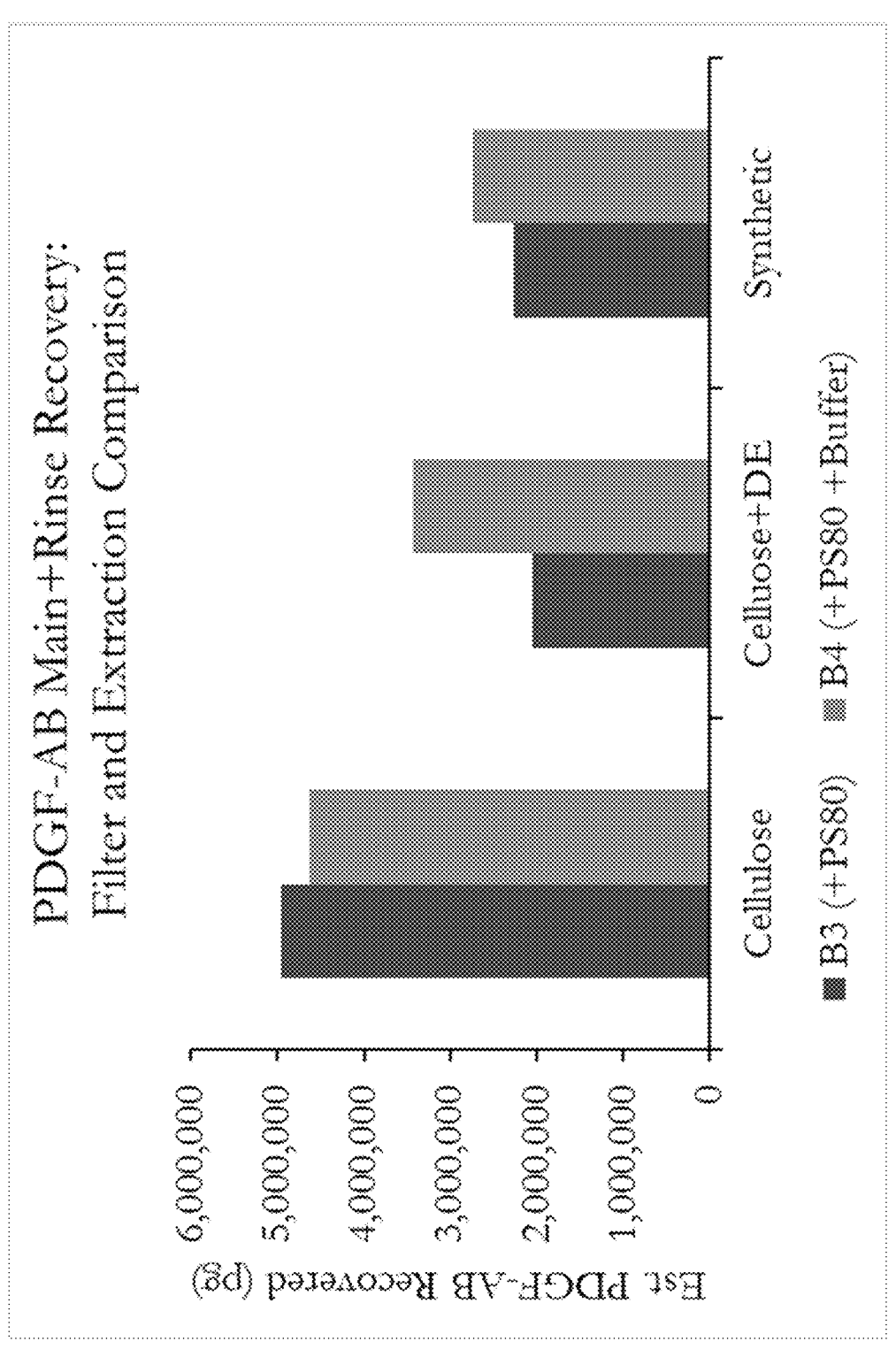
FIG. 24 provides a graph of PDGF-AB concentration of pooled whole blood following depth filtration with a polyacrylic fiber and silica, diatomaceous earth (DE) and cellulose, or cellulose filter.
Figure 25:
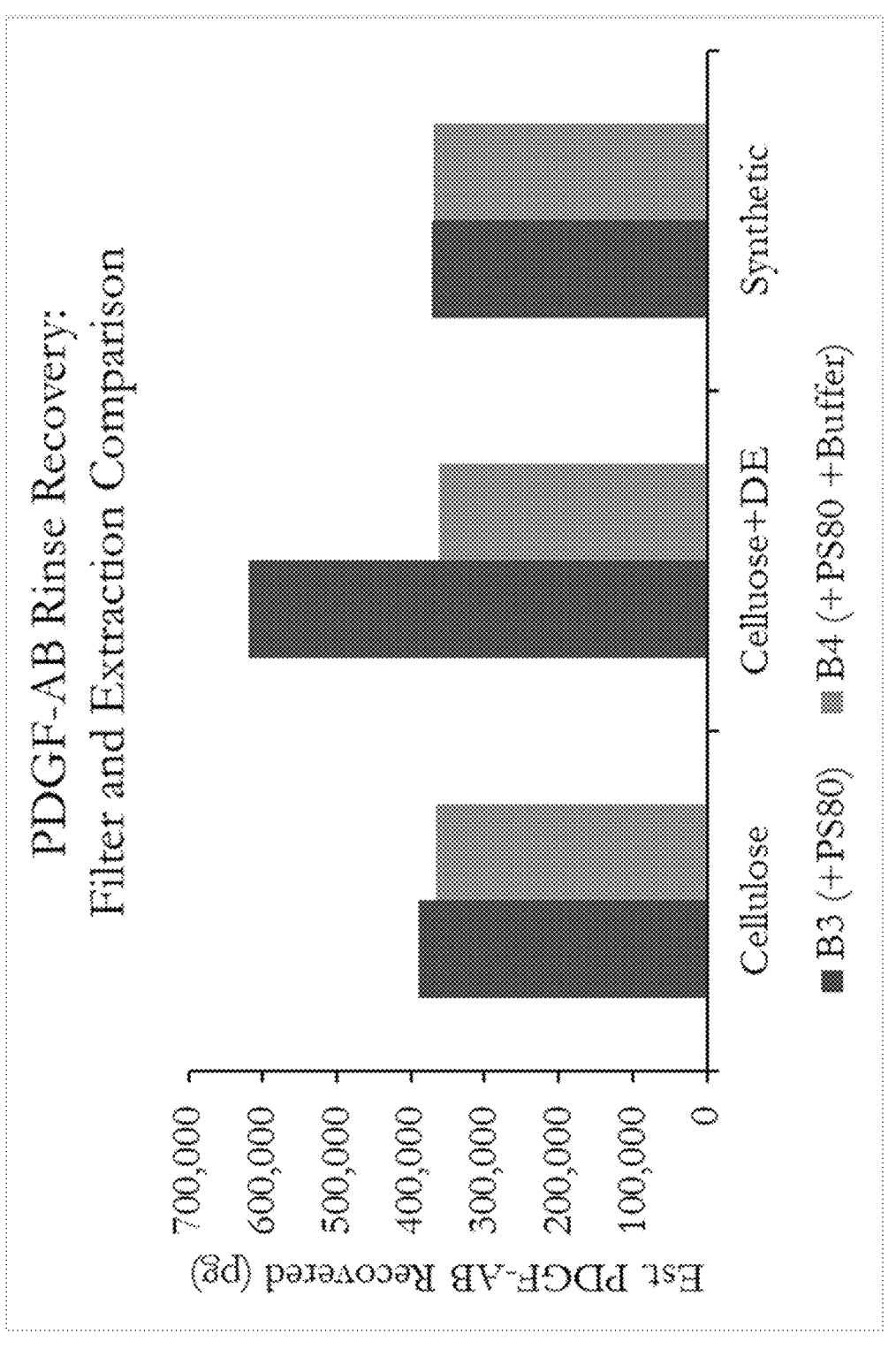
FIG. 25 provides a graph of PDGF-AB concentration of pooled whole blood following rinsing of a polyacrylic fiber and silica, diatomaceous earth (DE) and cellulose, or cellulose filter.

Following depth filtration, the opacities of the samples was evaluated. Samples that had been filtered with a polyacrylic fiber and silica appeared to be the least opaque. The total protein concentration and PDGF-AB concentration was quantified for the samples. Depth filtration with a cellulose filter resulted in the highest total protein concentration followed by DE and cellulose. A synthetic depth-filter resulted in the lowest protein concentration (FIG. 23). Adding buffer helped retain PDGF-AB during depth-filtration (FIG. 24). Further, rinsing the depth-filter after completion of depth-filtration resulted in recovery of PDGF-AB (FIG. 25).

Example 31. Characterization of Allogeneic Human Plasma and Platelet Derived Product Allogenic human plasma and platelet derived product (AHPPDP) was produced and characterized. The process to produce AHPPDP is depicted in FIG. 26 and described below:

Thawing: Platelet suspensions obtained from one or more human donors were thawed at about 4° C. for about 24 to about 60 hours.

Centrifugation: Thawed platelet suspensions were centrifuged at 1,500×g for 5 minutes at 21° C.

Pooling: Thawed platelet suspensions from at least 2 human donors were added to a peristaltic pump and mixed for 10 minutes. The platelet suspensions were then mixed overnight.

Filtration: Pooled platelet suspensions were filtered with a Clarisolve filter and Millistack filter.

Extraction, Viral Inactivation: Platelet proteins were extracted with an extraction buffer comprising 10 mM sodium citrate and 0.2 mM EDTA. Polysorbate 80 was added to a concentration of 0.2%, and the platelet extract was mixed at 21° C. for 3 hours. The platelet extract was then mixed at about 2 to about 8° C. overnight.

Centrifugation: The platelet extract was centrifuged at 4,200×g at 21° C. for 30 minutes.

Filtration: The platelet extract was filtered with a Sartopore Maxicap filter.

Viral Clearance: An S20N filter was used to remove viruses. The platelet extract was filtered three times.

Concentration: The platelet extract was concentrated and buffer exchanged with TFF.

Filtration: The concentrated platelet extract was sterile filtered with a 0.22 µm filter.

The AHPPDP was produced in 5 lots as described in Table 27 below.

TABLE 27

| AHPPDP Lots | |
| --- | --- |
| Lot Number | Batch Size |
| CUR-2401-3.75 L-JUL24 | 3.75 L |
| CUR-2401-6 L-SEP24 | 6 L |
| CUR-001-20 L-SEP24 | 20 L |
| CUR-001-20 L-NOV24 | 20 L |

The AHPPDP was characterized by various properties including but not limited to, protein concentration, bioburden, color and clarity, pH, and osmolality among others. The composition of AHPPDP was evaluated, and the concentrations of various growth factors was quantified via enzyme-linked immunosorbent assay (ELISA) or Meso Scale Discovery (MSD). Specifically, determination of proteins such as VEGF-a, EGF, FGF-2, HGF from AHPPDP was performed with a MSD multiplex panel (U-PLEX platform). Biotinylated capture reagents were coupled to U-PLEX Linkers. In this assay, capture reagents were specific for VEGF-a, EGF, FGF-2, HGF respectively. The U-PLEX Linkers then self-assembled onto unique spots on the U-PLEX plate. After the VEGF-a, EGF, FGF-2 and HGF in the sample were bound to the specific capture reagents, detection antibodies (specific for VEGF-a, EGF, FGF-2, HGF) conjugated with electrochemiluminescent labels (MSD GOLD SULFO-TAG) and were bound to the proteins to complete the sandwich immunoassay. Once the sandwich immunoassay was complete, the plate was placed into an MSD instrument where the amount of proteins present in the sample was measured.

The PDGF-AB assay employed the quantitative sandwich enzyme immunoassay technique. A monoclonal antibody specific for human PDGF-BB was pre-coated onto a microplate. Standards and samples were pipetted into the wells and any PDGF-AB present was bound by the immobilized antibody. After washing away any unbound substances, an enzyme-linked polyclonal antibody specific for human PDGF-AA was added to the wells. Following a wash to remove any unbound antibody-enzyme reagent, a substrate solution was added to the wells and color developed in proportion to the amount of PDGF-AB bound in the initial step. The color development was stopped, and the intensity of the color was measured.

Capillary electrophoresis (CE-SDS) was further employed to quantify the proteins present at the highest concentrations. Specifically, the CE-SDS separation technique used 50 m ID bare fused-silica capillary in a cartridge set for a total length of 30.2 cm.

The characteristics and composition of AHPPDP are outlined in Table 28 below.

TABLE 28

| | AHPPDP Characteristics | | | |
|---|---|---|---|---|
| Attribute | CUR-2401-3.75 L-JUL24 | CUR-2401-6 L-SEP24 | CUR-001-20 L-SEP24 | CUR-001-20 L-NOV24 |
| Total Protein Concentration as measured by BCA | 101 mg/mL | 141 mg/mL | 108 mg/mL | 117 mg/mL |
| PDGF-AB by ELISA | 50.2 ng/mL | 60.7 ng/mL | 57.4 ng/mL | 57.8 ng/mL |
| pH | 7.4 | 7.3 | 7.1 | 7.2 |
| Osmolality | 404 | 404 | 425 | 407 |
| % HSA as measured by CE-SDS | 61.1% | 65.5% | 60.5% | 61.3% |
| % Ig by CE-SDS | 18.8% | 12.2% | 13.4% | 14.0% |
| Visual Appearance | Greater than Brownish yellow color | Opalescent, Brownish yellow color | Ref Suspension IV, Brownish yellow color | Opalescent, Brownish yellow color |
| TGF-β by ELISA | — | 407.3 ng/mL | 362.8 ng/mL | On Test |
| VEGF-a by MSD | 611 pg/mL | 486 pg/mL | 582 pg/mL | On Test 537 pg/mL |
| EGF by MSD | 1355 pg/mL | 2766 pg/mL | 2637 pg/mL | 2690 pg/mL |
| FGF-2 (basic) by MSD | 749 pg/mL | 834 pg/mL | 901 pg/mL | 1010 pg/mL |
| HGF by MSD | 808 pg/mL | 295 pg/mL | 462 pg/mL | 675 pg/mL |
| Fibrinogen by ELISA | — | 1.63 mg/mL | 1.48 mg/mL | 1.98 mg/mL |

The stability of the AHPPDP compositions were also evaluated. The AHPPDP batches were stored at −80° C. for one month. After one month, the AHPPDP was characterized including but not limited to, protein concentration, composition, pH, and osmolality among others. AHPPDP remained stable following one month of storage (data not shown).

To further investigate the cytokines present in AHPPDP, a Luminex assay was performed (Eve Diagnostics, Alberta, Canada). The Luminex assay quantified cytokines including, IL-5, IL-1β, IL-6, IL-1RA, IL-10, IL-13, TNFα, IL-8, IL-12p40, and MCP-1. The concentrations of cytokines in each AHPPDP batch are outlined in Table 29 below.

TABLE 29

Cytokines in AHPPDP

| Analyte pg/mL | CUR-2401-6 L-SEP24 | CUR-001-20 L-SEP24 | CUR-001-20 L-NOV24 |
|---|---|---|---|
| IFNγ | 0.18 | 0.21 | 0.27 |
| IL-5 | 0.83 | 1.10 | 1.23 |
| IL-1β | 1.26 | 2.68 | 2.76 |
| IL-6 | 1.51 | 2.81 | 3.50 |
| IL-1RA | 4.24 | 3.37 | 5.45 |
| IL-10 | 3.45 | 3.51 | 7.26 |
| IL-13 | 2.82 | 5.76 | 7.05 |
| TNFα | 11.47 | 1.33 | 12.35 |
| IL-8 | 25.28 | 39.68 | 34.68 |
| IL-12p40 | 62.06 | 73 | 70.09 |
| MCP-1 | 229.2 | 247.6 | 238.1 |

Example 32. In Vitro Wound Closure

A scratch assay was developed to evaluate the effects of AHPPDP on wound closure. The test articles are outlined in Table 30 below. Briefly, AHPPDP was prepared based on the methods disclosed herein. AHPPDP (CUR-2401-20L-SEP24) was prepared as described in Example 31, FIG. 26 including concentration of platelet proteins through buffer exchange including removal of citrate and formulating in a suitable buffer.

TABLE 30

Test Articles

| Test Article | Concentration (mg/mL)$^a$ |
|---|---|
| Vehicle | NA |
| AHPPDP | 108 |

$^a$Total protein concentration.

3,000 normal human dermal fibroblasts (NHDF) cells were plated per well. 3.4 ng/mL PDGF-BB in cell media was the positive control. Vehicle at 9% concentration was the negative control. The NHDF cells were starved 48 hours prior to scratch initiation (Day 5) which allowed for higher potential for observing the wound closure effects of PDGF-BB and AHPPDP. Wound closure was measured at 6 and 24 hours after PDGF-BB or AHPPDP treatment.

The output measures of the scratch assay were, total number of nuclei per well, sum of cell area per well, and sum of empty area per well. Percent wound closure from AHPPDP was relative, and calculated with a PDGF treatment defined as 100%, and a vehicle condition defined as 0%.

Wound healing compared to vehicle condition was obtained after treatment with 3.7 ng/mL PDGF-BB indicating the positive control performed as expected. Addition of 9% (v/v) of vehicle after scratch initiation resulted in enhanced wound closure at 24 hours after treatment compared to a medium-only condition, in cells that are serum-starved since day 5. Treatment with concentrations of AHPPDP between 2.5 mg/mL and 0.625 mg/mL resulted in higher wound closure relative to vehicle. There were no abnormal observations of nuclei count, indicating there were no potential cytotoxic side effects (data not shown).

The invention claimed is:

1. A pharmaceutical composition comprising an allogeneic human plasma and platelet derived product, wherein cells and cell debris are removed from the product, wherein the product comprises:
   (a) human plasma proteins comprising human serum albumin, immunoglobulins, and fibrinogen; and
   (b) human platelet proteins comprising platelet derived growth factor (PDGF)-AB at a concentration of about 20 ng/ml to about 160 ng/mL,
   wherein the total protein concentration of the composition is greater than 50 mg/mL and less than or about 500 mg/mL.

2. The pharmaceutical composition of claim 1, wherein the amount of human serum albumin is about 60% to about 70% w/w total protein and the amount of immunoglobulins is about 10% to about 20% w/w total protein.

3. The pharmaceutical composition of claim 1, wherein the concentration of fibrinogen is about 0.5 mg/mL to about 5 mg/mL.

4. The pharmaceutical composition of claim 1, comprising one or more of transforming growth factor beta (TGF-β), vascular endothelial growth factor (VEGF), fibroblast growth factor (FGF), epidermal growth factor (EGF), and hepatocyte growth factor (HGF).

5. The pharmaceutical composition of claim 1, comprising one or more of TGF-β at a concentration of about 50 ng/mL to about 1000 ng/mL, VEGF at a concentration of about 50 pg/mL to about 1500 pg/mL, EGF at a concentration of about 100 pg/mL to about 6000 pg/mL, FGF at a concentration of about 100 pg/mL to about 3000 pg/mL, and HGF at a concentration of about 25 pg/mL to about 2500 pg/mL.

6. The pharmaceutical composition of claim 1, comprising one or more cytokines selected from interleukin (IL)-5, IL-1b, IL-6, IL-1Ra, IL-10, IL-13, tumor necrosis factor alpha (TNFα), IL-8, IL-12p40, and monocyte chemoattractant protein-1 (MCP-1).

7. The pharmaceutical composition of claim 1, comprising a pH of about 6.5 to about 8.5.

8. The pharmaceutical composition of claim 1, comprising an osmolality of about 200 mOsmo/kg to about 500 mOsmo/kg.

9. The pharmaceutical composition of claim 1, comprising a buffer.

10. The pharmaceutical composition of claim 1, wherein the total protein concentration is about 50 mg/mL to about 80 mg/mL and the PDGF-AB concentration is about 20 ng/ml to about 40 ng/mL.

11. The pharmaceutical composition of claim 10, wherein the amount of human serum albumin is about 60% to about 70% w/w total protein and the amount of immunoglobulins is about 10% to about 20% w/w total protein.

12. The pharmaceutical composition of claim 10, wherein the concentration of fibrinogen is about 0.5 mg/mL to about 1 mg/mL.

13. The pharmaceutical composition of claim 10, comprising one or more of TGF-β, VEGF, FGF, EGF, and HGF.

14. The pharmaceutical composition of claim 10, comprising one or more of TGF-β at a concentration of about 150 ng/ml to about 300 ng/ml, VEGF at a concentration of about 200 pg/mL to about 400 pg/mL, EGF at a concentration of about 1000 pg/mL to about 2000 pg/mL, FGF at a concentration of about 300 pg/mL to about 600 pg/mL, and HGF at a concentration of about 150 pg/mL to about 300 pg/mL.

15. The pharmaceutical composition of claim 10, comprising a buffer.

16. The pharmaceutical composition of claim 1, wherein the total protein concentration is about 80 mg/mL to about 160 mg/mL and the PDGF-AB concentration is about 40 ng/ml to about 80 ng/mL.

17. The pharmaceutical composition of claim 16, wherein the amount of human serum albumin is about 60% to about 70% w/w total protein and the amount of immunoglobulins is about 10% to about 20% w/w total protein.

18. The pharmaceutical composition of claim 16, wherein the concentration of fibrinogen is about 1 mg/mL to about 2 mg/mL.

19. The pharmaceutical composition of claim 16, comprising one or more of TGF-β, VEGF, FGF, EGF, and HGF.

20. The pharmaceutical composition of claim 16, comprising one or more of TGF-β at a concentration of about 300 ng/ml to about 500 ng/mL, VEGF at a concentration of about 400 pg/mL to about 800 pg/mL, EGF at a concentration of about 2000 pg/mL to about 4000 pg/mL, FGF at a concentration of about 600 pg/mL to about 1200 pg/mL, and HGF at a concentration of about 300 pg/mL to about 1000 pg/mL.

21. The pharmaceutical composition of claim 16, comprising a buffer.

22. The pharmaceutical composition of claim 1, wherein the total protein concentration is about 160 mg/mL to about 320 mg/mL and the PDGF-AB concentration is about 80 ng/ml to about 160 ng/mL.

23. The pharmaceutical composition of claim 22, wherein the amount of human serum albumin is about 60% to about 70% w/w total protein and the amount of immunoglobulins is about 10% to about 20% w/w total protein.

24. The pharmaceutical composition of claim 22, wherein the concentration of fibrinogen is about 2 mg/mL to about 5 mg/mL.

25. The pharmaceutical composition of claim 22, comprising one or more of TGF-β, VEGF, FGF, EGF, and HGF.

26. The pharmaceutical composition of claim 22, comprising a buffer.

27. The pharmaceutical composition of claim 1, wherein the product is derived from pooled platelet suspensions.

28. The pharmaceutical composition of claim 10, wherein the product is derived from pooled platelet suspensions.

29. The pharmaceutical composition of claim 16, wherein the product is derived from pooled platelet suspensions.

30. The pharmaceutical composition of claim 22, wherein the product is derived from pooled platelet suspensions.

\* \* \* \* \*